United States Patent
Chimenti et al.

(10) Patent No.: US 9,809,553 B2
(45) Date of Patent: Nov. 7, 2017

(54) ISOQUINOLINE COMPOUNDS, A PROCESS FOR THEIR PREPARATION, AND PHARMACEUTICAL COMPOSITIONS CONTAINING THEM

(71) Applicant: LES LABORATOIRES SERVIER, Suresnes (FR)

(72) Inventors: Stéfano Chimenti, Paris (FR); Christine Courchay, Igny (FR); Aimee Dessinges, Rueil Malmaison (FR); Françoise Gellibert, Bures-sur-Yvette (FR); Bertrand Goument, Viroflay (FR); Marc Konnert, Deuil-la-Barre (FR); Jean-Louis Peglion, Le Vesinet (FR); Christophe Poitevin, Paris (FR); Jean-Paul Vilaine, Chatenay Malabry (FR); Nicole Villeneuve, Rueil Malmaison (FR)

(73) Assignee: LES LABORATOIRES SERVIER, Suresnes (FR)

(*) Notice: Subject to any disclaimer, the term of this patent is extended or adjusted under 35 U.S.C. 154(b) by 0 days.

(21) Appl. No.: 15/119,173

(22) PCT Filed: Feb. 20, 2015

(86) PCT No.: PCT/FR2015/050415
§ 371 (c)(1),
(2) Date: Aug. 16, 2016

(87) PCT Pub. No.: WO2015/124877
PCT Pub. Date: Aug. 27, 2015

(65) Prior Publication Data
US 2017/0137385 A1   May 18, 2017

(30) Foreign Application Priority Data
Feb. 21, 2014 (FR) ...................................... 14 51389

(51) Int. Cl.
| C07D 217/02 | (2006.01) |
| C07D 217/04 | (2006.01) |
| C07D 405/06 | (2006.01) |
| A61K 31/472 | (2006.01) |
| C07D 217/24 | (2006.01) |

(52) U.S. Cl.
CPC ......... C07D 217/02 (2013.01); C07D 217/24 (2013.01); C07D 405/06 (2013.01)

(58) Field of Classification Search
None
See application file for complete search history.

(56) References Cited

U.S. PATENT DOCUMENTS
7,867,999 B1   1/2011   Chen et al.

FOREIGN PATENT DOCUMENTS
| WO | WO 02/13827 | 2/2002 |
| WO | WO 03/022835 A1 * | 3/2003 |
| WO | WO 2007/000240 | 1/2007 |

OTHER PUBLICATIONS

International Search Report with Written Opinion for PCT/FR2015/050415 of Mar. 31, 2015.
Lograsso, et al., Current Topics in Medicinal Chemistry, vol. 9, No. 8, p. 704-723, 2009.
Watson, et al, Bioorganic and Medicinal Chemistry, vol. 6, No. 6, p. 721-734, 1998.
International Preliminary Report for PCT/FR2015/050415 on Aug. 23, 2016.

* cited by examiner

Primary Examiner — Zinna Northington Davis
(74) Attorney, Agent, or Firm — Hueschen and Sage

(57) ABSTRACT

A compound of formula (I):

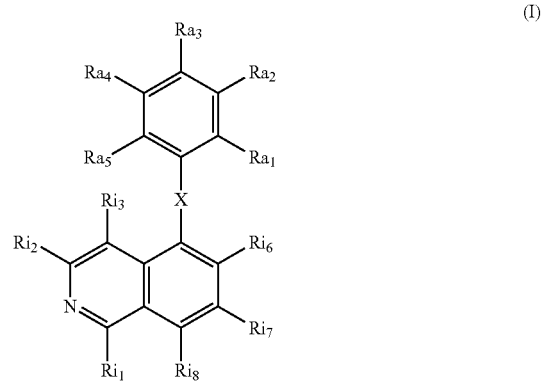

wherein the substituents are as defined in the description. Medicinal products containing the same which are useful in treating or preventing pathologies which are the result of activation of the RhoA/ROCK pathway and phosphorylation of the myosin light chain.

20 Claims, No Drawings

ISOQUINOLINE COMPOUNDS, A PROCESS FOR THEIR PREPARATION, AND PHARMACEUTICAL COMPOSITIONS CONTAINING THEM

The present invention relates to new isoquinoline compounds, to their synthesis and to their use in the prevention and/or treatment of pathologies which are the result of activation of the RhoA/ROCK pathway and phosphorylation of the myosin light chain.

Under the effect of agonists such as angiotensin II, 5-hydroxytryptamine or endothelin, the RhoA membrane protein, which belongs to the family of the small GTP-binding proteins, acquires the active GTP-bound configuration, under the control of specific adenyl nucleotide exchange factors. This active membrane form permits binding to the Rho-kinase protein and activation thereof.

Rho-kinase is a serine/threonine kinase with a molecular mass of 160 kdaltons and one of the many targets of the RhoA protein. Two isoforms of Rho-kinase, Rho-kinase/ROCK β/p160ROCK or ROCK1 and Rho-kinase α/ROCK α or ROCK2, which are coded for by two different genes, have been identified. The two isoforms are expressed ubiquitously, ROCK2 especially in the vascular smooth muscle cells, the heart and the brain. ROCK1 is expressed preferentially on the non-nervous tissues such as the lungs, the liver, the spleen, the kidneys and the testicles. These two isoforms share 92% homology in their kinase domain. The activation of ROCK by RhoA-GTP leads to phosphorylation and inhibition of a myosin phosphatase regulatory subunit and thus allows the myosin light chain to be maintained in a phosphorylated state, independently of the intracellular $Ca^{2+}$ concentration (a process known as $Ca^{2+}$ sensitisation). Phosphorylation of the myosin light chain is responsible for increasing the contractility of the actin cytoskeleton, which is the result of sliding between the actin and myosin filaments.

Activation of the RhoA/ROCK pathway is involved in the following dysfunctions and the pathologies associated therewith:

vasoconstriction by increase of the myogenic tone (Rattan et al, Pharmacological Sciences, 880:1-10, 2011),
formation of stress fibres and cellular contraction (Kaibuchi et al, Sciences, 275: 1308, 1997),
systemic arterial hypertension (Uehata et al, Nature, 389: 990-993, 1997; Pacaud et al, P. Nat. Rev. Cardiol., 7(11): 637-647, 2010),
pulmonary arterial hypertension (Jankov et al, Am J Physiol Heart Circ Physiol, 299:H1854-H1864, 2010; Fukumoto et al, Heart, 91: 391-392, 2005) and associated pulmonary fibrosis (Duong-Quy et al, J. Fran. Viet. Pneu., 03(08): 1-74, 2012),
increase in intraocular pressure, retinopathy and glaucoma resulting therefrom (Acott et al, Curr Opin Ophtalmol, 23(2): 135-43, 2012; Tanihara et al, Curr Eye Res, 36(10): 964-70, 2011; Rossetti et al, Expert. Opin. Investig. Drugs, 20(7):947-959, 2011; Chen et al, Clin. Ophtalmol, 5: 667-677, 2011; Rao et al, J Glaucoma, 21:530-538, 2012, Zhong et al, Int J Oncol, 43(5):1357-67, 2013; Van de Velde, Acta Ophtalmologica, 91: s252, 2013), dystrophy of the cornea due to proliferation of endothelial cells (Kinoshita et al, Cornea, 32(8): 1167-1170, 2013),
coronary artery vasospasm, angina pectoris, myocardial infarction (Kandabashi et al, Circulation, 101: 1319-1323, 2000; Shimokawa et al, Am. J. Physiol. Heart Circ. Physiol, 301: H287-H296, 2011),
endothelial dysfunction by negative regulation of NO production and atherosclerosis (Shimokawa et al, Cardiovasc. Res. 51: 169-177, 2001),
aortic aneurysm, occlusion of the peripheral arteries (Shimokawa et al, Am J Physiol Heart Circ Physiol, 301: H287-H296, 2011),
erectile dysfunction (Chitaley et al, Int J Impot Res, 24(2): 49-60, 2012),
proliferation, mobility of the endothelial cells and angiogenesis (Imamura et al, Biochem, Biophys Res, 269(2): 633-640, 2000),
increased blood viscosity and fibrinogen level (Zhang et al, Central South Pharmacy, 3,035, 2008),
differentiation of cardiac fibroblasts into myofibroblasts (Kalluri et al, J. Cell. Physiol. 225:631-637, 2010; Sabbadini et al, Circ. Res., 82: 303-312, 2009; Rohr, Heart Rhythm, 6(6): 848-856, 2009),
ventricular remodelling and cardiac fibrosis after myocardial infarction (Hattori et al, Circulation, 109: 2234-2239, 2004; Krum et al, Am J Physiol Heart Circ Physiol, 294: H1804-H1814, 2008; Entman et al, Cardiovasc. Res., 83: 511-518, 2009; Liu et al, Toxicology Letters, 211: 91-97, 2012) and heart failure (Kishi et al, Circulation, 111: 2741-2747, 2005),
proliferation of the smooth muscle cells and restenosis (Shimokawa et al, Am J Physiol Heart Circ Physiol, 301: H287-H296, 2011),
diabetes, hyperglycaemia, insulin resistance, diabetic nephropathies (Kikuchi et al, J. Endocrinol., 192: 595-603, 2007; Kolavennu et al, Diabetes, 57:714-723, 2008) and renal insufficiency, renal fibrosis, nephrosclerosis (Matsuoka et al, J Hypertens, 26(9):1837-48, 2008),
activation of the astrocytes of the liver and liver diseases such as cirrhosis, hepatitis and cancer (WO2000064478A1, 2000),
differentiation of human dermal fibroblasts in cutaneous systemic sclerosis (Distler et al, Arthritis and Rheumatism, 58(8): 2553-2564, 2008),
post-radiotherapy intestinal fibrosis by differentiation of the smooth muscle cells (Vozenin-Brotons et al, Gut, 54(3): 336-343, 2005),
adherence, migration, phagocytosis of the macrophages and inflammatory diseases (Schwartz et al, the EMBO Journal, 26: 505-515, 2007; Doe et al, J. Pharmacol. Exp. Ther., 320:89-98, 2007),
cerebral vasospasm and ischaemia resulting therefrom with neurological dysfunction (Shibuya et al, J. Neurol. Science, 238: 31-39, 2005),
neuronal degeneration such as Alzheimer's disease (Zhou et al, Science, 302: 1215-1217, 2003; Song et al, CNS Neurosci. Ther. 19, 603-610, 2013),
neuropathic pain (Xiao et al, Brain, Behaviour and Immunity, 23(8): 1083-88, 2009),
neurological recovery after spinal cord injury (Hara et al, J. Neurosurg. 93 (suppl.1):94-101, 2000; Dergham et al, J. Neurosci. 22, 6570-6577, 2002; Yamashita et al, Ther. Clin. Risk Manag., 4(3): 605-615, 2008),
cell proliferation and migration (Feng et al, Current Topics in Medical Chemistry, 9, 704-723, 2009; Utsunomiya et al, Biochemical and Biophysical Research Communication, 402:725-730, 2010),
formation of metastases and development of cancer of the breast, lung, colon, brain, head and neck (Liu et al, Cancer Res, 69: 8742-8751, 2009; Li et al, FEBS Lett. 580: 4252-4260, 2006; Vishnubhotla et al, Lab. Invest. 87: 1149-1158, 2007; Zohrabian et al, Anticancer Res. 29:

119-123, 2009; Torre et al, Arch. Otolaryngol. Head Neck Surg., 136: 493-501, 2010; Ying et al, Mol. Cancer Ther., 5: 2158-2164, 2006), activation of osteoclasts (migration) and of bone resorption (Hruska et al, J Biol chem, 278(31): 29086-97, 2003), contraction of the bronchial smooth muscle cells, chronic broncho-pulmonary diseases and asthma (Mori et al, Am. J. Resp. Cell. Mol. Biol., 20(6): 1190-1200, 1999; Kanaide et al, Br J Pharmacol, 132: 111-118, 2001), increase of the SREBP (sterol response binding element) signalling pathway under the effect of shear stress and activation of the gene coding for the LDL receptor (Lin et al, Cir. Res., 92(12): 1296-1304, 2003).

Accordingly, a compound which had the ability to inhibit Rho-kinase and phosphorylation of the myosin light chain might prevent or treat cardiovascular or non-cardiovascular diseases such as: systemic arterial hypertension, pulmonary arterial hypertension, glaucoma, retinopathies, degeneration of the optic nerve, pathologies of the cornea, coronary diseases such as angina, myocardial infarction, post-angioplasty restenosis, aortic aneurysm, occlusion of the peripheral arteries, atherosclerosis, cardiac fibrosis and heart failure, erectile dysfunction, broncho-obstructive pulmonary diseases such as asthma or respiratory distress syndrome in adults, post-radiation intestinal fibrosis, cutaneous systemic sclerosis, pulmonary fibrosis associated with pulmonary arterial hypertension, the prevention or treatment of hepatic diseases, renal fibrosis and glomerulo-sclerosis, diabetic nephropathies induced or not induced by hypertension, thrombotic diseases, cerebral vasospasm and resulting cerebral ischaemia, neuropathic pain, degenerative neuronal diseases such as Alzheimer's disease, inflammatory diseases, the development of cancer and its progression by metastases, osteoporosis, lipid metabolism.

Rho-kinase inhibitors having an isoquinoline skeleton are described in several patent applications.

There may be mentioned, for example, application WO2005/035 503, which describes Rho-kinase inhibitors for the treatment of glaucoma.

Application EP 0 187 371 describes Rho-kinase inhibitors having an isoquinoline skeleton with a sulphonamide functional group for the treatment of glaucoma, and in particular Fasudil.

Mention may also be made of patent applications WO2007/000 240, WO2007/012 421, WO2007/012 422, WO2008/077 550, WO2008/077 552, WO2008/077 553, WO2008/077 554, WO2008/077 555, WO2008/077 556, WO2009/156 092, WO2009/156 099 and WO2009/156 100, which describe Rho-kinase inhibitors for use in the treatment of hypertension and glaucoma.

The present invention relates to compounds of formula (I)

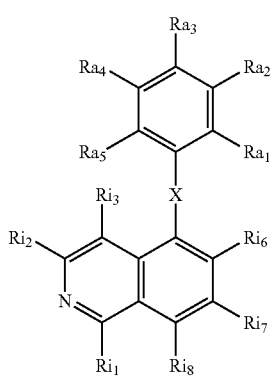

(I)

wherein:
X represents a group —C(=O), —CH(OH)— or —CH$_2$—,
Ri$_1$ represents a hydrogen atom or a hydroxyl group,
it being understood that the compounds of formula (I) wherein Ri$_1$ represents a hydroxyl group may be represented by the following tautomeric form:

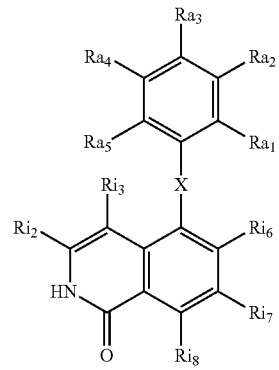

Ri$_2$ and Ri$_3$, which may be identical or different, each represent a hydrogen atom, a (C$_1$-C$_6$)alkyl group or a halogen atom,
Ri$_6$, Ri$_7$ and Ri$_8$, which may be identical or different, each represent a hydrogen atom or a halogen atom,
Ra$_1$ and Ra$_5$, which may be identical or different, each represent a hydrogen or halogen atom, a —O(C$_1$-C$_6$) alkyl group or a (C$_1$-C$_6$)alkyl group,
Ra$_2$ represents a hydrogen or halogen atom, a hydroxyl group, a —O(C$_1$-C$_6$)alkyl group, a —(C$_1$-C$_6$)alkyl group, a nitrogen-containing heterocycle having from 3 to 7 ring members, or a group —O—(CH$_2$)$_m$—NR'R",
Ra$_3$ represents a hydrogen atom, a —O(C$_1$-C$_6$)alkyl group, a —(C$_1$-C$_6$)alkyl group, a nitrogen-containing heterocycle having from 3 to 7 ring members, or a group —CRy$_1$Ry$_2$NH(Ry$_3$),
Ra$_4$ represents a hydrogen or halogen atom, a —O(C$_1$-C$_6$)alkyl group, a —(C$_1$-C$_6$)alkyl group, or a group —CRy$_1$Ry$_2$NH(Ry$_3$),
it being understood that:
Ra$_1$, Ra$_2$, Ra$_3$, Ra$_4$ and Ra$_5$ may not simultaneously represent a hydrogen atom,
Ra$_3$ and Ra$_4$ may not simultaneously represent a group —CRy$_1$Ry$_2$NH(Ry$_3$),
Ra$_1$ and Ra$_2$ can form together with the carbon atoms carrying them a heterocycle having from 4 to 7 ring members chosen from tetrahydrofuran, 1,4-dioxane, tetrahydropyran, tetrahydro-2H-pyran-4-amine and 1-(tetrahydro-2H-pyran-4-yl)methanamine, and
Ra$_2$ and Ra$_3$ can form together with the carbon atoms carrying them a hydrocarbon ring having from 4 to 7 ring members chosen from cyclopentane, cyclopentanamine, N-cyclopentylglycinamide and 1-methylcyclopentanamine,
m is an integer the value of which is fixed at 1, 2 or 3,
R' and R", which may be identical or different, each represent —(C$_1$-C$_6$)alkyl groups or form together with the nitrogen atom carrying them a heterocycle having from 3 to 7 ring members,
Ry$_1$ represents a hydrogen atom, a —(C$_1$-C$_6$)alkyl group, a —CH$_2$-cyclohexyl group, or a 3-methoxyphenyl group, $Ry_2$ represents a hydrogen atom or a —$(C_1$-$C_6)$alkyl group, $Ry_3$ represents:
- a hydrogen atom,
- a group —C(=O)—$CHRy_4$-$NHRy_5$ wherein $Ry_4$ represents a hydrogen atom or a $(C_1$-$C_6)$alkyl group and $Ry_5$ represents a hydrogen atom or a methyl group, or
- a —$(C_1$-$C_6)$alkyl group which can be substituted by a hydroxyl group, a —$O(C_1$-$C_3)$alkyl group, a cyclohexyl group or a methylsulphonyl group,
- or $Ry_1$ and $Ry_2$ form together with the carbon atom carrying them a cyclopropane, cyclobutane or tetrahydropyran group,
- or $Ry_2$ and $Ry_3$ form together with the carbon and nitrogen atoms carrying them, respectively, a pyrrolidine or piperidine group, their optical isomers, where they exist, and addition salts thereof with a pharmaceutically acceptable acid and hydrates thereof.

Among the pharmaceutically acceptable acids there may be mentioned, without implying any limitation, hydrochloric, hydrobromic, sulphuric, phosphoric, acetic, trifluoroacetic, lactic, pyruvic, malonic, succinic, glutaric, fumaric, tartaric, maleic, citric, ascorbic, oxalic, methanesulphonic, para-toluenesulphonic, benzenesulphonic, camphoric, pamoic, 1,5-naphthalenedisulphonic acids.

The $(C_1$-$C_6)$alkyl groups can be linear or branched.

The hydrocarbon rings or the heterocycles present in the compounds of formula (I) of the present invention can be substituted by one or more halogen atoms and/or by one or more of the following groups: —$NH_2$, hydroxyl, —$(C_1$-$C_6)$alkyl, —$O(C_1$-$C_6)$alkyl, —$NH(C_1$-$C_6)$alkyl, —$(C_1$-$C_6)$alkyl-$NH_2$, —NH—C(=O)—$(C_1$-$C_6)$alkyl-$NH_2$.

When R' and R" form together with the nitrogen carrying them a heterocycle, substituted or unsubstituted, having from 3 to 7 ring members, the heterocycle is preferably chosen from morpholine, pyrrolidine, piperidine and N-methylpiperidine.

When $Ra_2$ or $Ra_3$ represents a nitrogen-containing heterocycle having from 3 to 7 ring members, the heterocycle can be chosen from the following non-limiting list: aziridine, azetidine, imidazoline, pyrrolidine, piperidine, piperazine, imidazole, pyrrole, pyridine, pyrimidine, pyridazine, 1,2,3,4-tetrahydropyrimidine, hexahydropyrimidine, hexahydropyridazine.

One aspect of the invention relates to compounds of formula (I) wherein X represents a group —C(=O)—, their optical isomers, where they exist, and addition salts thereof with a pharmaceutically acceptable acid and hydrates thereof.

Another aspect of the invention relates to compounds of formula (I) wherein $Ri_1$ represents a hydroxyl group, their optical isomers, where they exist, and addition salts thereof with a pharmaceutically acceptable acid and hydrates thereof.

Another aspect of the invention relates to compounds of formula (I) wherein $Ri_2$ or $Ri_3$ represents a $(C_1$-$C_6)$alkyl group, more especially a methyl or ethyl group, their optical isomers, where they exist, and addition salts thereof with a pharmaceutically acceptable acid and hydrates thereof.

Another aspect of the invention relates to compounds of formula (I) wherein $Ri_2$ and/or $Ri_3$ represent a hydrogen atom, their optical isomers, where they exist, and addition salts thereof with a pharmaceutically acceptable acid and hydrates thereof.

Another aspect of the invention relates to compounds of formula (I) wherein $Ri_6$ and/or $Ri_7$ and/or $Ri_8$ represent a hydrogen atom, their optical isomers, where they exist, and addition salts thereof with a pharmaceutically acceptable acid and hydrates thereof.

Another aspect of the invention relates to compounds of formula (I) wherein $Ri_2$, $Ri_6$, $Ri_7$ and $Ri_8$ each represent a hydrogen atom, their optical isomers, where they exist, and addition salts thereof with a pharmaceutically acceptable acid and hydrates thereof.

Another aspect of the invention relates to compounds of formula (I) wherein $Ra_1$ and/or $Ra_5$ represent a hydrogen atom or a halogen atom, more especially a chlorine or fluorine atom, their optical isomers, where they exist, and addition salts thereof with a pharmaceutically acceptable acid and hydrates thereof.

Another aspect of the invention relates to compounds of formula (I) wherein $Ra_1$ and $Ra_5$ each represent a fluorine atom, their optical isomers, where they exist, and addition salts thereof with a pharmaceutically acceptable acid and hydrates thereof.

Another aspect of the invention relates to compounds of formula (I) wherein $Ra_2$ represents a hydrogen atom, their optical isomers, where they exist, and addition salts thereof with a pharmaceutically acceptable acid and hydrates thereof.

Another aspect of the invention relates to compounds of formula (I) wherein $Ra_3$ and $Ra_4$ represent a hydrogen atom or a group —$CRy_1Ry_2NH(Ry_3)$, it being understood that $Ra_3$ and $Ra_4$ may not simultaneously represent a group —$CRy_1Ry_2NH(Ry_3)$, their optical isomers, where they exist, and addition salts thereof with a pharmaceutically acceptable acid and hydrates thereof.

Another aspect of the invention relates to compounds of formula (I) wherein $Ra_3$ or $Ra_4$ represents a group —$CRy_1Ry_2NH(Ry_3)$, their optical isomers, where they exist, and addition salts thereof with a pharmaceutically acceptable acid and hydrates thereof.

Another aspect of the invention relates to compounds of formula (I) wherein $Ra_3$ or $Ra_4$ represents a group —$CRy_1Ry_2NH(Ry_3)$ and:
- $Ry_1$ represents a hydrogen atom or a —$(C_1$-$C_6)$alkyl group,
- $Ry_2$ represents a —$(C_1$-$C_6)$alkyl group,
- $Ry_3$ represents a hydrogen atom, their optical isomers, where they exist, and addition salts thereof with a pharmaceutically acceptable acid and hydrates thereof.

Another aspect of the invention relates to compounds of formula (I) wherein $Ra_3$ represents a group —$CRy_1Ry_2NH$ ($Ry_3$) and $Ra_1$ and $Ra_2$ form together with the carbon atoms carrying them a heterocycle having from 4 to 7 ring members, their optical isomers, where they exist, and addition salts thereof with a pharmaceutically acceptable acid and hydrates thereof.

Preferably, such a heterocycle is chosen from tetrahydrofuran, 1,4-dioxane and tetrahydropyran.

Another aspect of the invention relates to compounds of formula (I) wherein $Ra_3$ represents a hydrogen atom and $Ra_1$ and $Ra_2$ form together with the carbon atoms carrying them a heterocycle having from 4 to 7 ring members, their optical isomers, where they exist, and addition salts thereof with a pharmaceutically acceptable acid and hydrates thereof.

Preferably, such a heterocycle is chosen from tetrahydro-2H-pyran-4-amine and 1-(tetrahydro-2H-pyran-4-yl)methanamine.

kel2qAnother aspect of the invention relates to compounds of formula (I) wherein $Ra_2$ and $Ra_3$ form together with the carbon atoms carrying them a hydrocarbon ring having from 4 to 7 ring members, their optical isomers, where they exist, and addition salts thereof with a pharmaceutically acceptable acid and hydrates thereof.

Preferably, such a hydrocarbon ring is chosen from cyclopentane and its derivatives, more especially cyclopentanamine, N-cyclopentylglycinamide and 1-methylcyclopentanamine.

Another aspect of the invention relates to compounds of formula (I) wherein:
X represents a group —C(=O)—,
$Ri_1$ represents a hydrogen atom or a hydroxyl group,
$Ri_2$, $Ri_6$, $Ri_7$ and $Ri_8$ each represent a hydrogen atom and $Ri_3$ represents a hydrogen atom or a $(C_1-C_6)$alkyl group,
$Ra_1$ and $Ra_5$, which may be identical or different, each represent a hydrogen or fluorine atom or a $(C_1-C_6)$alkyl group,
$Ra_2$ represents a hydrogen atom or a —$(C_1-C_6)$alkyl group,
$Ra_3$ represents a hydrogen atom, a piperidine group or a group —$CRy_1Ry_2NH(Ry_3)$,
$Ra_4$ represents a hydrogen atom or a group —$CRy_1Ry_2NH(Ry_3)$, it being understood that $Ra_3$ and $Ra_4$ may not simultaneously represent a group —$CRy_1Ry_2NH(Ry_3)$, and that:
when $Ra_3$ represents a group —$CRy_1Ry_2NH(Ry_3)$, $Ra_1$ and $Ra_2$ can form together with the carbon atoms carrying them a tetrahydrofuran, 1,4-dioxane or tetrahydropyran group, or
when $Ra_3$ represents a hydrogen atom, $Ra_1$ and $Ra_2$ can form together with the carbon atoms carrying them a tetrahydro-2H-pyran-4-amine or 1-(tetrahydro-2H-pyran-4-yl)methanamine group, or
$Ra_2$ and $Ra_3$ can form together with the carbon atoms carrying them a cyclopentanamine or 1-methylcyclopentanamine group,
$Ry_1$ represents a hydrogen atom, a —$(C_1-C_6)$alkyl group or a —$CH_2$-cyclohexyl group,
$Ry_2$ represents a hydrogen atom or a —$(C_1-C_6)$alkyl group,
$Ry_3$ represents a hydrogen atom or a —$(C_1-C_6)$alkyl group which can be substituted by a hydroxyl group, their optical isomers, where they exist, and addition salts thereof with a pharmaceutically acceptable acid and hydrates thereof.

Another aspect of the invention relates to compounds of formula (I) chosen from:
[4-(1-aminoethyl)-2,6-difluorophenyl](isoquinolin-5-yl)methanone and its optical isomers and addition salts thereof with a pharmaceutically acceptable acid and hydrates thereof,
[4-((1R)-1-aminoethyl)-2,6-difluorophenyl](isoquinolin-5-yl)methanone and its addition salts thereof with a pharmaceutically acceptable acid and hydrates thereof,
[4-(1-aminoethyl)-2,6-difluorophenyl](1-hydroxyisoquinolin-5-yl)methanone and its optical isomers and addition salts thereof with a pharmaceutically acceptable acid and hydrates thereof,
1-[3,5-difluoro-4-(isoquinolin-5-ylmethyl)phenyl]ethanamine and its optical isomers and addition salts thereof with a pharmaceutically acceptable acid and hydrates thereof,
{4-[(1S)-1-aminoethyl]-2,6-difluorophenyl}(isoquinolin-5-yl)methanol and its addition salts with a pharmaceutically acceptable acid and hydrates thereof,
[4-(2-aminopropan-2-yl)-2,6-difluorophenyl](isoquinolin-5-yl)methanone and its addition salts with a pharmaceutically acceptable acid and hydrates thereof,
5-[4-(2-aminopropan-2-yl)-2,6-difluorobenzoyl]isoquinolin-1(2H)-one and its addition salts with a pharmaceutically acceptable acid and hydrates thereof,
5-[4-(1-aminoethyl)-2-fluoro-3-methoxybenzoyl]isoquinolin-1(2H)-one and its optical isomers and addition salts thereof with a pharmaceutically acceptable acid and hydrates thereof,
5-({5-[(1R)-1-aminoethyl]-3,4-dihydro-2H-chromen-8-yl}carbonyl)isoquinolin-1(2H)-one and its addition salts with a pharmaceutically acceptable acid and hydrates thereof,
5-{4-[(1R)-1-aminoethyl]-2-methylbenzoyl}isoquinolin-1(2H)-one and its addition salts with a pharmaceutically acceptable acid and hydrates thereof,
5-(2,6-difluoro-4-{1-[(2-hydroxyethyl)amino]ethyl}benzoyl)isoquinolin-1(2H)-one and its optical isomers and addition salts thereof with a pharmaceutically acceptable acid and hydrates thereof,
5-{4-[(1R)-1-aminoethyl]-2,6-difluorobenzoyl}-4-methylisoquinolin-1(2H)-one and its addition salts with a pharmaceutically acceptable acid and hydrates thereof,
5-{3-[(1R)-1-aminoethyl]-2,6-difluorobenzoyl}isoquinolin-1(2H)-one and its addition salts with a pharmaceutically acceptable acid and hydrates thereof,
5-[(1-amino-4,6-difluoro-2,3-dihydro-1H-inden-5-yl)carbonyl]isoquinolin-1(2H)-one and its optical isomers and addition salts thereof with a pharmaceutically acceptable acid and hydrates thereof,
5-{[(3R)-3-amino-4,6-difluoro-2,3-dihydro-1H-inden-5-yl]carbonyl}isoquinolin-1(2H)-one and its addition salts with a pharmaceutically acceptable acid and hydrates thereof,
5-({8-[(1R)-1-aminoethyl]-2,3-dihydro-1,4-benzodioxin-5-yl}carbonyl)isoquinolin-1(2H)-one and its addition salts with a pharmaceutically acceptable acid,
5-[2,6-difluoro-4-(piperidin-2-yl)benzoyl]isoquinolin-1(2H)-one and its optical isomers and addition salts thereof with a pharmaceutically acceptable acid and hydrates thereof,
5-[4-(1-amino-2-cyclohexylethyl)-2,6-difluorobenzoyl]isoquinolin-1(2H)-one and its optical isomers and addition salts thereof with a pharmaceutically acceptable acid and hydrates thereof,
5-{[4-(aminomethyl)-3,4-dihydro-2H-chromen-8-yl]carbonyl}isoquinolin-1(2H)-one and its optical isomers and addition salts thereof with a pharmaceutically acceptable acid and hydrates thereof.

Another aspect of the invention relates to a process for the synthesis of compounds of formula (Ia), particular cases of compounds of formula (I) wherein X represents a group —C(=O), starting from a compound of formula (II):

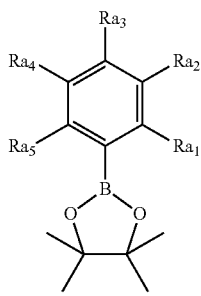

(II)

which is subjected to a coupling reaction with the compound of formula (III):

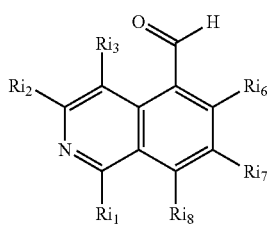

(III)

in the presence of a rhodium or palladium catalyst, of a phosphine and of a base in an organic solvent,
to yield the compound of formula (Ia):

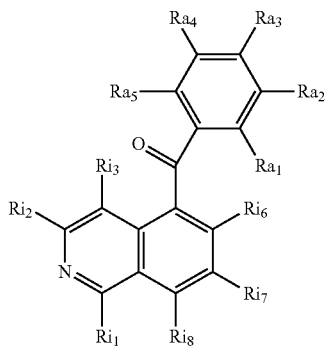

(Ia)

Among the rhodium and palladium catalysts which can be used to carry out the coupling reaction between the compound of formula (II) and the compound of formula (III) there may be mentioned, without implying any limitation, the following catalysts: ([Rh(CH$_2$CH$_2$)$_2$Cl]$_2$, Rh(acac)(coe)2 (coe=cyclooctene) and the tris(dibenzylidene-acetone)dipalladium/chloroform complex (Pd$_2$dba$_3$-CHCl$_3$).

Among the phosphines which can be used to carry out the coupling reaction between the compound of formula (II) and the compound of formula (III) there may be mentioned, without implying any limitation, tri-butylphosphine, 1,3-bis(diphenylphosphino)propane (dppp) and 1,1'-bis(diphenylphosphino)ferrocene (dppf).

Among the bases which can be used to carry out the coupling reaction between the compound of formula (II) and the compound of formula (III) there may be mentioned, without implying any limitation, potassium carbonate and potassium hydrogen carbonate.

Among the organic solvents which can be used to carry out the coupling reaction between the compound of formula (II) and the compound of formula (III) there may be mentioned, without implying any limitation, 1,4-dioxane, dimethoxyethane and toluene.

The compounds of formula (Ia) so obtained can then be converted into compounds of formula (Ib), particular cases of compounds of formula (I) wherein X represents —CH(OH)—, by a reduction reaction:

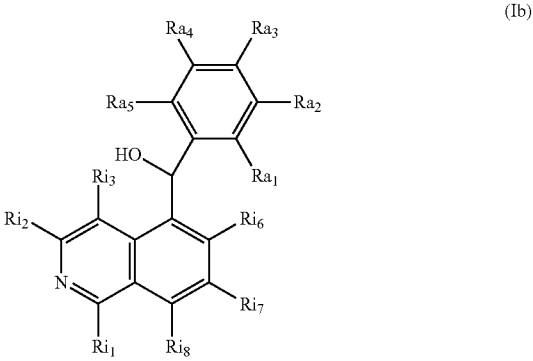

(Ib)

This reduction reaction can be carried out in the presence of hydride donors, such as sodium tetraborohydride (NaBH$_4$).

The compounds of formula (Ib) so obtained can then be converted into compounds of formula (Ic), particular cases of compounds of formula (I) wherein X represents —CH$_2$—, by a further reduction reaction, which can be carried out in the presence of trifluoroacetic acid and of triethylsilane:

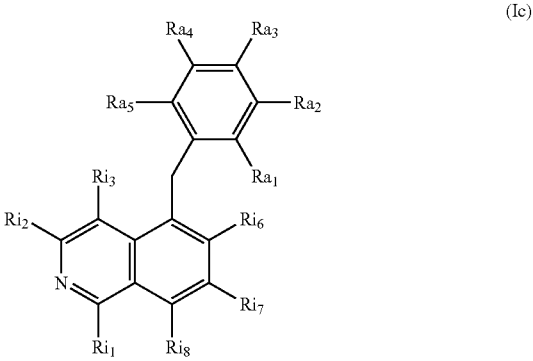

(Ic)

The optically active forms of the compounds of formula (I) are obtained either starting from optically active forms of the compound of formula (III) or by separating the racemic forms of the compounds of formula (I) according to methods known in the literature.

The present invention relates also to pharmaceutical compositions comprising as active ingredient a compound of formula (I), or an addition salt thereof with a pharmaceutically acceptable acid, in combination with one or more inert, non-toxic, pharmaceutically acceptable excipients or carriers.

Among the pharmaceutical compositions according to the invention there may be mentioned more especially those that are suitable for oral, parenteral (intravenous, intramuscular or subcutaneous), per- or trans-cutaneous, nasal, rectal, perlingual, ocular or respiratory administration, especially tablets or dragées, sublingual tablets, gelatin capsules, capsules, suppositories, creams, ointments, dermal gels, injectable or drinkable preparations, aerosols, eye or nasal drops.

In addition to the compound of formula (I), the pharmaceutical compositions according to the invention comprise one or more excipients or carriers such as diluents, lubricants, binders, disintegrators, absorbents, colourings, sweeteners.

Examples of excipients or carriers which may be mentioned include:
- for the diluents: lactose, dextrose, sucrose, mannitol, sorbitol, cellulose, glycerin,
- for the lubricants: silica, talc, stearic acid and its magnesium and calcium salts, polyethylene glycol,
- for the binders: aluminium and magnesium silicate, starch, gelatin, tragacanth, methylcellulose, sodium carboxymethylcellulose and polyvinylpyrrolidone,
- for the disintegrators: agar, alginic acid and its sodium salt, effervescent mixtures.

The percentage of active ingredient of formula (I) in the pharmaceutical composition is preferably from 5% to 50% by weight.

The dosage used varies according to the age and weight of the patient, the administration route, the nature and severity of the disorder and the taking of any associated treatments, and ranges from 0.5 mg to 500 mg in one or more administrations per day.

The following examples illustrate the invention.

LIST OF ABBREVIATIONS USED

AcOEt: ethyl acetate
Boc$_2$O: di-tert-butyl dicarbonate
DMF: dimethylformamide
DMSO: dimethyl sulphoxide
DTT: dithiothreitol
EDTA: ethylenediaminetetraacetic acid
EGTA ethylenebis(oxyethylenenitrilo)tetraacetic acid
ESI: electrospray ionization
eq.: equivalent(s)
GC: gas chromatography
Hepes: 4-(2-hydroxyethyl)-1-piperazineethanesulphonic acid
HRMS: high resolution mass spectrometry
IR: infrared
i.v.: intravenous
KHMDS: potassium hexamethyl-disilazane
LCMS: liquid chromatography-mass spectrometry
LDA: lithium diisopropylamide
m-CPBA: meta-chloroperbenzoic acid
MS: mass spectrometry
NEt$_3$: triethylamine
TMSCN: trimethylsilyl cyanide
SFC: supercritical fluid chromatography
NMR: nuclear magnetic resonance
tBuOK potassium tert-butanoate
THF: tetrahydrofuran
TMS: tetramethylsilane
TMSCN trimethylsilanecarbonitrile
Tris: trishydroxymethylaminomethane or 2-amino-2-hydroxymethyl-1,3-propanediol The presence of the symbol "*" next to a carbon atom in the chemical formulae emphasises that the carbon has a fixed absolute configuration, without the nature of that configuration having been identified.

The infrared spectra were recorded with the aid of a Bruker TENSOR 27 Fourier transform spectrometer in ATR mode.

The proton NMR spectra were recorded on Bruker DPX 400-B spectrometers. The chemical shifts are expressed in ppm and are determined relative to the TMS used as reference. The abbreviations used are:
- s: singlet
- d: doublet
- dd: doublet of doublets
- dt: doublet of triplets
- t: triplet
- td: triplet of doublets
- quad: quadruplet
- quint: quintuplet
- m: multiplet The mass spectra are recorded on a TSQ 7000 spectrometer.

GC monitoring was carried out on a HPS-J&W Scientific column 0.53×15 m with an Agilent 4890 GC chromatograph with flame ionisation detection (FID).

HPLC monitoring was carried out on Acquity UPLC BEH C18 1.7 µm columns 2.1×30 mm on 1200 Agilent HPLC with diode array detector (DAD).

SFC: The analyses of enantiomeric purity are carried out on a UPC2 (Waters).

Thin layer chromatography (TLC) was carried out on MERCK 60F-254 silica plates.

The chromatographies were carried out with a MERCK 60 silica gel (0.040-0.063 mm) or with Interchim or Grace prepacked silica columns.

The reverse phase separations were carried out on Interchim FHP RP C18 15 µm columns 275×60 mm with UV detection.

Filtrations were carried out on Millipore filters of type GVHP (0.22 µm) for the organic phases and on Whatman GF/A filters cat. No1820-070 for the aqueous phases.
Preparation of Compounds of the Invention
Preparation of Isoquinoline Precursors Protocol I: Preparation of 5-Halo-Isoquinoline Intermediates The following intermediates were prepared by bromation of commercial isoquinolines according to the protocol described by Brown, W. D.; Gouliaev, A. H., *Synthesis*, 2002, 1, 83-86 and *Organic Syntheses*, 2004, 81, 98-104.

Intermediate 2:
$^1$H NMR (300 MHz-DMSO-d$_6$): δ 9.40 (s, 1H), 8.70 (d, 1H), 8.22 (d, 1H), 8.18 (d, 1H), 7.93 (d, 1H), 7.65 (t, 1H)
IR (cm$^{-1}$): 1621-1579, 819-629;

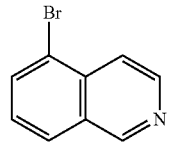

2

Intermediate 290:
$^1$H NMR (400 MHz-CDCl$_3$): δ 9.15 (s, 1H), 7.90 (2d, 2H), 7.80 (s, 1H), 7.35 (t, 1H), 2.75 (s, 3H)
IR (cm$^{-1}$): 1621-1584, 666
GC-EI (70 eV): M+.=221.

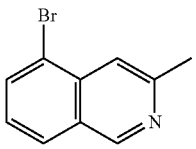

290

Intermediate 299:

¹H NMR (400 MHz-DMSO-d₆): δ 9.30 (s, 1H), 8.40 (s, 1H), 8.17 (t, 1H), 7.55 (t, 1H), 2.95 (s, 3H)

IR (cm⁻¹): 1609-1579

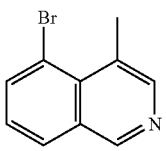

299

Intermediate 754 was prepared starting from intermediate 2 according to the following protocol:

To a solution of concentrated H₂SO₄ (48 mL) at ambient temperature there are added intermediate 2 (10 g, 48 mmoles), and then N-chlorosuccinimide (25 g, 187 mmoles). The mixture is heated at 80° C. for 5 days. The reaction mixture is poured into an ice/water mixture (33 g/300 mL), and then a 28% NH₄OH solution is added to pH 8. The precipitate that forms is filtered off and then dissolved in AcOEt, the organic phase is dried over MgSO₄, concentration in vacuo yields intermediate 754 in the form of a beige solid (11 g), which can be used without additional treatment in the following step.

¹H NMR (300 MHz-DMSO-d₆): δ 9.60 (s, 1H), 8.80 (d, 1H), 8.20 (d, 1H), 8.00 (d, 1H), 7.80 (d, 1H);

IR (cm⁻¹): 1607, 1568, 830, 631.

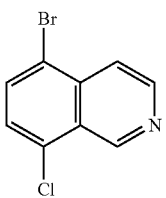

754

Protocol II: Preparation of
5-Halo-1-Alkoxisoquinoline Compounds

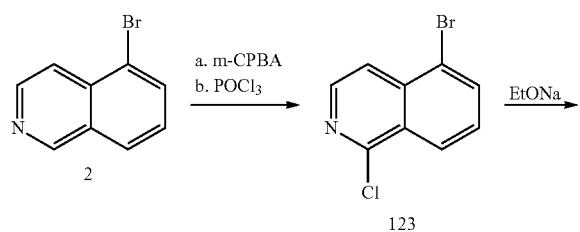

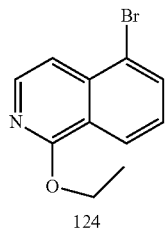

124

Intermediate 123:

To a solution of 2 (60 g, 288 mmoles) in methylene chloride (1.5 L) there are added (75 g, 436 mmoles) of 75% m-CPBA. The mixture is heated at 40° C. for 20 hours. After HPLC monitoring and return to ambient temperature, 75 g of sodium thiosulphate are added in the course of 10 minutes, followed by 300 mL of water. The whole is decanted, the organic phase is washed with a 1N sodium hydroxide solution, and the organic phase is dried by passage over MgSO₄. Evaporation under reduced pressure yields a white solid (42 g), which is used without additional treatment in the following step. A solution of the intermediate that forms (37 g, 165 mmoles) in methylene chloride (900 mL) and POCl₃ (37 mL) is stirred for 18 hours at 45° C. After HPLC and/or GC monitoring, the reaction mixture is concentrated in vacuo. The residue is treated carefully with water, and the aqueous phase is extracted with methylene chloride. The organic phase is washed carefully with a saturated NaHCO₃ solution and then with a saturated aqueous NaCl solution. Evaporation under reduced pressure yields intermediate 123 (33 g) in the form of a beige solid, which can be used without additional treatment in the following step.

¹H NMR (400 MHz-CDCl₃): δ 8.35 (2d, 2H), 8.00 (2d, 2H), 7.55 (t, 1H)

GC-EI (70 eV): M+.=241

Intermediate 124:

To a solution of sodium ethoxide, prepared by adding sodium (10.3 g) to ethanol (323 mL), there is added intermediate 123 in portions (15 g, 62 mmoles). The mixture is heated for 2 hours. After HPLC monitoring and return to ambient temperature, the reaction mixture is poured into a mixture of water and ice (3 kg): the product precipitates. Filtration of the solid yields a solid which, by recrystallisation from acetonitrile, yields intermediate 124 (8.06 g).

¹H NMR (400 MHz-DMSO-d₆): δ 8.20 (d, 1H), 8.15 (d, 1H), 8.10 (d, 1H), 7.55 (m, 1H), 7.45 (d, 1H), 4.55 (quad, 2H), 1.45 (t, 3H)

GC-EI (70 eV): M⁺=251

This procedure was used to prepare intermediates 293 and 302.

Intermediate 293:

Obtained starting from intermediate 290 according to protocol II

¹H NMR (400 MHz-DMSO-d₆): δ 8.20 (td, 1H), 7.85 (dd, 1H), 7.35 (m, 1H), 7.30 (t, 1H), 4.55 (quad, 2H), 2.55 (s, 3H), 1.50 (t, 3H)

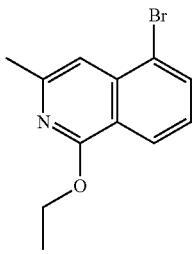

293

Intermediate 302:
Obtained starting from 299 according to protocol II

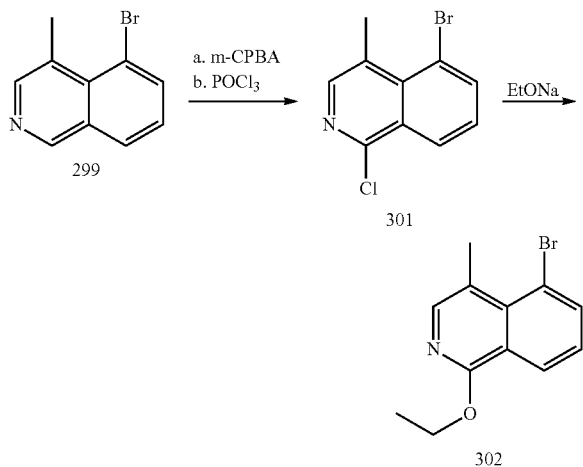

Intermediate 301:
¹H NMR (400/500 MHz, dmso-d6): δ 8.29 (d, 1H), 8.26 (d, 1H), 8.22 (s, 1H), 7.66 (m, 1H), 2.94 (s, 3H).
IR (cm⁻¹): 1603.
GC-EI (70 eV): M+.=254.9

Intermediate 302:
¹H NMR (400 MHz-DMSO-d₆): δ 8.30 (dd, 1H), 8.10 (dd, 1H), 7.90 (broad s, 1H), 7.50 (t, 1H), 4.50 (quad, 2H), 2.80 (s, 3H), 1.40 (t, 3H)

Protocol III: Preparation of Carbonylated Isoquinoline Intermediates According to a Halogen-Metal Exchange Reaction Followed by Formylation By way of example, the synthesis of intermediate 125 is described below:

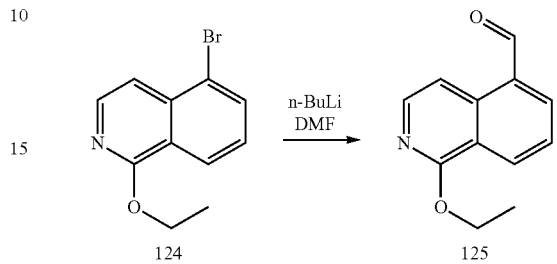

Intermediate 125:
A solution of intermediate 124 (21 g, 84 mmoles) in THF (106 mL) is added in the course of 35 minutes to a 2.5N solution of n-BuLi in hexane (67 mL, 168 mmoles) previously introduced into a THF/ethyl ether mixture (270 mL/270 mL) at −78° C. The reaction mixture is stirred for 1 hour at −78 C, and then a solution of DMF (10 mL) in THF (30 mL) previously cooled to −70 C is then introduced into the medium by means of a cannula in the course of 5 minutes. The reaction mixture is stirred for 35 minutes. Addition of 73 mL of ethanol and then 73 mL of a saturated aqueous NH₄Cl solution. Return to ambient temperature. The aqueous phase is extracted with ethyl ether and dried over MgSO₄, and evaporation under reduced pressure yields a yellow solid, which is purified on silica gel (eluant AcOEt/methylene chloride 10/90). Intermediate 125 (9 g) is obtained in the form of a yellow solid.
¹H NMR (400 MHz; DMSO-d₆): δ 10.41 (s, 1H), 8.53 (ddd, 1H), 8.44 (dd, 1H), 8.41 (dd, 1H), 8.19 (d, 1H), 7.85 (dd, 1H), 4.55 (quad, 2H), 1.45 (t, 3H).
IR (cm⁻¹): 1691.

This protocol was used to prepare the intermediates of the table below:

| Int. | Obtained from | Nomenclature Analytical description |
|---|---|---|
| 3 | 2 | isoquinoline-5-carbaldehyde<br>¹H NMR (300 MHz; DMSO-d₆): δ 10.50 (s, 1H), 9.50 (d, 1H), 8.90 (d, 1H), 8.70 (d, 1H), 8.50 (t and d, 1H), 7.95 (dd, 1H)<br>IR (cm⁻¹): 1693-1679 |
| 294 | 293 | 1-ethoxy-3-methyl-isoquinoline-5-carbaldehyde<br>¹H NMR (400 MHz; DMSO-d₆): δ 10.37 (s, 1H), 8.46 (d, 1H), 8.34 (d, 1H), 8.30 (s, 1H), 7.73 (dd, 1H), 4.53 (quad, 2H), 2.53 (s, 3H), 1.45 (t, 3H)<br>IR (cm⁻¹): 1684 |
| 303 | 302 | 1-ethoxy-4-methyl-isoquinoline-5-carbaldehyde<br>¹H NMR (400 MHz; DMSO-d₆): δ 10.90 (s, 1H), 8.50 (dd, 1H), 8.20 (dd, 1H), 8.00 (s, 1H), 7.75 (t, 1H), 4.50 (quad, 2H), 2.60 (s, 3H), 1.45 (t, 3H)<br>IR (cm⁻¹): 1677 |
| 321 | 299 | 4-methyl-isoquinoline-5-carbaldehyde<br>¹H NMR (400 MHz; DMSO-d₆): δ 10.90 (s, 1H), 9.20 (s, 1H), 8.50 (s, 1H), 8.25-8.20 (2d, 2H), 7.70 (t, 1H), 2.80 (s, 3H) |
| 755 | 754 | 8-chloroisoquinoline-5-carbaldehyde<br>¹H NMR (400 MHz; DMSO-d₆): δ 10.50 (s, 1H), 9.70 (s, 1H), 9.00 (d, 1H), 8.40 (d, 1H), 8.35 (d, 1H), 8.10 (d 1H)<br>IR (cm⁻¹): 1679 |

Protocol IV: Preparation of Intermediate 655

Intermediate 653:

To a solution (degassed with nitrogen) of intermediate 2 (45 g, 216 mmoles) in DMF (450 mL) there are added Zn(CN)$_2$ (30 g) and Pd(PPh$_3$)$_4$ (9.8 g). The mixture is heated at 100° C. for 2 hours. After return to ambient temperature, the mixture is taken up in AcOEt (200 mL) and water (2 L). The mixture is brought to pH>8 by addition of a 20% aqueous NaOH solution. After addition of AcOEt (200 mL), the organic phase is recovered by decantation, filtered over Celite®, washed with a saturated aqueous NaCl solution and then dried over MgSO$_4$ before being concentrated in vacuo. The solid is ground and dried in vacuo and taken up in a 1N aqueous HCl solution (1 L), and the acidic aqueous phase is washed with AcOEt and then treated with a 20% aqueous NaOH solution, the precipitate that forms is collected and dissolved in methylene chloride. The solution is dried over MgSO$_4$, and evaporation in vacuo yields intermediate 653 in the form of a beige solid (24 g).

$^1$H NMR (400 MHz; DMSO-d$_6$): δ 9.53 (s, 1H), 8.76 (d, 1H), 8.54 (d, 1H), 8.45 (d, 1H), 7.96 (d, 1H), 7.87 (t, 1H)

IR (cm$^{-1}$): 2226.

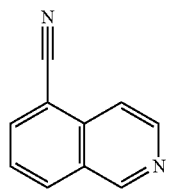

653

Intermediate 654:

To a 37% HCl solution (137 mL) there is added intermediate 653, and the mixture is heated at reflux for 20 h. After return to ambient temperature, the precipitate is collected on a frit, washed with acetone and dried in an oven at 50° C. in vacuo (10$^{-2}$ mbar). The hydrochloride of intermediate 654 is obtained in the form of a white solid (33 g), which is used in the following step without additional purification.

$^1$H NMR (300 MHz; DMSO-d$_6$): δ 10.00 (s, 1H), 9.20 (d, 1H), 8.00 (m, 3H), 8.10 (t, 1H)

IR (cm$^{-1}$): 1695, 1214

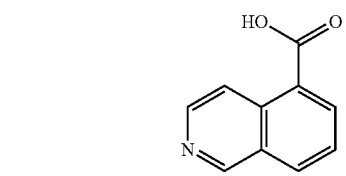

654

Intermediate 655:

Intermediate 654 (20 g, 95 mmoles) is added carefully to thionyl chloride (200 mL). The mixture is heated for 15 hours at 80° C. After return to ambient temperature, the mixture is filtered; (careful) concentration in vacuo of the filtrate yields the hydrochloride of 655 in the form of a brown solid, which is quickly used in the aromatic electrophilic substitution step (Protocol XXIII). The product can be analysed in its methyl ester form (by derivation from methanol).

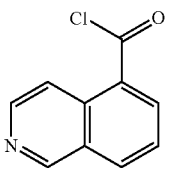

655

Preparation of Phenyl Precursors—General Protocols

Protocol V: Preparation of Amine Intermediates Starting from Phenylacetonitrile Intermediates By way of example, the synthesis of intermediate 601 is described below:

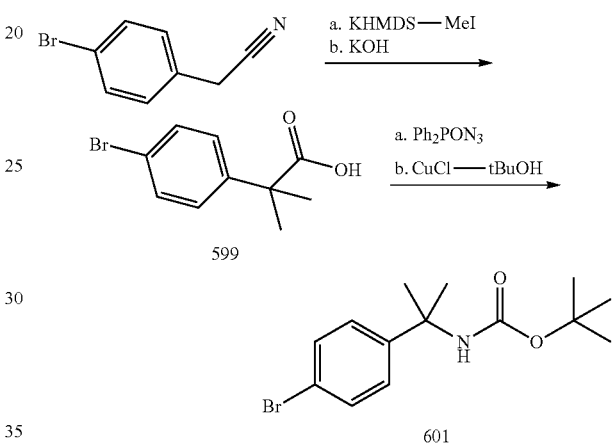

Intermediate 599:

Step 1

To a solution of KHMDS (50 g) in THF (300 mL) cooled to 0° C. there is added slowly a solution of commercial (4-bromophenyl)acetonitrile (16 g, 81 mmoles) in THF (90 mL), the temperature being maintained below 3° C. The mixture is stirred for 40 minutes at 0° C., and then methyl iodide (11.7 mL) is added in the course of 50 minutes at a temperature below 8° C. The mixture is stirred at ambient temperature for 20 hours and then poured carefully into ice-water (1.5 L). The aqueous phase is extracted with Et$_2$O, and the organic phase is washed with a saturated aqueous NaCl solution, dried and concentrated in vacuo. The residue is chromatographed on silica gel (eluant CH$_2$Cl$_2$/cyclohexane (60/40)). The expected intermediate (13 g) is obtained in the form of a white solid.

$^1$H NMR (300 MHz, CDCl$_3$): δ 7.52 (d, 2H), 7.36 (d, 2H), 1.75 (s, 6H)

IR (cm$^{-1}$): 2237

Step 2

A solution of the intermediate obtained above (5 g, 22 mmoles) and of KOH (2.4 g) in a mixture of ethanol (25 mL) and water (7.5 mL) is heated at reflux for 20 hours. The reaction mixture is concentrated in vacuo, and the residue is taken up with ethyl ether (100 mL) and water (60 mL). The aqueous phase (free of organic solvent) is cooled to 10° C. and then acidified with a 37% HCl solution. The precipitate that forms is collected on a frit and dried in vacuo. Intermediate 599 (5.3 g) is obtained in the form of a white solid.

$^1$H NMR (400 MHz, CDCl$_3$): δ 9.00-8.00 (1H), 7.75 (d, 2H), 7.25 (d, 2H), 1.60 (s, 6H)
IR (cm$^{-1}$): 3347-2235, 1697

Intermediate 601:

Step 1

To a solution of intermediate 599 (2.6 g, 10.7 mmoles) in toluene (60 mL) there are added NEt$_3$ (1.6 mL) and PhO$_2$PON$_3$ (2.3 mL). The resulting mixture is heated at reflux for 20 hours. After return to ambient temperature, a saturated aqueous NaHCO$_3$ solution is added. The organic phase is extracted with Et$_2$O, washed with a saturated aqueous NaCl solution, dried and concentrated in vacuo. The residue is chromatographed on silica gel (eluant CH$_2$Cl$_2$/cyclohexane (50/50)). The expected intermediate (1.8 g) is obtained in the form of a colourless oil.

$^1$H NMR (300 MHz, CDCl$_3$): δ 7.50 (d, 2H), 7.35 (d, 2H), 1.70 (s, 6H)
IR (cm$^{-1}$): 2248

Step 2

To a mixture of tert-butanol (3.5 mL) and CuCl (0.74 g) in DMF (30 mL) there is added a solution of the intermediate obtained above (1.8 g, 7.5 mmoles) in DMF (10 mL). The mixture is stirred at ambient temperature for 5 hours. The reaction mixture is extracted with Et$_2$O. The organic phase is washed with a saturated NaCl solution, dried and concentrated in vacuo. The residue is chromatographed on silica gel (eluant CH$_2$Cl$_2$/AcOEt (100/0 to 95/5)). Intermediate 601 (1.2 g) is obtained in the form of a white solid.

$^1$H NMR (300 MHz; CDCl$_3$): δ 7.45 (d, 2H); 7.30 (d, 2H); 4.90 (m, 1H); 1.60 (s, 6H); 1.35 (broad s, 9H)
IR (cm$^{-1}$): 3265; 1698

Protocol VI: Preparation of Protected Amine Intermediates Starting from Benzonitrile Intermediates By way of example, the synthesis of intermediate 158 (tert-butyl [2-(4-bromo-3,5-difluorophenyl)propan-2-yl]carbamate) is described below:

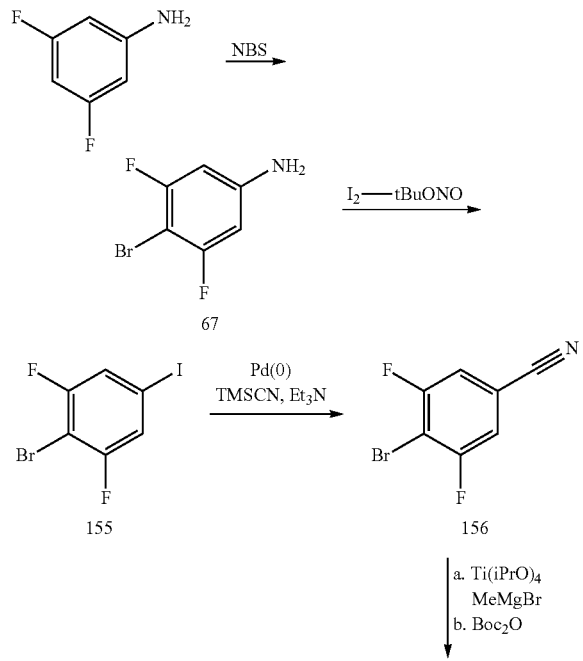
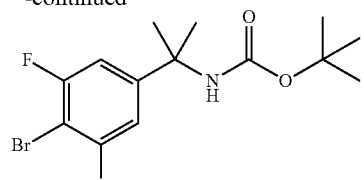

Intermediate 67:

2-Bromo-1,3-difluoro-5-aniline

To a solution of commercial 3,5-difluoroaniline (100 g, 770 mmoles) in DMF (310 mL) there is added a solution of N-bromosuccinimide (140 g, 786 mmoles) in DMF (310 mL) in the course of 40 minutes. The resulting solution is stirred at ambient temperature for 1½ hours. The whole is transferred to 8 L of water, which causes the desired intermediate to precipitate. The solid is filtered over a frit and then rinsed with copious amounts of water. The solid obtained is dried in the air for 48 hours: 148 g of the expected intermediate in the form of a white solid are obtained and used without additional treatment in the following step.

$^1$H NMR (400 MHz, DMSO-d$_6$): δ 6.3 (2d, 2H), 3.90 (m, 2H)
IR (cm$^{-1}$): 3479-3392;

Intermediate 155:

2-Bromo-1,3-difluoro-5-iodobenzene

Diiodine (365.48 g; 1.44 moles) and tert-butyl nitrite (85 mL) are dissolved in acetonitrile (320 mL). A solution of the intermediate obtained above (100 g; 0.48 mole) in acetonitrile (210 mL) is added slowly to the reaction mixture (Tmax: 35° C.). The mixture is stirred at ambient temperature for 50 minutes. An aqueous Na$_2$S$_2$O$_3$ solution is then added until the reaction mixture is discoloured. The aqueous phase is then extracted with Et$_2$O and then dried over MgSO$_4$ and concentrated under reduced pressure. The residue is purified by chromatography on silica (solid deposit (100% cyclohexane)). Intermediate 155 (143 g) is obtained in the form of a yellow solid.

$^1$H NMR (400 MHz, DMSO-d$_6$): δ 7.72 (d, 2H)
IR (cm$^{-1}$): 3080

Intermediate 156:

4-Bromo-3,5-difluorobenzonitrile

To a solution of intermediate 155 (10 g, 31 mmoles) in triethylamine (63 mL) there are added TMSCN (6.2 mL) and then Pd(PPh$_3$)$_4$(1.8 g). The reaction mixture is brought to 80° C., and 1.8 g of Pd(PPh$_3$)$_4$ are again added. The solution colours and a precipitate forms. After GC monitoring, the reaction mixture is returned to ambient temperature and then 50 mL of toluene are added. The mixture is filtered, and the filter is rinsed twice with 50 mL of toluene. The filtrate is treated with 300 mL of 1N HCl, and then with a saturated aqueous NaCl solution. Evaporation under reduced pressure yields 19 g of a solid. The residue is purified by chromatography on silica (solid deposit (100% cyclohexane)). Intermediate 156 (5.6 g) is obtained in the form of a yellow solid.

$^1$H NMR (300 MHz, DMSO-d$_6$): δ 7.98 (m, 2H)
IR (cm$^{-1}$): 2236, 1032; GC-EI (70 eV): 216.9

Intermediate 158:
Step 1

To a solution of intermediate 156 (13.6 g, 62 mmoles) in ethyl ether (330 mL) there is added CH$_3$MgBr (3M in Et$_2$O) (65 mL, 195 mmoles). The mixture is stirred for 35 minutes at ambient temperature, and then Ti(OiPr)$_4$ (19 mL, 64 mmoles) is added. The reaction mixture is stirred overnight at ambient temperature and then treated carefully with a 20% aqueous NaOH solution (50 mL). The mixture was decanted in the presence of AcOEt and of a saturated aqueous NaCl solution, and the organic phase is dried over MgSO$_4$ and then concentrated in vacuo. The residue is chromatographed on silica (eluant CH$_2$Cl$_2$/EtOH (100/0 to 95/05)). The expected intermediate 157 (6.2 g) is obtained in the form of an oil.

$^1$H NMR (400 MHz, DMSO-d$_6$): δ 7.41 (d, 2H), 2.0 (broad s, 2H), 1.34 (s, 6H)

IR (cm$^{-1}$): 3375-3288, 1021.

Step 2

To a solution of the intermediate obtained above (4.2 g, 16.8 mmoles) in methylene chloride (80 mL) there is added carefully di-tert-butyl dicarbonate (3.56 g, 16.3 mmoles). The reaction mixture is stirred at ambient temperature for 3 days before being treated with a 1N HCl solution. The organic phase is dried and then concentrated in vacuo. The residue is chromatographed on silica gel using an eluant mixture CH$_2$Cl$_2$/cyclohexane (50/50 to 100/0). Intermediate 158 (4.3 g) is obtained in the form of an amorphous solid.

$^1$H NMR (300 MHz; DMSO-d$_6$): δ 7.13 (d, 2H); 6.85 (m, 1H); 1.50 (s, 6H); 1.30 (s, 9H)

IR (cm$^{-1}$): 3318; 1683

Protocol VII: Preparation of Ketones by Sandmeyer Reaction

By way of example, the synthesis of intermediate 681 is described below:

Intermediate 681:

To a mixture of commercial 4-bromo-3-methoxyaniline (10.2 g, 50.6 mmoles) in HCl$_{cc}$/H$_2$O (11/25 mL) previously cooled to −5° C. there is added in portions NaNO$_2$ (3.48 g). The reaction mixture is stirred for 1 h at 0° C. before being transferred to a mixture of acetaldoxime (6.02 g), CuSO$_4$ (2.52 g), AcONa.3H$_2$O (36.64 g) in water (20.5 mL) at 0° C. The resulting mixture is stirred between 0° C. and 10° C. for 2 h, and then 37% HCl (23 mL) is added and the mixture is refluxed for 2 hours. After return to ambient temperature, the mixture is extracted with heptane, and the organic phase is dried over MgSO$_4$. Evaporation of the organic phase in vacuo yields a residue, which is chromatographed on silica gel (eluant CH$_2$Cl$_2$/cyclohexane (50/50 to 90/10)). Intermediate 681 (5.9 g) is obtained in the form of an amorphous solid.

$^1$H NMR (400 MHz; CDCl$_3$): δ 7.55 (d, 1H); 7.50 (d, 1H); 7.40 (dd, 1H); 3.95 (s, 3H); 2.60 (s, 3H)

IR (cm$^{-1}$): 1681

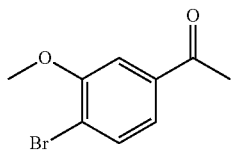

681

Protocol VIII: Obtaining Ketones by Reaction of a Magnesium Compound with Benzonitriles By way of example, the synthesis of intermediate 9 is described below:

Intermediate 9:

At ambient temperature, methylmagnesium iodide (3 M in diethyl ether) (17 mL, 51 mmoles) is added dropwise to a solution of commercial 4-bromo-3-methylbenzonitrile (10 g, 51 mmoles) in diethyl ether (100 mL). The reaction mixture is heated at reflux for 16 hours. After return to ambient temperature, 60 mL of 6N hydrochloric acid are added, and the mixture is then heated at reflux for 6 hours. After cooling, the aqueous and organic phases are separated, and the aqueous phase is extracted with 40 mL of ethyl acetate. The organic phases are combined, washed with a saturated aqueous NaCl solution (2×40 mL), dried over MgSO$_4$ and then concentrated under reduced pressure. 4.5 g of intermediate 9 are obtained in the form of a brown oil.

$^1$H NMR (300 MHz, CDCl$_3$): δ 7.80 (s, 1H), 7.62 (s, 2H), 2.60 (s, 3H), 2.45 (s, 3H)

IR (cm$^{-1}$): 1681

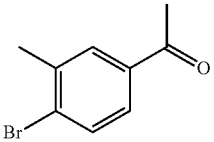

9

Protocol IX: Obtaining Ketones by Weinreb Reaction

By way of example, the synthesis of intermediate 37 is described below:

Intermediate 36:

To a suspension of commercial 4-bromo-3-fluoro-benzoic acid (5 g, 22.8 mmoles) in methylene chloride (70 mL) there are added DMF (0.1 mL) and then oxalyl chloride (2.1 mL). The mixture is stirred at ambient temperature for 4 hours, and then it is concentrated in vacuo. The residue is taken up in methylene chloride (220 mL), and N-methyl-methoxylamine hydrochloride is added thereto. The mixture is cooled to 5° C., and pyridine is added (4 mL). The mixture was stirred for 2 hours and then washed with a 2N aqueous HCl solution, and the organic phase is dried over MgSO$_4$ and then concentrated in vacuo. Intermediate 36 is obtained in the form of a solid (5.4 g).

$^1$H NMR (300 MHz, DMSO-d$_6$): δ 7.85 (dd, 1H), 7.60 (dd, 1H), 7.40 (dd, 1H), 3.59 (s, 3H), 3.29 (s, 3H)

IR (cm$^{-1}$): 1657

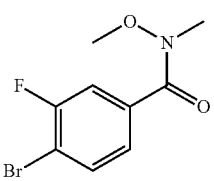

36

Intermediate 37:

At −70° C., intermediate 36 (5.4 g, 20.6 mmoles) in solution in THF (75 mL) is treated with a solution of methylmagnesium bromide (3 M in diethyl ether) (8.1 mL, 24 mmoles). The mixture is stirred with return to ambient temperature for 3 hours before being poured into a 1N aqueous HCl solution at 0° C. The product is extracted with AcOEt, and the organic phase is washed with a saturated aqueous NaCl solution, dried over MgSO₄ and then concentrated in vacuo. Intermediate 37 is obtained in the form of a solid (3.6 g).

¹H NMR (300 MHz; CDCl₃): δ 7.7-7.6 (m, 3H), 2.58 (s, 3H)

IR (cm⁻¹): 1679

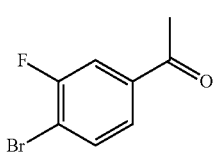

37

Protocol X: Obtaining Ketones by Stille Reaction

By way of example, the synthesis of compound 61 is described below:

Intermediate 61:

To a solution, degassed with nitrogen, of 44 g (137 mmoles, 1 eq.) of intermediate 155 in 1.7 L of DMF there are added tri-butyl-(1-ethoxyvinyl)tin (65 mL, 179 mmoles) and then PdCl₂(PPh₃)₂(13 g, 0.18 mmole). The mixture is heated at 80° C. until the starting intermediate has disappeared (GC monitoring). After return to ambient temperature, the reaction mixture is decanted with 3 L of water and 1 L of Et₂O. The organic phase is dried over MgSO₄ and then concentrated. The residue so obtained is taken up in 300 mL of THF and stirred for 1 hour in the presence of a 1N aqueous HCl solution (100 mL). The mixture is then decanted in the presence of 1 L of Et₂O, and the organic phase is dried over MgSO₄. Evaporation under reduced pressure yields 56 g of an oil. The oil is chromatographed on silica gel (cyclohexane/methylene chloride 80/20 to 50/50). Intermediate 61 (27 g) is obtained in the form of a beige solid, which is used without additional treatment in the following step.

¹H NMR (300 MHz, CDCl₃): δ 7.50 (d, 2H), 2.60 (s, 3H)

IR (cm⁻¹): 1694

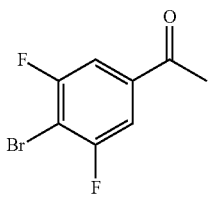

61

Protocol XI: Obtaining Ketones by Fries Rearrangement

By way of example, the synthesis of intermediate 547 is described below:

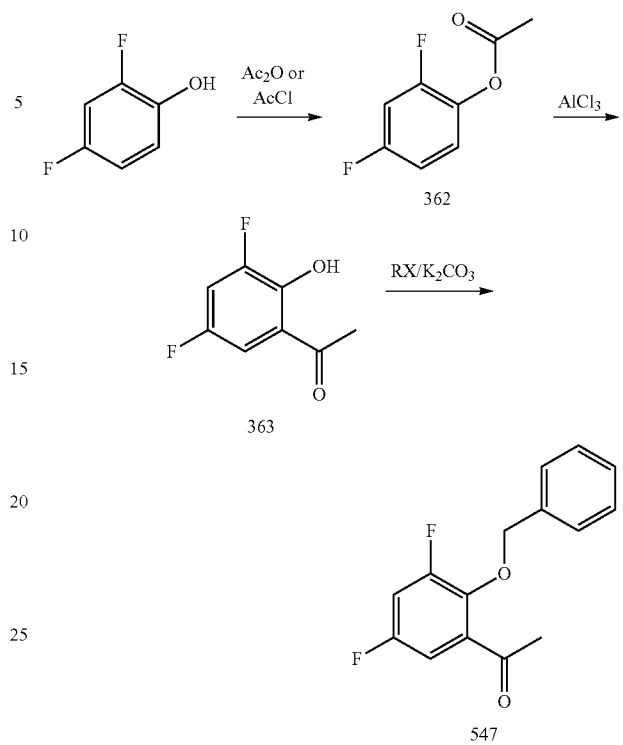

Intermediate 362:

To a mixture of commercial 2,4-difluorophenol (15 g, 115 mmoles) and pyridine (10.2 mL) in methylene chloride (156 mL) there is added acetyl chloride (8.6 mL), the temperature being maintained below 30° C. The resulting mixture (formation of a precipitate) is stirred for 1 hour at ambient temperature before being hydrolysed. The mixture is decanted, and the organic phase is washed in succession with a 1N aqueous HCl solution and a saturated aqueous NaHCO₃ solution and is then dried over MgSO₄. Evaporation under reduced pressure yields intermediate 362 in the form of an oil (19.4 g), which is used in the following step.

¹H NMR (300 MHz, CDCl₃): δ 7.10 (m, 1H), 6.90 (m, 2H), 2.30 (s, 3H)

IR (cm⁻¹): 1770

Intermediate 363:

A mixture of intermediate 362 (2 g, 11.6 mmoles) and AlCl₃ (2.8 g) is heated under argon at 150° C. for 30 minutes. After return to ambient temperature, there are added carefully ice and then a 1N aqueous HCl solution. The mixture is decanted in the presence of toluene, and the organic phase is washed with water and then with a saturated aqueous NaCl solution. After drying, evaporation under reduced pressure yields intermediate 363 in the form of a solid (1.5 g).

¹H NMR (300 MHz, CDCl₃): δ 12.00 (m, 1H), 7.25 (m, 1H), 7.10 (m, 1H), 2.65 (s, 3H)

IR (cm⁻¹): 1651

Intermediate 547:

To a solution of intermediate 363 (15 g, 87 mmoles) in acetone (150 mL) there are added K₂CO₃ (24 g) and then benzyl bromide (10.8 mL, 91 mmoles). The mixture is stirred at ambient temperature for 24 hours. The salts are filtered off and the filtrate is evaporated off. The residue is taken up in Et₂O and then washed with water and with a saturated aqueous NaCl solution. After drying over MgSO₄, evaporation under reduced pressure yields intermediate 547 in the form of an oil (22.5 g).

$^{1}$H NMR (400 MHz, CDCl$_{3}$): δ 7.40 (m, 5H), 7.15 (m, 1H), 7.00 (m, 1H), 5.10 (s, 2H), 2.50 (s, 3H)

IR (cm$^{-1}$): 1687

Protocol XII: Conversion of Ketones into Racemic Amines

By way of example, the synthesis of intermediate 48 is described below:

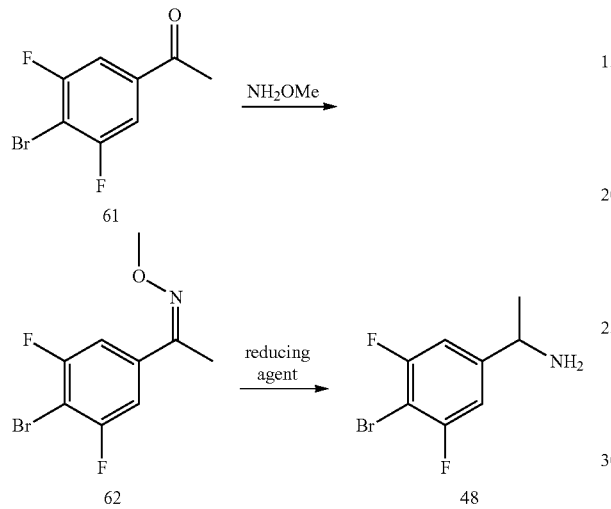

Intermediate 62:

To a mixture of 26 g (110 mmoles) of intermediate 61 in 53 mL of ethanol there are added 107 mL of water, 11.8 g (141 mmoles) of methoxylamine hydrochloride and 11.8 g (142 mmoles) of sodium acetate. The mixture is heated for 3 hours at 70° C. The mixture is returned to ambient temperature and then extracted with AcOEt (0.5 L) in the presence of a saturated aqueous NaCl solution. The organic phase is dried over MgSO$_{4}$. Evaporation under reduced pressure yields 27.7 g of the mixture of oximes 62 in the form of a light-brown solid, which is used without additional treatment in the following step.

IR (cm$^{-1}$): 1025

Intermediate 48:

At ambient temperature, 210 mL (210 mmoles, 2 eq.) of a 1M solution of BH$_{3}$.THF in THF are added in the course of 10 minutes to a solution of 27 g (105 mmoles, 1 eq.) of the mixture of oximes 62 in 114 mL of THF. The solution obtained is heated at 70° C. for 212 h. After HPLC monitoring, the mixture is returned to ambient temperature. A 2N solution of HCl in ether (2 eq.) is added carefully to the mixture. The mixture is heated for 1 h at 40° C. Filtration of the solid yields 11.8 g of the hydrochloride of intermediate 48.

$^{1}$H NMR (400 MHz; DMSO-d$_{6}$): δ 8.65 (m, 3H), 7.53 (d, 2H), 4.46 (quad, 1H), 1.51 (d, 3H)

IR (cm$^{-1}$): 3200-2500

This procedure is used to prepare the racemic amines in the form of hydrochlorides or of free bases.

Protocol XIIb: Alternative Process for the Conversion of Ketones into Racemic Amines By way of example, the synthesis of intermediate 341 is described below:

Intermediate 341:

To a solution of commercial 5,7-difluoro-2,3-dihydro-1H-inden-1-one (6 g, 35 mmoles) in pyridine (60 mL) at ambient temperature there is added methoxylamine hydrochloride (3.0 g, 37 mmoles). The reaction mixture is stirred for 20 hours at ambient temperature. The pyridine is evaporated off in vacuo, and the residue is stirred in water (30 mL) for 1 hour and then collected on a frit. The solid is rinsed with water and then dried in vacuo at 50° C. The oxime intermediate is obtained in the form of a white solid (6.5 g), which is then reduced to intermediate 341 according to the process described for intermediate 48.

$^{1}$H NMR (300 MHz; DMSO-d$_{6}$): δ 7.10 (m, 2H), 6.50 (m, 3H), 4.80 (m, 1H), 3.25 (m, 1H), 2.95 (m, 1H), 2.50 (m, 1H), 2.15 (m, 1H)

$^{19}$F NMR: −107.6, −110.8 (quad and dd, 2F)

IR (cm$^{-1}$): 3380-2500

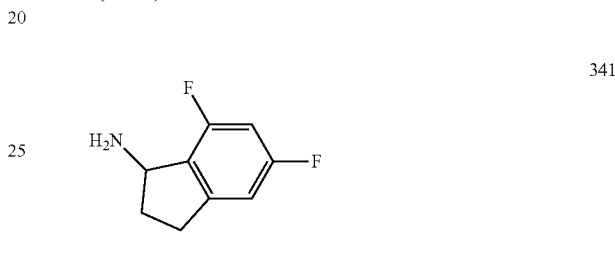

Protocol XIII: Conversion of Ketones into Chiral tert-butanesulphinylamine Intermediates Bibliographical reference: John T. Colyer, Neil G. Andersen,* Jason S. Tedrow, Troy S. Soukup, and Margaret M. Faul. *J. Org. Chem.* 2006, 71, 6859-6862 By way of example, the synthesis of intermediate 286 is described below:

Intermediate 286:

To a solution of commercial 1-(3,5-difluorophenyl)ethanone (20 g, 120 mmoles) in THF (332 mL) there are added in succession Ti(OEt)$_{4}$ (34 mL, 163 mmoles) and then (R)-(+)-2-methyl-2-propanesulphinamide (14.5 g, 119 mmoles). The mixture is heated for 24 hours at 70° C. The mixture, cooled to −40° C., is transferred by cannulation to a suspension of NaBH$_{4}$ (18.1 g; 374 mmoles) in THF (220 mL). The reaction mixture at ambient temperature is treated carefully with methanol (56 mL) and then diluted with AcOEt (300 mL) and an aqueous NaCl solution (700 mL). The resulting mixture is filtered over Celite®, which is rinsed with THF and AcOEt. The filtrate is decanted, and the organic phase is dried over MgSO$_{4}$. Evaporation under reduced pressure yields a white solid, which is purified on silica gel using an AcOEt/methylene chloride elution gradient 0/100 to 40/60. The diastereoisomer 286 (18 g) is isolated in the form of a white solid.

$^{1}$H NMR (400 MHz; DMSO-d$_{6}$): δ 7.15 (m, 2H), 7.08 (m, 1H), 5.29 (d, 1H), 4.40 (m, 1H), 1.38 (d, 3H), 1.10 (s, 9H)

IR (cm$^{-1}$): 3146, 1043

GC-EI (70 eV): M$^{+}$=261.1

Diastereoisomeric purity: de>99%

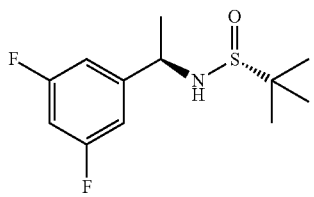

286

Protocol XIIIb: Alternative Method for the Preparation of Chiral tert-butanesulphinylamine Intermediates The preparation of chiral tert-butanesulphinylamine intermediates can be broken down according to the sequence described for intermediate 331.

Intermediate 330:

To a solution of commercial 1-(2,4-difluorophenyl)ethanone (4 g, 25.6 mmoles) in 80 mL of THF there are added in succession Ti(OEt)$_4$ (13.1 g, 46 mmoles) and then (R)-(+)-2-methyl-2-propanesulphinamide (3.1 g, 25 mmoles). The mixture is heated for 24 hours at 70° C. The reaction mixture, cooled to about 15° C., is poured into a saturated aqueous NaCl solution, and then ethyl acetate is added. After stirring (30 minutes), the mixture is filtered over Celite® and washed with 2 times 80 mL of ethyl acetate. The filtrate is decanted, and the organic phase is dried over MgSO$_4$, filtered and evaporated to dryness. The residue is purified by flash chromatography on silica (eluant: CH$_2$Cl$_2$/AcOEt: 95/5). Intermediate 330 (5.2 g) is obtained in the form of a yellow liquid.

$^1$H NMR (400 MHz; DMSO-d$_6$): δ 7.80 (m, 1H), 7.40 (m, 1H), 7.20 (m, 1H), 2.70 (s, 3H), 1.20 (s, 9H)

IR (cm$^{-1}$): 1603, 1080

GC-EI (70 eV): M$^+$=259.1

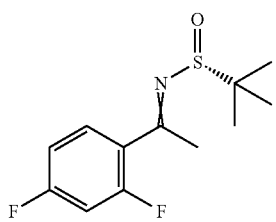

330

Intermediate 331:

To a solution of intermediate 330 (2.5 g, 9.64 mmoles) in 50 mL of THF, cooled to −60° C., there is added NaBH$_4$ (366 mg, 9.64 mmoles). After return to ambient temperature, the reaction mixture is treated carefully with methanol and then concentrated in vacuo. The residue is taken up in water and extracted with ether. The organic phase is washed with a saturated aqueous NaCl solution and then dried over MgSO$_4$. The residue is purified by flash chromatography on silica (eluant: CH$_2$Cl$_2$/AcOEt: 80/20). Intermediate 331 is obtained (1.85 g) in the form of a white crystalline solid.

$^1$H NMR (300 MHz; DMSO-d$_6$): δ 7.60 (m, 1H), 7.20 (m, 1H), 7.10 (m, 1H), 5.75 (d, 1H), 4.60 (quint, 1H), 1.4 (d, 3H), 1.1 (s, 9H)

IR (cm$^{-1}$): 3243, 1603, 853, 814

Diastereoisomeric purity: de>99%

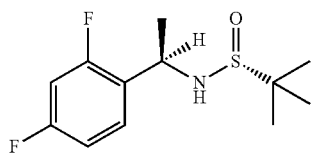

331

Protocol XIV: Conversion of Commercial Aldehydes into Chiral tert-butanesulphinylamine Intermediates By way of example, the synthesis of intermediate 497 N-[1-(3,5-difluorophenyl)-2-methylpropyl]-2-methylpropane-2-sulphinamide) is described below:

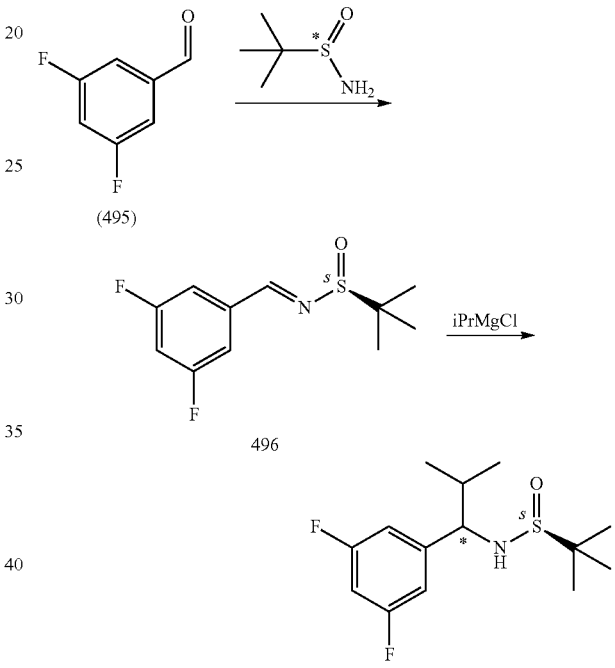

Intermediate 496:

To a solution of (S)-(−)-2-methylpropane-2-sulphinamide (44.7 g, 368 mmoles) in methanol (500 mL) there is added at ambient temperature tBuOK (3.93 g). After 15 minutes' stirring at ambient temperature, commercial 3,5-difluorobenzaldehyde (50 g, 0.35 mole) is added. The reaction mixture is stirred at ambient temperature for 1 hour and then it is hydrolysed with a saturated aqueous NH$_4$Cl solution. Evaporation of the methanol in vacuo allows a solid to crystallise, which solid is taken up in 300 mL of water, filtered and washed with water. The solid is dissolved in ether, washed with a saturated aqueous NaCl solution, dried over MgSO$_4$, filtered and concentrated in vacuo. Intermediate 496 (74.5 g) is obtained in the form of an oil, which crystallises.

$^1$H NMR (400 MHz, DMSO-d$_6$): δ 8.58 (s, 1H), 7.70 (broad d, 2H), 7.50 (t, 1H), 1.25 (s, 9H)

IR (cm$^{-1}$): 1620, 1142, 1078

Intermediate 497:

To a solution of intermediate 496 (3 g, 12 mmoles) in THF (60 mL), cooled to −65° C., there is added a solution of isopropylMgBr (3M/ether) (9 mL, 27 mmoles) in the course of 20 minutes. After monitoring, the reaction mixture is hydrolysed at −40° C. with a saturated aqueous NH$_4$Cl solution. The mixture is decanted in the presence of ethyl ether, and the organic phase is washed with a saturated NaCl solution, dried over MgSO$_4$ and then concentrated. Chromatography on silica (eluant CH$_2$Cl$_2$/AcOEt 99/1 to 85/15) yields intermediate 497 (2.7 g) in the form of an oil.

$^1$H NMR (400 MHz, DMSO-d$_6$): δ 7.05 (m, 3H), 5.35 (d, 1H), 4.0 (t, 1H), 2.0 (m, 1H), 1.05 (s, 9H), 1.0-0.8 (2d, 6H) IR (cm$^{-1}$): 3189, 1116, 1040

Protocol XV: Preparation of tert-butylcarbamate Compounds

The chiral auxiliary was cleaved in an acidic medium according to the following protocol:
Intermediate 287:

A solution of intermediate 286 (18 g, 69 mmoles) in ethyl ether (580 mL) is treated with hydrochloric acid in Et$_2$O (2M solution, 59 mL). The reaction mixture is stirred for 20 hours at ambient temperature. The precipitate is filtered over a frit and then dried in vacuo. The hydrochloride of 287 (11.5 g, ee>99%) is obtained in the form of a white solid.

$^1$H NMR (300 MHz, DMSO-d$_6$): δ 8.68 (broad s, 3H), 7.32 (m, 2H), 7.27 (m, 1H), 4.45 (quad, 1H), 1.50 (d, 3H) IR (cm$^{-1}$): 3100-2500

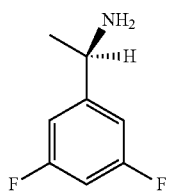

287

The amines obtained are protected in the form of tert-butylcarbamates according to the procedure described for intermediate 158 (protocol VI).

When hydrochlorides are obtained, they are treated with 1N sodium hydroxide and the amines obtained are protected as indicated above.

Protocol XVI: Preparation of Trifluoroacetamide Compounds

By way of example, the procedure for preparing intermediate 17 is described below:
Intermediate 17:

To a solution of commercial (R)-(+)-1-(3-methoxyphenyl)ethylamine (50 g, 330 mmoles) in methylene chloride (400 mL) at ambient temperature there is added slowly a solution of trifluoroacetic anhydride (46 mL, 330 mmoles). The mixture is stirred at ambient temperature for 212 hours. The reaction mixture is washed with a 1N aqueous HCl solution (400 mL). The whole is decanted, and the organic phase is dried by passage over MgSO$_4$. Evaporation under reduced pressure yields intermediate 17 (84 g) in the form of a solid, which is used without additional treatment in the following step.

$^1$H NMR (400 MHz, CDCl$_3$): δ 7.30 (m, 1H), 6.90 (2d and s, 3H), 6.45 (broad s, 1H),
5.10 (m, 1H), 3.80 (s, 3H), 1.60 (d, 3H) IR (cm$^{-1}$): 3293, 1696, 1612, 1588

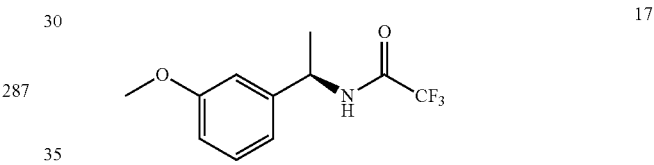

17

Protocol XVII

By way of example, the preparation of 94 is described below:

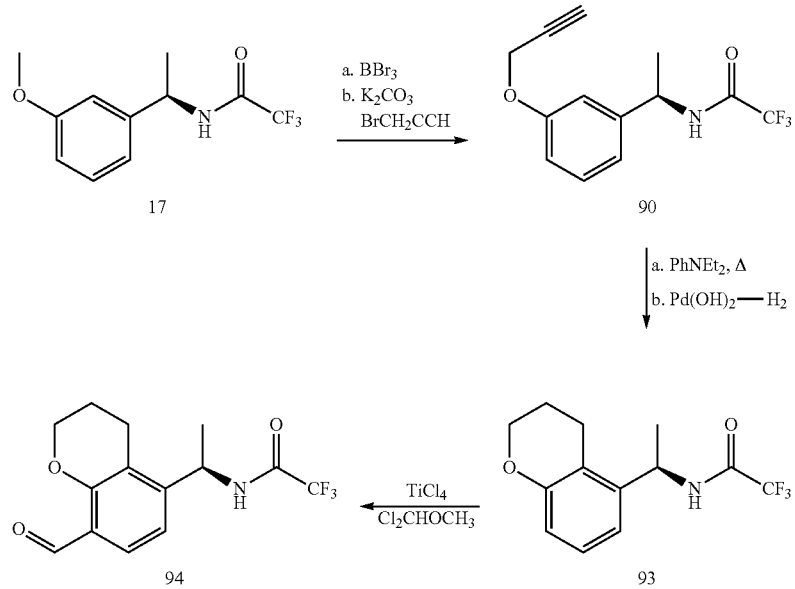

Intermediate 90:

To a solution of intermediate 17 (65 g, 262 mmoles) in methylene chloride (800 mL) at −70° C. there is added slowly a solution of BBr$_3$ (1M in CH$_2$Cl$_2$) (480 mL, 480 mmoles). The mixture is brought to ambient temperature over a period of 2 hours. After HPLC monitoring, the reaction mixture is cooled to −70° C. and treated carefully with methanol (200 mL). The solution is concentrated in vacuo, the residue is taken up carefully in water (300 mL), and the mixture is treated with NaOAc until pH 4-5 is reached. The whole is decanted in the presence of methylene chloride (500 mL), and the organic phase is dried by passage over MgSO$_4$. Evaporation under reduced pressure yields intermediate 90 (64 g) in the form of a beige solid, which is used without additional treatment in the following step.

$^1$H NMR (300 MHz, DMSO-d$_6$): δ 9.70 (m, 1H), 9.20 (s, 1H), 7.12 (t, 1H), 6.75 (s, 1H), 6.78 (m, 1H), 6.65 (dd, 1H), 4.90 (quint, 1H), 1.42 (d, 3H)

IR (cm$^{-1}$): 3298, 1702, 1153

Intermediate 93:

Step 1

To a solution of intermediate 90 (21 g, 90 mmoles) in DMF (450 mL) there are added K$_2$CO$_3$ (15 g, 108 mmoles) and then propargyl bromide (11 mL, 98 mmoles). The mixture is stirred at 60° C. for 4 hours. After HPLC monitoring, the reaction mixture, cooled to ambient temperature, is poured into a water/ice mixture (1 L/1 kg). The solid is filtered over a frit and washed with water. Drying in vacuo yields the expected intermediate (24 g) in the form of a beige solid, which is used without additional treatment in the following step.

$^1$H NMR (300 MHz, DMSO-d$_6$): δ 9.70 (broad s, 1H), 7.28 (t, 1H), 6.92 (m, 3H), 5.00 (quad, 1H), 4.78 (s, 2H), 3.42 (t, 1H), 1.45 (d, 3H)

IR (cm$^{-1}$): 3301, 1693, 1158

Step 2

A suspension of the intermediate obtained above (5 g, 11 mmoles, 1 eq) in diethylaniline (7 mL) is heated in a microwave oven (CEM, DISCOVER, standard mode) for 40 minutes at 210° C. The reaction mixture is poured into a water/ice/AcOEt mixture (0.2 L/0.2 kg/0.2 L), with stirring, and is then treated with 12N HCl until a stable pH 1 is reached, and the organic phase is washed with a saturated NaCl solution (1L) and then dried by passage over MgSO$_4$. Evaporation under reduced pressure yields an oil, which is chromatographed on silica gel using an eluant mixture CH$_2$Cl$_2$/cyclohexane (30/70 to 50/50). The mixture of two compounds a and b (2.3 g) is obtained in the form of a yellow oil (ratio a/b: 56/43).

Intermediate a:

$^1$H NMR (400 MHz, DMSO-d$_6$): δ 9.90 (s, 1H), 7.15 (t, 1H), 6.9-6.7 (2d, 2H), 6.80 (d, 1H), 6.00 (m, 1H), 5.20 (m, 1H), 4.70 (m, 2H), 1.40 (d, 3H)

IR (cm$^{-1}$): 3284, 1692

Step 3

To a solution of a/b (7.1 g, 26.1 mmoles, 1 eq) in methanol (700 mL) there is added Pd(OH)$_2$ (2.9 g, 40% by weight). The resulting mixture is stirred at atmospheric pressure and at ambient temperature until the starting material has disappeared (GC monitoring).

The reaction mixture is filtered. Evaporation under reduced pressure of the filtrate yields a mixture of intermediates 93a/93b (5.8 g), which is used without additional treatment in the following step.

Intermediate 93a:

$^1$H NMR (300 MHz, DMSO-d$_6$): δ 9.80 (d, 1H), 7.10 (t, 1H), 6.90 (broad d, 1H), 6.65 (broad d, 1H), 5.10 (quint, 1H), 4.10 (t, 2H), 2.85-2.6 (m, 2H), 1.95 (m, 2H), 1.40 (d, 3H)

IR (cm$^{-1}$): 3276, 1691, 1181

Intermediate 94:

2,2,2-Trifluoro-N-[(1R)-1-(8-formyl-3,4-dihydro-2H-chromen-5-yl)ethyl]acetamide

To a solution of 93a/93b (2.58 g, 9.4 mmoles) in methylene chloride (40 mL) at 0° C. there are added TiCl$_4$ (1.8 mL, 16 mmoles) and then Cl$_2$CHOMe (0.78 mL, 8.6 mmoles). The resulting mixture is stirred at ambient temperature for 20 hours and then poured into a water/ice mixture (250 mL/250 g). The whole is decanted in the presence of methylene chloride (500 mL), and the organic phase is dried by passage over MgSO$_4$. Evaporation under reduced pressure yields an oil, which is chromatographed on silica gel (eluant CH$_2$Cl$_2$/AcOEt (97/3)). Intermediate 94 (0.9 g) is obtained in the form of an oil.

$^1$H NMR (500 MHz, CDCl$_3$): δ 10.30 (s, 1H), 10.00 (1H), 7.55 (d, 1H), 7.05 (d, 1H), 5.10 (quad, 1H), 4.28 (t, 2H), 2.9-2.78 (m, 2H), 2.05 (m, 2H), 1.40 (dd, 3H)

IR (cm$^{-1}$): 3303, 1716, 1660

Preparation of Phenyl Precursors—Examples

Intermediate 64:

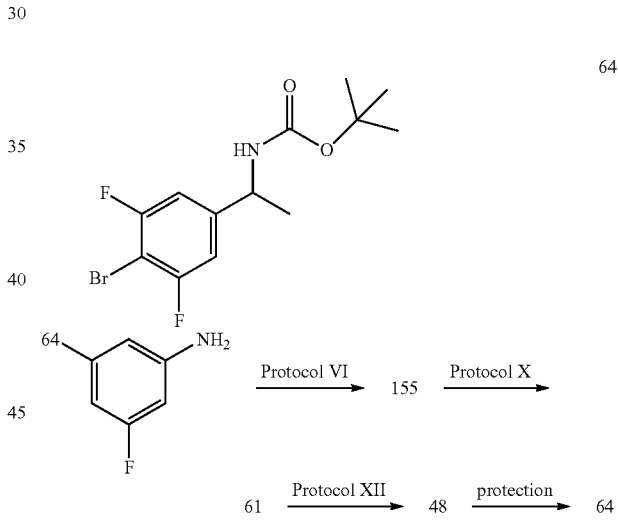

Obtained by protection of amine 48 according to the protocol described for intermediate 158

$^1$H NMR (300 MHz, CDCl$_3$): δ 6.90 (d, 2H), 4.70 (2m, 2H), 1.40 (m and d, 12H)

IR (cm$^{-1}$): 3420, 1680

Intermediates 145 and 146:

Intermediate 64 (11 g) was chromatographed by high pressure chromatography on a chiral support (ChiralPak IC column, eluant heptane/THF 100/5, detection UV 270 nm) to give intermediates 145 (4 g) and 146 (4 g).

Intermediate 145:

tert-Butyl [(1R)-1-(4-bromo-3,5-difluorophenyl)ethyl]carbamate $^1$H NMR (400 MHz, DMSO-d$_6$): 7.45 (broad d, 1H), 7.20 (d, 2H), 4.65 (m, 1H), 1.40 (s, 9H), 1.30 (d, 3H)

IR (cm$^{-1}$): 3368, 1678

Attribution of chirality carried out by IR-VCD on the basis of the infrared spectra of (1R)-1-(4-bromophenyl)ethanamine.

Intermediate 146:

tert-Butyl [(1S)-1-(4-bromo-3,5-difluorophenyl)ethyl]carbamate $^1$H NMR (300 MHz, DMSO-d$_6$): 7.14 (m, 2H), 7.01 (m, 1H), 4.62 (m, 1H), 1.35 (s, 9H), 1.32 (d, 3H)
IR (cm$^{-1}$): 3366, 1678

Attribution of chirality carried out by IR-VCD on the basis of the infrared spectra of (1S)-1-(4-bromophenyl)ethanamine.

Intermediates 145 and 146 can also be obtained starting from intermediates 166 and 161, respectively, using the conditions of protocol XV.

Intermediate 166:
Obtained by reaction of intermediate 61 and (R)-(+)-2-methyl-2-propanesulphinamide according to protocol XIIIb
LC/MS: [M+H]+ measured 339
chemical purity 85%.

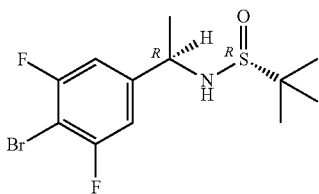

166

Intermediate 161:
Obtained by reaction of intermediate 61 and (S)-(−)-2-methyl-2-propanesulphinamide according to protocol XIIIb
$^1$H NMR (400 MHz, DMSO-d$_6$): δ 7.34 (d, 2H), 5.81 (d, 1H), 4.41 (quint, 1H), 1.38 (d, 3H), 1.12 (s, 9H)
IR (cm$^{-1}$): 3174

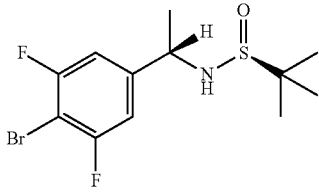

161

Intermediate 5:

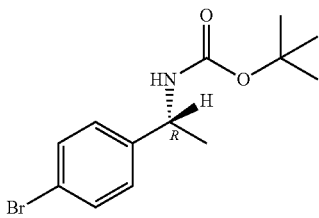

5

Obtained by protection of commercial (1R)-1-(4-bromophenyl)ethanamine according to the protocol described for intermediate 158

$^1$H NMR (300 MHz, DMSO-d$_6$): δ 7.50 (d, 2H), 7.25 (d, 2H), 7.40 (d, 1H), 4.60 (m, 1H), 1.40 (s, 9H), 1.30 (d, 3H)
IR (cm$^{-1}$): 3373, 1681.

Intermediates 13 and 313:

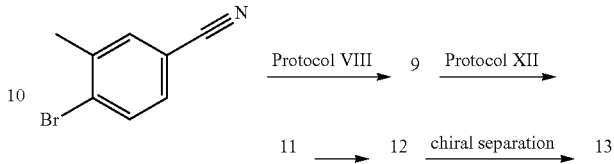

Intermediate 11:
Obtained starting from intermediate 9 according to protocol XII
$^1$H NMR (300 MHz; CDCl$_3$): 7.45 (d, 1H), 7.20 (d, 1H); 7.05 (dd, 1H); 4.05 (quad, 1H); 2.40 (s, 3H); 1.35 (d, 3H); 1.55 (m, 2H)

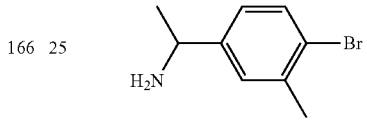

11

Intermediate 12:
To a solution of intermediate 11 (28 g, 131 mmoles) in methylene chloride (1.4 L) at ambient temperature there is added a solution of di-tert-butyl dicarbonate (28 g, 131 mmoles) in methylene chloride (0.36 L). The reaction mixture is stirred for 312 hours, and then a 1N aqueous HCl solution is added. The organic phase is dried over MgSO$_4$ and then concentrated in vacuo. The solid residue is stirred in pentane for 1 hour, and the solid is collected on a frit. Intermediate 12 is obtained in the form of a white solid.
$^1$H NMR (400 MHz, DMSO-d$_6$): δ 7.50 (d, 1H), 7.37 (d, 1H), 7.26 (d, 1H), 7.05 (dd, 1H), 4.54 (m, 1H), 2.32 (s, 3H), 1.36 (s, 9H), 1.27 (d, 3H)
IR (cm$^{-1}$): 3374, 1684

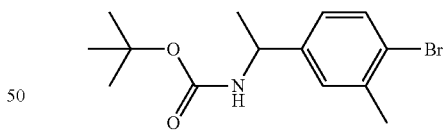

12

Intermediate 12 (122 g) was then chromatographed by high pressure chromatography on a chiral support (Chiral-Pak (R,R) WHELK column, eluant iPrOH, detection: 220 nm) to yield enantiomers 313 (48 g) and 13 (57 g).

Intermediate 313:
α$_D$ (589 nM)=−69.9 (c=0.010 g/mL, MeOH) at 20° C.
Optical purity: >99%, intermediate 13<1%.

Intermediate 13:
$^1$H NMR (400 MHz, DMSO-d$_6$): 7.50 (d, 1H), 7.37 (d, 1H), 7.26 (d, 1H), 7.05 (dd, 1H), 4.54 (m, 1H), 2.32 (s, 3H), 1.36 (s, 9H), 1.27 (d, 1H)
IR (cm$^{-1}$): 3374, 1684
α$_D$ (589 nM)=+71.80 (c=0.010 g/mL, MeOH) at 20° C.
Optical purity: >99%, intermediate 313<1%

Intermediate 13 can also be obtained starting from intermediate 459 using the conditions of protocol XV.

Intermediate 459:

Obtained by reaction of intermediate 9 and (R)-(+)-2-methyl-2-propanesulphinamide according to protocol XIIIb $^1$H NMR (400 MHz, DMSO-d$_6$): δ 7.50 (d, 1H), 7.35 (d, 1H), 7.15 (dd, 1H), 5.60 (d, 1H), 4.30 (quint, 1H), 2.30 (s, 3H), 1.40 (d, 3H), 1.10 (s, 9H)

IR (cm$^{-1}$): 3207, 1052

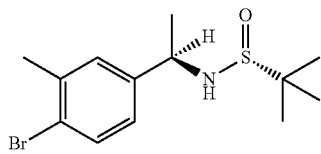

459

Intermediate 32:

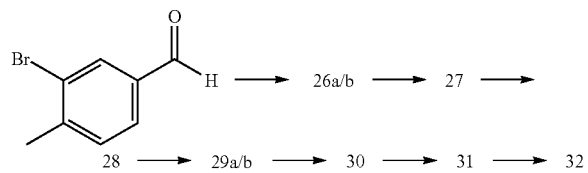

Intermediates 26a/b:

To a solution of sodium ethoxide prepared by adding sodium (9.1 g, 396 mmoles) to ethanol (400 mL) previously cooled to 0° C. there is added (EtO)$_2$POCH$_2$CN (63 mL, 396 mmoles). The resulting mixture is stirred at 0° C. for 30 minutes, and then commercial 3-bromo-4-methylbenzaldehyde (77 g, 391 mmoles) is added slowly (approximately 20 minutes). The reaction mixture is stirred at ambient temperature until the starting material has disappeared, and it is then poured into water (4 L). The precipitate is filtered off over a frit, rinsed with water and dried in vacuo. The mixture of intermediates 26a/b (mixture of the Z and E forms) is obtained (81 g) and used in the following step.

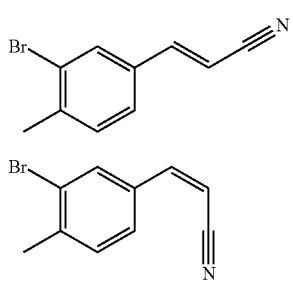

26a

26b

Intermediate 27:

To a solution of intermediates 26a/b (75 g, 338 mmoles) in isopropanol (1 L) there is added NaBH$_4$ (51 g, 1.35 mole). The reaction mixture is heated at 90-100° C. for 48 hours and stirred with return to ambient temperature for 2 days. The solvent is evaporated off, and the residue is taken up in water, neutralised carefully with concentrated HCl and extracted with AcOEt. The organic phase is washed in succession with water and with a saturated aqueous NaCl solution and is then dried over MgSO$_4$ and concentrated in vacuo. The oil is chromatographed on silica gel (methylene chloride 100%). Intermediate 27 (58 g) is obtained in the form of an oil.

$^1$H NMR (400 MHz; CDCl$_3$): δ 7.40 (d, 1H); 7.20 (d, 1H); 7.10 (dd, 1H); 2.90 (t, 2H); 2.60 (t, 2H); 2.40 (s, 3H)

IR (cm$^{-1}$): 2247, 1040.

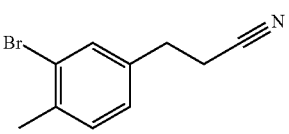

27

Intermediate 28:

Intermediate 27, treated according to the protocol described for intermediate 599 (protocol V), yields intermediate 28 (60 g).

$^1$H NMR (400 MHz; CDCl$_3$): δ 11.0 (m, 1H); 7.40 (d, 1H); 7.15 (d, 1H); 7.00 (dd, 1H); 2.90 (t, 2H); 2.65 (t, 2H); 2.35 (s, 3H).

IR (cm$^{-1}$): 3400, 2100, 1697.

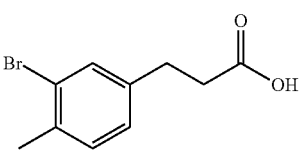

28

Intermediates 29a/b:

To a mixture of P$_2$O$_5$(14 g, 100 mmoles) and methanesulphonic acid (142 mL) previously heated at 60° C. for 2 hours there is added intermediate 28 (12 g, 50 mmoles). The reaction mixture is stirred for 35 minutes at 60° C. and is then poured carefully into ice. The mixture is extracted with AcOEt, and the organic phase is washed in succession with water, with a 4N aqueous NaOH solution, again with water and with a HCl solution. The organic phase is dried over MgSO$_4$ and concentrated in vacuo. The residue is solidified in isopropyl ether. The mixture of intermediates 29a/b (5 g) obtained is used in the following step.

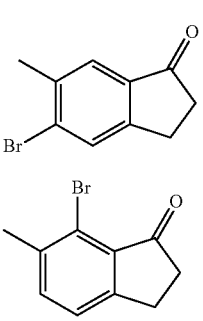

29a

29b

Intermediate 30:

The mixture of intermediates 29a/b (5.2 g, 23 mmoles) is treated according to the protocol described for Example 341, methoxylamine hydrochloride being replaced by o-benzyl-hydroxylamine hydrochloride. After treatment and chromatography (SiO$_2$, eluant: toluene/CH$_2$Cl$_2$ 80/20), intermediate 30 (2.5 g) is obtained.

¹H NMR (300 MHz; CDCl₃): δ 7.55 (s, 1H); 7.50 (s, 1H); 7.4-7.25 (m, 5H); 5.20 (s, 2H); 2.90 (2m, 4H); 2.40 (s, 3H).

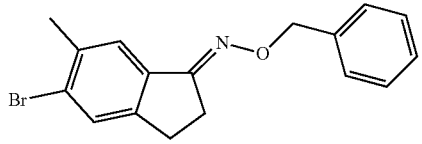
30

Intermediate 31:
Obtained starting from intermediate 30 according to the process described for intermediate 48 (protocol XII) ¹H NMR (300 MHz; CDCl₃): 7.40 (s, 1H), 7.20 (s, 1H); 4.30 (t, 1H); 2.90 (m, 1H); 2.75 (m, 1H); 2.50 (m, 1H); 2.40 (s, 3H); 1.70 (m, 1H); 1.50 (m, 2H)

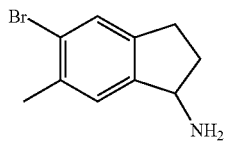
31

Intermediate 32:
Obtained by protection of intermediate 31 according to the protocol described for intermediate 158 (protocol VI)
¹H NMR (400 MHz, CDCl₃): δ 7.40 (s, 1H), 7.20 (s, 1H), 5.10 (quad, 1H), 4.70 (broad d, 1H), 2.90 (m, 1H), 2.80 (m, 1H), 2.55 (m, 1H), 2.40 (s, 3H), 1.80 (m, 1H), 1.50 (s, 9H)
IR (cm⁻¹): 3299, 1674

32

Intermediate 40:

The synthesis of intermediate 37 is described by way of example for protocol IX.

Intermediate 39:
Obtained starting from intermediate 37 according to protocol XII
¹H NMR (300 MHz; CDCl₃): 7.49 (t, 1H), 7.18 (dd, 1H), 7.01 (dd, 1H), 4.11 (quad, 1H), 1.50 (s, 2H), 1.35 (d, 3H)
IR (cm⁻¹): 3372, 3288

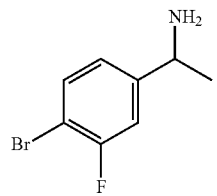
39

Intermediate 40:
Obtained by protection of intermediate 39 according to the protocol described for intermediate 158 (protocol VI)
¹H NMR (300 MHz, DMSO-d₆): δ 7.65 (t, 1H), 7.45 (d, 1H), 7.30 (dd, 1H), 7.09 (dd, 1H), 4.60 (m, 1H), 1.40 (s, 9H), 1.30 (d, 3H)
IR (cm⁻¹): 3365, 1678

40

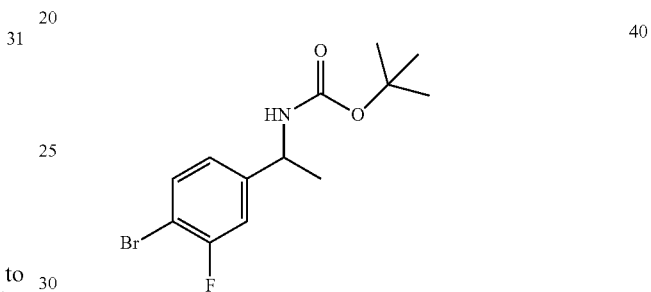

Intermediate 676:
Obtained starting from intermediate 39 according to protocol XVI
¹H NMR (300 MHz, DMSO-d₆): δ 9.80 (d, 1H), 7.70 (dd, 1H), 7.40 (dd, 1H), 7.15 (dd, 1H), 5.00 (quint, 1H), 1.45 (d, 3H)
IR (cm⁻¹): 3267, 1702, 1556, 1205, 1146

676

Intermediate 60b:

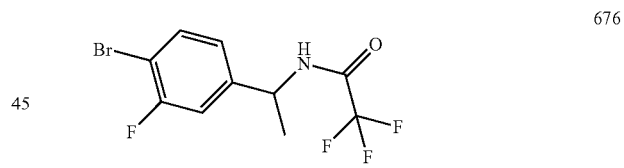

Intermediate 60:

4-Bromo-3-fluoro-5-methylaniline

Obtained by bromation of commercial 3-fluoro-5-methylaniline according to the protocol described for intermediate 67 (protocol VI)

Intermediate 680:

Obtained starting from 4-bromo-3-fluoro-5-methylaniline 60 according to protocol VII $^1$H NMR (300 MHz; CDCl$_3$): δ 7.60 (dd, 1H); 7.50 (dd, 1H); 2.60 (s, 3H); 2.50 (broad s, 3H)

IR (cm$^{-1}$): 1687

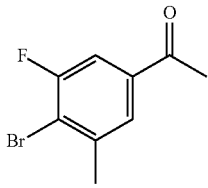

Intermediate 60b:

Obtained starting from intermediate 680 according to protocol XII $^1$H NMR (300 MHz; DMSO-d$_6$): 7.20 (m, 2H), 3.90 (quad, 1H), 2.40 (s, 3H), 1.85 (m, 2H), 1.20 (d, 3H)

IR (cm$^{-1}$): 3650-3030

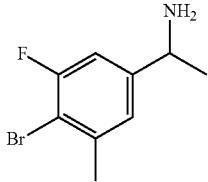

Intermediate 73:

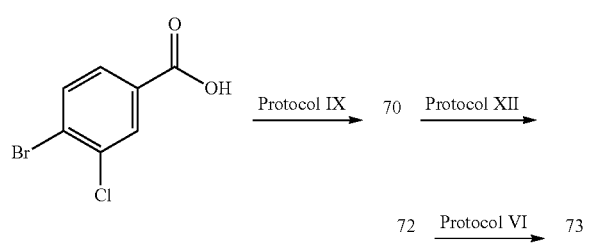

Intermediate 70:

Obtained starting from commercial 4-bromo-3-chlorobenzoic acid and methylmagnesium bromide according to protocol IX $^1$H NMR (400 MHz; CDCl$_3$): δ 8.00 (d, 1H), 7.70 (d, 1H), 7.65 (dd, 1H), 2.60 (s, 3H)

IR (cm$^{-1}$): 1680

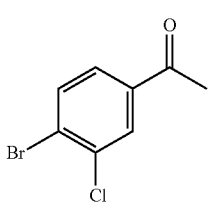

Intermediate 72:

Obtained starting from intermediate 70 according to protocol XII $^1$H NMR (400 MHz; CDCl$_3$): 7.55 (d, 1H), 7.50 (sd, 1H); 7.10 (dd, 1H) 4.10 (quad, 1H); 1.60 (m, 2H); 1.35 (d, 3H)

IR (cm$^{-1}$): 3650, 3000

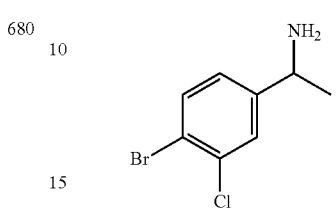

Intermediate 73:

Obtained by protection of intermediate 72 according to the protocol described for intermediate 158 (protocol VI)

$^1$H NMR (300 MHz, CDCl$_3$): δ 7.55 (d, 1H), 7.40 (sd, 1H), 7.05 (dd, 1H), 4.70 (m, 2H), 1.40 (m, 12H)

IR (cm$^{-1}$): 3365, 1681

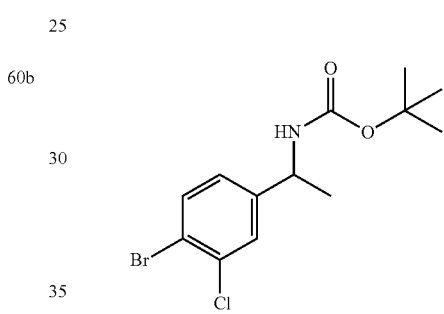

Intermediate 87:

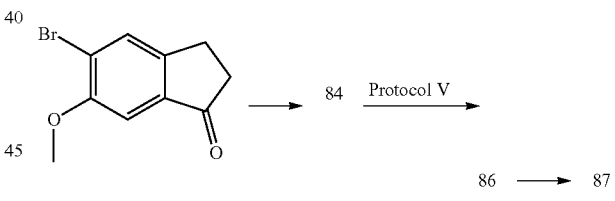

Intermediate 84:

To a mixture of 5-bromo-6-methoxy-2,3-dihydro-1H-inden-1-one (10 g, 41 mmoles) and LiCN (0.27 g, 8.3 mmoles) in THF (105 mL) there is added (Et$_2$O)$_2$POCN (9.5 mL, 62 mmoles). The mixture is stirred at ambient temperature for 5 hours and then concentrated in vacuo. The residue is taken up in AcOEt and washed with water and then with a saturated aqueous NaCl solution. The organic phase is dried over MgSO$_4$ and concentrated in vacuo. The residue is taken up in toluene (100 mL) and then treated with BF$_3$.OEt$_2$ (10.2 mL, 82.96 mmoles) for 5 hours. The mixture is washed with water and then with a saturated aqueous NaCl solution. The organic phase is dried over MgSO$_4$ and then concentrated in vacuo. Intermediate 83 (5-bromo-6-methoxy-3H-indene-1-carbonitrile) so obtained (11.9 g) is used in the following step without additional purification. A solution of 83 (10 g, 41 mmoles) in THF (70 mL) is added in the course of 10 minutes to a mixture of NaBH$_4$ (4.7 g, 124 mmoles) in THF (100 mL), this addition is exothermic (Tmax 48° C.). The mixture is heated at 50° C. for 212 hours and then cooled to about 0° C. A 4N HCl solution (30 mL) is added, followed by Et₂O (250 mL) and water (50 mL). The organic phase is extracted, dried over MgSO₄ and concentrated in vacuo. The residue is purified by chromatography on silica (eluant CH₂Cl₂/cyclohexane 50/50). Intermediate 84 (3 g) is obtained in the form of a yellow solid.

¹H NMR (300 MHz; CDCl₃): δ 7.45 (s, 1H); 6.95 (s, 1H), 4.05 (t, 1H), 3.90 (s, 3H), 3.0-2.9 (2m, 2H), 2.6-2.4 (2m, 2H)

IR (cm⁻¹): 2238

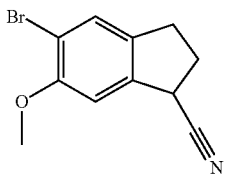

84

Intermediate 86:

Obtained starting from intermediate 84 according to the protocol described for the preparation of intermediate 599 (protocol V)

¹H NMR (300 MHz; DMSO-d₆): δ 13.0-11.0 (m, 1H), 7.40 (s, 1H); 6.95 (s, 1H), 3.80 (s, 3H), 3.0-2.75 (m, 2H), 2.55 (m, 1H), 1.90 (m, 1H), 1.45 (s, 3H).

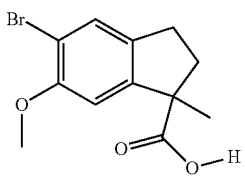

86

Intermediate 87:

To a solution of tBuOH (18.3 mL) and Boc₂O (1.56 g, 7.1 mmoles) which has previously been heated for 2 hours at 90° C. and then returned to ambient temperature there are added in succession intermediate 86 (2.31 g, 8 mmoles), NEt₃ (1.13 mL, 8 mmoles) and PhO₂PON₃ (1.75 mL). The mixture is heated at 90° C. for 3 days and is then concentrated in vacuo. The residue is purified by chromatography on silica (eluant CH₂Cl₂ 100%) to give intermediate 87 (1.5 g).

¹H NMR (300 MHz; DMSO-d₆): δ 7.35 (s, 1H); 7.00 (m, 1H), 6.95 (d, 1H), 3.80 (s, 3H), 2.85-2.65 (m, 2H), 2.45 (m, 1H), 2.00 (m, 1H), 1.40 (s, 3H), 1.30 (broad s, 9H)

IR (cm⁻¹): 3356, 1694

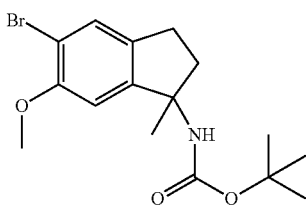

87

Intermediate 116a:

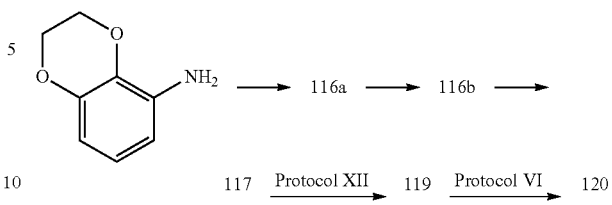

To a solution of 2,3-dihydro-1,4-benzodioxin-5-amine (40 g, 260 mmoles) in DMF (750 mL) cooled to −30° C. there is added dropwise a solution of N-bromosuccinimide (47 g) in DMF (250 mL). The mixture is stirred for 1 hour and is then poured into a water/ice mixture (500 mL/500 g); the precipitate that forms is dissolved in methylene chloride. The organic phase is dried over MgSO₄ and then concentrated in vacuo. Intermediate 116a is obtained in the form of a violet solid (30 g).

¹H NMR (400 MHz, DMSO-d₆): δ 6.78 (d, 1H), 6.20 (d, 1H), 4.25 (m, 4H), 4.90 (s, 2H)

IR (cm⁻¹): 3480

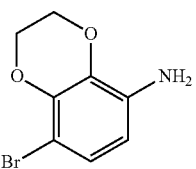

116a

Intermediate 116b:

To a mixture of intermediate 116a (7 g, 30 mmoles) in water (20 mL) there is added HCl_c(20 mL), the resulting mixture is cooled to 0° C., and a solution of NaNO₂ (2.2 g) in water (10 mL) is added. The mixture is stirred for 1½ h at 0° C., and then an aqueous KI solution (5 g in 7 mL) is added and the whole is heated gradually to 90° C. After return to ambient temperature, the mixture is poured into ice and the precipitate that forms is dissolved in AcOEt. The organic phase is washed with a 0.1N sodium thiosulphate solution, dried over MgSO₄ and then evaporated in vacuo. Intermediate 116b is obtained in the form of a brown solid (7 g) (which can be chromatographed on silica gel (cyclohexane/methylene chloride 80/20 to 0/100)).

¹H NMR (400 MHz, DMSO-d₆): δ 7.25 (d, 1H), 6.95 (d, 1H), 4.40 (s, 4H)

IR (cm⁻¹): 1734

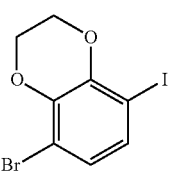

116b

Intermediate 117:

To a solution, degassed with nitrogen, of intermediate 116b (15 g, 44 mmoles) in DMF (500 mL) there is added tri-butyl-(1-ethoxyvinyl)-tin (15 mL, 44 mmoles). The solution is brought to 70° C., and then PdCl₂(PPh₃)₂(3.7 g) is added. The mixture is heated at 70° C. until the starting intermediate has disappeared. After return to ambient temperature, the reaction mixture is treated in succession with 10 g of KF in water (1 L) and with ethyl ether. The salts are filtered off, and the organic phase is concentrated in vacuo. The residue so obtained is dissolved in THF and stirred for 1 hour in the presence of 30 mL of a 1N aqueous HCl solution. The mixture is then decanted in the presence of 1 L of Et₂O, and the organic phase is dried over MgSO₄. Evaporation under reduced pressure yields an oil, which is chromatographed on silica gel using a cyclohexane/methylene chloride elution gradient (50/50 to 20/80). Intermediate 117 is obtained in the form of an orange solid (4.6 g).

¹H NMR (400 MHz, DMSO-d₆): δ 7.2-7.1 (2d, 2H), 4.40 (s, 4H), 2.55 (s, 3H); 7.25 (d, 1H), 6.95 (d, 1H), 4.40 (s, 4H)

IR (cm⁻¹): 1664

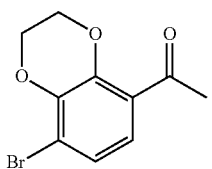

117

Intermediate 119:

Obtained starting from intermediate 117 according to protocol XII

¹H NMR (400 MHz; DMSO-d₆): 7.08 (d, 1H), 6.95 (d, 1H), 4.30 (m, 4H), 4.20 (quad, 1H), 1.20 (d, 3H)

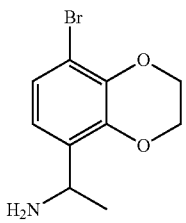

119

Intermediate 120:

Obtained by protection of intermediate 119 according to the protocol described for intermediate 158 (protocol VI)

¹H NMR (400 MHz, DMSO-d₆): δ 7.33 (d, 1H), 7.09 (d, 1H), 6.78 (d, 1H), 4.82 (m, 1H), 4.30 (m, 4H), 1.35 (s, 9H), 1.20 (d, 3H)

IR (cm⁻¹): 3368, 1684

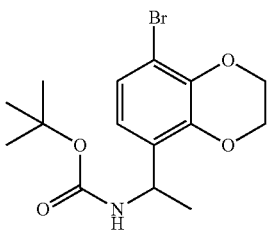

120

Intermediate 370:

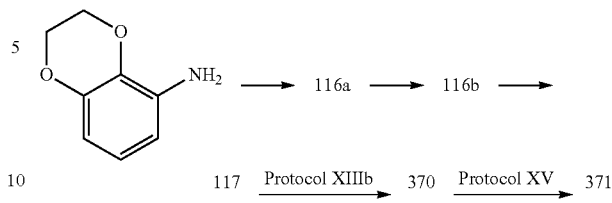

Obtained starting from intermediate 117 and (S)-(−)-2-methyl-2-propanesulphinamide according to protocol XIIIb ¹H NMR (400 MHz, DMSO-d₆): δ 7.12 (d, 1H), 6.95 (d, 1H), 5.59 (d, 1H), 4.63 (m, 1H), 4.32 (m, 4H), 1.33 (d, 3H), 1.10 (s, 9H)

IR (cm⁻¹): 3500, 3000, 1056

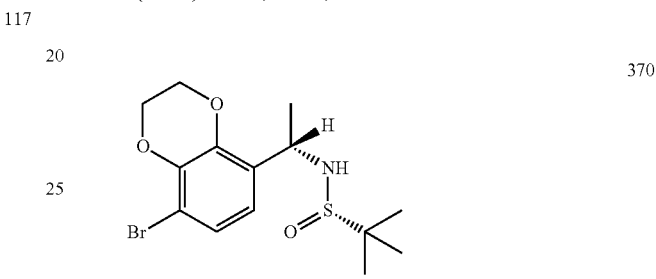

370

Intermediate 371:
Obtained starting from intermediate 370 according to protocol XV ¹H NMR (400 MHz, DMSO-d6): δ 7.35 (d, 1H), 7.09 (d, 2H), 6.79 (d, 2H), 4.85 (m, 1H), 4.33 (m, 4H), 1.37 (s, 9H), 1.21 (d, 3H)

IR (cm⁻¹): 3260, 1695, 1676

Enantiomeric excess >99%

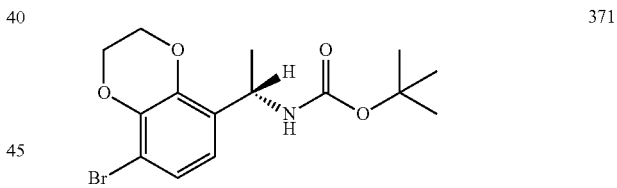

371

Intermediate 349b:

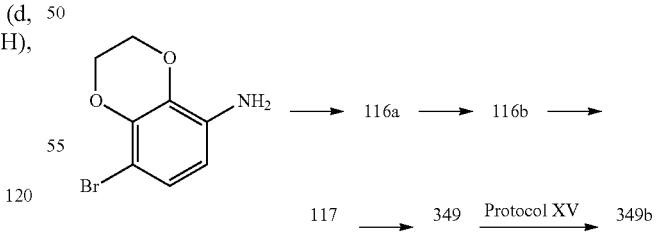

Intermediate 349:
To a solution of intermediate 117 (10.7 g, 41 mmoles) in 160 mL of THF there are added in succession Ti(OEt)₄ (30 mL, 143 mmoles) and then (R)-(+)-2-methyl-2-propanesulphinamide (5 g, 41 mmoles). The mixture is heated for 48 hours at 55° C. The mixture, cooled to −40° C., is transferred by cannulation to a suspension of NaBH₄ (3.1 g; 82 mmoles) in 46 mL of THF. The reaction mixture, at ambient temperature, is treated carefully with methanol and then diluted with 300 mL of ethyl acetate and 700 mL of a saturated aqueous NaCl solution. The resulting mixture is filtered over Celite®, which is rinsed with THF and AcOEt. The filtrate is decanted, and the organic phase is dried by passage over MgSO$_4$. Evaporation under reduced pressure yields a white solid, which is purified on silica using an AcOEt/methylene chloride elution gradient 0/100 to 40/60. The diastereoisomer 349 (7 g) is isolated in the form of a white solid.

$^1$H NMR (400 MHz; DMSO-d$_6$): δ 7.12 (d, 1H), 6.95 (d, 1H), 5.59 (d, 1H), 4.63 (m, 1H), 4.32 (m, 4H), 1.33 (d, 3H); 1.10 (s, 9H)

IR (cm$^{-1}$): 3265, 1057

GC-EI (70 eV): M$^+$=361

Diastereoisomeric purity: de>99%

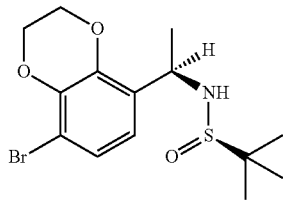

Intermediate 349b:

Obtained starting from intermediate 349 according to protocol XV $^1$H NMR (400 MHz, DMSO-d$_6$): δ 7.33 (broad d, 1H), 7.08 (d, 1H), 6.78 (d, 1H), 4.83 (m, 1H), 4.32 (broad m, 4H), 1.35 (broad s, 9H), 1.21 (d, 3H)

Enantiomeric excess >99%

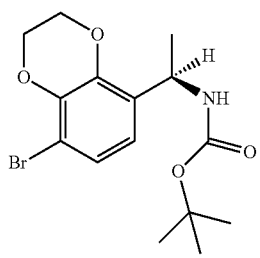

Intermediate 135:

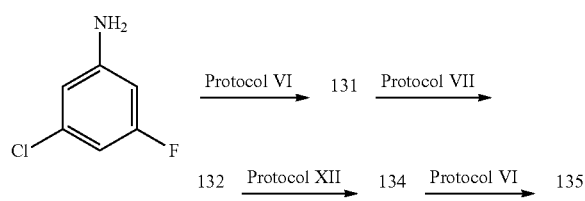

Intermediate 131

4-Bromo-3-chloro-5-fluoroaniline

Obtained by bromation of commercial 3-chloro-5-fluoroaniline according to the protocol described for intermediate 67 (protocol VI)

Intermediate 132:

Obtained starting from intermediate 131 according to protocol VII $^1$H NMR (300 MHz, CDCl$_3$): δ 7.85 (s, 1H), 7.60 (d, 1H), 2.60 (s, 3H)

IR (cm$^{-1}$): 1692, 1206.

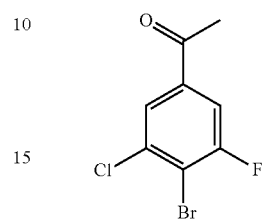

Intermediate 134:

Obtained starting from intermediate 132 according to protocol XII $^1$H NMR (300 MHz; CDCl$_3$): 7.30 (s, 1H), 7.05 (d, 1H) 4.10 (quad, 1H); 1.35 (d, 3H)

IR (cm$^{-1}$): 3600, 2500

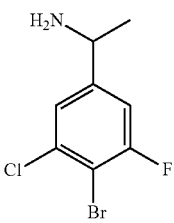

Intermediate 135:

Obtained by protection of intermediate 134 according to the protocol described for intermediate 158 (protocol VI)

$^1$H NMR (400 MHz, CDCl$_3$): δ 7.20 (s, 1H), 7.00 (d, 1H), 4.75 (broad s, 1H), 4.70 (m, 1H), 1.40 (s and d, 12H)

IR (cm$^{-1}$): 3367, 1682, 1163

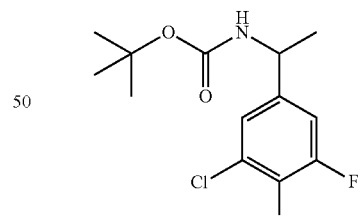

Intermediate 174:

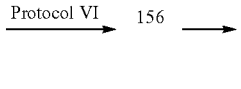

Intermediate 173:
Intermediate 173 was prepared by reduction with BH$_3$.THF of intermediate 156 (4-bromo-3,5-difluorobenzonitrile).
$^1$H NMR (300 MHz, DMSO-d$_6$): δ 8.60 (m, 3H), 7.50 (d, 2H), 4.05 (s, 2H)
IR (cm$^{-1}$): 3450-2400.

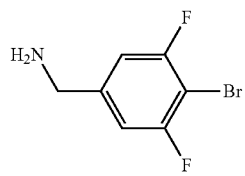

Intermediate 174:
Obtained by protection of intermediate 173 according to the protocol described for intermediate 158 (protocol VI)
$^1$H NMR (300 MHz, DMSO-d$_6$): δ 7.50 (t, 1H), 7.10 (d, 2H), 4.10 (d, 2H), 1.40 (s, 9H)
IR (cm$^{-1}$): 3323, 1681

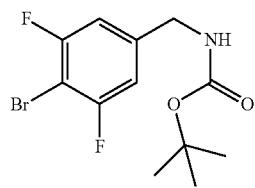

Intermediate 112:

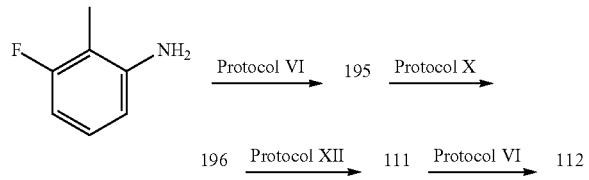

Intermediate 195:

1-Bromo-2-fluoro-4-iodo-3-methylbenzene

Obtained starting from commercial 3-fluoro-2-methylaniline according to the protocol described for intermediate 155 (protocol VI)

Intermediate 196:
Obtained starting from intermediate 195 according to protocol X
$^1$H NMR (400 MHz, CDCl$_3$): δ 7.45 (dd, 1H), 7.30 (d, 1H), 2.60 (s, 3H), 1.40 (s, 3H)
IR (cm$^{-1}$): 1684

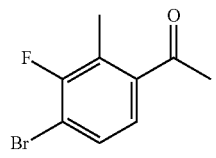

Intermediate 111
Obtained starting from intermediate 196 according to protocol XII
$^1$H NMR (400 MHz; CDCl$_3$): 7.40 (dd, 1H), 7.20 (d, 1H); 4.30 (quad, 1H); 2.30 (s, 3H), 1.60 (m, 2H); 1.30 (d, 3H)
IR (cm$^{-1}$): 3750, 2900

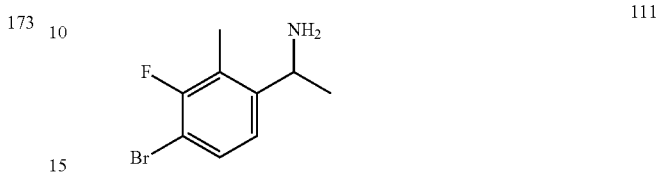

Intermediate 112:
Obtained by protection of intermediate 111 according to the protocol described for intermediate 158 (protocol VI)
$^1$H NMR (300 MHz, DMSO-d$_6$): δ 7.50 (dd, 1H), 7.10 (d, 1H), 4.75 (quint, 1H), 2.25 (m, 3H), 1.35 (m, 9H), 1.25 (d, 3H)
IR (cm$^{-1}$): 3301, 1690-1664

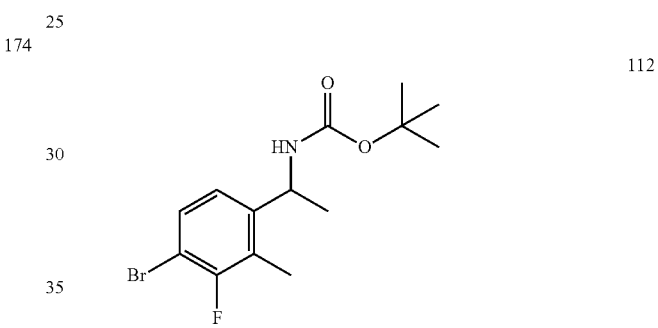

Intermediate 187:

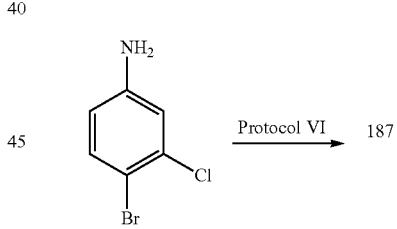

Obtained starting from commercial 4-bromo-3-chloroaniline according to protocol VI
$^1$H NMR (400 MHz; DMSO-d$_6$): δ 7.70 (d, 1H); 7.50 (d, 1H); 7.30 (s, 1H); 7.20 (dd, 1H); 1.45 (s, 6H); 1.30 (s, 9H)
IR (cm$^{-1}$): 3264-2972; 1698.

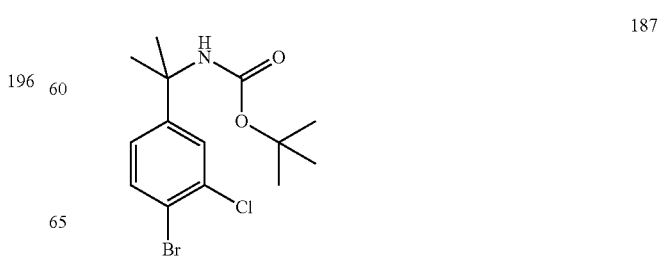

Intermediate 193:

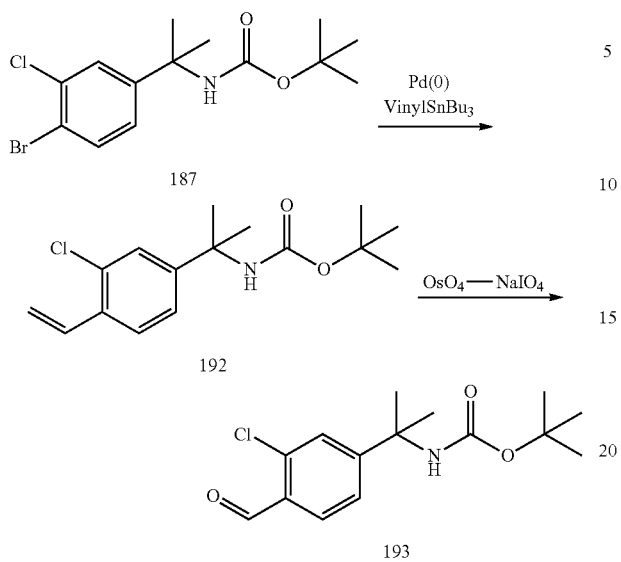

Intermediate 192:
To a solution (degassed with nitrogen) of intermediate 187 (12 g, 34 mmoles) in DMF (240 mL) there are added tri-butyl-vinyltin (10 mL, 34 mmoles) and Pd(PPh$_3$)$_4$(2.47 g). The reaction mixture is heated at 100° C. for 20 h. After return to ambient temperature, the mixture is treated with a 10% aqueous KF solution, the resulting salts are filtered off, and the filtrate is extracted with ethyl acetate. The organic phase is washed with a saturated aqueous NaCl solution, dried over MgSO$_4$ and concentrated in vacuo. The residue is chromatographed on silica gel (eluant CH$_2$Cl$_2$ (100%)). Intermediate 192 (4.7 g) is obtained in the form of a yellow solid.
$^1$H NMR (400 MHz, DMSO-d$_6$): δ 7.60 (d, 1H), 7.36 (d, 1H), 7.30 (dd, 1H), 6.99 (dd, 1H), 6.85 (m, 1H), 5.82 (d, 1H), 5.40 (d, 1H), 1.52 (s, 6H), 1.31 (s, 9H)
IR (cm$^{-1}$): 3327, 1689

Intermediate 193:
To a mixture of intermediate 192 (4.7 g, 15 mmoles) in dioxane (95 mL) and water (5 mL) there are added OsO$_4$ (2.5% by weight in butanol) (3.2 g), 2,6-lutidine (3.7 g, 31 mmoles) and NaIO$_4$ (13.6 g, 63 mmoles). The reaction mixture is stirred for 1 h at ambient temperature. After addition of AcOEt and of a saturated NaCl solution, the solid is filtered off and the filtrate is extracted with ethyl acetate. The organic phase is washed with a saturated NaCl solution, dried over MgSO$_4$ and concentrated in vacuo. The residue is chromatographed on silica gel using a CH$_2$Cl$_2$ eluant (100). Intermediate 193 (4.2 g) is obtained in the form of a colourless oil.
$^1$H NMR (400 MHz, DMSO-d$_6$): δ 10.40 (s, 1H), 7.81 (d, 1H), 7.50 (m, 2H), 7.40 (m, 1H), 1.50 (s, 6H), 1.35 (m, 9H)
IR (cm$^{-1}$): 3350, 1688193

Intermediate 200:

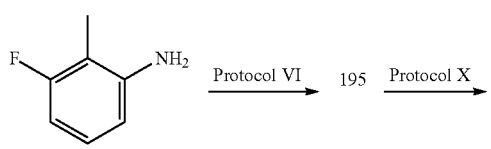

Intermediate 195:
1-Bromo-2-fluoro-4-iodo-3-methylbenzene

Obtained starting from commercial 3-fluoro-2-methylaniline according to the protocol described for intermediate 155 (protocol VI)

Intermediate 196:
Obtained starting from intermediate 195 according to protocol X
$^1$H NMR (400 MHz, CDCl$_3$): δ 7.45 (dd, 1H), 7.30 (d, 1H), 2.60 (s, 3H), 1.40 (s, 3H)
IR (cm$^{-1}$): 1684

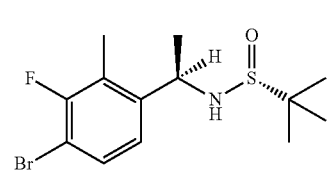

Intermediate 197:
Obtained by reaction of intermediate 196 and (R)-(+)-2-methyl-2-propanesulphinamide according to protocol XIIIb
$^1$H NMR (400 MHz, CDCl$_3$): δ 7.40 (m, 1H), 7.05 (d, 1H), 4.75 (m, 1H), 2.30 (d, 3H), 1.45 (d, 3H), 1.20 (s, 9H), 3.30 (m, 1H)
IR (cm$^{-1}$): 3378, 3290, 1620

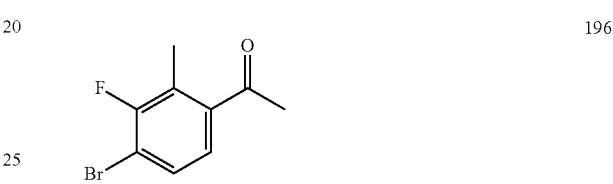

Intermediate 200:
Obtained starting from intermediate 197 according to protocol XV
$^1$H NMR (400 MHz, DMSO-d$_6$): δ 7.50 (2m, 2H), 7.10 (d, 1H), 4.75 (m, 1H), 2.25 (d, 3H), 1.35 (s, 9H), 1.25 (d, 3H)
IR (cm$^{-1}$): 3373, 1681
Enantiomeric excess >99%

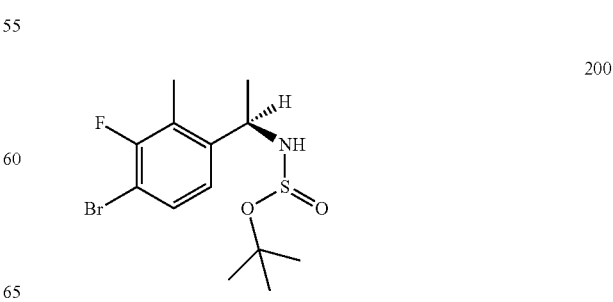

Intermediate 211:

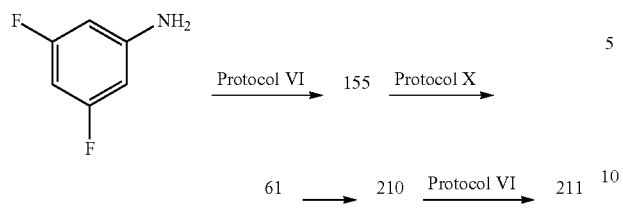

To a mixture of TiOiPr₄ (16 mL, 54 mmoles) in ethanol (70 mL) there are added NEt₃ (7.7 mL, 55.3 mmoles), methylamine hydrochloride (3.7 g, 54.8 mmoles) and intermediate 61 (7 g, 27.8 mmoles). The mixture is stirred at ambient temperature for 40 hours, and then NaBH₄ (1.56 g, 41.4 mmoles) is added in portions. After 20 hours' stirring, the reaction mixture is poured carefully into a 2N aqueous NH₄OH solution, and the resulting precipitate is filtered off and rinsed with methylene chloride. The filtrate is decanted, the organic phase is washed with a 2N aqueous HCl solution, and the acidic phase is brought to basic pH by means of a 20% sodium hydroxide solution. The product is extracted with methylene chloride, the organic phase is dried over MgSO₄, and evaporation under reduced pressure yields an oil, which is purified on silica gel using a methylene chloride/ethanol elution gradient 100/0 to 95/5. Intermediate 210 is isolated in the form of an oil (1.5 g).

¹H NMR (400 MHz; DMSO-d₆): δ 7.25 (d, 2H), 3.6 (q, 1H), 2.5-2.15 (m, 1H), 2.10 (s, 3H), 1.20 (d, 3H)

IR (cm⁻¹): 3280-3360

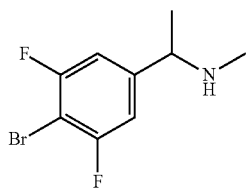

210

Intermediate 211:

Obtained by protection of intermediate 210 according to the protocol described for intermediate 158 (protocol VI)

¹H NMR (400 MHz, DMSO-d₆): δ 7.12 (m, 2H), 5.20 (broad s, 1H), 2.63 (s, 3H), 1.45 (d, 3H), 1.39 (broad s, 9H)

IR (cm⁻¹): 1686

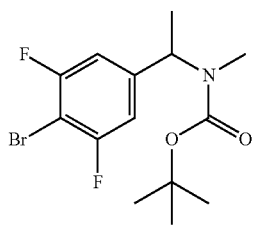

211

Intermediate 217:

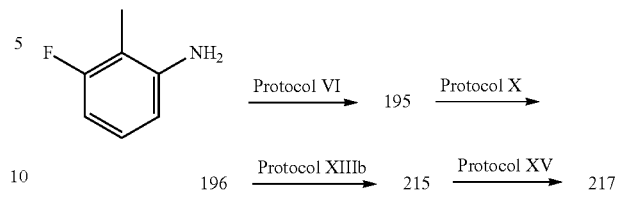

Intermediate 195:

1-Bromo-2-fluoro-4-iodo-3-methylbenzene

Obtained starting from commercial 3-fluoro-2-methylaniline according to the protocol described for intermediate 155 (protocol VI)

Intermediate 196:

Obtained starting from intermediate 195 according to protocol X

¹H NMR (400 MHz, CDCl₃): δ 7.45 (dd, 1H), 7.30 (d, 1H), 2.60 (s, 3H), 1.40 (s, 3H)

IR (cm⁻¹): 1684

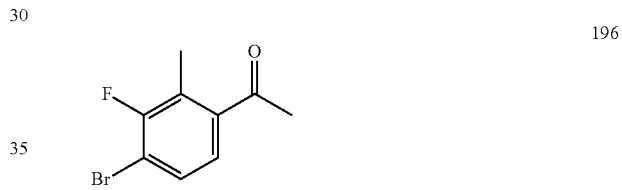

196

Intermediate 215:

Obtained by reaction of intermediate 196 and (S)-(−)-2-methyl-2-propanesulphinamide according to protocol XIIIb ¹H NMR (300 MHz, DMSO-d₆): δ 7.50 (dd, 1H), 7.25 (d, 1H), 5.70 (d, 1H), 4.55 (quint, 1H), 2.25 (d, 3H), 1.35 (d, 3H), 1.10 (s, 9H)

IR (cm⁻¹): 3353, 3298, 1121

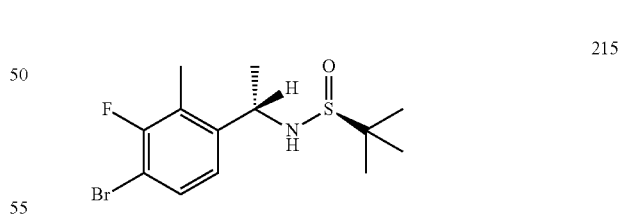

215

Intermediate 217:

Obtained starting from intermediate 215 according to protocol XV

¹H NMR (400 MHz, DMSO-d₆): δ 7.50 (t and m, 2H), 7.10 (d, 1H), 4.75 (m, 1H), 2.25 (d, 3H), 1.35 (s, 9H), 1.25 (d, 3H)

IR (cm⁻¹): 3373, 1681

Enantiomeric excess >99%

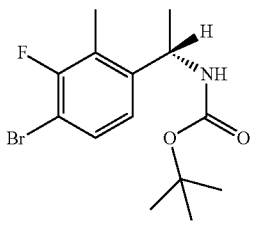

Intermediates 615a and 615b:

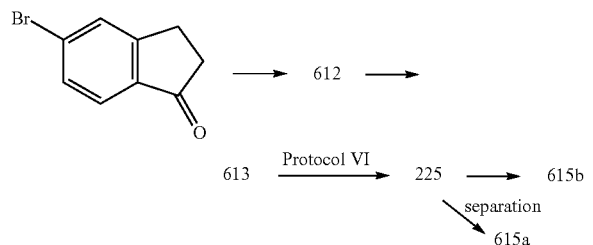

Intermediate 612:

To a solution of commercial 5-bromo-2,3-dihydro-1H-inden-1-one (5 g, 23 mmoles) in ethanol (47 mL) there are added in succession hydroxylamine hydrochloride (3.1 g, 44 mmoles) and pyridine (9.5 mL). The reaction mixture is stirred for 8 hours at 80° C. The pyridine is evaporated off in vacuo, and the residue is taken up in water and then extracted with methylene chloride. After drying of the organic phase over MgSO$_4$ and concentration, intermediate 612 is obtained in the form of a solid (5.13 g), which is used without additional treatment in the following step.

$^1$H NMR (300 MHz; DMSO-d$_6$): δ 11.0 (s, 1H), 7.60 (s, 1H), 7.45 (2d, 2H), 3.0-2.8 (2m, 4H)

IR (cm$^{-1}$): 3100

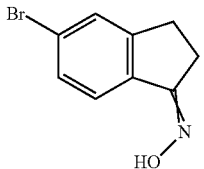

Intermediate 613:

At 0° C., a mixture of 612 (0.5 g, 2.2 mmoles) and MoO$_3$ (0.42 g, 2.9 mmoles) in methanol (22 mL) is treated carefully with NaBH$_4$ (0.84 g, 2.2 mmoles), the temperature being maintained below 36° C. The reaction mixture is stirred for 1 hour at 0° C. and then at ambient temperature for 18 hours before being concentrated in vacuo. The residue is taken up carefully in a 1N aqueous HCl solution and ethyl acetate, the salts are filtered off and the filtrate is decanted. The aqueous phase is rendered basic and then extracted with methylene chloride. After drying over MgSO$_4$ and concentration in vacuo, intermediate 613 is obtained (0.28 g).

$^1$H NMR (300 MHz; DMSO-d$_6$): δ 7.35 (s, 1H), 7.35 (d, 1H), 4.15 (t, 1H), 2.85-2.7 (m, 2H), 2.3-1.55 (m, 2H), 2.00 (m, 2H)

IR (cm$^{-1}$): 3400-3300

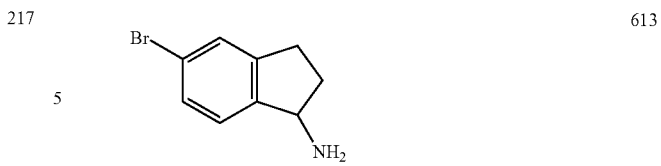

Intermediate 225:

Obtained by protection of intermediate 613 according to the protocol described for intermediate 158 (protocol VI)

$^1$H NMR (400 MHz, CDCl$_3$): δ 7.36 (broad s, 1H), 7.33 (broad d, 1H), 7.19 (d, 1H), 5.12 (quad, 1H), 4.69 (m, 1H), 2.93 (ddd, 1H), 2.82 (ddd, 1H), 2.57 (m, 1H), 1.79 (m, 1H), 1.48 (s, 9H)

IR (cm$^{-1}$): 3316, 1682

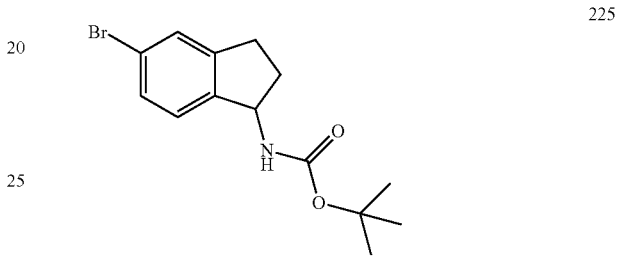

Intermediate 225 (18 g) was purified by high pressure chromatography on a chiral support (ChiralPak T101 column, eluant iPrOH/CH$_3$CN 10/90, detection: 275 nm) to give enantiomers 615a (9.8 g) and 615b (7.4 g).

Intermediate 615a: α$_D$ (589 nM)=76.78 (c=0.011 g/mL, MeOH) at 20° C.

Intermediate 615b: α$_D$ (589 nM)=−77.52 (c=0.011 g/mL, MeOH) at 20° C.

Intermediate 245:

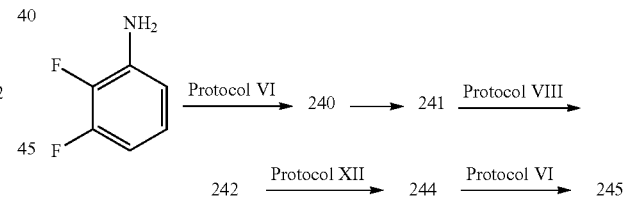

Intermediate 240:

4-Bromo-2,3-difluorobenzonitrile

Obtained starting from commercial 2,3-difluoroaniline according to the protocol described for the preparation of intermediate 156 (protocol VI)

Intermediate 241:

Obtained by treatment of intermediate 240 (0.5 g, 2.3 mmoles) in methanol (12 mL) at 0° C. in the presence of sodium methoxide (0.25 g, 4.6 mmoles).

The reaction mixture is stirred for 72 hours at ambient temperature and then poured into water. The precipitate collected on a frit is dried in vacuo. Intermediate 241 (0.3 g) is obtained.

$^1$H NMR (400 MHz, CDCl$_3$): δ 7.30 (dd, 1H), 7.22 (d, 1H), 4.16 (s, 3H)

IR (cm$^{-1}$): 3091, 2233, 1674 GC-EI (70 eV): M+.=229

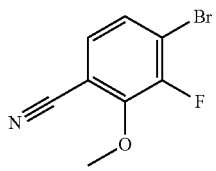

241

Intermediate 242:

Obtained starting from intermediate 241 according to protocol VIII $^1$H NMR (400 MHz; DMSO-d$_6$): δ 7.52 (dd, 1H), 7.39 (dd, 1H), 3.97 (s, 3H), 2.55 (s, 3H)

IR (cm$^{-1}$): 1681

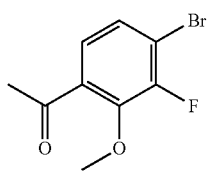

242

Intermediate 244:

Obtained starting from intermediate 242 according to protocol XII $^1$H NMR (400 MHz; DMSO-d$_6$): 8.45 (s, 3H), 7.55 (m, 1H), 7.35 (d, 1H), 4.60 (quad, 1H), 3.95 (s, 3H), 1.50 (d, 3H)

IR (cm$^{-1}$): 3170-2400

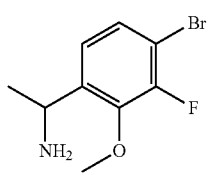

244

Intermediate 245:

Obtained by protection of intermediate 244 according to the protocol described for intermediate 158 (protocol VI)

$^1$H NMR (300 MHz, DMSO-d$_6$): δ 7.47 (broad d, 1H), 7.41 (dd, 1H), 7.10 (d, 1H), 4.88 (m, 1H), 3.90 (s, 3H), 1.36 (s, 9H), 1.25 (d, 3H)

19F NMR: −125

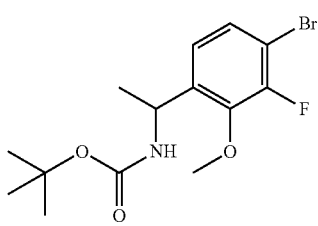

245

Intermediate 255:

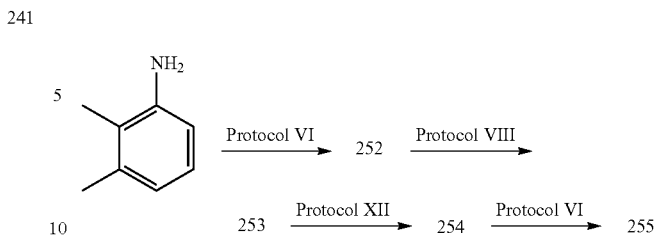

Intermediate 252:

Obtained starting from commercial 2,3-dimethylaniline according to the procedure described for intermediate 156 (protocol VI) Intermediate 253:

Obtained starting from intermediate 252 according to protocol VIII $^1$H NMR (300 MHz; DMSO-d$_6$): δ 7.55 (d, 1H), 7.40 (d, 1H), 2.55 (s, 3H), 2.40 (s, 3H), 2.30 (s, 3H)

IR (cm$^{-1}$): 1684

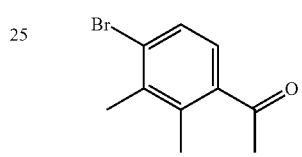

253

Intermediate 254:

Obtained starting from intermediate 253 according to protocol XII $^1$H NMR (400 MHz; DMSO-d$_6$): 8.45 (s, 3H), 7.55 (d, 1H), 7.35 (d, 1H), 4.60 (quad, 1H), 2.4-2.3 (2s, 6H), 1.45 (d, 3H)

IR (cm$^{-1}$): 3200, 2430

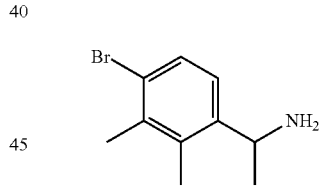

254

Intermediate 255:

Obtained by protection of intermediate 254 according to the protocol described for intermediate 158 (protocol VI)

$^1$H NMR (300 MHz, DMSO-d$_6$): δ 7.45 (dl, 1H), 7.41 (d, 1H), 7.10 (d, 1H), 4.81 (m, 1H), 2.35-2.28 (2s, 6H), 1.35 (s, 9H), 1.20 (d, 3H)

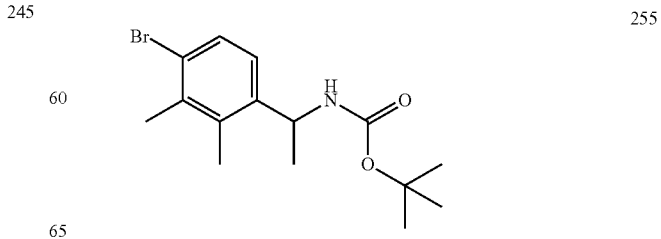

255

Intermediate 310:

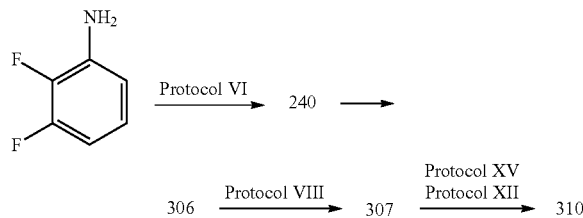

Intermediate 240:
4-Bromo-2,3-difluorobenzonitrile
Obtained starting from commercial 2,3-difluoroaniline according to the protocol described for the preparation of intermediate 156 (protocol VI)

Intermediate 306:

4-Bromo-2-ethoxy-3-fluorobenzonitrile

Obtained by treatment of intermediate 240 (0.5 g, 2.3 mmoles) in ethanol (12 mL) at 0° C. in the presence of sodium ethoxide (0.31 g, 4.6 mmoles).
The reaction mixture is stirred for 72 hours at ambient temperature and then poured into water. The precipitate collected on a frit is dried in vacuo.
$^1$H NMR (400 MHz, DMSO-d6): δ 7.60 (s, 2H), 4.35 (q, 2H), 1.35 (t, 3H)
IR (cm$^{-1}$): 3085, 2237

Intermediate 307:
Obtained starting from intermediate 306 according to protocol VIII
$^1$H NMR (300 MHz; CDCl$_3$): δ 7.33 (d, 1H), 7.28 (dd, 1H), 4.26 (quad, 2H), 2.62 (s, 3H), 1.45 (t, 3H)
IR (cm$^{-1}$): 1685

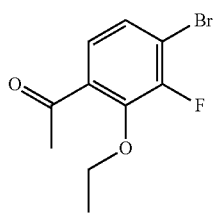

307

Intermediate 310:
Obtained starting from intermediate 307 according to protocol XV, which intermediate 307 is converted beforehand into the amine (not isolated) according to protocol XII
$^1$H NMR (400 MHz, DMSO-d$_6$): δ 7.45 (d, 1H), 7.40 (dd, 1H), 7.10 (d, 1H), 4.90 (m, 1H), 4.10 (m, 2H), 1.35 (m, 12H), 1.20 (d, 3H)
IR (cm$^{-1}$): 3480-3280, 1694

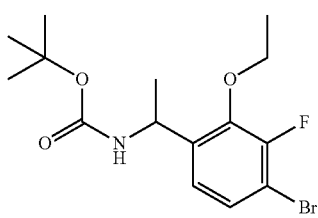

310

Intermediate 540:

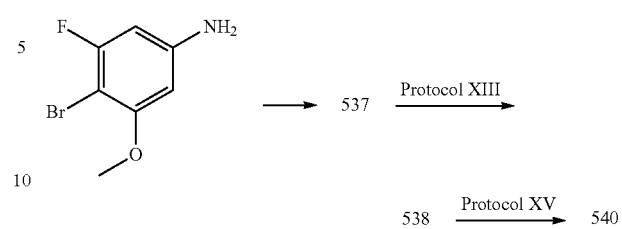

Intermediate 537:
Obtained starting from 4-bromo-3-fluoro-5-methoxyaniline, prepared by bromation of 3-fluoro-5-methoxyaniline, according to the protocol described for intermediate 117
$^1$H NMR (300 MHz, DMSO-d$_6$): δ 7.55 (dd, 1H), 7.40 (d, 1H), 4.00 (s, 3H), 2.60 (s, 3H)
IR (cm$^{-1}$): 1682, 1229

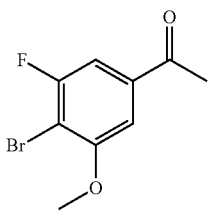

537

Intermediate 538:
Obtained by reaction of intermediate 537 and (R)-(+)-2-methyl-2-propanesulphinamide according to protocol XIII
$^1$H NMR (400 MHz, DMSO-d$_6$): δ 7.05-7.00 (2m, 2H), 5.75 (d, 1H), 4.38 (m, 1H), 3.88 (s, 3H), 1.39 (d, 3H), 1.12 (s, 9H)
IR (cm$^{-1}$): 3265, 1058

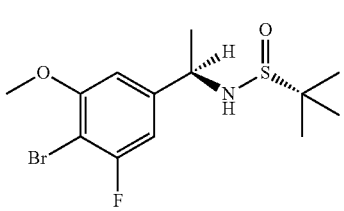

538

Intermediate 540:
Obtained starting from intermediate 538 according to protocol XV
$^1$H NMR (400 MHz, DMSO-d$_6$): δ 7.40 (d, 1H), 6.92 (broad s, 1H), 6.88 (dd, 1H), 4.6 (m, 1H), 3.87 (s, 3H), 1.35 (broad s, 9H), 1.3 (d, 3H)
Optical purity: >99%

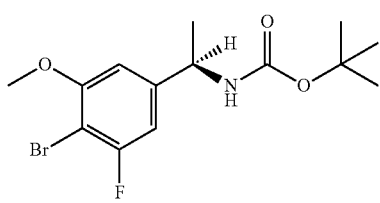

540

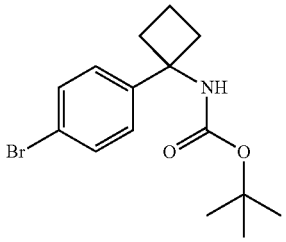

608

Intermediate 589:

Obtained by protection of commercial 1-(4-bromophenyl) ethanamine according to the protocol described for intermediate 158 (protocol VI)

$^1$H NMR (300 MHz, DMSO-d$_6$): δ 7.50 (d, 2H), 7.40 (d, 1H), 7.25 (d, 2H), 4.60 (m, 1H), 1.40 (s, 9H), 1330 (d, 3H)

IR (cm$^{-1}$): 3373, 1681

Intermediate 623:

Obtained starting from (4-bromophenyl)acetonitrile according to protocol V in the presence of 1-bromo-2-(2-bromoethoxy)ethane in the first step $^1$H NMR (300 MHz; DMSO-d$_6$): δ 7.50 (d, 2H); 7.30 (d, 2H); 3.75-3.55 (m, 4H); 2.20 (m, 2H); 1.85 (m, 2H); 1.30 (broad s, 9H)

IR (cm$^{-1}$): 3255-3135, 1692

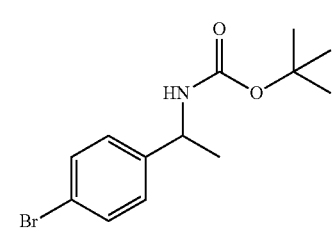

589

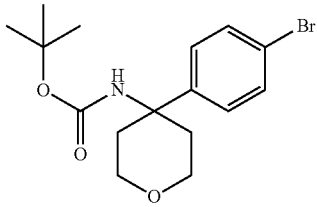

623

Intermediate 633:

Obtained starting from commercial 5-bromoindene-1-one according to the procedure used to prepare intermediate 87

$^1$H NMR (400 MHz, CDCl$_3$): δ 7.31 (d and s, 1H), 7.12 (d, 1H), 4.80 (s, 1H), 3.00 (m, 1H), 2.85 (m, 1H), 2.60 (m, 1H), 2.12 (m, 1H), 1.50 (s, 3H), 1.38 (s, 9H)

IR (cm$^{-1}$): 3347, 1694

Intermediate 594:

Obtained by protection of commercial (1S)-1-(4-bromophenyl)ethanamine according to the protocol described for intermediate 158 (protocol VI)

$^1$H NMR (300 MHz, DMSO-d$_6$): δ 7.50 (d, 2H), 7.40 (d, 1H), 7.25 (d, 2H), 4.60 (m, 1H), 1.40 (s, 9H), 1.30 (d, 3H)

IR (cm$^{-1}$): 3373, 1681

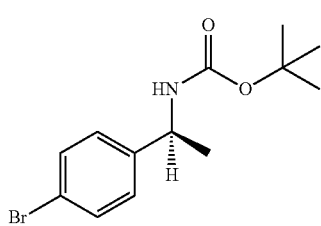

594

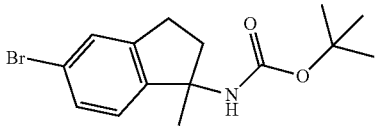

633

Intermediate 645:

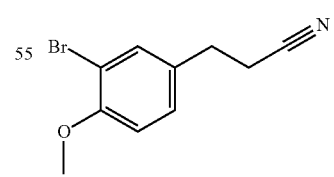

Intermediate 608:

Obtained starting from (4-bromophenyl)acetonitrile according to protocol V in the presence of 1,3-dibromopropane in the first step $^1$H NMR (300 MHz; DMSO-d$_6$): δ 7.65 (m, 1H); 7.50-7.30 (dd, 4H); 2.35 (m, 4H); 2.00-1.75 (m, 2H); 1.30 (m, 9H)

IR (cm$^{-1}$): 3346, 1683

Intermediate 81:

Obtained starting from commercial 3-(3-bromo-4-methoxyphenyl)propanenitrile according to the protocol described for obtaining intermediate 599 (protocol V)

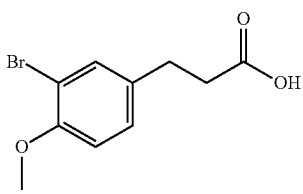

81

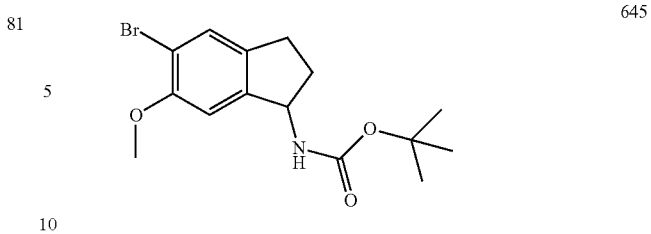

645

Intermediate 684:

Intermediate 82:

Intermediate 81 is stirred in the presence of $PCl_5$ (44 g, 211 mmoles) for 2½ hours, and then the mixture is carefully concentrated in vacuo. The residue, diluted in methylene chloride (960 mL) and cooled to 0° C., is treated with $AlCl_3$ (28 g, 211 mmoles). The reaction mixture is stirred for 2 hours at 15° C. and then poured carefully into ice. The mixture is extracted with AcOEt, and the organic phase is washed in succession with water, with a 4N aqueous NaOH solution, again with water and with an HCl solution. The organic phase is dried over $MgSO_4$ and concentrated in vacuo. The residue is solidified in isopropyl ether. Intermediate 82 (39 g) is obtained in the form of a solid.

$^1$H NMR (300 MHz; $CDCl_3$): δ 7.70 (s, 1H); 7.20 (s, 1H); 3.92 (s, 3H); 3.06 (t, 2H); 2.70 (t, 2H).

IR ($cm^{-1}$): 1698

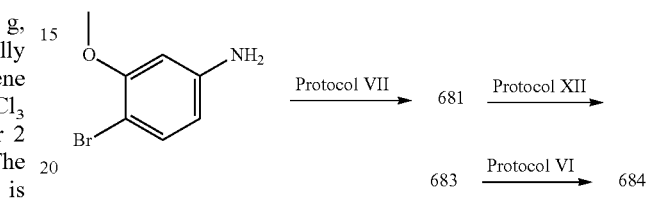

The synthesis of intermediate 681 is described in protocol VII Intermediate 683:

Obtained starting from intermediate 681 according to protocol XII $^1$H NMR (300 MHz; $CDCl_3$): 7.40 (d, 1H), 7.15 (d, 1H); 6.90 (dd, 1H), 4.00 (quad, 1H); 3.85 (s, 3H), 1.90 (m, 2H), 1.20 (d, 3H)

IR ($cm^{-1}$): 3750, 3000

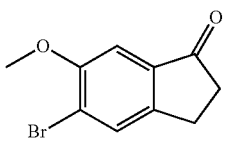

82

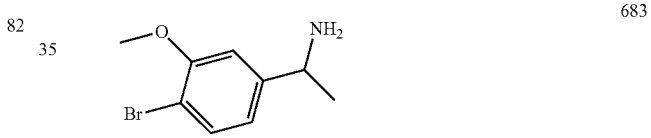

683

Intermediate 644:

Obtained starting from intermediate 82 according to protocol XIIb $^1$H NMR (300 MHz; $CDCl_3$): 7.35 (s, 1H); 6.90 (s, 1H), 4.30 (t, 1H); 3.90 (s, 3H), 2.85-2.7 (2m, 2H), 2.50 (m, 1H), 1.70 (m, 1H), 1.50 (m, 2H)

Intermediate 684:

Obtained by protection of intermediate 683 according to the protocol described for intermediate 158 (protocol VI)

$^1$H NMR (400 MHz, DMSO-$d_6$): δ 7.50 (d, 1H), 7.40 (d, 1H), 7.05 (d, 1H), 6.80 (dd, 1H), 4.60 (quint, 1H), 3.80 (s, 3H), 1.38 (m, 9H), 1.30 (d, 3H)

IR ($cm^{-1}$): 3286, 1690

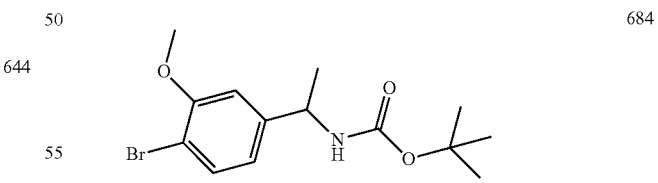

684

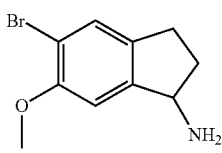

644

Intermediate 714:

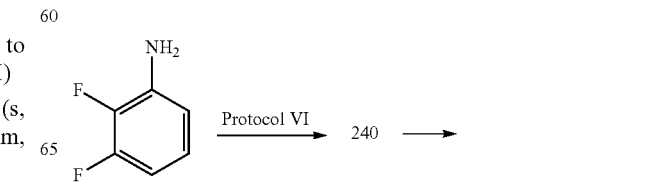

Intermediate 645:

Obtained by protection of intermediate 644 according to the protocol described for intermediate 158 (protocol VI)

$^1$H NMR (300 MHz, DMSO-d6): δ 7.35 (s, 1H), 6.90 (s, 1H), 4.90 (m, 1H), 3.80 (s, 3H), 2.9-2.6 (2m, 2H), 2.35 (m, 1H), 1.80 (m, 1H), 1.45 (s, 9H)

IR ($cm^{-1}$): 3309, 1682

711 →(Protocol VIII)→ 712 →(Protocol XII)→ 714

Intermediate 240:

4-Bromo-2,3-difluorobenzonitrile

Obtained starting from commercial 2,3-difluoroaniline according to the protocol described for the preparation of intermediate 156 (protocol VI)

Intermediate 711:

4-Bromo-3-fluoro-2-(2-methylpropoxy)benzonitrile

Obtained starting from intermediate 240 (5 g, 23 mmoles) and isobutanol (2.1 mL, 23 mmoles) in DMF (100 mL) at 0° C. in the presence of 60% sodium hydride in oil (0.92 g).

The reaction mixture is stirred for 72 hours at ambient temperature and then poured into water and extracted with ethyl ether. The organic phase is washed with water, dried over MgSO$_4$ and then concentrated. The residue is purified on silica gel (eluant cyclohexane/methylene chloride 70/30 to 0/100). Intermediate 711 (4.1 g) is obtained.

$^1$H NMR (400 MHz, DMSO-d6): δ 7.60 (s, 1H), 4.10 (d, 2H), 2.05 (m, 1H), 1.00 (d, 6H)

IR (cm$^{-1}$): 2240

GC-EI (70 eV): M+.=271

Intermediate 712:

Obtained starting from intermediate 711 according to protocol VIII $^1$H NMR (400 MHz; DMSO-d$_6$): δ 7.50 (m, 1H), 7.35 (dd, 1H), 3.90 (d, 2H), 2.55 (s, 3H), 2.05 (m, 1H), 1.00 (d, 6H)

IR (cm$^{-1}$): 1686

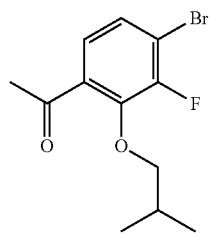

712

Intermediate 714:

Obtained starting from intermediate 712 according to protocol XII $^1$H NMR (400 MHz; DMSO-d$_6$): 8.70 (broad s, 3H), 7.55 (m, 1H), 7.45 (d, 1H), 4.60 (quad, 1H), 4.0-3.8 (2dd, 2H), 2.05 (m, 1H), 1.50 (d, 3H), 1.00 (d, 6H)

$^{19}$F NMR: −123 (1F)

IR (cm$^{-1}$): 3154, 2000

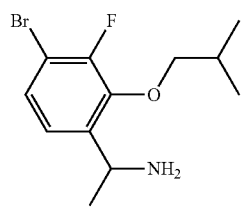

714

Intermediate 726:

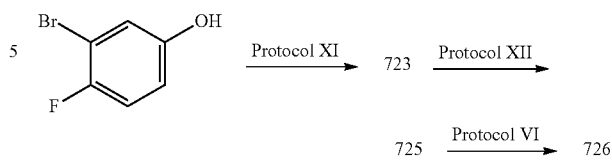

723 →(Protocol XII)→ 725 →(Protocol VI)→ 726

Intermediate 723:

Obtained starting from commercial 3-bromo-4-fluorophenol according to protocol XI $^1$H NMR (400 MHz, DMSO-d6): δ 7.68 (d, 1H), 7.54 (d, 1H), 7.51 (d, 2H), 7.44 (t, 2H), 7.38 (t, 1H), 5.28 (s, 2H), 2.51 (s, 3H)

$^{19}$F NMR: −117.49 (1F)

IR (cm$^{-1}$): 1662

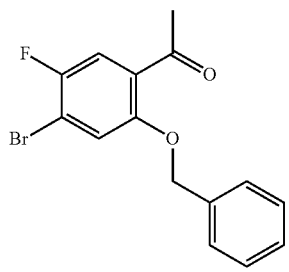

723

Intermediate 725:

Obtained starting from intermediate 723 according to protocol XII $^1$H NMR (300/400 MHz: DMSO-d$_6$): 7.46 (d, 1H), 7.5-7.35 (m, 5H), 7.31 (d, 1H), 5.15 (2d, 2H), 4.26 (quad, 1H), 1.85 (broad s, 2H), 1.19 (d, 3H)

$^{19}$F NMR: −117.8 (dd, 1F)

IR (cm$^{-1}$): 3154, 2000.

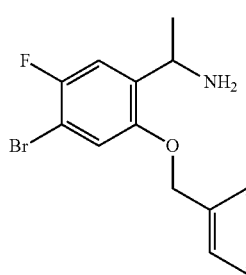

725

Intermediate 726:

Obtained by protection of intermediate 725 according to the protocol described for intermediate 158 (protocol VI)

$^1$H NMR (300 MHz, DMSO-d$_6$): δ 7.40 (m and d, 6H), 7.25 (d, 1H), 5.20 (s, 2H), 4.95 (m, 1H), 1.35 (broad s, 9H), 1.25 (d, 3H)

IR (cm$^{-1}$): 3303, 1675

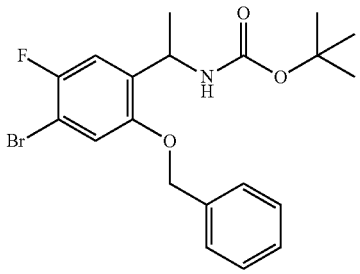

Intermediate 331b:

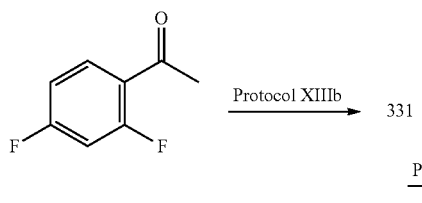

The synthesis of intermediate 331 is described in protocol XIIIb.

Intermediate 331b:

Obtained starting from intermediate 331 according to protocol XV $^1$H NMR (400 MHz, DMSO-d$_6$): δ 7.46 (broad d, 1H), 7.40 (m, 1H), 7.14 (m, 1H), 7.06 (m, 1H), 4.83 (m, 1H), 1.34 (broad s, 9H), 1.27 (d, 3H)

IR (cm$^{-1}$): 3373, 1678

Enantiomeric excess >99%

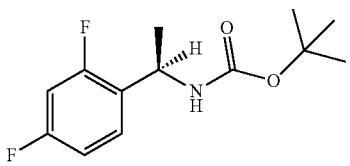

Intermediate 234:

Obtained by reaction of commercial 4,6-difluoro-2,3-dihydro-1H-inden-1-one and (+/−)-2-methyl-2-propanesulphinamide according to protocol XIII $^1$H NMR (400/500 MHz, DMSO-d$_6$): δ 7.28 (d, 1H), 7.04 (t, 1H), 5.90 (d, 1H), 4.78 (quad, 1H), 2.9-2.7 (2m, 2H), 2.45-1.98 (2m, 2H), 1.16 (s, 9H)

IR (cm$^{-1}$): 3246

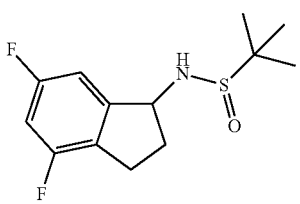

Intermediate 260:

Obtained by reaction of commercial 5,7-difluoro-2,3-dihydro-1H-inden-1-one and (+/−)-2-methyl-2-propanesulphinamide according to protocol XIII $^1$H NMR (400 MHz, DMSO-d$_6$): δ 6.98 (m, 2H), 5.64 (d, 1H), 4.89 (m, 1H), 3.13 (m, 1H), 2.8 (m, 1H), 2.34 (m, 1H), 2.13 (m, 1H), 1.07 (s, 9H)

IR (cm$^{-1}$): 3209, 1048

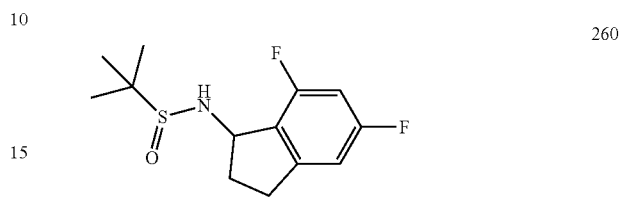

Intermediates 343 and 346:

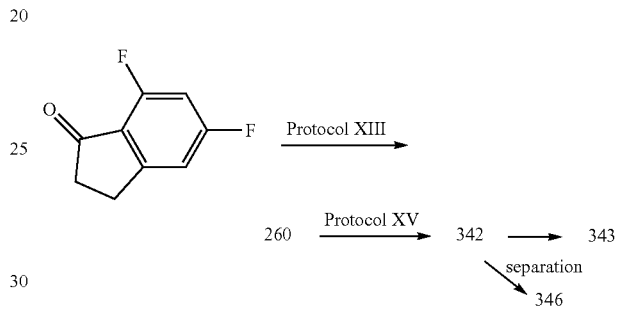

Intermediate 342:

Obtained starting from intermediate 260 according to protocol XV $^1$H NMR (400 MHz, DMSO-d$_6$): δ 7.26 (d, 1H), 6.95 (m, 2H), 5.16 (quad, 1H), 3.00 (m, 1H), 2.77 (m, 1H), 2.38 (m, 1H), 1.87 (m, 1H), 1.41 (s, 9H)

IR (cm$^{-1}$): 3241, 1708-1680

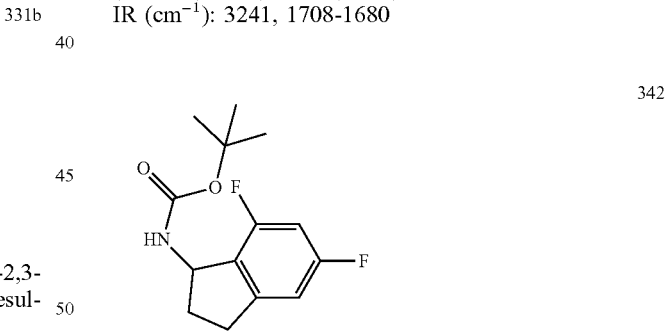

Intermediate 342 (7.9 g) was purified by high pressure chromatography on a chiral support (ChiralPak IC column, eluant ethanol/n-heptane 10/90, detection: 260 nm) to give enantiomers 343 (3.7 g) and 346 (3.7 g).

Intermediate 343:

optical purity (ChiralPak IC3 column: 3 μm, 4.6×250 mm, eluant ethanol/n-heptane 10/90, detection: 210 nm): >99%, intermediate 346<1%

IR (cm$^{-1}$): 3355, 1680

α$_D$ (589 nM)=+60.7 (c=0.013 g/mL, EtOH) at 20° C.

Intermediate 346:

Optical purity (ChiralPak IC3 column: 3 μm, 4.6×250 mm, eluant ethanol/n-heptane 10/90, detection: 210 nm): >99%, intermediate 343<1%

IR (cm$^{-1}$): 3354, 1678

α_D (589 nM)=−60.7 (c=0.013 g/mL, EtOH) at 20° C.

Intermediate 269:

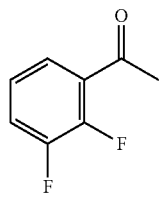

Intermediate 268:
Obtained starting from commercial 1-(2,3-difluorophenyl)ethanone according to protocol XII $^1$H NMR (400 MHz; DMSO-d$_6$): 7.40 (ddd, 1H), 7.25 (m, 1H), 7.20 (m, 1H), 4.30 (quad, 1H), 1.95 (m, 2H), 1.25 (d, 3H)

IR (cm$^{-1}$): 3750, 3000.

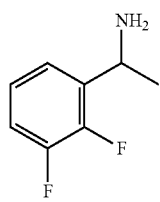

Intermediate 269:
Obtained by protection of intermediate 268 according to the protocol described for intermediate 158 (protocol VI)

$^1$H NMR (400 MHz, DMSO-d$_6$): δ 7.53 (d, 1H), 7.20 (m, 3H), 4.90 (m, 1H), 1.35 (m, 9H), 1.30 (d, 3H), IR (cm$^{-1}$): 3377, 1681

$^{19}$F NMR: −140, −146

GC-EI (70 eV) 257.1

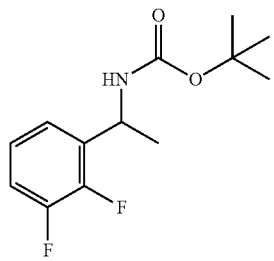

Intermediate 288:

The preparations of intermediates 286 and 287 are described in protocols XIII and XV, respectively.

Intermediate 288:
Obtained by protection of intermediate 287 according to the protocol described for intermediate 158 (protocol VI)

$^1$H NMR (300 MHz, DMSO-d$_6$): δ 7.42 (d, 1H), 7.03 (m, 1H), 7.00 (m, 2H), 4.61 (m, 1H), 1.37 (s, 9H), 1.30 (d, 3H)

IR (cm$^{-1}$): 3369, 1682

α_D (589 nM)=58.22 (c=0.0087 g/mL, methanol) at 20° C.

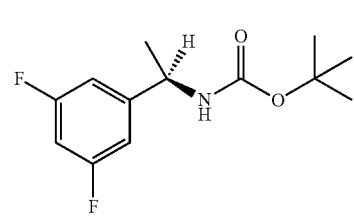

Intermediate 317:
Obtained by reaction of commercial 4,6-difluoro-2,3-dihydro-1H-inden-1-one and (R)-(+)-2-methyl-2-propanesulphinamide according to protocol XIIIb $^1$H NMR (400 MHz, DMSO-d$_6$): δ 7.29 (d, 1H), 7.05 (t, 1H), 5.91 (d, 1H), 4.79 (m, 1H), 2.9-2.7 (m, 2H), 2.45-1.99 (m, 2H), 1.15 (s, 9H)

IR (cm$^{-1}$): 3207

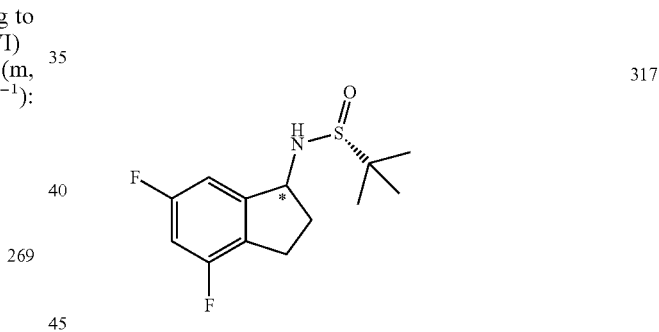

Intermediate 324:

Intermediate 322:
Obtained by reaction of commercial 3,5-difluoroacetophenone and (S)-(−)-2-methyl-2-propanesulphinamide according to protocol XIIIb $^1$H NMR (300 MHz, DMSO-d$_6$): δ 7.14 (d, 2H), 7.05 (tt, 1H), 4.40 (m, 1H), 3.80 (d, 1H), 1.38 (d, 3H), 1.13 (s, 9H)

IR (cm$^{-1}$): 3125, 1624, 1598, 1117, 853, 699

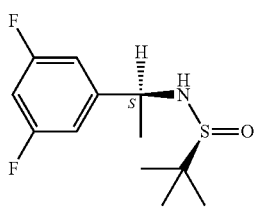

322

Intermediate 324:

Obtained starting from intermediate 322 according to protocol XV $^1$H NMR (400 MHz, DMSO-d$_6$): δ 7.40 (d, 1H), 7.05 (m, 1H), 7.00 (m, 2H), 4.65 (m, 1H), 1.35 (broad s, 9H), 1.30 (d, 3H)

IR (cm$^{-1}$): 3364, 1683

Enantiomeric excess >99%

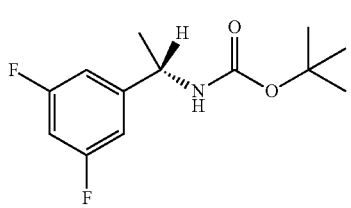

324

Intermediate 334:

Obtained by reaction of commercial 1-(2,4-difluorophenyl)ethanone and (R)-(+)-2-methyl-2-propanesulphinamide and then reduction with L-selectride (1M in THF) according to protocol XIII $^1$H NMR (300 MHz, DMSO-d$_6$): δ 7.6 (m, 1H), 7.20 (m, 1H), 7.10 (m, 1H), 5.45 (d, 1H), 4.65 (quint, 1H), 1.5 (d, 3H), 1.10 (s, 9H)

IR (cm$^{-1}$): 3214

$^{19}$F NMR: −111, −114 (2m)

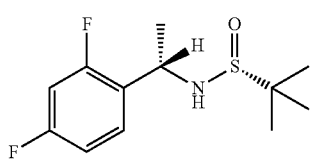

334

Intermediate 337:

Obtained by reaction of commercial 4,6-difluoro-2,3-dihydro-1H-inden-1-one and (S)-(−)-2-methyl-2-propanesulphinamide according to protocol XIIIb $^1$H NMR (400 MHz, DMSO-d$_6$): δ 7.3 (dd, 1H), 7.05 (td, 1H), 5.95 (d, 1H), 4.80 (quad, 1H), 2.9-2.7 (m, 2H), 2.45-2.0 (m, 2H), 1.15 (s, 9H)

IR (cm$^{-1}$): 3207

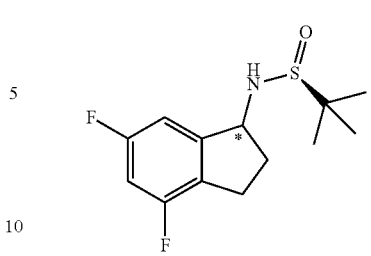

337

Intermediate 478:

Obtained starting from N-[(2,4-difluorophenyl)methylidene]-2-methylpropane-2-sulphinamide (precursor of intermediate 334 before reduction) and EtMgCl according to protocol XIV $^1$H NMR (300 MHz, DMSO-d$_6$): δ 7.49 (m, 1H), 7.09 (m, 1H), 5.44 (d, 1H), 4.39 (m, 1H), 4.37 (m, 1H), 1.9 (m, 1H), 1.71 (m, 1H), 1.07 (s, 9H), 0.81 (s, 3H)

$^{19}$F NMR: −112.2, −115.4

IR (cm$^{-1}$): 3205, 1049

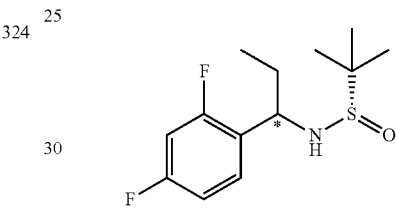

478

Intermediate 367:

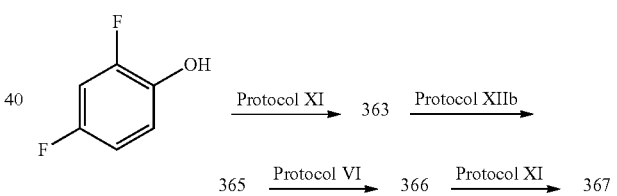

The preparation of intermediate 363 is described in protocol XI.

Intermediate 365:

Obtained starting from intermediate 363 according to protocol XIIb $^1$H NMR (400 MHz; DMSO-d$_6$): 7.00 (m, 1H), 6.80 (m, 1H), 7.00-5.0 (m, 3H), 4.20 (quad, 1H), 1.30 (d, 3H)

IR (cm$^{-1}$): 3300-2000

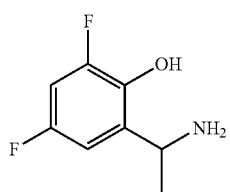

365

Intermediate 366:

Obtained by protection of intermediate 365 according to the protocol described for intermediate 158 (protocol VI)

¹H NMR (400 MHz, DMSO-d₆): δ 9.40 (m, 1H), 7.35 (dl, 1H), 7.05 (m, 1H), 6.90 (dd, 1H), 4.95 (quint, 1H), 2.39 (s, 3H), 1.35 (d, 9H), 1.20 (d, 3H)
IR (cm⁻¹): 3500, 2600, 1690, 1672.

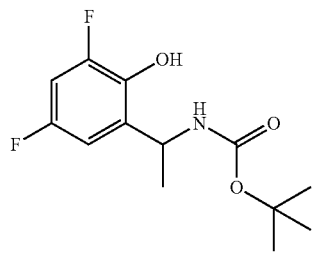

366

Intermediate 367:
Obtained starting from intermediate 366 according to the protocol described for intermediate 384 (Protocol XI)
¹H NMR (400 MHz, DMSO-d₆): δ 7.43 (d, 1H), 7.15 (m, 1H), 7.00 (m, 1H), 4.93 (m, 1H), 3.82 (s, 3H), 1.36 (s, 9H), 1.21 (d, 3H)
IR (cm⁻¹): 3368, 1681

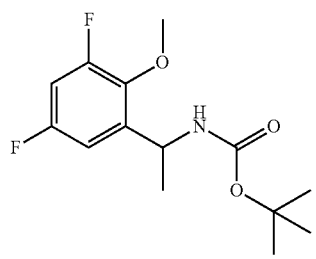

367

Intermediate 430:
Obtained starting from intermediate 366 according to the protocol described for intermediate 562 (Protocol XXI)
¹H NMR (400 MHz, DMSO-d₆): δ 7.50 (d, 1H), 7.05 (dd, 1H), 7.00 (td, 1H), 4.85 (quint, 1H), 2.70 (m, 1H), 2.60 (m, 1H), 1.35 (m, 9H), 1.30 (d, 3H), 1.15 (t, 3H)
IR (cm⁻¹): 3380, 1671

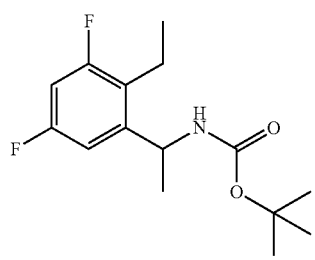

430

Intermediate 378:
Obtained starting from commercial 3,5-difluorobenzonitrile according to protocol VI
¹H NMR (400 MHz; DMSO-d₆): δ 7.28 (m, 1H); 7.00 (m, 1H); 6.98 (m, 2H); 1.48 (s, 6H); 1.30 (m, 9H)
IR (cm⁻¹): 3314; 1685; 1523

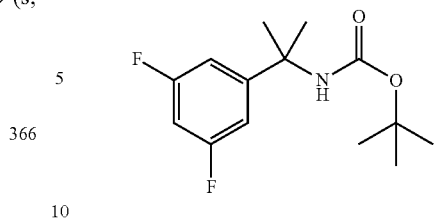

378

Intermediate 387:

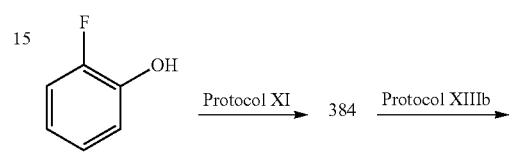

Intermediate 384:
Obtained starting from commercial 2-fluorophenol according to protocol XI, in the presence of methyl iodide in the last step
¹H NMR (400 MHz, DMSO-d₆): δ 7.50 (dd, 1H), 7.40 (dd, 1H), 7.20 (m, 1H), 3.90 (s, 3H), 2.55 (s, 3H)
IR (cm⁻¹): 1685

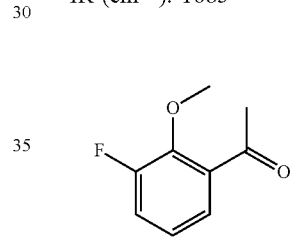

384

Intermediate 385:
Obtained by reaction of intermediate 384 and (R)-(+)-2-methyl-2-propanesulphinamide according to protocol XIIIb
¹H NMR (400 MHz, DMSO-d₆): δ 7.30 (d, 1H), 7.12 (m, 2H), 5.63 (d, 1H), 4.72 (m, 1H), 3.89 (d, 3H), 1.36 (d, 3H), 1.11 (s, 9H)
¹⁹F NMR: −130.0
IR (cm⁻¹): 3500, 3000, 1056

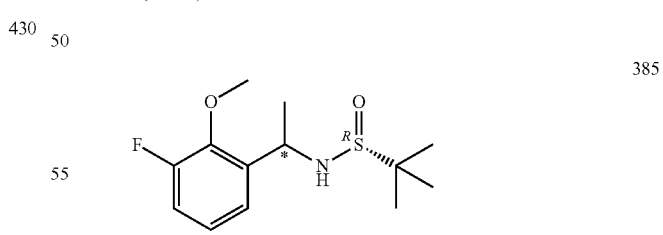

385

Intermediate 387:
Obtained starting from intermediate 385 according to protocol XV
¹H NMR (400 MHz, DMSO-d₆): δ 7.42 (broad d, 1H), 7.16 (broad d, 1H), 7.10 (m, 2H), 4.95 (m, 1H), 3.87 (s, 3H), 1.36 (s, 9H), 1.25 (d, 3H)
IR (cm⁻¹): 3346, 1695
Enantiomeric excess >99%

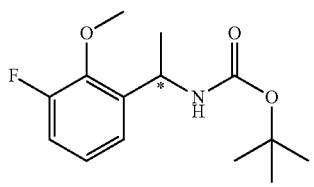

387

Intermediate 739:
Intermediate 737:
Obtained by reaction of intermediate 384 and (S)-(−)-2-methyl-2-propanesulphinamide according to protocol XIIIb
¹H NMR (400 MHz, DMSO-d₆): δ 7.30 (d, 1H), 7.12 (m, 2H), 5.63 (d, 1H), 4.72 (m, 1H), 3.89 (d, 3H), 1.36 (d, 3H), 1.11 (s, 9H)
¹⁹F NMR: −130.02
IR (cm⁻¹): 3219, 1050.

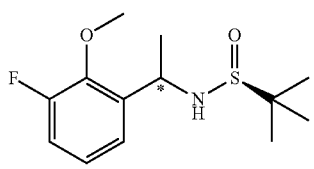

737

Intermediate 739:
Obtained starting from intermediate 737 according to protocol XV
¹H NMR (300 MHz, DMSO-d₆): δ 7.2-7.0 (m, 3H), 6.95 (m, 1H), 4.98 (quint, 1H), 3.90 (s, 3H), 1.35 (s, 9H), 1.30 (d, 3H)
IR (cm⁻¹): 3353, 1697

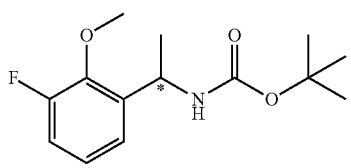

739

Intermediate 401:

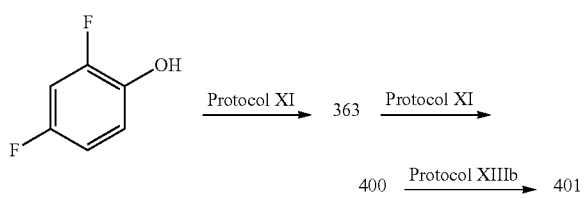

The preparation of intermediate 363 is described in protocol XI.
Intermediate 400:
Obtained starting from intermediate 363 according to protocol XI, in the presence of methyl iodide in the last step
¹H NMR (400 MHz, CDCl₃): δ 7.20 (ddd, 1H), 7.00 (ddd, 1H), 4.00 (s, 3H), 2.65 (s, 3H)
IR (cm⁻¹): 1674

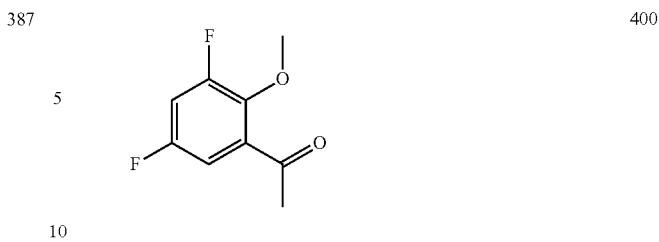

400

Intermediate 401:
Obtained by reaction of intermediate 400 and (R)-(+)-2-methyl-2-propanesulphinamide according to protocol XIIIb
¹H NMR (400 MHz, DMSO-d₆): δ 7.2 (m, 2H), 5.70 (s, 1H), 4.70 (quint, 1H), 3.85 (d, 3H), 1.35 (d, 3H), 1.10 (s, 9H)
IR (cm⁻¹): 3150
Diastereoisomeric purity: de>99%

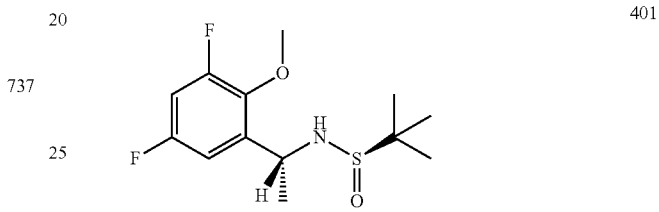

401

Intermediate 404:
Obtained by reaction of intermediate 400 and (S)-(−)-2-methyl-2-propanesulphinamide and then reduction with L-selectride (1M in THF) according to protocol XIII
¹H NMR (400 MHz, DMSO-d₆): δ 7.2 (m, 1H), 7.1 (ddd, 1H), 5.40 (d, 1H), 4.75 (quint, 1H), 3.85 (s, 3H), 1.4 (d, 3H), 1.10 (s, 9H)
IR (cm⁻¹): 3260

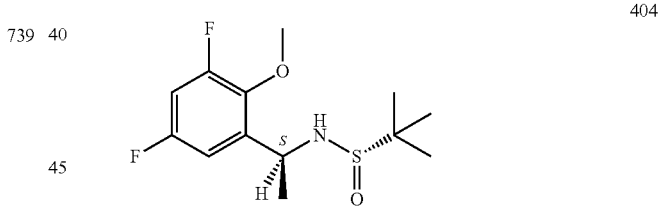

404

Intermediates 423 and 415:

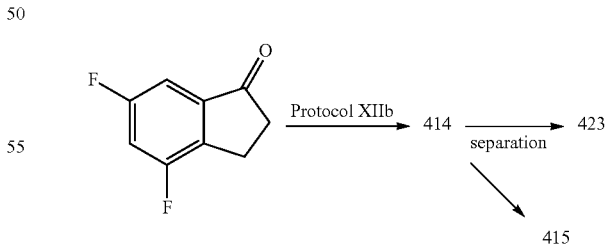

Intermediate 414:
Obtained starting from commercial 4,6-difluoro-2,3-dihydro-1H-inden-1-one according to protocol XIIb
¹H NMR (400 MHz; DMSO-d₆): 8.85 (m, 3H), 7.50 (dd, 1H), 7.20 (td, 1H), 4.75 (t, 1H), 3.05 (m, 1H), 2.85 (m, 1H), 2.55 (m, 1H), 2.10 (m, 1H)
IR (cm⁻¹): 3450-2440

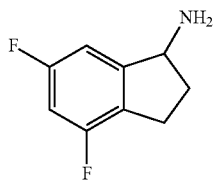

414

Intermediate 414 (11 g) was purified by high pressure chromatography on a chiral support (ChiralPak T304 column, eluant acetonitrile: 100: detection 260 nm) to give enantiomers 415 (5.2 g) and 423 (5.5 g).

Intermediate 415:

$^1$H NMR (400 MHz, DMSO-$d_6$): 7.00 (td, 1H), 6.80 (dd, 1H), 5.00 (m, 1H), 2.90 (m, 1H), 2.70 (m, 1H), 2.40 (m, 1H), 1.90 (m, 1H), 1.40 (s, 9H)

Optical purity (SFC: Kromasil-3-amy coat 3 µM column 4.6×250 mm; CO$_2$/(ethanol/diethylamine: 100/0.5): 80/20; Detection: 260 nm): >99%, intermediate 423<1%

Intermediate 423:

Optical purity (SFC: Kromasil-3-amy coat 3 µM column 4.6×250 mm; CO$_2$/(ethanol/diethylamine: 100/0.5): 80/20; Detection: 260 nm): >99%, intermediate 415<1%.

Intermediate 444:

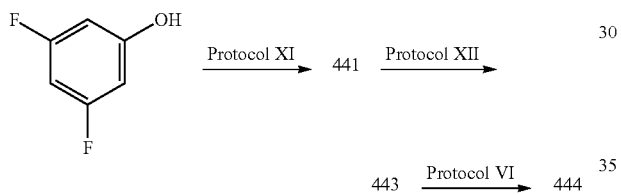

Intermediate 441:

Obtained starting from commercial 3,5-difluorophenol according to protocol XI $^1$H NMR (400 MHz, DMSO-d6): δ 7.50-7.30 (m, 6H), 7.05 (d, 1H), 6.95 (t, 1H), 5.20 (s, 2H), 2.45 (s, 3H)

IR (cm$^{-1}$): 1699

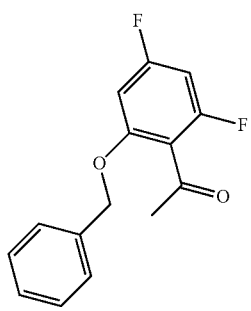

441

Intermediate 443:

Obtained starting from intermediate 441 according to protocol XII $^1$H NMR (400 MHz; DMSO-$d_6$): 8.30 (m, 3H), 7.50 (d, 2H), 7.40 (t, td, 3H), 7.00 (dd, 1H), 6.95 (td, 1H), 5.30 (s, 2H), 4.65 (quad, 1H), 1.50 (d, 3H)

IR (cm$^{-1}$): 3500-2450

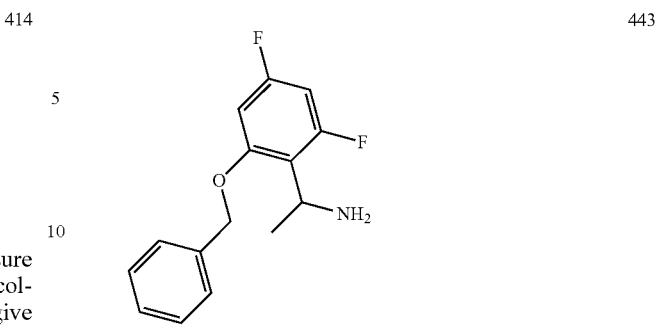

443

Intermediate 444:

Obtained by protection of intermediate 443 according to the protocol described for intermediate 158 (protocol VI)

$^1$H NMR (400 MHz, DMSO-$d_6$): δ 7.50 (d, 2H), 7.40 (t, 2H), 7.35 (td, 1H), 6.85 (dd, 1H), 6.80 (d, 1H), 6.75 (td, 1H), 5.20 (s, 2H), 5.10 (quint, 1H), 1.45-1.15 (m, 12H)

IR (cm$^{-1}$): 3475, 1709

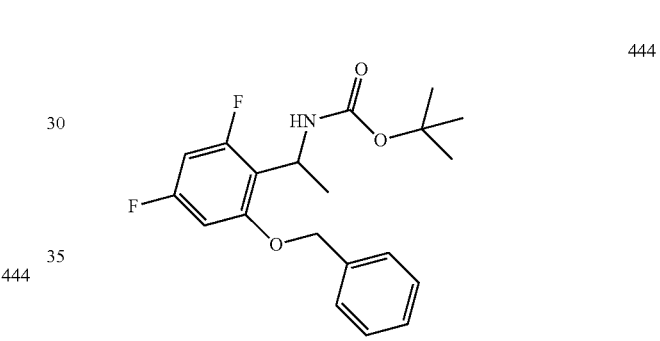

444

Intermediate 558:

Obtained starting from intermediate 444 according to the following procedure: 6.3 g of intermediate 444 are engaged in a debenzylation reaction in the presence of 10% by mass of 10% Pd/C in ethyl acetate to obtain 4.5 g of the phenolic intermediate 556. The 4.5 g of intermediate 556 yielded intermediate 557 (5.2 g of triflate) (flash chromatography on SiO$_2$, cyclohexane/methylene chloride gradient 10/90 to 100% methylene chloride). Intermediate 557 (4.3 g) was converted into intermediate 558 according to the following procedure:

A mixture of 557 (1 g, 2.47 mmoles), trimethyl-boroxine (0.62 g, 5 mmoles), K$_2$CO$_3$ (1.36 g, 9.8 mmoles) in 1,4-dioxane (10 mL) degassed by N$_2$ for 15 minutes is treated with Pd(PPh$_3$)$_4$(0.57 g, 0.5 mmoles). The mixture is heated at reflux for 1 hour. After return to ambient temperature, the solid is filtered off and the filtrate is concentrated in vacuo. Intermediate 558 (0.55 g) is obtained after purification on silica (2.4 g of methyl obtained after flash chromatography on SiO$_2$, gradient methylene chloride 100% to methylene chloride/AcOEt 90/10).

$^1$H NMR (400 MHz, DMSO-$d_6$): δ 7.24-6.95 (broad d and m, 1H), 6.95 (ddd, 1H), 6.86 (broad d, 1H), 4.85 (quint, 1H), 2.39 (s, 3H), 1.35 (d, 3H), 1.33-1.19 (2 broad s, 9H)

IR (cm$^{-1}$): 3468, 1705

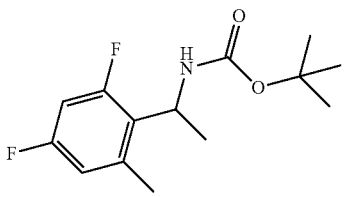

Intermediate 465:

Obtained starting from commercial 2,4-difluorobenzonitrile according to protocol VI $^1$H NMR (300 MHz; DMSO-d$_6$): δ 7.30 (m, 1H); 7.20 (m, 1H); 7.10 (m, 1H); 7.00 (m, 1H); 1.50 (s, 6H); 1.30 (m, 9H)
IR (cm$^{-1}$): 3410; 1697; 1613; 1160; 848-700.

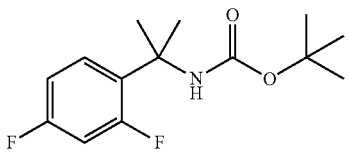

Intermediate 484:

N-[(2,4-Difluorophenyl)methylidene]-(2S)-2-methylpropane-2-sulphinamide

Obtained by reaction of 2,4-difluorobenzaldehyde with (S)-(−)-2-methylpropane-2-sulphinamide according to protocol XIV

Intermediate 482:

To a solution of N-[(2,4-difluorophenyl)methylidene]-(2S)-2-methylpropane-2-sulphinamide (5.1 g, 20 mmoles) in THF (30 mL), cooled to −60° C., there is added a solution of 2-(1,3-dioxolan-2-yl)ethyl-MgBr in methylene chloride (32 mL) prepared by reaction of magnesium (0.42 g) and 2-(2-bromoethyl)-1,3-dioxolane. The reaction mixture is stirred at −60° C. for 20 minutes and is then hydrolysed at −40° C. with a saturated aqueous NH$_4$Cl solution. The mixture is decanted in the presence of ethyl ether, and the organic phase is washed with a saturated NaCl solution, dried over MgSO$_4$ and then concentrated. Chromatography on silica (eluant CH$_2$Cl$_2$/THF 95/5) yields 1.7 g of intermediate 482 in the form of an oil.

$^1$H NMR (300 MHz, DMSO-d$_6$): δ 7.58 (m, 1H), 7.15 (m, 1H), 7.09 (m, 1H), 5.71 (d, NH), 4.78 (t, 1H), 4.45 (m, 1H), 3.85-3.73 (2m, 4H), 1.95-1.4 (m, 4H), 1.09 (s, 9H)
IR (cm$^{-1}$): 3230, 1048
Optical purity (SFC: AD 5 μM column 4.6×250 mm; CO$_2$/MeOH: 90/10; Detection: 260 nm): >98.6%

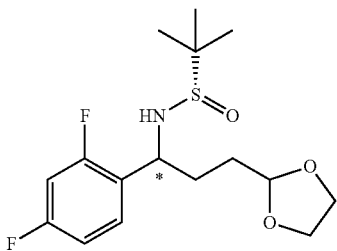

Intermediate 483:

To a solution of intermediate 482 (5.2 g, 15 mmoles) in an EtOH/H$_2$O mixture (50 mL/50 mL) there are added trifluoroacetic acid (10 mL) and PtO$_2$ (0.5 g). The mixture is hydrogenated at atmospheric pressure and at ambient temperature for 22 hours. The catalyst is filtered off and the filtrate is concentrated. The residue is taken up in water and extracted with ethyl ether. The aqueous phase is brought to basic pH using a 10N NaOH solution. After extraction with ethyl ether, washing with a saturated aqueous NaCl solution and drying over MgSO$_4$, evaporation under reduced pressure yields intermediate 483 (2.2 g).

$^1$H NMR (300 MHz, DMSO-d$_6$): δ 7.59 (m, 1H), 7.11 (m, 1H), 7.0 (m, 1H), 4.25 (m, 1H), 2.9 (m, 2H), 2.75 (broad s, NH), 1.72 (quint, 2H), 1.4 (m, 1H), 1.12 (m, 1H)
IR (cm$^{-1}$): 3286, 1097, 846

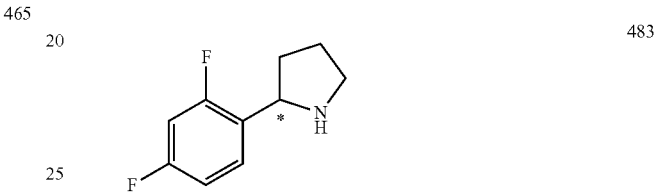

Intermediate 484:

Obtained by protection of intermediate 483 according to the protocol described for intermediate 158 (protocol VI)

$^1$H NMR (300 MHz, DMSO-d$_6$): δ 7.21 (dt, 1H), 7.09 (t, 1H), 7.00 (t, 1H), 4.94 (dd, 1H), 3.50 (t, 2H), 2.32 (m, 1H), 1.85 (quint, 2H), 1.73 (m, 1H), 1.23 (s, 9H)
IR (cm$^{-1}$): 1687, 1117
Enantiomeric excess >99%

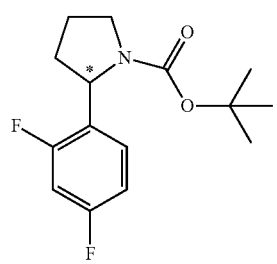

Intermediate 521:

N-[(2,4-Difluorophenyl)methylidene]-(2R)-2-methylpropane-2-sulphinamide

Obtained by reaction of 2,4-difluorobenzaldehyde with (R)-(+)-2-methylpropane-2-sulphinamide according to protocol XIV.

Intermediate 520, the optical antipode of intermediate 483, was obtained according to the protocol described for intermediate 483 starting from N-[(2,4-difluorophenyl)methylidene]-(2R)-2-methylpropane-2-sulphinamide, via intermediate 519.

Intermediate 519:

$^1$H NMR (400 MHz, DMSO-d$_6$): δ 7.60 (m, 1H), 7.15 (m, 1H), 7.1 (m, 1H), 5.7 (d, 2H), 4.8 (m, 1H), 4.45 (m, 1H), 3.85-3.75 (2m, 4H), 1.95-1.6 (m, 4H), 1.1 (s, 9H)
IR (cm$^{-1}$): 3230, 1047

Optical purity (SFC: AD 5 µM column 4.6×250 mm; CO$_2$/MeOH: 90/10; Detection: 260 nm): >99%.

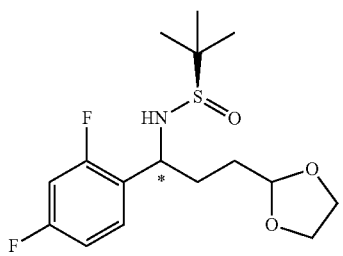
519

Intermediate 520:

$^1$H NMR (300 MHz, DMSO-d$_6$): δ 7.59 (m, 1H), 7.11 (m, 1H), 7.0 (m, 1H), 4.25 (m, 1H), 2.9 (m, 2H), 2.75 (broad s, NH), 1.72 (quint, 2H), 1.4 (m, 1H), 1.12 (m, 1H).

IR (cm$^{-1}$): 3286, 1097, 846.

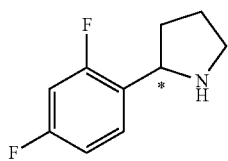
520

Intermediate 521:

Obtained by protection of intermediate 520 according to the protocol described for intermediate 158

$^1$H NMR (400 MHz, DMSO-d$_6$): δ 7.3-7.1 (2m, 1H), 7.05 (m, 1H), 5.0-4.85 (m, 1H), 3.6-3.35 (m, 2H), 2.32-1.7 (2m, 2H), 1.85 (m, 2H), 1.35-1.1 (2s, 9H)

IR (cm$^{-1}$): 1687

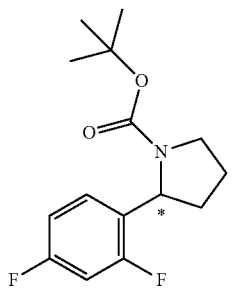
521

Intermediate 492:

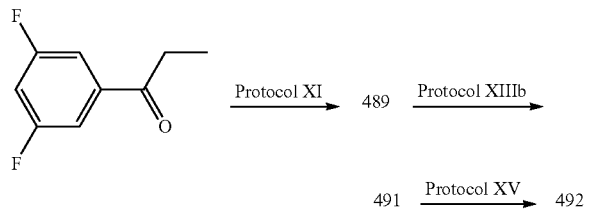

Intermediate 489:

Obtained starting from commercial 3,5-difluorobenzoic acid and ethylmagnesium bromide according to protocol IX GC-EI (70 eV): M$^+$=170.

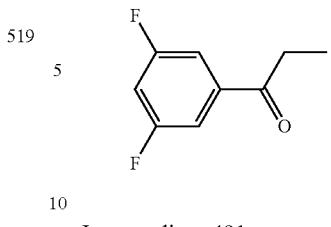
489

Intermediate 491:

Obtained by reaction of intermediate 489 and (R)-(+)-2-methyl-2-propanesulphinamide according to protocol XIIIb $^1$H NMR (400 MHz, DMSO-d6): δ 7.15 (dd, 2H), 7.05 (td, 1H), 5.70 (d, 1H), 4.10 (dd, 1H), 1.85-1.65 (m, 2H), 1.15 (s, 9H), 0.85 (t, 3H)

IR (cm$^{-1}$): 3151, 1040

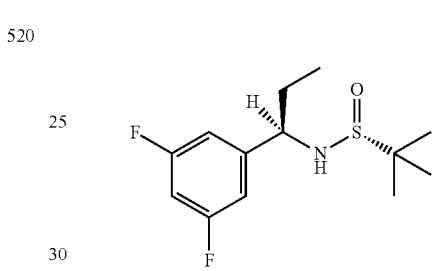
491

Intermediate 492:

Obtained starting from intermediate 491 according to protocol XV $^1$H NMR (400 MHz, DMSO-d$_6$): δ 7.05 (td, 1H), 7.00 (broad d, 2H), 4.40 (m, 1H), 1.60 (quint, 2H), 1.35 (s, 9H), 0.80 (t, 3H)

IR (cm$^{-1}$): 3371, 1679

Enantiomeric excess >99%

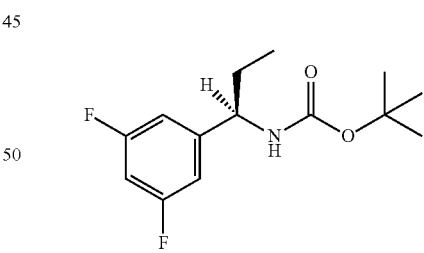
492

Intermediate 499:

The preparation of intermediate 497 is described in protocol XIV.

Intermediate 499:

Obtained starting from intermediate 497 according to protocol XV $^1$H NMR (400 MHz, DMSO-d$_6$): δ 7.05 (m, 3H), 7.40 (d, 1H), 4.25 (t, 1H), 1.85 (m, 1H), 1.40-1.2 (s, 9H), 0.9-0.7 (2d, 6H)

IR (cm$^{-1}$): 3365, 1678, 1161

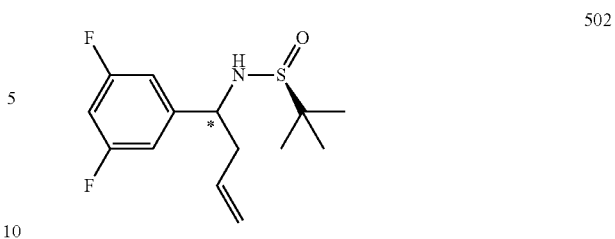

Intermediate 503:

Obtained starting from intermediate 502 in the presence of 10% Pd/C in methanol under hydrogen for 2 days (2.9 g of intermediate 502 used, 2.9 g of intermediate 503 obtained).

$^1$H NMR (400 MHz, DMSO-d6): δ 7.1 (d, 3H), 5.45 (d, 1H), 4.25 (quad, 1H), 1.85-1.6 (m, 2H), 1.35-1.15 (m, 2H), 1.1 (s, 9H), 1.85 (t, 3H)

IR (cm$^{-1}$): 3208, 1052

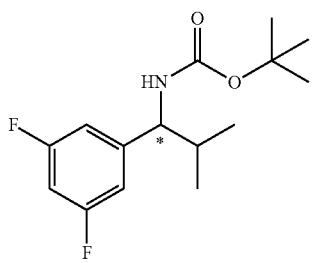

Intermediate 505:

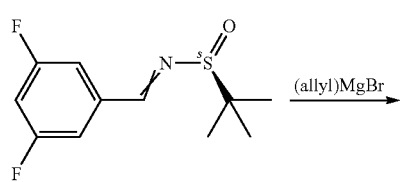

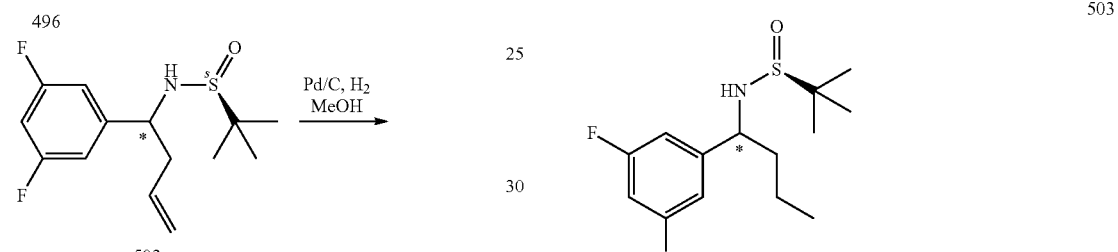

Intermediate 505:

Obtained starting from intermediate 503 according to protocol XV $^1$H NMR (400 MHz, DMSO-d$_6$): δ 7.38 (d, 1H), 7.1-7.0 (m, 3H), 4.45 (quad, 1H), 1.55 (m, 2H), 1.35 (s, 9H), 1.4-1.3 (m, 2H), 0.85 (t, 3H)

IR (cm$^{-1}$): 3372, 1681

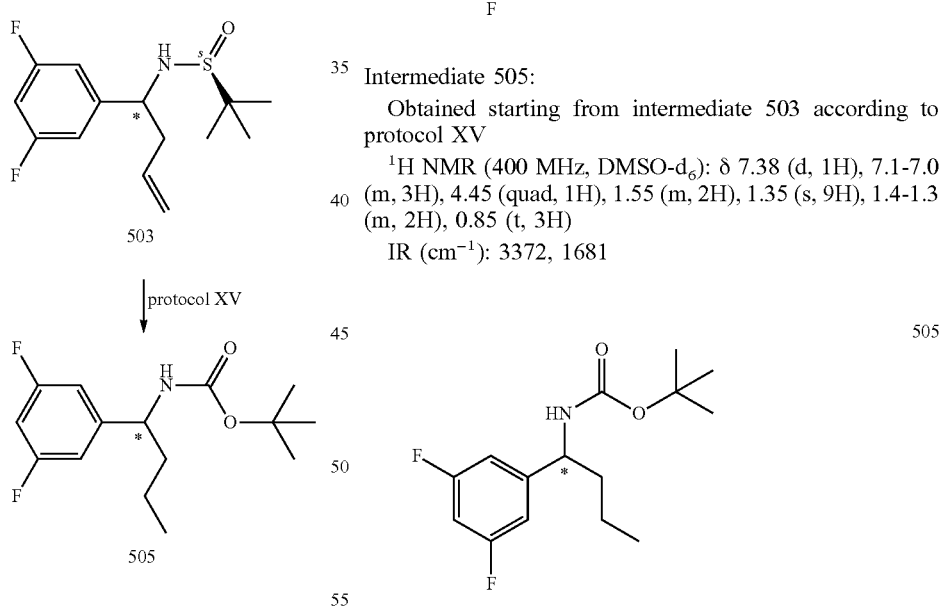

The preparation of intermediate 496 is described in protocol XIV.

Intermediate 502:

Obtained starting from intermediate 496 and (allyl)MgBr according to protocol XIV (see preparation of intermediate 497)

$^1$H NMR (400 MHz, DMSO-d$_6$): δ 7.1 (m, 3H), 5.7 (m, 1H), 5.05 (m, 2H), 4.35 (quad, 1H), 2.65-2.45 (m, 2H), 1.1 (s, 9H)

IR (cm$^{-1}$): 3205, 1053.

Intermediate 510:

The preparation of intermediate 496 is described in protocol XIV.

Intermediate 508:

Obtained starting from intermediate 496 and i-BuMgCl according to protocol XIV $^1$H NMR (400 MHz, DMSO-d$_6$): δ 7.1 (m, 3H), 5.45 (d, 1H), 4.3 (quad, 1H), 1.75-1.5 (m, 2H), 1.5 (m, 1H), 1.1 (s, 9H), 0.9 (2d, 6H)

IR (cm$^{-1}$): 3200, 1725, 1057

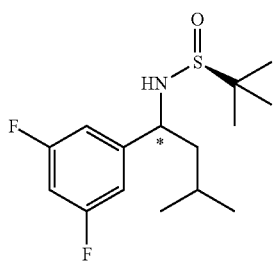

508

Intermediate 510:

Obtained starting from intermediate 508 according to protocol XV $^1$H NMR (400 MHz, DMSO-d$_6$): δ 7.35 (broad d, 1H), 7.0 (m, 3H), 4.55 (m, 1H), 1.55 (m, 2H), 1.40 (s, 9H), 1.35 (m, 1H), 0.95 (d, 6H)

IR (cm$^{-1}$): 3367, 1681, 1253

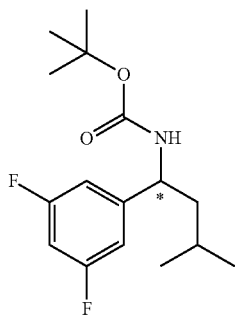

510

Intermediate 526:

Intermediate 525:

Obtained by reaction of (S)-2-methylpropane-2-sulphinamide with commercial 3-bromo-2-fluoro-benzaldehyde according to protocol XIV Intermediate 526:

Obtained by treatment with MeMgBr (3M/ether) of intermediate 525 according to protocol XIV $^1$H NMR (400 MHz, DMSO-d$_6$): δ 7.60-7.5 (m, 1H), 7.5 (m, 1H), 7.18 (m, 1H), 5.51 (d, 1H), 4.7 (m, 1H), 1.5 (d, 3H), 1.1 (s, 9H)

IR (cm$^{-1}$): 3206, 1048

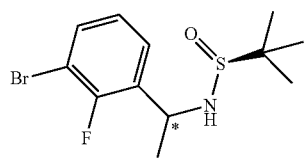

526

Intermediate 550:

The preparation of intermediate 547 is described in protocol XI.

Intermediate 548:

Obtained by reaction of intermediate 547 and (R)-(+)-2-methyl-2-propanesulphinamide according to protocol XIII $^1$H NMR (400 MHz, DMSO-d$_6$): δ 7.50-7.35 (m, 5H), 7.22 (td, 1H), 7.10 (dd, 1H), 5.42 (d, 1H), 5.05 (s, 2H), 4.75 (m, 1H), 1.35 (d, 3H), 1.10 (s, 9H)

IR (cm$^{-1}$): 3206

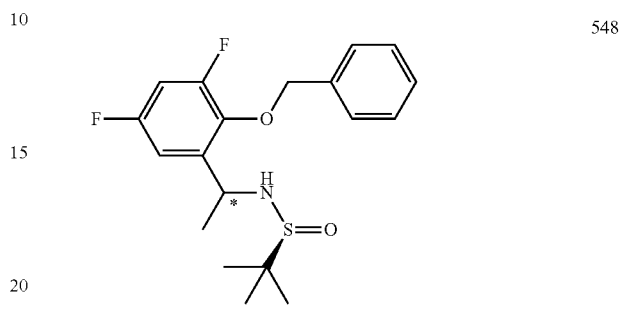

548

Intermediate 550:

Obtained starting from intermediate 548 according to protocol XV $^1$H NMR (400 MHz, DMSO-d$_6$): δ 7.49 (m, 3H), 7.42 (t, 2H), 7.37 (t, 1H), 7.20 (m, 1H), 7.05 (m, 1H), 5.04 (m, 3H), 1.36 (s, 9H), 1.19 (d, 3H)

IR (cm$^{-1}$): 3329, 1699

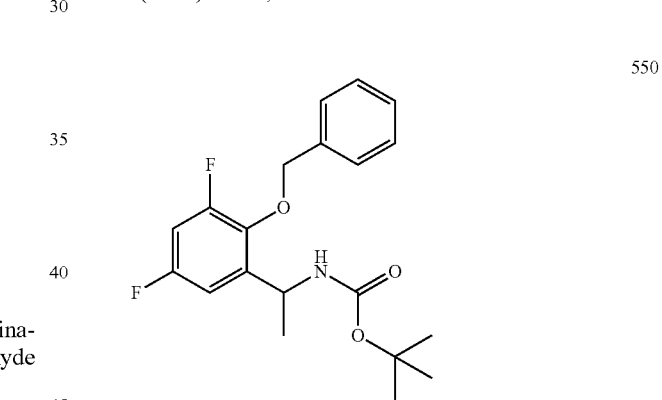

550

Intermediate 696:

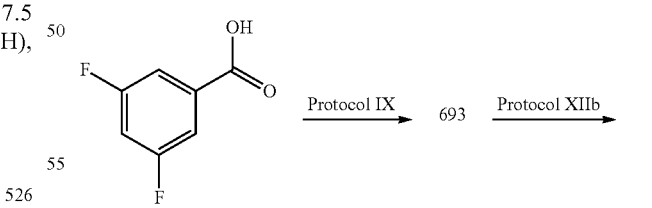

Intermediate 693:

Obtained starting from commercial 3,5-difluorobenzoic acid and 3-methoxyphenylmagnesium bromide according to protocol IX $^1$H NMR (400 MHz; DMSO-d$_6$): δ 7.60 (m, 1H), 7.50 (t, 1H), 7.40 (m, 2H), 7.30 (m, 3H), 3.85 (s, 1H)

IR (cm$^{-1}$): 1665

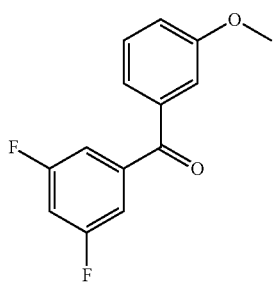

693

Intermediate 695:

Obtained starting from intermediate 693 according to protocol XIIb

¹H NMR (300 MHz; DMSO-d$_6$): 7.20 (t, 1H), 7.10 (m, 2H); 7.00 (m, 2H), 6.95 (d, 1H), 6.75 (dd, 1H), 5.05 (s, 1H), 3.75 (s, 3H), 2.35 (broad s, 2H)

IR (cm$^{-1}$): 3385-3309, 1594, 1254

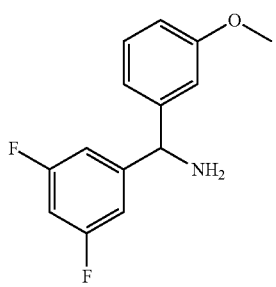

695

Intermediate 696:

Obtained by protection of intermediate 695 according to the protocol described for intermediate 158 (protocol VI)

¹H NMR (300 MHz, DMSO-d$_6$): δ 8.00 (broad d, 1H), 7.25 (t, 1H), 7.10 (m, 3H), 6.95 (m, 2H), 6.80 (dd, 1H), 5.70 (broad d, 1H), 3.75 (s, 3H), 1.40 (broad s, 9H)

IR (cm$^{-1}$): 3357, 1684, 1162

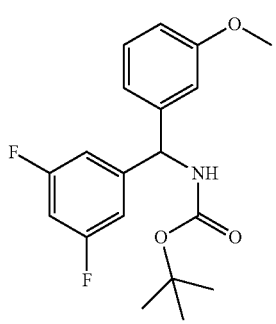

696

Intermediate 702:

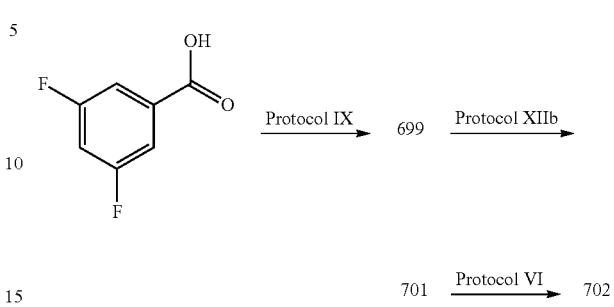

Intermediate 699:

Obtained starting from commercial 3,5-difluorobenzoic acid and methyl-cyclohexylmagnesium bromide according to protocol IX ¹H NMR (400 MHz; DMSO-d$_6$): δ 7.64 (m, 2H), 7.56 (tt, 1H), 2.90 (d, 2H), 1.83 (m, 1H), 1.6-1.1-0.99 (3m, 10H)

IR (cm$^{-1}$): 1688

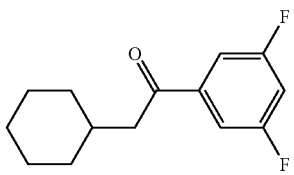

699

Intermediate 701:

Obtained starting from intermediate 699 according to protocol XIIb

¹H NMR (400 MHz; DMSO-d$_6$): 8.57 (broad s, 3H), 7.35 (m, 2H); 7.28 (tt, 1H), 4.35 (dd, 1H), 1.85-1.67 (m, 3H), 1.6-0.88 (3m, 10H)

IR (cm$^{-1}$): 3200-2500, 1126.

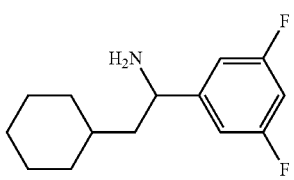

701

Intermediate 702:

Obtained by protection of intermediate 701 according to the protocol described for intermediate 158 (protocol VI)

¹H NMR (400 MHz, DMSO-d$_6$): δ 7.00 (m, 3H), 7.38 (d, 1H), 4.60 (m, 1H), 1.78-1.55 (2m, 2H), 1.7-0.8 (m, 11H), 1.40 (s, 9H)

IR (cm$^{-1}$): 3280, 1677

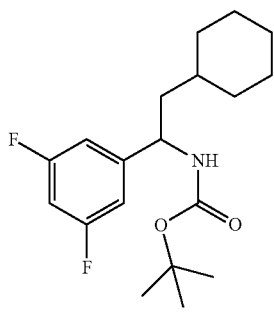

702

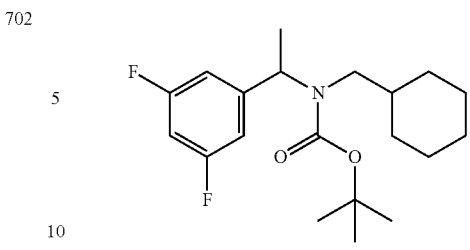

706

Intermediate 278:
Obtained starting from intermediate 489 according to protocol XII ¹H NMR (400 MHz; CDCl₃): 6.88 (d, 2H); 6.65 (tt, 1H), 4.10 (quad, 2H); 1.53 (broad s, 2H), 1.35 (d, 3H)

IR (cm⁻¹): 3371, 3298

Intermediate 706:
Intermediate 705:

A solution of commercial 1-(3,5-difluorophenyl)ethanone (5 g, 32 mmoles) and cyclohexanemethylamine (3.6 g, 32 mmoles) in toluene (50 mL) is heated for 40 hours at reflux in an azeotropic assembly. The toluene is evaporated off and the residue is dissolved in ethanol (40 mL). The solution is cooled to 10° C., and then NaBH₄ (1.2 g, 32 mmoles) is added in portions; the reaction mixture is stirred for 2 hours, and NaBH₄ (0.12 g) is again added. After stirring for 30 minutes, a 3N aqueous HCl solution is added carefully, and the ethanol is evaporated off in vacuo. The residue is taken up in toluene (200 mL) and washed with a 40% aqueous NaOH solution. The organic phase is dried over MgSO₄, and evaporation under reduced pressure yields intermediate 705 (4.4 g), which is used without additional treatment in the following step.

¹H NMR (300 MHz, DMSO-d₆): δ 7.00 (m, 3H), 3.70 (quad, 1H), 2.20 (dd, 1H), 2.05 (dd, 1H), 1.80-1.70 (3m, 10H), 1.30 (m, 1H), 1.20 (d, 3H)

IR (cm⁻¹): 2922-2850, 1114

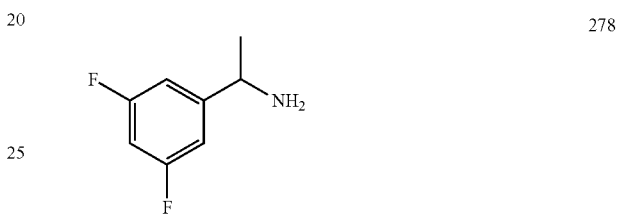

278

Intermediate 104:

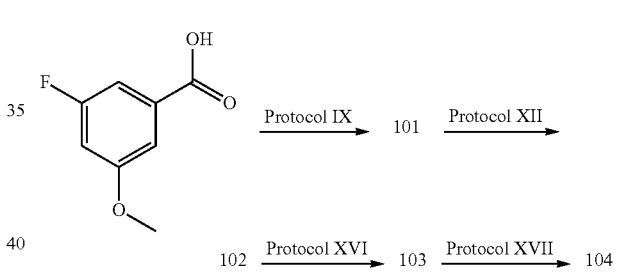

Intermediate 101:
Obtained starting from commercial 3-fluoro-5-methoxy-benzoic acid and methylmagnesium bromide according to protocol IX ¹H NMR (CDCl₃): δ 7.20 (s, 1H), 7.14 (d, 1H), 6.73 (d, 1H), 3.77 (s, 3H), 2.50 (s, 3H)

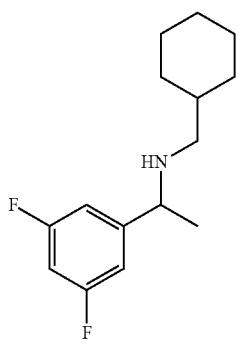

705

101

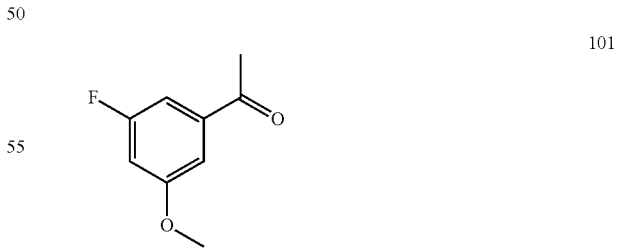

Intermediate 706:
Obtained by protection of intermediate 705 according to the protocol described for intermediate 158 (protocol VI)

¹H NMR (300 MHz, DMSO-d₆): δ 7.10 (tt, 1H), 6.95 (d, 2H), 4.90 (broad s, 1H), 3.00 (broad s, 2H), 1.50 (d, 3H), 1.30 (broad s, 9H), 1.70-0.75 (2m, 11H). 19F NMR: −110.7

IR (cm⁻¹): 1686, 1147

Intermediate 102:
Obtained starting from intermediate 101 according to protocol XII ¹H NMR (300 MHz; DMSO-d₆): 6.75 (t and d, 2H), 6.60 (d and t, 1H), 3.90 (quad, 1H), 3.75 (s, 3H), 1.80 (m, 2H), 1.20 (d, 6H)

IR (cm⁻¹): 3750-2750

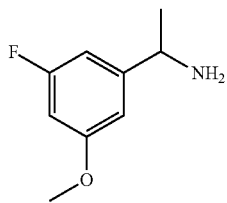

102

Intermediate 103:

Obtained starting from intermediate 102 according to protocol XVI $^{1}$H NMR (300 MHz, CDCl$_{3}$): δ 6.60 (2m, 2H), 6.55 (t, 1H), 6.40 (m, 1H), 5.10 (quint, 1H), 3.80 (s, 3H), 1.55 (d, 3H)

IR (cm$^{-1}$): 3240, 1694, 1627, 1595, 1558

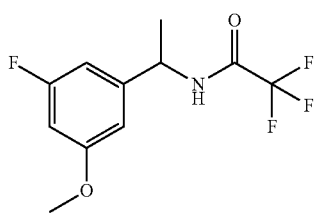

103

Intermediate 104:

Obtained starting from intermediate 103 according to the procedure used to convert intermediate 93a into intermediate 94 (Protocol XVII)

$^{1}$H NMR (500 MHz, DMSO-d$_{6}$): 10.30 (s, 1H), 9.90 (1, 1H), 7.08 (d, 1H), 6.87 (d, 1H), 5.05 (m, 1H), 3.92 (s, 3H), 1.48 (dd, 3H)

IR (cm$^{-1}$): 3294, 1688

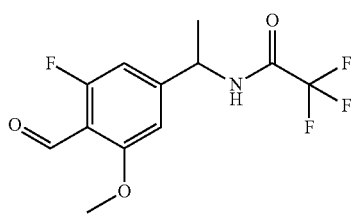

104

Intermediate 18:

The preparation of intermediate 17 is described in protocol XVI.

Intermediate 18:

Obtained starting from intermediate 17 according to the procedure used to convert intermediate 93a into intermediate 94 (Protocol XVII)

$^{1}$H NMR (400 MHz, DMSO-d$_{6}$): δ 10.31 (s, 1H), 9.94 (m, 1), 7.68 (d, 1H), 7.22 (broad s, 1H) 7.05 (broad d, 1H), 5.06 (quad, 1H), 3.93 (s, 3H), 1.48 (d, 3H)

IR (cm$^{-1}$): 3299, 1703, 1672

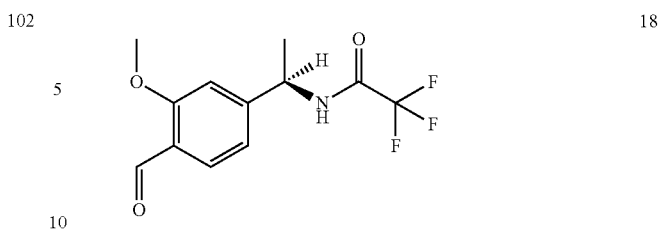

18

Intermediate 357:

2,2,2-Trifluoro-N-[(1S)-1-(8-formyl-3,4-dihydro-2H-chromen-5-yl)ethyl]acetamide

Obtained starting from (S)-(−)-1-(3-methoxyphenyl)ethylamine according to protocols XVI and XVII $^{1}$H NMR (400 MHz, DMSO-d$_{6}$): δ 10.30 (s, 1H), 10.00 (s, 1H), 7.55 (d, 1H), 7.05 (d, 1H), 5.12 (quad, 1H), 4.25 (t, 2H), 2.9-2.78 (m, 2H), 2.05 (m, 2H), 1.40 (d, 3H)

$^{19}$F NMR: −72 (dd, 1F)

IR (cm$^{-1}$): 3298, 1701, 1673.

Intermediate 453:

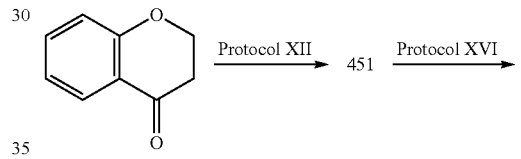

Intermediate 451:

Obtained starting from commercial 2,3-dihydro-4H-chromen-4-one according to protocol XII $^{1}$H NMR (300 MHz; DMSO-d$_{6}$): 8.70 (m, 3H), 7.60 (d, 1H), 7.25 (t, 1H), 6.95 (t, 1H), 6.85 (d, 1H), 4.50 (m, 1H), 4.25 (m, 2H), 2.20 (m, 2H)

IR (cm$^{-1}$): 3400-2250

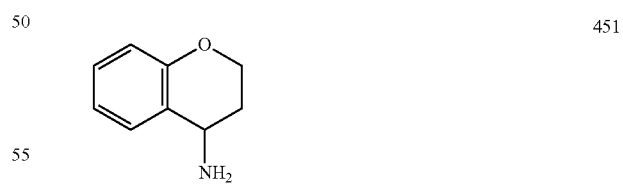

451

Intermediate 452:

Obtained starting from intermediate 451 according to protocol XVI $^{1}$H NMR (300 MHz, DMSO-d$_{6}$): δ 9.90 (d, 1H), 7.20 (td, 1H), 7.10 (dd, 1H), 6.90 (td, 1H), 6.80 (d, 1H), 5.10 (m, 1H), 4.20 (m, 2H), 2.10 (2m, 2H)

IR (cm$^{-1}$): 3266, 1699, 1546, 754, 711

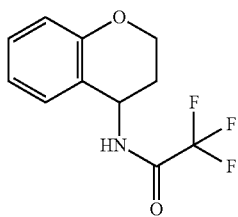

452

Intermediate 453:
Obtained starting from intermediate 452 according to the procedure used to convert intermediate 93a into intermediate 94 (Protocol XVII)
$^1$H NMR (500 MHz, CDCl$_3$): 10.35 (s, 1H), 9.95 (s, 1H), 7.65 (dd, 1H), 7.45 (dd, 1H), 7.05 (t, 1H), 5.20 (m, 1H), 4.4-4.35 (2m, 2H), 2.20 (2m, 2H)

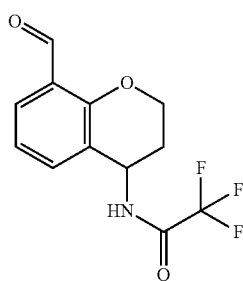

453

Intermediate 639:

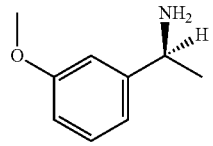

Intermediate 352:
Obtained by protection of commercial (1S)-1-(3-methoxyphenyl)ethanamine according to protocol XVI
$^1$H NMR (400 MHz, CDCl$_3$): δ 7.30 (m, 1H), 6.90 (d, 1H), 6.85 (m, 2H), 6.68 (m, 1H), 5.10 (quint, 1H), 3.80 (s, 3H), 1.58 (d, 3H)
IR (cm$^{-1}$): 3294, 1697, 1151

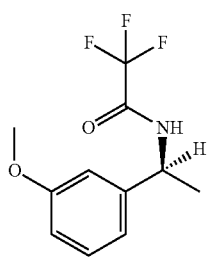

352

Intermediate 639:
Obtained starting from intermediate 352 according to the procedure used to convert intermediate 93a into intermediate 94 (Protocol XVII)

$^1$H NMR (500 MHz, DMSO-d$_6$): 10.50 (s, 1H), 7.80 (d, 1H), 6.95 (dd, 1H), 6.90 (d, 1H), 6.60 (broad s, 1H), 5.18 (m, 1H), 3.95 (s, 3H), 1.60 (dd, 3H)
IR (cm$^{-1}$): 3324, 1692-1660

639

Intermediate 53:

Intermediate 47:
Obtained starting from commercial 3-methoxy-5-methyl-benzoic acid and methylmagnesium bromide according to le protocol IX
$^1$H NMR (CDCl$_3$): δ 7.26 (s, 1H), 7.20 (s, 1H), 6.84 (s, 1H), 3.74 (s, 3H), 2.49 (s, 3H), 2.29 (s, 3H)

47

Intermediate 52:
Obtained starting from intermediate 47 according to protocol XII
$^1$H NMR (400/500 MHz; DMSO-d$_6$): 6.72 (s, 1H), 6.56 (s, 1H), 3.90 (quad, 1H), 3.70 (s, 3H), 2.25 (s, 3H), 1.70 (s, 2H), 1.20 (s, 3H)
IR (cm$^{-1}$): 3750-2750

52

Intermediate 53:

Obtained starting from intermediate 52 according to protocol XVI

¹H NMR (400 MHz, DMSO-d₆): δ 9.80 (d, 1H), 6.70-6.65 (3 broad s, 3H), 4.95 (quint, 1H), 3.70 (s, 3H), 2.25 (s, 3H), 1.40 (d, 3H)

IR (cm⁻¹): 3295, 1694, 1596, 1558, 1185, 1152, 847-685

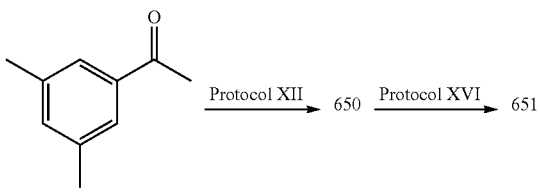

53

Intermediate 651:

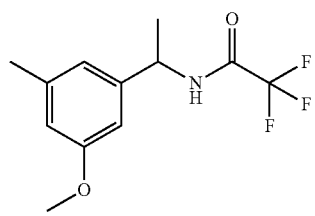

Intermediate 650:

Obtained starting from commercial 1-(3,5-dimethylphenyl)ethanone according to protocol XII ¹H NMR (300 MHz; CDCl₃): 7.00 (m, 2H); 6.90 (m, 1H), 4.05 (quad, 1H); 2.30 (s, 6H), 1.50 (m, 2H), 1.35 (d, 3H)

IR (cm⁻¹): 3364, 3290

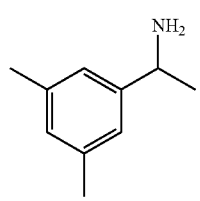

650

Intermediate 651:

Obtained starting from intermediate 650 according to protocol XVI

¹H NMR (400 MHz, CDCl₃): δ 6.98 (s, 1H), 6.92 (s, 2H), 6.40 (broad s, 1H), 5.05 (quint, 1H), 2.30 (s, 6H), 1.55 (d, 3H)

IR (cm⁻¹): 3298, 1694, 1161

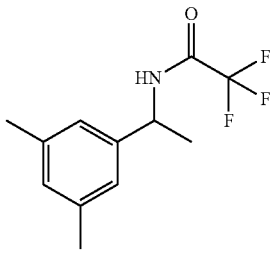

651

Intermediate 664:

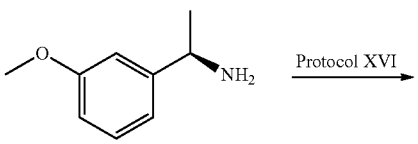

Intermediate 664 was prepared starting from intermediate 90 (which was in turn prepared according to Protocol XVII, starting from intermediate 17, which was prepared according to protocol XVI) according to the following sequence:

Intermediate 660:

To a solution of intermediate 90 (1 g, 4.3 mmoles) in DMF (25 mL) there are added potassium carbonate (0.7 g) and then allyl bromide (0.4 mL, 4.5 mmoles). The mixture is stirred at ambient temperature for 5 hours and then poured into an ice/water mixture. After decantation in the presence of ethyl ether, the organic phase is dried over MgSO₄ and then concentrated. The residue obtained is chromatographed on silica (eluant: CH₂Cl₂ 100%), intermediate 660 (0.7 g) is obtained in the form of a solid.

¹H NMR (300 MHz, DMSO-d₆): 9.70 (broad s, NH), 7.25 (t, 1H), 6.95-6.80 (m, 3H), 6.10-5.95 (m, 1H), 5.30 (2dd, 2H), 4.95 (quad, 1H), 4.55 (d, 2H), 1.45 (d, 3H)

IR (cm⁻¹): 3319, 1693, 1662, 1157

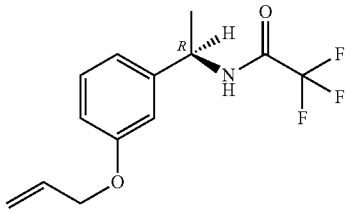

660

Intermediate 662:

A mixture of intermediate 660 (0.7 g) in diethylaniline (7 mL) is heated at 210° C. for 20 hours. The reaction mixture is washed with a 1N HCl solution and then extracted with methylene chloride. The organic phase is dried over MgSO₄ and then concentrated. The mixture of isomers 661 and 662 is chromatographed on silica (eluant: CH₂Cl₂ 100%), isomer 662 (0.15 g) is obtained.

¹H NMR (300 MHz, DMSO-d₆): 10.0-9.0 (2 broad s, NH—OH), 7.05 (t, 1H), 6.90 (d, 1H), 6.75 (d, 1H), 5.95 (m, 1H), 5.18 (quad, 1H), 4.90 (m, 2H), 3.45 (d, 2H), 1.40 (d, 3H)

IR (cm⁻¹): 3461, 3293, 1698, 1156

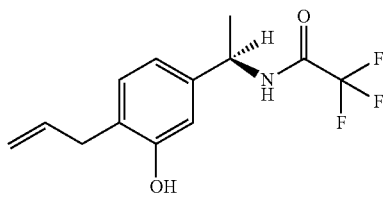

661

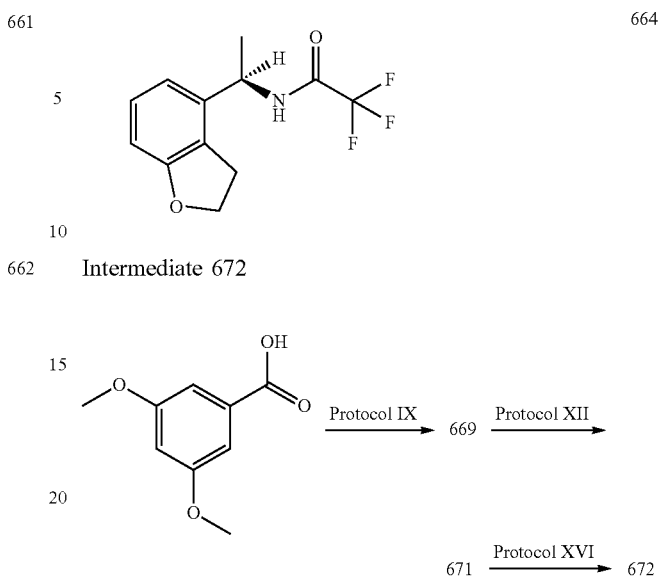

662

664

Intermediate 672

Intermediate 663:

To a solution of intermediate 662 (2 g) in a mixture of 1,4-dioxane (90 mL) and water (30 mL) there are added in succession OsO$_4$ (2.5% in t-BuOH) (1.48 g), 2,6-lutidine (1.68 mL) and NaIO$_4$ (6 g). The reaction mixture is stirred at ambient temperature for 20 hours. After decantation by AcOEt, the organic phase is washed with water, with a 1N aqueous HCl solution and with a saturated aqueous NaCl solution, and the organic phase is dried over MgSO$_4$ and then concentrated. The residue (1 g), taken up in toluene (100 mL), was treated with para-toluenesulphonic acid (0.5 g). The reaction mixture is heated for 1 hour at reflux. The mixture is concentrated in vacuo and the residue is chromatographed on silica (eluant 100% CH$_2$Cl$_2$). Intermediate 663 (1 g) is obtained in the form of a white solid.

$^1$H NMR (300 MHz, DMSO-d$_6$): 9.80 (d, 1H), 7.95 (d, 1H), 7.50 (broad d, 1H), 7.30 (t, 1H), 7.20 (broad d, 1H), 7.10 (broad d, 1H), 5.30 (quint, 1H), 1.55 (d, 3H)

IR (cm$^{-1}$): 3276, 1695

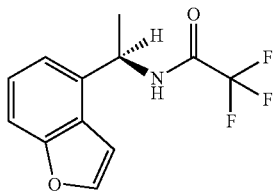

663

Intermediate 664:

Intermediate 663 (0.9 g, 3.5 mmoles) in solution in ethanol (90 mL) is hydrogenated at atmospheric pressure and ambient temperature in the presence of Pd(OH)$_2$ (0.25 g). The catalyst is filtered off, and concentration of the filtrate yields intermediate 664 (0.8 g), which is used in the following step without additional purification.

$^1$H NMR (300 MHz, DMSO-d$_6$): 9.90 (broad s, NH), 7.10 (t, 1H), 6.82 (d, 1H), 6.66 (d, 1H), 4.93 (m, 1H), 4.52 (t, 1H), 3.20 (t, 2H), 1.45 (d, 3H).

IR (cm$^{-1}$): 3272, 1696

Intermediate 669:

Obtained starting from commercial 3,5-dimethoxybenzoic acid and methylmagnesium bromide according to protocol IX $^1$H NMR (300 MHz; DMSO-d$_6$): δ 7.05 (d, 2H), 6.75 (m, 1H), 3.80 (s, 6H), 2.55 (s, 1H)

IR (cm$^{-1}$): 1681

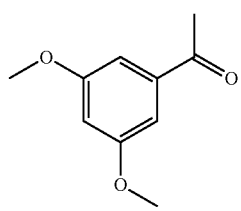

669

Intermediate 671:

Obtained starting from intermediate 669 according to protocol XII $^1$H NMR (300 MHz; CDCl$_3$): 6.50 (d, 2H); 6.32 (t, 1H), 4.02 (quad, 1H); 3.80 (s, 6H), 1.50 (s, 2H), 1.35 (d, 3H)

IR (cm$^{-1}$): 3359, 3295

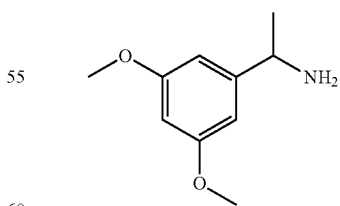

671

Intermediate 672:

Obtained starting from intermediate 671 according to protocol XVI $^1$H NMR (300 MHz, DMSO-d$_6$): δ 9.60 (d, 1H), 6.50 (d, 2H), 6.40 (t, 1H), 4.92 (m, 1H), 3.74 (s, 6H), 1.45 (d, 3H)

IR (cm$^{-1}$): 3321, 1698, 1608, 1553, 1182-1144

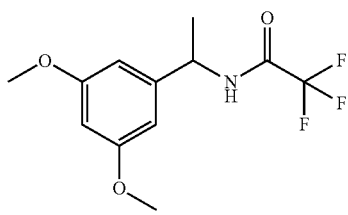

Intermediate 566:

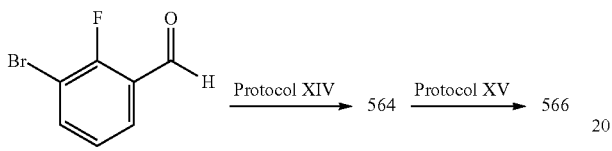

Intermediate 563:

Obtained by reaction of (R)-2-methylpropane-2-sulphinamide with commercial 3-bromo-2-fluoro-benzaldehyde according to protocol XIV Intermediate 564:

Obtained by treatment with MeMgBr (3M/ether) of intermediate 563 according to protocol XIV $^1$H NMR (400 MHz, DMSO-d$_6$): δ 7.60-7.50 (2m, 2H), 7.16 (t, 1H), 5.53 (d, 1H), 4.7 (m, 1H), 1.48 (d, 3H), 1.09 (s, 9H)

IR (cm$^{-1}$): 3189, 1040

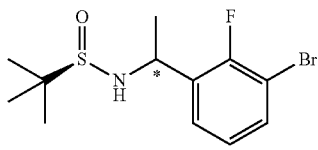

Intermediate 566:

Obtained starting from intermediate 564 according to protocol XV $^1$H NMR (400 MHz, DMSO-d$_6$): δ 7.55 (2m, 2H), 7.36 (t, 1H), 7.15 (t, 1H), 4.85 (m, 1H), 1.35 (broad s, 9H), 1.3 (d, 3H)

IR (cm$^{-1}$): 3360, 1676

α$_D$ (589 nM)=35.09 (0.005 g/mL/MeOH) at 20° C.

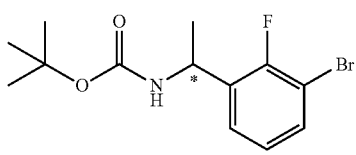

Intermediate 585:

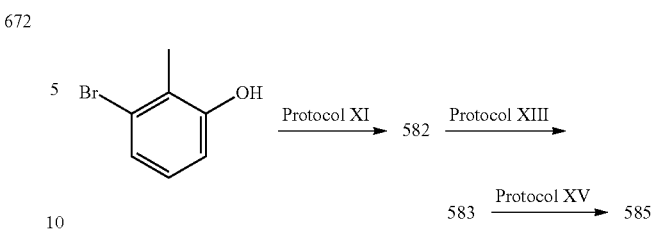

Intermediate 582:

Obtained starting from commercial 3-bromo-2-methylphenol according to protocol XI, in the presence of methyl iodide in the last step $^1$H NMR (400 MHz, DMSO-d$_6$): δ 7.45 (d, 1H), 7.35 (d, 1H), 3.72 (s, 3H), 5.10 (s, 2H), 2.58 (s, 3H), 2.35 (s, 3H)

IR (cm$^{-1}$): 1681

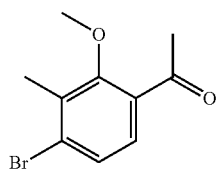

Intermediate 583:

Obtained by reaction of intermediate 582 and (R)-(+)-2-methyl-2-propanesulphinamide according to protocol XIII $^1$H NMR (400 MHz, DMSO-d6): δ 7.40 (d, 1H), 7.31 (d, 1H), 5.62 (d, 1H), 4.64 (m, 1H), 3.71 (s, 3H), 2.29 (s, 3H), 1.33 (d, 3H), 1.10 (s, 9H)

IR (cm$^{-1}$): 3215, 1009

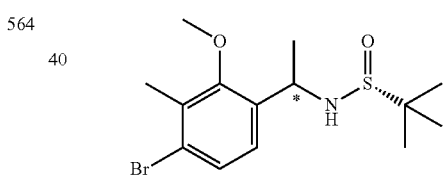

Intermediate 585:

Obtained starting from intermediate 583 according to protocol XV $^1$H NMR (400 MHz, DMSO-d$_6$): δ 7.43 (d, 1H), 7.37 (d, 1H), 7.15 (d, 1H), 4.88 (m, 1H), 3.75 (s, 3H), 2.28 (s, 3H), 1.35 (broad s, 9H), 1.21 (d, 3H)

IR (cm$^{-1}$): 3353, 1695

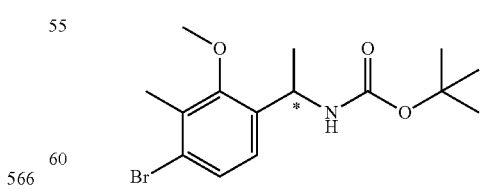

Intermediate 748:
Intermediate 743:

To a solution of commercial 2,3-dihydro-4H-chromen-4-one (20 g, 135 mmoles) in methylene chloride (400 mL) there are added ZnI$_2$ (0.8 g) and TMSCN (20 g, 201 mmoles). The reaction mixture is stirred at ambient temperature for 20 hours, and then the organic phase is washed with an aqueous NaHCO₃ solution (400 mL), dried over MgSO₄, filtered and concentrated in vacuo. Intermediate 743 is obtained (32 g) in the form of an oil, which is used in the following step.

¹H NMR (400 MHz, CDCl₃): 7.47 (dd, 1H), 7.18 (dd, 1H), 6.88 (td, 1H), 6.75 (dd, 1H), 4.25 (m, 2H), 2.30 (m, 2H), 0.08 (s, 9H)

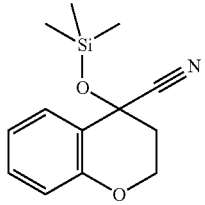

743

Intermediate 745 and intermediate 746:

To a solution of intermediate 743 (2.7 g, 11 mmoles) in THF (20 mL) there is added a solution of LiAlH₄ (1M/THF) (23 mmoles) diluted in THF (10 mL) and previously cooled to 0° C. The reaction mixture is stirred for 90 minutes at 5° C. and is then treated in succession with water, with a 20% aqueous sodium hydroxide solution and with water. The salts are filtered off, the filtrate is washed with a saturated aqueous NaCl solution, and the organic phase is dried over MgSO₄ and then concentrated. The residue (2.4 g) obtained, dissolved in methylene chloride (20 mL), is treated with a solution of trifluoroacetic anhydride (2 mL) in methylene chloride (15 mL). The reaction mixture is stirred for 20 hours at ambient temperature and then concentrated in vacuo. The residue obtained is chromatographed on silica (eluant: cyclohexane/CH₂Cl₂ 30/70 to 0/100). A mixture of intermediates 745 (exo) and 746 (endo) is obtained, which mixture is used in the following step.

Intermediate 745:

¹H NMR (400 MHz, DMSO-d₆): 10.8 (s, 1H), 7.61 (d, 1H), 7.15 (m, 2H), 6.89 (t, 1H), 6.72 (d, 1H), 4.15 (t, 2H), 2.75 (t, 2H)

IR (cm⁻¹): 3350, 1693

Intermediate 746:

¹H NMR (400 MHz, DMSO-d₆): 9.80 (s, 1), 7.22 (t, 1H), 7.15 (d, 1H), 6.92 (t, 1H), 6.80 (d, 1H), 5.75 (t, 1H), 4.75 (broad s, 2H), 4.2 (broad s, 2H)

IR (cm⁻¹): 3300, 1702, 1150

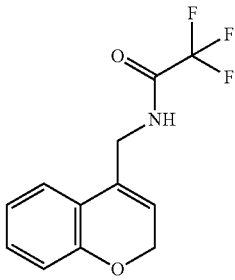

745

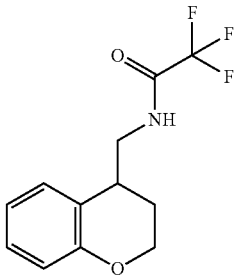

746

Intermediate 747:

The mixture of intermediates 745 and 746 (12 g, 46 mmoles) in solution in ethanol (600 mL) is hydrogenated at atmospheric pressure and ambient temperature in the presence of 10% Pd/C (1.2 g). The catalyst is filtered off, and concentration of the filtrate yields compound 747 (10 g), which is used in Protocol XVII without additional purification.

¹H NMR (400 MHz, DMSO-d₆): 9.70 (t, 1), 7.15 (d, 1H), 7.10 (t, 1H), 6.85 (t, 1H), 6.75 (d, 1H), 4.15-4.1 (m, 2H), 3.55-3.3 (m, 2H), 3.00 (m, 1H), 1.9-1.8 (m, 2H)

IR (cm⁻¹): 3300, 1702, 1150

747

Intermediate 748:

Obtained starting from intermediate 747 according to the procedure used to convert intermediate 93a into intermediate 94 (Protocol XVII)

¹H NMR (300 MHz, DMSO-d₆): 10.30 (s, 1H), 9.70 (m, 1), 7.57 (dd, 1H), 7.48 (m, 1H), 7.00 (t, 1H), 4.39 (m, 1H), 4.28 (m, 1H), 3.55 (m, 1H), 3.40 (m, 1H), 3.09 (m, 1H), 2.02 (m, 1H), 1.85 (m, 1H), 1.48 (d, 3H)

IR (cm⁻¹): 3300, 1700, 1672

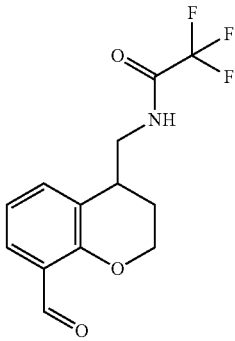

748

Coupling Reactions Yielding Compounds of the Invention

Protocol XX: Preparation of Compounds of Formula (I) Wherein X Represents —C(=O)

Compounds of formula (I) wherein X represents —C(=O) can be prepared by coupling reaction via a halogen-metal exchange according to the example of the synthesis of intermediate 127:

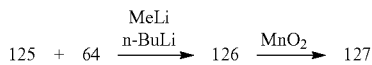

Intermediate 126:

tert-Butyl (1-{4-[(1-ethoxyisoquinolin-5-yl)(hydroxy)methyl]-3,5-difluorophenyl}-ethyl)carbamate To a solution of intermediate 64 (3 g, 8.92 mmoles) in 36 mL of THF previously cooled to −78° C. there are added 5.5 mL (8.8 mmoles) of a 1.6N solution of MeLi in pentane, an internal temperature below −75° C. being maintained. After 15 minutes' contact, 3.54 mL (8.8 mmoles) of a 2.5N solution of n-BuLi in hexane are added, the internal temperature being maintained below −75° C. After one hour's contact, a solution of intermediate 125 (1.9 g, 9.83 mmoles) in 80 mL of THF is added, the temperature being maintained below −75° C. The mixture is stirred at −78° C. for 1 hour, and then a solution of THF with 20% water is added to the mixture. After return to ambient temperature, the mixture is decanted in the presence of ethyl acetate and of a saturated NaCl solution. The organic phase is dried over MgSO₄. Evaporation under reduced pressure yields an oil, which is purified on silica gel (eluant AcOEt/methylene chloride 10/90). Intermediate 126 (2.05 g) is obtained in the form of a colourless amorphous solid.

$^1$H NMR (400 MHz, DMSO-d$_6$): δ 8.17-8.14 (m, 2H), 7.94 (m, 1H), 7.67 (dd, 1H), 7.38 (broad d, 1H), 7.18 (broad d, 1H), 6.95 (m, 2H), 6.52 (broad s, 1H), 6.34 (broad s, 1H), 4.57 (m, 1H), 1.41 (t, 3H), 1.24 (d, 3H), 4.49 (quad, 2H), 1.34-1.15 (2 broad s, 9H)

IR (cm$^{-1}$): 3312, 1685, 1161, 1009, 855-804-757

Intermediate 127:

tert-Butyl (1-{4-[(1-ethoxyisoquinolin-5-yl)carbonyl]-3,5-difluorophenyl}ethyl)-carbamate A solution of intermediate 126 (2.05 g, 4.47 mmoles) in 490 mL of methylene chloride is treated with 7.4 g (85 mmoles) of MnO₂, and the mixture is stirred for 20 hours. The mixture is filtered over Celite®, and the Celite® is rinsed with CH₂Cl₂ and then with AcOEt. Evaporation under reduced pressure yields 1.85 g of intermediate 127 in the form of a white solid, which can be used without additional treatment in the following step or can be purified on silica (eluant AcOEt/methylene chloride 5/95).

$^1$H NMR (300 MHz, DMSO-d$_6$): δ 8.55 (d, 1H), 8.1-8.2 (dd, 2H), 8.05 (d, 1H), 7.7 (m, 1H), 7.55 (d, 1H), 7.20 (d, 2H), 4.75 (m, 1H), 4.55 (quad, 2H), 1.45 (t, 3H), 1.3-1.45 (d and s, 12H)

IR (cm$^{-1}$): 3362-3309, 1675, 1523, 1255-1160, 856-811-788-752

This sequence was used to prepare the following intermediates:

Intermediate 7:

tert-Butyl {1-[4-(isoquinolin-5-ylcarbonyl)phenyl]ethyl}carbamate

Obtained by oxidation of the intermediate resulting from the coupling of 5 and 3

$^1$H NMR (300 MHz, DMSO-d$_6$): δ 9.45 (s, 1H), 8.55 (d, 1H), 8.35 (d, 1H), 7.95 (d, 1H), 7.75 (m, 4H), 7.50 (d, 1H), 7.45 (d, 2H), 4.70 (m, 1H), 1.35 (s, 9H), 1.30 (d, 3H)

IR (cm$^{-1}$): 1697, 1654

Intermediate 15:

tert-Butyl {(1R)-1-[4-(isoquinolin-5-ylcarbonyl)-3-methylphenyl]ethyl}carbamate

Obtained by oxidation of the intermediate resulting from the coupling of 13 and 3:

$^1$H NMR (400 MHz, DMSO-d$_6$): δ 9.46 (s, 1H), 8.61 (d, 1H), 8.39 (d, 1H), 8.17 (d, 1H), 7.82 (d, 1H), 7.75 (t, 1H), 7.47 (d, 1H), 7.32 (broad s, 1H), 7.28 (d, 1H), 7.20 (dl, 1H), 4.65 (m, 1H), 2.39 (s, 3H), 1.38 (s, 9H), 1.33 (d, 3H)

IR (cm$^{-1}$): 3359, 1680, 1656

Intermediate 34:

tert-Butyl [5-(isoquinolin-5-ylcarbonyl)-6-methyl-2,3-dihydro-1H-inden-1-yl]-carbamate Obtained by oxidation of the intermediate resulting from the coupling of 32 and 3

$^1$H NMR (300 MHz, DMSO-d$_6$): δ 9.45 (s, 1H), 8.60 (d, 1H), 8.35 (d, 1H), 8.20 (d, 1H), 7.80 (m, 1H), 7.70 (m, 1H), 7.20 (s, 1H), 7.15 (s, 1H), 7.10-6.90 (m, 1H), 5.00 (m, 1H), 2.90-2.60 (2m, 2H), 2.35 (m, 1H), 2.30 (s, 3H), 1.85 (m, 1H), 1.40 (s, 9H)

Intermediate 42:

tert-Butyl [5-(isoquinolin-5-ylcarbonyl)-6-methyl-2,3-dihydro-1H-inden-1-yl]-carbamate Obtained by oxidation of the intermediate resulting from the coupling of 40 and 3:

$^1$H NMR (300 MHz, DMSO-d$_6$): δ 9.45 (s, 1H), 8.62 (d, 1H), 8.42 (d, 1H), 8.20 (d, 1H), 7.95 (d, 1H), 7.78 (t, 1H), 7.68 (t, 1H), 7.52 (broad d, 1H), 7.32 (d, 1H), 7.25 (d, 1H), 4.71 (m, 1H), 1.35 (s, 9H), 1.35 (t, 3H)

Intermediate 51:

tert-Butyl {1-[3,5-difluoro-4-(isoquinolin-5-ylcarbonyl)phenyl]ethyl}carbamate

Obtained by oxidation of the intermediate resulting from the coupling of 64 and 3:

$^1$H NMR (300 MHz, DMSO-d$_6$): δ 9.50 (s, 1H), 8.70 (d, 1H), 8.63 (d, 1H), 8.50 (d, 1H), 8.10 (d, 1H), 7.80 (t, 1H), 7.52 (d, 1H), 7.25 (d, 2H), 4.70 (m, 1H), 1.40 (s, 9H), 1.35 (d, 3H)

IR (cm$^{-1}$): 3360, 1684, 1667, 1634, 1248-1167, 862-824-761

Intermediate 60c:

tert-Butyl {1-[3-fluoro-4-(isoquinolin-5-ylcarbonyl)-5-methylphenyl]ethyl}carbamate Obtained by oxidation of the intermediate resulting from the coupling of the carbamate of intermediate 60b and 3:

¹H NMR (300 MHz, DMSO-d₆): δ 9.40 (s, 1H), 8.70 (m, 2H), 8.45 (d, 1H), 7.95 (dd, 1H), 7.80 (t, 1H), 7.45 (m, 1H), 7.20 (d, 1H), 7.10 (dd, 1H), 4.70 (m, 1H), 2.10 (s, 3H), 1.40 (broad s, 9H), 1.35 (d, 3H)

IR (cm⁻¹): 3500-3080, 1695, 1664, 1619, 1516, 1164, 837-680

Intermediate 75:

tert-Butyl {1-[3-chloro-4-(isoquinolin-5-ylcarbonyl)phenyl]ethyl}carbamate

Obtained by oxidation of the intermediate resulting from the coupling of 73 and 3

¹H NMR (300 MHz, DMSO-d₆): δ 9.40 (s, 1H), 8.70 (d, 1H), 8.50 (d, 1H), 8.45 (d, 1H), 7.90 (dd, 1H), 7.75 (t, 1H), 7.60 (d, 1H), 7.50 (broad s, 1H), 7.40 (dd, 1H), 4.70 (quint, 1H), 1.40 (m, 12H)

IR (cm⁻¹): 3500-3060, 1695, 1664, 1600, 1510, 1163, 834-647

Intermediate 89:

tert-Butyl [5-(isoquinolin-5-ylcarbonyl)-6-methoxy-1-methyl-2,3-dihydro-1H-inden-1-yl]carbamate Obtained by oxidation of the intermediate resulting from the coupling of 87 and 3

¹H NMR (300 MHz, DMSO-d₆): δ 9.40 (s, 1H), 8.55 (d, 1H), 8.30 (broad d, 1H), 8.20 (d, 1H), 7.80 (broad d, 1H), 7.70 (t, 1H), 7.30 (s, 1H), 7.00 (s, 1H), 6.85 (m, 1H), 3.40 (s, 3H), 3.00-2.70 (m, 2H), 2.55 (m, 1H), 2.05 (m, 1H), 1.45 (s, 3H), 1.30 (s, 9H)

IR (cm⁻¹): 3390-3240, 1702, 1654

Intermediate 114:

tert-Butyl {1-[3-fluoro-4-(isoquinolin-5-ylcarbonyl)-2-methylphenyl]ethyl}carbamate Obtained by oxidation of the intermediate resulting from the coupling of 112 and 3

¹H NMR (300 MHz, DMSO-d₆): δ 9.50 (s, 1H), 8.60 (d, 1H), 8.40 (d, 1H), 8.20 (d, 1H), 7.95 (d, 1H), 7.80 (t, 1H), 7.62 (d, 1H), 7.50 (t, 1H), 7.35 (d, 1H), 4.90 (m, 1H), 2.22 (s, 3H), 1.40 (s, 9H), 1.30 (d, 3H)

IR (cm⁻¹): 3360, 1680, 1655, 1615, 1525

Intermediate 122:

tert-Butyl {1-[8-(isoquinolin-5-ylcarbonyl)-2,3-dihydro-1,4-benzodioxin-5-yl]ethyl}-carbamate Obtained by oxidation of the intermediate resulting from the coupling of 120 and 3

¹H NMR (400/500 MHz, DMSO-d₆): δ 9.40 (1H), 8.60 (1H), 8.35 (1H), 8.30 (1H), 7.92 (1H), 7.75 (1H), 7.45 (1H), 7.05-7.00 (2H), 4.95 (1H), 4.28-4.00 (4H), 1.40 (9H), 1.30 (3H)

IR (cm⁻¹): 3358, 1677, 1246-1161-1058, 833-787-760

Intermediate 137:

tert-Butyl {1-[3-chloro-5-fluoro-4-(isoquinolin-5-ylcarbonyl)phenyl]ethyl}carbamate Obtained by oxidation of the intermediate resulting from the coupling of 135 and 3

¹H NMR (300 MHz, DMSO-d₆): δ 9.50 (s, 1H), 8.80 (d, 1H), 8.50 (d, 1H), 8.02 (d, 1H), 7.80 (t, 1H), 7.53 (d, 1H), 7.45 (s, 1H), 7.38 (d, 1H), 4.72 (m, 1H), 1.40 (broad s, 9H), 1.38 (d, 3H), 1.40 (s, 9H), 1.38 (d, 3H)

IR (cm⁻¹): 3400, 1675, 1615-1569, 1245-1164, 837-761

Intermediate 160:

tert-Butyl {2-[3,5-difluoro-4-(isoquinolin-5-ylcarbonyl)phenyl]propan-2-yl}carbamate Obtained by oxidation of the intermediate resulting from the coupling of 158 and 3

¹H NMR (400 MHz, DMSO-d₆): δ 9.50 (s, 1H), 8.70 (d, 1H), 8.65 (d, 1H), 8.05 (broad d, 1H), 7.80 (t, 1H), 7.50 (d, 1H), 7.35 (broad s, 1H), 7.20 (d, 2H), 1.55 (s, 6H), 1.35 (broad s, 9H)

IR (cm⁻¹): 3256, 3206, 1708, 1663, 1633

Intermediate 165:

tert-Butyl [(1S)-1-{4-[(1-ethoxyisoquinolin-5-yl)carbonyl]-3,5-difluorophenyl}ethyl]-carbamate Obtained by oxidation of the intermediate resulting from the coupling of 146 and 125

¹H NMR (400/500 MHz, DMSO-d₆): δ 8.55 (d, 1H), 8.20 (d, 1H), 8.15 (d, 1H), 8.05 (broad d, 1H), 7.70 (t, 1H), 7.55 (broad d, 1H), 7.25 (d, 2H), 4.75 (m, 1H), 4.55 (quad, 2H), 1.45 (t, 3H), 1.40 (s, 9H), 1.35 (d, 3H)

IR (cm⁻¹): 3300, 1677, 1260

Intermediate 170:

tert-Butyl [(1R)-1-{4-[(1-ethoxyisoquinolin-5-yl)carbonyl]-3,5-difluorophenyl}ethyl]-carbamate Obtained by oxidation of the intermediate resulting from the coupling of 145 and 125

¹H NMR (400 MHz, DMSO-d₆): δ 8.55 (d, 1H), 8.20 (d, 1H), 8.15 (d, 1H), 8.05 (d, 1H), 7.75 (m, 1H), 7.55 (d, 1H), 7.25 (m, 2H), 4.75 (m, 1H), 4.55 (quad, 2H), 1.45 (t, 3H), 1.40 (s, 9H), 1.35 (d, 3H)

IR (cm⁻¹): 3363, 1681

Intermediate 172:

tert-Butyl (2-{4-[(1-ethoxyisoquinolin-5-yl)carbonyl]-3,5-difluorophenyl}propan-2-yl)-carbamate Obtained by oxidation of the intermediate resulting from the coupling of 158 and 125

¹H NMR (400 MHz, DMSO-d₆): δ 8.55 (d, 1H), 8.20-8.10 (dd, 2H), 8.00 (d, 1H), 7.75 (t, 1H), 7.35 (m, 1H), 7.20 (d, 2H), 4.55 (q, 2H), 1.50 (s, 6H), 1.45 (t, 3H), 1.35 (broad s, 9H)

IR (cm⁻¹): 1712, 1682, 1670

Intermediate 176:

tert-Butyl {4-[(1-ethoxyisoquinolin-5-yl)carbonyl]-3,5-difluorobenzyl}carbamate

Obtained by oxidation of the intermediate resulting from the coupling of 174 and 125

¹H NMR (400 MHz, DMSO-d₆): δ 8.54 (dt, 1H), 8.19 (d, 1H), 8.14 (broad d, 1H), 8.05 (broad d, 1H), 7.71 (dd, 1H), 7.56 (t, 1H), 7.14 (m, 2H), 4.57 (quad, 2H), 4.24 (d, 2H), 1.46 (t, 3H), 1.41 (broad s, 9H)

IR (cm⁻¹): 3327, 1673, 1251-1160, 1040

Intermediate 178:

tert-Butyl (1-{4-[(1-ethoxyisoquinolin-5-yl)carbonyl]-3-fluoro-2-methylphenyl}ethyl)-carbamate Obtained by oxidation of the intermediate resulting from the coupling of 112 and 125

¹H NMR (400 MHz, DMSO-d6): δ 8.45 (dt, 1H), 8.10 (d, 1H), 7.90 (d, 1H), 7.70 (m, 1H), 7.65 (m, 1H), 7.60 (d, 1H), 7.50 (t, 1H), 7.30 (d, 1H), 4.85 (m, 1H), 4.55 (q, 2H), 2.20 (s, 3H), 1.45 (t, 3H), 1.35 (s, 9H), 1.30 (d, 3H)
IR (cm⁻¹): 3340, 1703, 1660.
Intermediate 180:

tert-Butyl (1-{4-[(1-ethoxyisoquinolin-5-yl)carbonyl]-3-fluorophenyl}ethyl)carbamate Obtained by oxidation of the intermediate resulting from the coupling of 40 and 125
¹H NMR (400 MHz, DMSO-d₆): δ 8.47 (d, 1H), 8.10 (d, 1H), 7.90 (d, 1H), 7.70 (t and m, 2H), 7.65 (d, 1H), 7.55 (broad d, 1H), 7.31 (d, 1H), 7.27 (d, 1H), 4.71 (quint, 1H), 4.55 (quad, 2H), 1.48 (t, 3H), 1.45 (d, 3H), 1.40 (s, 9H)
IR (cm⁻¹): 3344, 1681, 1655
Intermediate 189:

tert-Butyl {2-[3-chloro-4-(isoquinolin-5-ylcarbonyl)phenyl]propan-2-yl}carbamate Obtained by oxidation of the intermediate resulting from the coupling of 187 and 3
¹H NMR (400 MHz, DMSO-d₆): δ 9.48 (s, 1H), 8.68 (d, 1H), 8.49 (d, 1H), 8.44 (broad d, 1H), 7.83 (broad d, 1H), 7.76 (t, 1H), 7.57 (d, 1H), 7.48 (broad s, 1H), 7.46 (broad d, 1H), 7.37 (broad s, 1H), 1.55 (s, 6H), 1.35 (broad s, 9H)
IR (cm⁻¹): 3265, 1707-1657
Intermediate 202:

tert-Butyl [(1R)-1-{4-[(1-ethoxyisoquinolin-5-yl)carbonyl]-3-fluoro-2-methylphenyl}-ethyl]carbamate Obtained by oxidation of the intermediate resulting from the coupling of 200 and 125
¹H NMR (400 MHz, DMSO-d₆): δ 8.44 (d, 1H), 8.10 (d, 1H), 7.85 (d, 1H), 7.70 (t, 1H), 7.66 (m, 1H), 7.60 (d, 1H), 7.50 (t, 1H), 7.35 (d, 1H), 4.85 (m, 1H), 4.55 (quad, 2H), 2.20 (s, 3H), 1.47 (t, 3H), 1.38 (s, 9H), 1.30 (d, 3H)
IR (cm⁻¹): 3366, 1681, 1670, 1615-1572, 1291-1265-1251-1167, 808-781-755
Intermediate 213:

tert-Butyl (1-{4-[(1-ethoxyisoquinolin-5-yl)carbonyl]-3,5-difluorophenyl}ethyl)methylcarbamate Obtained by oxidation of the intermediate resulting from the coupling of 211 and 125
¹H NMR (400 MHz, DMSO-d₆): δ 8.55 (d, 1H), 8.20 (d, 1H), 8.20 (d, 1H), 8.05 (d, 1H), 7.71 (t, 1H), 7.15 (d, 2H), 5.30 (m, 1H), 4.59 (quad, 2H), 2.70 (s, 3H), 1.52 (d, 3H), 1.49 (t, 3H), 1.43 (s, 9H)
IR (cm⁻¹): 1673, 1632, 1615
Intermediate 219:

tert-Butyl [(1S)-1-{4-[(1-ethoxyisoquinolin-5-yl)carbonyl]-3-fluoro-2-methylphenyl}-ethyl]carbamate Obtained by oxidation of the intermediate resulting from the coupling of 217 and 125
¹H NMR (400 MHz, DMSO-d₆): δ 8.44 (d, 1H), 8.09 (d, 1H), 7.87 (dl, 1H), 7.69 (t, 1H), 7.67 (m, 1H), 7.62 (dl, 1H), 7.51 (t, 1H), 7.34 (d, 1H), 4.87 (m, 1H), 4.56 (quad, 2H), 2.21 (s, 3H), 1.46 (t, 3H), 1.37 (broad s, 9H), 1.29 (d, 3H)
IR (cm⁻¹): 3362, 1738, 1681-1666, 1527, 1291-1165

Intermediate 227:

tert-Butyl {(1S)-5-[(1-ethoxyisoquinolin-5-yl)carbonyl]-2,3-dihydro-1H-inden-1-yl}-carbamate Obtained by oxidation of the intermediate resulting from the coupling of 615b and 125
¹H NMR (300 MHz, DMSO-d₆): δ 8.40 (d, 1H), 8.00 (d, 1H), 7.82 (d, 1H), 7.72 (t, 1H), 7.60 (s, 1H), 7.58 (d, 1H), 7.34 (d, 1H), 7.32 (d, 1H), 7.23 (d, 1H), 5.03 (m, 1H), 4.55 (quad, 2H), 2.90 (dd, 1H), 2.80 (dd, 1H), 2.38 (m, 1H), 1.85 (m, 1H), 1.42 (s, 9H)
IR (cm⁻¹): 3330, 1708-1694, 1656, 1266-1244, 810-756
Intermediate 247:

tert-Butyl (1-{4-[(1-ethoxyisoquinolin-5-yl)carbonyl]-3-fluoro-2-methoxyphenyl}-ethyl)carbamate Obtained by oxidation of the intermediate resulting from the coupling of 245 and 125
¹H NMR (400 MHz, DMSO-d₆): δ 8.45 (d, 1H), 8.10 (d, 1H), 7.95 (d, 1H), 7.70 (m, 2H), 7.55 (d, 1H), 7.40 (m, 1H), 7.30 (d, 1H), 5.00 (m, 1H), 4.55 (quad, 2H), 3.85 (s, 3H), 1.45 (t, 3H), 1.35 (s, 9H), 1.30 (d, 3H)
IR (cm⁻¹): 3341, 1702, 1666
Intermediate 257:

tert-Butyl (1-{4-[(1-ethoxyisoquinolin-5-yl)carbonyl]-2,3-dimethylphenyl}ethyl)-carbamate Obtained by oxidation of the intermediate resulting from the coupling of 255 and 125
¹H NMR (400 MHz, DMSO-d₆): δ 8.45 (d, 1H), 8.10 (d, 1H), 7.90 (d, 1H), 7.75 (d, 1H), 7.65 (m, 1H), 7.50 (d, 1H), 7.30 (d, 1H), 7.10 (d, 1H), 4.95 (m, 1H), 4.55 (quad, 2H), 2.30 (2s, 6H), 1.45 (t, 3H), 1.35 (s, 9H), 1.25 (d, 3H)
IR (cm⁻¹): 3346, 1701, 1659
Intermediate 273:

tert-Butyl [(1R)-1-{4-[(1-ethoxyisoquinolin-5-yl)carbonyl]-3-methylphenyl}ethyl]-carbamate Obtained by oxidation of the intermediate resulting from the coupling of 13 and 125
¹H NMR (300/400 MHz, DMSO-d₆): δ 8.42 (d, 1H), 8.06 (d, 1H), 7.75 (d, 1H), 7.70 (t, 1H), 7.60 (d, 1H), 7.45 (dl, 1H), 7.30 (broad s, 1H), 7.25 (d, 1H), 7.18 (broad d, 1H), 4.65 (quint, 1H), 4.55 (quad, 2H), 2.40 (s, 3H), 1.45 (t, 3H), 1.40 (broad s, 9H), 1.32 (d, 3H)
IR (cm⁻¹): 3336, 1697, 1657
Intermediate 312:

tert-Butyl (1-{2-ethoxy-4-[(1-ethoxyisoquinolin-5-yl)carbonyl]-3-fluorophenyl}ethyl)-carbamate Obtained by oxidation of the intermediate resulting from the coupling of 310 and 125
¹H NMR (400 MHz, DMSO-d₆): δ 8.45 (d, 1H), 8.10 (d, 1H), 7.90 (d, 1H), 7.70 (m, 2H), 7.55 (d, 1H), 7.35 (m, 1H), 7.30 (d, 1H), 5.00 (m, 1H), 4.55 (quad, 2H), 4.05 (m, 2H), 1.45 (t, 3H), 1.40 (s, 9H), 1.35 (d, 3H), 1.30 (d, 3H)
IR (cm⁻¹): 3348, 1710, 1661
Intermediate 315:

tert-Butyl [(1S)-1-{4-[(1-ethoxyisoquinolin-5-yl)carbonyl]-3-methylphenyl}ethyl]-carbamate Obtained by oxidation of the intermediate resulting from the coupling of 313 and 125

¹H NMR (400 MHz, DMSO-d₆): δ 8.45 (d, 1H), 8.05 (d, 1H), 7.80 (d, 1H), 7.70 (m, 1H), 7.60 (d, 1H), 7.45 (d, 1H), 7.30 (s, 1H), 7.25 (d, 1H), 7.20 (dd, 1H), 4.65 (m, 1H), 4.55 (quad, 2H), 2.40 (s, 3H), 1.45 (t, 3H), 1.35 (s, 9H), 1.30 (d, 3H)
IR (cm⁻¹): 3392-3355, 1685, 1649

Intermediate 351:

tert-Butyl [(1R)-1-{8-[(1-ethoxyisoquinolin-5-yl)carbonyl]-2,3-dihydro-1,4-benzodioxin-5-yl}ethyl]carbamate Obtained by oxidation of the intermediate resulting from the coupling of 349b and 125
¹H NMR (400 MHz, DMSO-d₆): δ 8.41 (d, 1H), 8.07 (d, 1H), 7.85 (d, 1H), 7.77 (d, 1H), 7.65 (dd, 1H), 7.42 (d, 1H), 7.03 (d, 1H), 6.98 (d, 1H), 4.93 (m, 1H), 4.55 (quad, 2H), 4.25 (m, 2H), 4.02 (m, 2H), 1.45 (t, 3H), 1.38 (s, 9H), 1.26 (d, 3H)
IR (cm⁻¹): 3346, 1703, 1656, 1614

Intermediate 373:

tert-Butyl [(1S)-1-{8-[(1-ethoxyisoquinolin-5-yl)carbonyl]-2,3-dihydro-1,4-benzodioxin-5-yl}ethyl]carbamate Obtained by oxidation of the intermediate resulting from the coupling of 371 and 125
¹H NMR (400 MHz, DMSO-d₆): δ 8.41 (d, 1H), 8.07 (d, 1H), 7.85 (d, 1H), 7.76 (d, 1H), 7.66 (dd, 1H), 7.43 (d, 1H), 7.03 (d, 1H), 6.98 (d, 1H), 4.93 (m, 1H), 4.55 (quad, 2H), 4.25 (m, 2H), 4.02 (m, 2H), 1.45 (t, 3H), 1.38 (s, 9H), 1.26 (d, 3H)
IR (cm⁻¹): 3346, 1703, 1656, 1614

Intermediate 391:

tert-Butyl [(1S)-1-{8-[(1-ethoxyisoquinolin-5-yl)carbonyl]-2,3-dihydro-1,4-benzodioxin-5-yl}ethyl]carbamate Obtained by oxidation of the intermediate resulting from the coupling of 13 and 294
¹H NMR (400 MHz, DMSO-d₆): δ 8.36 (d, 1H), 7.69 (d, 1H), 7.56 (t, 1H), 7.51 (s, 1H), 7.44 (broad d, 1H), 7.30 (s, 1H), 7.24 (d, 1H), 7.18 (d, 2H), 4.64 (m, 1H), 4.54 (quad, 2H), 2.46 (s, 3H), 2.38 (s, 3H), 1.45 (t, 3H), 1.37 (broad s, 9H), 1.32 (d, 3H)
IR (cm⁻¹): 3350, 1677, 1658

Intermediate 408:

tert-Butyl [(1S)-1-{4-[(1-ethoxy-4-methylisoquinolin-5-yl)carbonyl]-3-methylphenyl}-ethyl]carbamate Obtained by oxidation of the intermediate resulting from the coupling of 313 and 301
¹H NMR (400 MHz, DMSO-d₆): δ 8.40 (d, 1H), 7.85 (s, 1H), 7.70 (t, 1H), 7.60 (dd, 1H), 7.45 (d, 1H), 7.35 (s, 1H), 7.25 (d, 1H), 7.15 (dd, 1H), 4.65 (m, 1H), 4.50 (quad, 2H), 2.60 (s, 3H), 2.10 (s, 3H), 1.50 (t, 3H), 1.35 (m, 9H), 1.30 (d, 3H)
IR (cm⁻¹): 3410, 1700, 1662

Intermediate 462:

tert-Butyl [(1R)-1-{4-[(1-ethoxy-4-methylisoquinolin-5-yl)carbonyl]-3-methylphenyl}-ethyl]carbamate Obtained by oxidation of the intermediate resulting from the coupling of 13 and 302
¹H NMR (400 MHz, DMSO-d₆): δ 8.40 (d, 1H), 7.85 (s, 1H), 7.70 (t, 1H), 7.60 (dd, 1H), 7.45 (d, 1H), 7.35 (s, 1H), 7.25 (d, 1H), 7.15 (dd, 1H), 4.65 (m, 1H), 4.50 (quad, 2H), 2.60 (s, 3H), 2.10 (s, 3H), 1.50 (t, 3H), 1.35 (m, 9H), 1.30 (d, 3H)
IR (cm⁻¹): 3335, 1698, 1662

Intermediate 542:

tert-Butyl [(1R)-1-{4-[(1-ethoxyisoquinolin-5-yl)carbonyl]-3-fluoro-5-methoxyphenyl}-ethyl]carbamate Obtained by oxidation of the intermediate resulting from the coupling of 540 and 125
¹H NMR (400 MHz, DMSO-d₆): δ 8.5 (d, 1H), 8.25 (d, 1H), 8.2 (d, 1H), 7.9 (d, 1H), 7.7 (t, 1H), 7.5 (d, 1H), 7.0 (s, 1H), 6.9 (d, 1H), 4.7 (m, 1H), 4.55 (quad, 2H), 3.7 (s, 3H), 1.45 (t, 3H), 1.4 (s, 9H), 1.35 (d, 3H).
IR (cm⁻¹): 3389, 1680, 1168

Intermediate 591:

tert-Butyl {1-[4-(isoquinolin-5-ylcarbonyl)phenyl]ethyl}carbamate

Obtained by oxidation of the intermediate resulting from the coupling of 589 and 3
¹H NMR (300 MHz, DMSO-d₆): δ 9.45 (s, 1H), 8.55 (d, 1H), 8.35 (d, 1H), 7.95 (d, 1H), 7.75 (m, 4H), 7.50 (d, 1H), 7.45 (d, 2H), 4.70 (m, 1H), 1.35 (s, 9H), 1.30 (d, 3H)
IR (cm⁻¹): 1697, 1654

Intermediate 596:

tert-Butyl {(1S)-1-[4-(isoquinolin-5-ylcarbonyl)phenyl]ethyl}carbamate

Obtained by oxidation of the intermediate resulting from the coupling of 594 and 3
¹H NMR (300 MHz, DMSO-d₆): δ 9.45 (s, 1H), 8.55 (d, 1H), 8.35 (d, 1H), 7.95 (d, 1H), 7.75 (m, 4H), 7.50 (d, 1H), 7.45 (d, 2H), 4.70 (m, 1H), 1.35 (s, 9H), 1.30 (d, 3H)
IR (cm⁻¹): 1697, 1654

Intermediate 603:

tert-Butyl {2-[4-(isoquinolin-5-ylcarbonyl)phenyl]propan-2-yl}carbamate

Obtained by oxidation of the intermediate resulting from the coupling of 601 and 3
¹H NMR (300 MHz, DMSO-d₆): δ 9.50 (s, 1H), 8.55 (d, 1H), 8.35 (d, 1H), 7.90 (broad d, 1H), 7.80 (m, 2H), 7.75-7.5 (dd, 4H), 7.30 (m, 1H), 1.55 (s, 6H), 1.30 (m, 9H)
IR (cm⁻¹): 1697, 1654
LCMS [M+H]+=391

Intermediate 610:

tert-Butyl {1-[4-(isoquinolin-5-ylcarbonyl)phenyl]cyclobutyl}carbamate

Obtained by oxidation of the intermediate resulting from the coupling of 608 and 3
¹H NMR (300 MHz, DMSO-d₆): δ 9.50 (s, 1H), 8.55 (d, 1H), 8.40 (d, 1H), 7.9-7.7 (m, 4H), 7.8-7.5 (dd, 4H), 2.40 (m, 4H), 2.05-1.8 (m, 2H), 1.30 (m, 9H)
IR (cm⁻¹): 1697, 1654
LCMS [M+H]+=403

Intermediate 617:

tert-Butyl [(1R)-5-(isoquinolin-5-ylcarbonyl)-2,3-dihydro-1H-inden-1-yl]carbamate Obtained by oxidation of the intermediate resulting from the coupling of 615a and 3

$^1$H NMR (300 MHz, DMSO-d$_6$): δ 9.50 (s, 1H), 8.55 (d, 1H), 8.35 (d, 1H), 7.90 (d, 1H), 7.80 (dd, 1H), 7.80 (d, 1H), 7.65 (d and s, 2H), 7.35 (broad t, 1H), 5.05 (m, 1H), 2.9-2.8 (m, 2H), 2.4-1.85 (m, 2H), 1.45 (s, 9H)

IR (cm$^{-1}$): 3300, 1692-1654

Optical purity (OJ-H column, eluant: n-propyl alcohol/heptane/diethylamine: 10/90/0.1, detection 270 nm): 99%.

Intermediate 619:

tert-Butyl [(1S)-5-(isoquinolin-5-ylcarbonyl)-2,3-dihydro-1H-inden-1-yl]carbamate Obtained by oxidation of the intermediate resulting from the coupling of 615b and 3

$^1$H NMR (300 MHz, DMSO-d$_6$): δ 9.40 (s, 1H), 8.55 (d, 1H), 8.35 (d, 1H), 7.90 (d, 1H), 7.85 (d, 1H), 7.80 (d, 1H), 7.65 (m, 2H), 7.35 (d, 1H), 5.05 (m, 1H), 3.0-2.7 (2m, 2H), 2.41-1.9 (2m, 2H), 1.45 (s, 9H)

IR (cm$^{-1}$): 3300, 1692-1654

Optical purity (OJ-H column, eluant: n-propyl alcohol/heptane/diethylamine 10/90/0.1,
 detection 270 nm): >98%

Intermediate 625:

tert-Butyl {4-[4-(isoquinolin-5-ylcarbonyl)phenyl]tetrahydro-2H-pyran-4-yl}-carbamate Obtained by oxidation of the intermediate resulting from the coupling of 623 and 3

$^1$H NMR (400 MHz, DMSO-d$_6$): δ 9.45 (s, 1H), 8.54 (d, 1H), 8.38 (d, 1H), 7.92 (d, 1H), 7.80 (d and t, 2H), 7.76/7.55 (2d, 4H), 7.40 (broad s, 1H, NH), 3.70 (m, 4H), 2.2/1.9 (2m, 4H), 1.35 (broad s, 9H)

IR (cm$^{-1}$): 3300, 1708-1695, 1655

Intermediate 635:

tert-Butyl [5-(isoquinolin-5-ylcarbonyl)-1-methyl-2,3-dihydro-1H-inden-1-yl]-carbamate Obtained by oxidation of the intermediate resulting from the coupling of 633 and 3

$^1$H NMR (300 MHz, DMSO-d$_6$): δ 9.40 (s, 1H), 8.55 (d, 1H), 8.35 (d, 1H), 7.90 (d, 1H), 7.80 (m, 2H), 7.60 (m, 2H), 7.35 (d, 1H), 7.20 (broad s, 1H, NH), 3.00-2.8 (m, 2H), 2.55-1.95 (2m, 2H), 1.40 (s, 3H), 1.30 (broad s, 9H)

IR (cm$^{-1}$): 3340-3230, 1700, 1653, 1616

Intermediate 637:

tert-Butyl {(1S)-1-[4-(isoquinolin-5-ylcarbonyl)-3-methylphenyl]ethyl}carbamate

Obtained by oxidation of the intermediate resulting from the coupling of 313 and 3

$^1$H NMR (400 MHz, DMSO-d$_6$): δ 9.46 (s, 1H), 8.61 (d, 1H), 8.39 (d, 1H), 8.17 (d, 1H), 7.82 (d, 1H), 7.75 (t, 1H), 7.47 (d, 1H), 7.32 (broad s, 1H), 7.28 (d, 1H), 7.20 (dl, 1H), 4.65 (m, 1H), 2.39 (s, 3H), 1.38 (s, 9H), 1.33 (d, 3H)

Intermediate 647:

tert-Butyl [5-(isoquinolin-5-ylcarbonyl)-6-methoxy-2,3-dihydro-1H-inden-1-yl]-carbamate Obtained by oxidation of the intermediate resulting from the coupling of 645 and 3

$^1$H NMR (300 MHz, DMSO-d$_6$): δ 9.30 (d, 1H), 8.55 (d, 1H), 8.30 (d, 1H), 8.25 (d, 1H), 7.80 (d, 1H), 7.70 (t, 1H), 7.35 (s, 1H), 7.10 (m, 1H, NH), 6.95 (s, 1H), 5.00 (m, 1H), 3.45 (s, 3H), 2.75-2.90 (2m, 2H), 2.40 (m, 1H), 1.90 (m, 1H), 1.45 (s, 9H)

IR (cm$^{-1}$): 3400-3200, 1700, 1651

Intermediate 686:

tert-Butyl {1-[4-(isoquinolin-5-ylcarbonyl)-3-methoxyphenyl]ethyl}carbamate

Obtained by oxidation of the intermediate resulting from the coupling of 684 and 3

$^1$H NMR (400 MHz, DMSO-d$_6$): δ 9.40 (s, 1H), 8.60 (d, 1H), 8.35 (d, 1H), 8.25 (d, 1H), 7.80 (d, 1H), 7.70 (t, 1H), 7.45 (d, 2H), 7.10 (s, 1H), 7.05 (d, 1H), 4.70 (tl, 1H), 3.50 (s, 3H), 1.40 (s, 9H), 1.35 (d, 3H)

IR (cm$^{-1}$): 3400-3150, 1702-1656, 1607, 1243, 1164, 1032, 832-760

Intermediate 718:

tert-Butyl (1-{4-[(1-ethoxyisoquinolin-5-yl)carbonyl]-3-fluoro-2-(2-methylpropoxy)-phenyl}ethyl)carbamate Obtained by oxidation of the intermediate resulting from the coupling of the tert-butylcarbamate intermediate of 714 and 125

$^1$H NMR (300 MHz, DMSO-d$_6$): δ 8.45 (d, 1H), 8.10 (d, 1H), 7.90 (d, 1H), 7.70 (t and m, 2H), 7.53 (d, 1H, NH), 7.34 (dd, 1H), 7.32 (d, 1H), 5.02 (m, 1H), 4.68 (quad, 2H), 3.78 (m, 2H), 2.03 (m, 1H), 1.46 (t, 3H), 1.36 (broad s, 9H), 1.30 (d, 3H), 0.98 (d, 6H)

IR (cm$^{-1}$): 3354, 1704, 1662, 1264, 1161, 813, 759

Intermediate 728:

tert-Butyl (1-{2-(benzyloxy)-4-[(1-ethoxyisoquinolin-5-yl)carbonyl]-5-fluorophenyl}-ethyl)carbamate Obtained by oxidation of the intermediate resulting from the coupling of 726 and 125

$^1$H NMR (400 MHz, DMSO-d$_6$): δ 8.46 (d, 1H), 8.09 (d, 1H), 7.90 (dl, 1H), 7.70 (dd, 1H), 7.66 (dl, 1H), 7.51 (dl, 1H, NH), 7.45-7.30 (m, 6H), 5.21 (dd, 2H), 5.08 (m, 1H), 4.58 (quad, 2H), 1.48 (t, 3H), 1.39 (s, 9H), 1.30 (d, 3H)

IR (cm$^{-1}$): 3350, 1679, 1657, 1619

Intermediate 757:

tert-Butyl [(1R)-1-{4-[(8-chloroisoquinolin-5-yl)carbonyl]phenyl}ethyl]carbamate Obtained by oxidation of the intermediate resulting from the coupling of 5 and 755

$^1$H NMR (300 MHz, DMSO-d$_6$): δ 9.70 (s, 1H), 8.68 (d, 1H), 7.95 (d, 1H), 7.90 (d, 1H), 7.88 (d, 1H), 7.77 (d, 2H), 7.53 (d, 1H, NH), 7.47 (d, 2H), 4.70 (quint, 1H), 1.36 (s, 9H), 1.32 (d, 3H)

IR (cm$^{-1}$): 3378, 1674, 1669, 1245, 1168, 1062, 836

Intermediate 182:
Obtained in two steps starting from intermediate 75

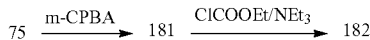

Intermediate 181:

tert-Butyl (1-{3-chloro-4-[(2-oxidoisoquinolin-5-yl)carbonyl]phenyl}ethyl)carbamate Intermediate 75, treated according to the protocol described for intermediate 123, was converted into 181.
MS (DEI 70 eV)=426.1
Intermediate 182:

tert-Butyl (1-{3-chloro-4-[(1-ethoxyisoquinolin-5-yl)carbonyl]phenyl}ethyl)carbamate To a solution of intermediate 181 (1.1 g, 2.57 mmoles) in ethanol (680 mL), at ambient temperature, there are added in succession ethyl chloroformate (0.9 mL) and then, after 5 minutes, $NEt_3$ (1.9 mL). The reaction mixture is stirred for 10 minutes at ambient temperature, and then ethyl chloroformate (0.9 mL) is again added. After 10 minutes' stirring at ambient temperature, the reaction mixture is concentrated in vacuo. The residue is taken up in water and extracted in the presence of methylene chloride. The organic phase is dried over $MgSO_4$ and concentrated. By chromatography on silica (eluant $CH_2Cl_2$/AcOEt 100/0 to 90/10), intermediate 182 is obtained (0.5 g).
$^1$H NMR (400 MHz, DMSO-$d_6$): δ 8.50 (d, 1H), 8.15 (d, 1H), 8.00 (d, 1H), 7.80 (d, 1H), 7.70 (m, 1H), 7.55 (d, 1H), 7.55 (broad s, 1H), 7.50 (s, 1H), 7.40 (d, 1H), 4.70 (m, 1H), 4.55 (quad, 2H), 1.45 (t, 3H), 1.40 (s, 9H), 1.35 (d, 3H)
IR (cm$^{-1}$): 3336, 1694, 1668
This procedure was applied to prepare intermediate 191 obtained from intermediate 189:
Intermediate 191:

tert-Butyl (2-{3-chloro-4-[(1-ethoxyisoquinolin-5-yl)carbonyl]phenyl}propan-2-yl)-carbamate $^1$H NMR (400 MHz, DMSO-$d_6$): δ 8.48 (d, 1H), 8.15 (d, 1H), 7.96 (d, 1H), 7.78 (broad d, 1H), 7.69 (t, 1H), 7.54 (d, 1H), 7.46 (broad s, 1H), 7.45 (broad d, 1H), 7.36 (broad s, 1H), 4.57 (quad, 2H), 1.54 (s, 6H), 1.46 (t, 3H), 1.35 (broad s, 9H)
IR (cm$^{-1}$): 3350, 1698, 1666, 1243-1159
Intermediate 395:
Obtained in three steps starting from intermediate 127

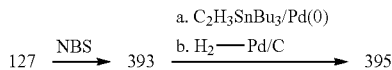

Intermediate 393:

tert-Butyl (1-{4-[(4-bromo-1-ethoxyisoquinolin-5-yl)carbonyl]-3,5-difluorophenyl}-ethyl)carbamate To a solution of intermediate 127 (2.7 g, 5.9 mmoles) in DMF (65 mL) there is added N-bromosuccinimide (1 g, 6 mmoles). The reaction mixture is stirred at ambient temperature for 24 hours. The mixture is taken up in AcOEt and water, and the organic phase is washed with a saturated aqueous NaCl solution, dried over $MgSO_4$ and concentrated. By chromatography on silica (eluant $CH_2Cl_2$/AcOEt 100/0 to 95/5), intermediate 393 is obtained in the form of an amorphous solid (1.35 g).
$^1$H NMR (400 MHz, DMSO-$d_6$): δ 8.43 (d, 1H), 8.31 (s, 1H), 7.86 (d, 1H), 7.74 (t, 1H), 7.52 (broad d, 1H), 7.16 (d, 2H), 4.69 (m, 1H), 4.56 (quad, 2H), 1.46 (t, 3H), 1.37 (broad s, 9H), 1.30 (d, 3H)
IR (cm$^{-1}$): 3346, 1708, 1678
Intermediate 395:

tert-Butyl (1-{4-[(1-ethoxy-4-ethylisoquinolin-5-yl)carbonyl]-3,5-difluorophenyl}-ethyl)carbamate Step 1:
To a solution, degassed with $N_2$, of intermediate 393 (1.6 g) in DMF (33 mL) there are added vinyl-tributyl-tin (0.89 mL) and Pd(PPh$_3$)$_4$ (56 mg). The mixture is heated at 100° C. for 5 hours. After return to ambient temperature, the mixture is treated with a 10% aqueous KF solution, the salts are filtered off, and the filtrate is extracted with AcOEt. The organic phase is dried over $MgSO_4$ and concentrated in vacuo. The expected product is obtained by chromatography on silica (eluant $CH_2Cl_2$/AcOEt 100/0 to 90/10) in the form of an amorphous solid (0.9 g).
$^1$H NMR (400 MHz, DMSO-$d_6$): δ 8.45 (d, 1H), 8.09 (s, 1H), 7.85 (d, 1H), 7.70 (t, 1H), 7.51 (d, 1H), 7.13 (d, 2H), 6.61 (dd, 1H), 5.43 (d, 1H), 5.08 (d, 1H), 4.67 (m, 1H), 4.57 (quad, 2H), 1.46 (t, 3H), 1.37 (broad s, 9H), 1.30 (d, 3H)
IR (cm$^{-1}$): 3344, 1710, 1673, 1631
Step 2:
A solution of the intermediate obtained in step 1 above (0.94 g, 1.95 mmoles) in ethanol (90 mL) is hydrogenated at atmospheric pressure of $H_2$ and at ambient temperature in the presence of 10% Pd/C (0.2 g) for 24 hours. A fresh batch of 10% Pd/C is added, and the mixture is hydrogenated for a further 24 hours, the catalyst is then filtered off, and the filtrate is concentrated in vacuo. By chromatography on silica (eluant $CH_2Cl_2$/cyclohexane 20/80 to 100/0 then $CH_2Cl_2$/AcOEt 95/5), intermediate 395 is obtained in the form of an amorphous solid (0.5 g).
$^1$H NMR (300 MHz, DMSO-$d_6$): δ 8.45 (d, 1H), 8.00 (s, 1H), 7.80 (d, 1H), 7.65 (t, 1H), 7.50 (broad d, 1H), 7.20 (d, 2H), 4.70 (m, 1H), 4.55 (quad, 2H), 2.65 (quad, 2H), 1.50 (t, 3H), 1.35 (broad s, 9H), 1.32 (d, 3H), 1.20 (t, 3H)
IR (cm$^{-1}$): 3340, 1678
Intermediate 433 was obtained by chlorination (with N-chlorosuccinimide) of intermediate 170 or tert-butyl (1-{4-[(4-chloro-1-ethoxyisoquinolin-5-yl)carbonyl]-3,5-difluorophenyl}-ethyl)carbamate.
Intermediate 433:

tert-Butyl (1-{4-[(4-chloro-1-ethoxyisoquinolin-5-yl)carbonyl]-3,5-difluorophenyl}-ethyl)carbamate To a solution of 170 (1 g, 2.19 mmoles) in $CH_3CN$ (30 mL) there is added N-chlorosuccinimide (0.3 g, 2.3 mmoles). The reaction mixture is heated at reflux for 24 hours, and then the solvent is evaporated off in vacuo. The residue is taken up in AcOEt and washed with water, and the organic phase is dried over $MgSO_4$ and concentrated. By chromatography on silica (eluant $CH_2Cl_2$/AcOEt 98/2), intermediate 433 is obtained in the form of an amorphous solid (0.6 g).
$^1$H NMR (400 MHz, DMSO-$d_6$): δ 8.43 (dd, 1H), 8.18 (s, 1H), 7.88 (d, 1H), 7.77 (t, 1H), 7.52 (d, 1H), 7.16 (d, 2H), 4.69 (m, 1H), 4.57 (quad, 2H), 1.47 (t, 3H), 1.38 (s, 9H), 1.31 (d, 3H)
IR (cm$^{-1}$): 3350, 1712-1680

Intermediate 434:

tert-Butyl [(1S)-1-{4-[(4-chloro-1-ethoxyisoquinolin-5-yl)carbonyl]-3,5-difluorophenyl}ethyl]carbamate Obtained starting from 165 according to the protocol described for the preparation of intermediate 433.

$^1$H NMR (400 MHz, DMSO-$d_6$): δ 8.43 (dd, 1H), 8.18 (s, 1H), 7.88 (d, 1H), 7.77 (t, 1H), 7.52 (d, 1H), 7.16 (d, 2H), 4.69 (m, 1H), 4.57 (quad, 2H), 1.47 (t, 3H), 1.38 (s, 9H), 1.31 (d, 3H)

IR (cm$^{-1}$): 3500-3400, 1679-1632

Intermediate 688:

tert-Butyl {1-[3-hydroxy-4-(isoquinolin-5-ylcarbonyl)phenyl]ethyl}carbamate

Obtained in two steps, by treatment of intermediate 686 with BBr$_3$ in methylene chloride, and treatment of the phenol intermediate formed 687 in the presence of Boc$_2$O and NEt$_3$.

$^1$H NMR (400 MHz, DMSO-$d_6$): δ 11.30, 9.50, 8.60, 8.40, 7.95, 7.90, 7.82, 7.50, 7.32, 6.97, 6.88, 4.62, 1.40, 1.35

IR (cm$^{-1}$): 3330, 1699

LCMS [M+H]+=392

Intermediate 230:

(4-Bromo-2,5-difluorophenyl)(isoquinolin-5-yl)methanone

Obtained by oxidation of intermediate 229 resulting from the coupling of 228 and 125 according to the following protocol:

Step 1:

500 mg (1.83 mmoles) of 1,4-dibromo-2,5-difluorobenzene 228 are dissolved in 10 mL of anhydrous THF. The mixture is cooled to −50° C., under argon, and there is added dropwise 1 mL (2 mmoles, 1.1 eq.) of a 2M solution in THF of isopropylmagnesium chloride. The temperature is maintained between −50° C. and −40° C. Stirring is carried out for 30 minutes at −50° C., and the progress of the reaction is monitored by HPLC (approximately 75%). There is then added, still at −50° C., a solution of 0.37 g (1.83 mmoles, 1 eq.) of 125 in 3 mL of anhydrous THF. The temperature is allowed to rise to −10° C. Monitoring of the reaction by HPLC shows the formation of 68% of the desired alcohol. Hydrolysis is carried out with 15 mL of 1N HCl. Extraction with 3 times 25 ml of ether is carried out, and the organic phase is washed with a saturated aqueous NaCl solution, dried over MgSO$_4$, filtered and evaporated to dryness. The residue obtained crystallises in dichloromethane. The solid is then filtered off and dried to give 280 mg of expected product in the form of a solid. The crystallisation liquors are evaporated to dryness and purified by flash chromatography on 40 g of silica, eluant: CH$_2$Cl$_2$—AcOEt gradient: 99-1 to 90-10 to give 200 mg of the purified intermediate.

$^1$H NMR (400/500 MHz, DMSO-$d_6$): δ 8.18 (d, 1H), 8.01 (d, 1H), 7.73 (d, 1H), 7.61 (t, 1H), 7.67 (dd, 1H), 7.53 (d, 1H), 7.47 (dd, 1H), 6.51 (d, 1H), 6.41 (d, 1H), 4.52 (quad, 2H), 1.45 (t, 3H).

IR (cm$^{-1}$): 1621

Step 2:

Oxidation with MnO$_2$ of the intermediate obtained above yields intermediate 230:

$^1$H NMR (400 MHz, DMSO-$d_6$): δ 8.50 (d, 1H), 8.13 (d, 1H), 8.01 (d, 1H), 7.93 (dd, 1H), 7.82 (d, 1H), 7.73 (dd, 1H), 7.70 (t, 1H), 4.58 (quad, 2H), 1.46 (t, 3H)

IR (cm$^{-1}$): 3211, 1652

Intermediate 232:

tert-Butyl [3-fluoro-4-(isoquinolin-5-ylcarbonyl)benzyl]carbamate

Obtained starting from 230 according to the following protocol:

Step 1:

There are dissolved in 2 ml of anhydrous DMF, degassed with argon, 220 mg (0.558 mmole) of intermediate 230. There are added to the solution, under argon, 11 mg (0.055 mmole, 0.1 eq.) of CuI, 92 mg (0.558 mmole, 1 eq.) of potassium iodide and 20 mg (0.11 mmole, 0.2 eq.) of phenanthroline. The whole is heated at 110° C. for 18 h. HPLC monitoring shows 90% conversion to the iodine-containing compound. There are then added 36 mg (0.0558 mmole, 1 eq.) of potassium cyanide, and heating is continued at 110° C. for 3 hours. The conversion is incomplete and 20% of iodine-containing compound remain. A further 5 mg (0.077 mmole, 0.13 eq.) of KCN are added. Heating is carried out for a further 3 hours at 110° C. The reaction mixture is cooled and hydrolysed on 10 mL of water. The mixture is filtered, and the solid is rinsed 3 times with water. There are then added to the filtrate a 5% aqueous ammonia solution and ethyl acetate. A solid precipitates. It is filtered off and washed with ethyl acetate and water. The ethyl acetate phase is decanted and washed with water and then with a saturated aqueous NaCl solution. The organic phase is then dried over MgSO$_4$, filtered and evaporated to give 170 mg of a residue, which is purified by flash chromatography on 12 g of silica, eluant=CH$_2$Cl$_2$ 100% to give 100 mg of the expected intermediate.

$^1$H NMR (400 MHz, DMSO-$d_6$): δ 8.55 (d, 1H), 8.20 (dd, 1H), 8.20 (d, 1H), 8.05 (m, 3H), 7.95 (dd, 1H), 7.70 (m, 1H), 4.60 (quad, 2H), 1.45 (t, 3H)

IR (cm$^{-1}$): 2244, 1663

Step 2:

Reduction of the intermediate obtained in step 1 according to the protocol described for intermediate 223 yields intermediate 232

$^1$H NMR (400 MHz, DMSO-$d_6$): δ 8.49 (d, 1H), 8.10 (d, 1H), 7.95 (d, 1H), 7.72 (d, 1H), 7.70 (t, 1H), 7.52 (m, 1H), 7.51 (m, 1H), 7.20 (m, 1H), 4.55 (quad, 2H), 4.22 (m, 2H), 1.45 (t, 3H), 1.40 (s, 9H)

$^{19}$F NMR: −123, −117

IR (cm$^{-1}$): 3351, 1676-1662.

Intermediate 730:

tert-Butyl (1-{2-[2-(dimethylamino)ethoxy]-4-[(1-ethoxyisoquinolin-5-yl)carbonyl]-5-fluorophenyl}ethyl)carbamate Intermediate 730 was obtained in two steps starting from 728:

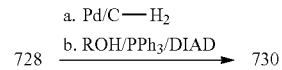

Step 1:

Intermediate 728 or tert-butyl (1-{2-(benzyloxy)-4-[(1-ethoxyisoquinolin-5-yl)carbonyl]-5-fluorophenyl}ethyl)carbamate was converted into the corresponding phenolic compound according to the conditions described for obtaining compound 553 (intermediate of 555).

Step 2:

The phenolic intermediate obtained above (1 g, 2.2 mmoles) is dissolved in THF and, in the presence of commercial dimethyl-ethanol-amine (0.22 mL), is treated with triphenylphosphine (0.87 g, 3.3 mmoles) and diisopropyl azodicarboxylate (0.65 mL, 3.3 mmoles). The reaction mixture was stirred at ambient temperature for 3 days. After concentration in vacuo, the residue is chromatographed on silica (eluant: $CH_2Cl_2$/EtOH 90/10), and the solid obtained is recrystallised from methanol. Intermediate 730 is obtained in the form of a solid (0.36 g).

$^1$H NMR (300 MHz, DMSO-$d_6$): δ 8.45 (d, 1H), 8.10 (d, 1H), 7.90 (d, 1H), 7.70 (m, 2H), 7.55 (d, 1H, NH), 7.30 (d, 1H), 7.20 (d, 1H), 5.00 (quint, 1H), 4.60 (quad, 2H), 4.10 (t, 2H), 2.65 (m, 2H), 2.20 (s, 6H), 1.50 (t, 3H), 1.40 (broad s, 9H), 1.30 (d, 3H)

IR (cm$^{-1}$): 3410, 1679, 1630, 1533, 1166

The ketone intermediates obtained by protocol XX were deprotected in an acidic medium to yield the final products, such as in the example of product P110:

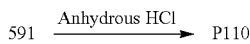

Product P110:

[4-(1-Aminoethyl)phenyl](isoquinolin-5-yl)methanone hydrochloride

To a solution of intermediate 591 (2.9 g, 7.7 mmoles) in $Et_2O$ (60 mL) there is added a solution of 2N HCl in ether (30 mL). The resulting suspension is stirred at ambient temperature for 4 days. The precipitate collected on a frit is dried in vacuo, and product P110 is obtained in the form of a white solid (2.05 g).

The 1-ethoxyisoquinolin-5-yl ketone intermediates were then deprotected according to one of the two examples described below for P17 and P68:

Product P17:

[4-(1-Aminoethyl)-2,6-difluorophenyl](1-hydroxyisoquinolin-5-yl)methanone hydrochloride A mixture of 11.86 g (36 mmoles) of intermediate 127 in 710 mL of 4N HCl is heated at 80° C. for 48 h. After HPLC monitoring, the mixture is cooled to 0° C. and the solid is filtered over a frit, which yields 8.2 g of product P17 in the form of a white solid (1.1% of deamination product).

Product P68:

5-{4-[(1R)-1-Aminoethyl]-2-methylbenzoyl}-3-methylisoquinolin-1(2H)-one methanesulphonate A solution of intermediate 391 (0.7 g, 1.58 mmoles) in a 1,4-dioxane/water mixture (14 mL/4 mL) and of methanesulphonic acid (0.51 mmole) is heated at 80° C. for 24 hours.

The reaction mixture is concentrated in vacuo, and the residue is taken up in $CH_3CN$. The resulting solid is filtered off and dried in vacuo. Product P68 is obtained in the form of a solid.

| Product | Obtained from | Nomenclature Analytical description |
|---|---|---|
| P1 | 7 | {4-[(1R)-1-Aminoethyl]phenyl}(isoquinolin-5-yl)-methanone dihydrochloride<br>$^1$H NMR (400 MHz, DMSO-$d_6$): δ 9.80 (s, 1H), 8.75 (m, 3H), 8.65 (2d, 2H), 8.20 (d, 1H), 8.15 (d, 1H), 8.00 (t, 1H), 7.88 (t, 2H), 7.75 (d, 2H), 4.50 (m, 1H), 1.55 (d, 3H)<br>IR (cm$^{-1}$): 3000-2000, 1650<br>HRMS (ESI): theoretical m/z for $C_{18}H_{17}N_2O$ [M + H]$^+$ 277.1341, measured 277.1357<br>Optical purity: (ADH 5 μm column 4.6 × 250 mm, eluant: EtOH/triethylamine 1000/1, detection: 265 nm): >99%. (absence of P111) |
| P2 | 15 | {4-[(1R)-1-Aminoethyl]-2-methylphenyl}(isoquinolin-5-yl)methanone hydrochloride<br>$^1$H NMR (400 MHz, DMSO-$d_6$): δ 9.88 (s, 1H), 8.74 (m, 4H), 8.68 (d, 1H), 8.59 (d, 1H), 8.04 (d, 1H), 7.98 (t, 1H), 7.62 (broad s, 1H), 7.48 (broad d, 1H), 7.42 (d, 1H), 4.46 (m, 1H), 2.43 (s, 3H), 1.56 (d, 3H)<br>IR (cm$^{-1}$): 3000-2000, 1654<br>HRMS (ESI): theoretical m/z for $C_{19}H_{19}N_2O$ [M + H]$^+$ 291.1497, measured 291.1525<br>Optical purity: (ADH 5 μm column 4.6 × 250 mm, eluant: EtOH/diethylamine 100/0.1, detection: 270 nm): >99%. (absence of P121)<br>$α_D$ (589 nM) = 7 (c = 0.004 g/mL, MeOH) at 20° C. |
| P4 | 34 | (1-Amino-6-methyl-2,3-dihydro-1H-inden-5-yl)-(isoquinolin-5-yl)methanone dihydrochloride<br>$^1$H NMR (300 MHz, DMSO-$d_6$): δ 9.85 (s, 1H), 8.88-8.55 (3d, 3H), 8.75 (m, 3H), 8.00 (d and t, 2H), 7.70 (s, 1H), 7.30 (s, 1H), 5.05 (m, 1H), 4.75 (m, 1H), 3.00-2.80 (2m, 2H), 2.40 (s, 3H), 2.50-2.02 (2m, 2H)<br>IR (cm$^{-1}$): 3100-2200, 1657<br>HRMS (ESI): theoretical m/z for $C_{20}H_{19}N_2O$ [M + H]$^+$ 303.1497, measured 303.1511 |
| P5 | 42 | [4-(1-Aminoethyl)-2-fluorophenyl](isoquinolin-5-yl)-methanone dihydrochloride |

| Product | Obtained from | Nomenclature Analytical description |
|---|---|---|
| | | ¹H NMR (300 MHz, DMSO-d$_6$): δ 9.95 (s, 1H), 9.00 (broad s, 3H), 8.80 (2dd, 2H), 8.62 (d, 1H), 8.21 (dd, 1H), 8.05 (t, 1H), 7.80 (m, 1H), 7.72-7.58 (m, 2H), 7-6.50 (m, 1H), 4.60 (m, 1H), 1.60 (d, 3H)<br>IR (cm⁻¹): 3000-2000, 1663<br>HRMS (ESI): theoretical m/z for C$_{18}$H$_{16}$F$_1$N$_2$O [M + H]⁺ 295.1247, measured 295.1249 |
| P6 | 51 | [4-(1-Aminoethyl)-2,6-difluorophenyl](isoquinolin-5-yl)methanone dihydrochloride<br>¹H NMR (300 MHz, DMSO-d$_6$): δ 9.70 (s, 1H) 8.90 (d, 1H) 8.80 (d and m, 4H) 8.70 (d, 1H) 8.25 (d, 1H) 7.95 (t, 1H) 7.60 (d, 2H) 4.60 (sept, 1H) 1.60 (d, 3H)<br>IR (cm⁻¹): 3280-2000, 1673<br>HRMS (ESI): theoretical m/z for C$_{18}$H$_{15}$F$_2$N$_2$O [M + H]⁺ 313.1152, measured 313.1167 |
| P8 | 60c | [4-(1-Aminoethyl)-2-fluoro-6-methylphenyl]-(isoquinolin-5-yl)methanone dihydrochloride<br>¹H NMR (300 MHz, DMSO-d$_6$): δ 9.90 (m, 1H), 9.10 (m, 1H), 8.80 (m, 4H), 8.70 (d, 2H), 8.60 (d, 1H), 8.00 (t, 1H), 7.50 (s and d, 2H), 4.50 (m, 1H), 2.30 (s, 3H), 1.60 (d, 3H)<br>IR (cm⁻¹): 3385-1900, 1660<br>HRMS (ESI): theoretical m/z for C$_{19}$H$_{18}$F$_1$N$_2$O [M + H]⁺ 309.1403, measured 309.1403 |
| P11 | 75 | [4-(1-Aminoethyl)-2-chlorophenyl](isoquinolin-5-yl)-methanone dihydrochloride<br>¹H NMR (300 MHz, DMSO-d$_6$): δ 9.90 (s and d and m, 5H), 8.80 (d, 1H), 8.70 (d, 2H), 8.10 (d, 1H), 8.00 (t, 1H), 7.90 (broad s, 1H), 7.70 (m, 2H), 4.55 (m, 1H), 1.60 (d, 3H)<br>IR (cm⁻¹): 3290-1910, 1663<br>HRMS (ESI): theoretical m/z for C$_{18}$H$_{16}$Cl$_1$N$_2$O [M + H]⁺ 310.0873, measured 310.0859 |
| P12 | 89 | (1-Amino-6-methoxy-1-methyl-2,3-dihydro-1H-inden-5-yl)(isoquinolin-5-yl)methanone dihydrochloride<br>¹H NMR (300 MHz, DMSO-d$_6$): δ 9.60 (s, 1H), 8.70 (m, 3H), 8.65 (d, 1H), 8.44 (d, 2H), 7.90 (d, 1H), 7.82 (t, 1H), 7.60 (s, 1H), 7.45 (s, 1H), 3.10-2.85 (m, 4H), 2.40-2.20 (m, 2H), 1.65 (s, 3H)<br>IR (cm⁻¹): 2800-2056, 1654<br>HRMS (ESI): theoretical m/z for C$_{21}$H$_{21}$N$_2$O$_2$ [M + H]⁺ 333.1603, measured 333.1616 |
| P15 | 114 | [4-(1-Aminoethyl)-2-fluoro-3-methylphenyl]-(isoquinolin-5-yl)methanone dihydrochloride<br>¹H NMR (300 MHz, DMSO-d$_6$): δ 9.95 (s, 1H), 8.80 (m, 4H), 8.25 (d, 1H), 8.52 (d, 1H), 8.10 (d, 1H), 7.95 (t, 1H), 7.65 (m, 2H), 4.70 (m, 1H), 2.78 (s, 3H), 1.55 (d, 3H)<br>IR (cm⁻¹): 3400-2200, 1668<br>HRMS (ESI): theoretical m/z for C$_{19}$H$_{18}$FN$_2$O [M + H]⁺ 309.1403, measured 309.1391 |
| P16 | 122 | [8-(1-Aminoethyl)-2,3-dihydro-1,4-benzodioxin-5-yl]-(isoquinolin-5-yl)methanone dihydrochloride<br>¹H NMR (300 MHz, DMSO-d$_6$): δ 9.90 (s, 1H), 8.75 (d, 1H), 8.70 (m, 6H), 8.15 (d, 1H), 8.00 (t, 1H), 7.25 (d, 1H), 7.20 (d, 1H), 4.60 (d, 1H), 4.30 (m, 2H), 4.05 (m, 2H), 1.55 (d, 3H)<br>IR (cm⁻¹): 3200-2400, 165<br>HRMS (ESI): theoretical m/z for C$_{20}$H$_{19}$N$_2$O$_3$ [M + H]⁺ 335.1396, measured 335.1392 |
| P17 | 127 | [4-(1-Aminoethyl)-2,6-difluorophenyl](1-hydroxy-isoquinolin-5-yl)methanone hydrochloride<br>¹H NMR (300 MHz, DMSO-d$_6$): δ 11.60 (broad s, 1H), 8.52 (dd, 1H), 8.50 (m, 3H), 7.90 (dd, 1H), 7.58 (t, 1H), 7.40 (s, 2H), 7.50 (d, 2H), 4.53 (quad, 1H), 1.55 (d, 3H)<br>IR (cm⁻¹): 3000-2500, 1674<br>HRMS (ESI): theoretical m/z for C$_{18}$H$_{15}$F$_2$N$_2$O$_2$ [M + H]⁺ 329.1102, measured 329.1102 |
| P18 | 137 | [4-(1-Aminoethyl)-2-chloro-6-fluorophenyl]-(isoquinolin-5-yl)methanone dihydrochloride<br>¹H NMR (300 MHz, DMSO-d$_6$): δ 10.80 (s, 1H), 9.05 (d, 1H), 8.70 (d, 1H), 8.85 (broad d, 4H), 8.20 (d, 1H), 7.95 (t, 1H), 7.80 (s, 1H), 7.75 (d, 1H), 4.55 (t, 1H), 1.60 (d, 3H)<br>IR (cm⁻¹): 3100-2400, 1675<br>HRMS (ESI): theoretical m/z for C$_{18}$H$_{15}$ClFN$_2$O [M + H]⁺ 329.0857, measured 329.0846 |
| P24 | 160 | [4-(2-Aminopropan-2-yl)-2,6-difluorophenyl]-(isoquinolin-5-yl)methanone dihydrochloride |

| Product | Obtained from | Nomenclature Analytical description |
|---|---|---|
| | | $^1$H NMR (400 MHz, DMSO-$d_6$): δ 9.84 (s, 1H), 9.10 (m, 4H), 8.94 (d, 1H), 8.82 (d, 1H), 7.73 (d, 1H), 8.32 (d, 1H), 7.99 (t, 1H), 7.64 (d, 2H), 1.71 (s, 6H)<br>IR (cm$^{-1}$): 3200-2300, 1674.<br>HRMS (ESI): theoretical m/z for $C_{19}H_{17}F_2N_2O$ [M + H]$^+$ 327.1309, measured 327.129 |
| P25 | 165 | {4-[(1S)-1-Aminoethyl]-2,6-difluorophenyl}(1-hydroxy-isoquinolin-5-yl)methanone hydrochloride<br>$^1$H NMR (400 MHz, DMSO-$d_6$): δ 11.70 (s, 1H), 8.90 (broad s, 3H), 8.55 (d, 1H), 7.90 (d, 1H), 7.60 (m, 3H), 7.40 (s, 2H), 4.55 (quad, 1H), 1.60 (d, 3H)<br>IR (cm$^{-1}$): 3200-2300, 1673, 1631<br>HRMS (ESI): theoretical m/z for $C_{18}H_{15}F_2N_2O_2$ [M + H]$^+$ 329.1102, measured 329.1112<br>Optical purity (SFC: Chiralpak ID 3 μM 4.6 × 250 mm; eluant: $CO_2$/(isopropanol/diethylamine: 100/0.5): 65/35; detection: 255 nm): >99%.<br>(absence of P26) |
| P26 | 170 | {4-[(1R)-1-Aminoethyl]-2,6-difluorophenyl}(1-hydroxy-isoquinolin-5-yl)methanone hydrochloride<br>$^1$H NMR (400 MHz, DMSO-$d_6$): δ 11.70 (m, 1H), 8.80 (m, 3H), 8.55 (d, 1H), 7.90 (d, 1H), 7.55 (t and m, 3H), 7.40 (m, 2H), 4.55 (quad, 1H), 1.60 (d, 3H)<br>IR (cm$^{-1}$): 3500-3000, 2863, 1673<br>HRMS (ESI): theoretical m/z for $C_{18}H_{15}F_2N_2O_2$ [M + H]$^+$ 329.1102, measured 329.1119<br>Optical purity (SFC: Chiralpak ID 3 μM 4.6 × 250 mm; eluant: $CO_2$/(isopropanol/diethylamine: 100/0.5): 65/35; detection: 255 nm): >99%.<br>(absence of P25)<br>[P26 in the form of methanesulphonate $α_D$ (589 nM) = +2.48 (c = 0.01 g/mL, MeOH) at 20° C. |
| P27 | 172 | 5-[4-(2-Aminopropan-2-yl)-2,6-difluorobenzoyl]-isoquinolin-1(2H)-one hydrochloride<br>$^1$H NMR (300 MHz, DMSO-$d_6$): δ 11.70 (m, 1H), 9.00 (m, 3H), 8.55 (dd, 1H), 7.90 (dd, 1H), 7.60 (t and d, 3H), 7.40 (m, 2H), 1.70 (broad s, 6H)<br>IR (cm$^{-1}$): 3400-2400, 1677, 1631<br>HRMS (ESI): theoretical m/z for $C_{19}H_{17}F_2N_2O_2$ [M + H]$^+$ 343.1258, measured 343.1271 |
| P28 | 176 | [4-(Aminomethyl)-2,6-difluorophenyl](1-hydroxy-isoquinolin-5-yl)methanone hydrochloride<br>$^1$H NMR (400 MHz, DMSO-$d_6$): δ 11.67 (broad s, 1H), 8.55 (broad s, 3H), 8.54 (dd, 1H), 7.88 (broad d, 1H), 7.58 (t, 1H), 7.50 (m, 2H), 7.40 (m, 2H), 4.16 (s, 2H)<br>IR (cm$^{-1}$): 3250-1950, 1671<br>HRMS (ESI): theoretical m/z for $C_{17}H_{13}F_2N_2O_2$ [M + H]$^+$ 314.0867, measured 314.0865 |
| P29 | 178 | 5-[4-(1-Aminoethyl)-2-fluoro-3-methylbenzoyl]-isoquinolin-1(2H)-one hydrochloride<br>$^1$H NMR (400 MHz, DMSO-$d_6$): δ 11.60 (m, 1H), 9.00-8.50 (m, 3H), 8.45 (dd, 1H), 7.75 (dd, 1H), 7.70-7.55 (2m, 3H), 7.30 (m, 1H), 6.95 (d, 1H), 4.65 (quad, 1H), 2.25 (s, 3H), 1.55 (d, 3H)<br>IR (cm$^{-1}$): 3300-2000, 1668, 1629<br>MS (DEI 70 eV): m/z measured for $C_{19}H_{18}FN_2O_2$ 324.10 |
| P30 | 180 | 5-[4-(1-Aminoethyl)-2-fluorobenzoyl]isoquinolin-1(2H)-one hydrochloride<br>$^1$H NMR (400 MHz, DMSO-$d_6$): δ 11.56 (broad s, 1H), 8.60 (broad s, 3H), 8.46 (d, 1H), 7.76 (d, 1H), 7.73 (t, 1H), 7.60-7.50 (m, 3H), 7.30 (dd, 1H), 6.91 (d, 1H), 4.53 (quad, 1H), 1.55 (d, 3H)<br>IR (cm$^{-1}$): 3200-2400, 1684-1659, 1625<br>HRMS (ESI): theoretical m/z for $C_{18}H_{16}FN_2O_2$ [M + H]$^+$ 311.1196, measured 311.1205 |
| P31 | 182 | 5-[4-(1-Aminoethyl)-2-chlorobenzoyl]isoquinolin-1(2H)-one hydrochloride<br>$^1$H NMR (400 MHz, DMSO-$d_6$): δ 11.62 (broad s, 1H), 8.58 (broad s, 3H), 8.49 (d, 1H), 7.80 (s, 1H), 7.66 (m, 3H), 7.55 (t, 1H), 7.37 (broad d 1H), 7.28 (d, 1H), 4.53 (quad, 1H), 1.56 (d, 3H)<br>IR (cm$^{-1}$): 3300-2500, 1661, 1631<br>HRMS (ESI): theoretical m/z for $C_{18}H_{16}ClN_2O_2$ [M + H]$^+$ 327.0900, measured 327.0902 |
| P32 | 191 | 5-[4-(2-Aminopropan-2-yl)-2-chlorobenzoyl]-isoquinolin-1(2H)-one hydrochloride |

| Product | Obtained from | Nomenclature Analytical description |
|---|---|---|
| | | $^1$H NMR (400 MHz, DMSO-d$_6$): δ 11.63 (d, 1H), 8.82 (broad s, 3H), 8.49 (d, 1H), 7.81 (broad s, 1H), 7.68 (m, 3H), 7.55 (t, 1H), 7.38 (dd, 1H), 7.29 (d, 1H), 1.69 (s, 6H)<br>IR (cm$^{-1}$): 3500-2400, 1662-1651, 1623<br>HRMS (ESI): theoretical m/z for C$_{19}$H$_{18}$ClN$_2$O$_2$ [M + H]$^+$ 341.1057, measured 341.1062 |
| P33 | 202 | 5-{4-[(1R)-1-Aminoethyl]-2-fluoro-3-methylbenzoyl}-isoquinolin-1(2H)-one hydrochloride<br>$^1$H NMR (400 MHz, DMSO-d$_6$): δ 11.60 (d, 1H), 8.80-8.60 (m, 3H), 8.45 (d, 1H), 7.75 (d, 1H), 7.65-7.55 (m, 3H), 7.30 (m, 1H), 6.95 (d, 1H), 4.65 (m, 1H), 2.25 (s, 3H), 1.50 (d, 3H)<br>IR (cm$^{-1}$): 3500-2000, 1650-1630<br>HRMS (ESI): theoretical m/z for C$_{19}$H$_{18}$FN$_2$O$_2$ [M + H]$^+$ 325.1352, measured 325.1354.<br>Optical purity (ASH 5 μM column 4.6 × 250 mm; eluant: EtOH/heptane/diethylamine: 70/30/0.1; detection: 620 nm): >99%. (absence P36) |
| P34 | 189 | [4-(2-Aminopropan-2-yl)-2-chlorophenyl](isoquinolin-5-yl)methanone dihydrochloride<br>$^1$H NMR (400 MHz, DMSO-d6): δ 9.90 (s, 1H), 9.40-8.90 (m, 3H), 8.90 (d, 1H), 8.80 (d, 1H), 8.70 (broad d, 1H), 8.05 (dd, 1H), 7.95 (t, 1H), 7.90 (s, 1H), 7.75 (m, 2H), 1.70 (s 6H)<br>IR (cm$^{-1}$): 3200-2000, 1662<br>HRMS (ESI): theoretical m/z for C$_{19}$H$_{18}$ClN$_2$O [M + H]$^+$ 325.1108, measured 325.1116 |
| P35 | 213 | 5-{2,6-Difluoro-4-[1-(methylamino)ethyl]benzoyl}-isoquinolin-1(2H)-one hydrochloride<br>$^1$H NMR (400 MHz, DMSO-d$_6$): δ 11.68 (s, 1H), 9.68 (broad s, 2H), 8.54 (dd, 1H), 7.98 (broad d, 1H), 7.59 (m, 2H), 7.58 (t, 1H), 7.42 (m, 2H), 4.44 (quad, 1H), 2.47 (s, 3H), 1.61 (d, 3H)<br>IR (cm$^{-1}$): 3250-3200, 1672-1668, 1632<br>HRMS (ESI): theoretical m/z for C$_{19}$H$_{17}$F$_2$N$_2$O$_2$ [M + H]$^+$ 343.1258, measured 343.1258 |
| P36 | 219 | 5-{4-[(1S)-1-Aminoethyl]-2-fluoro-3-methylbenzoyl}-isoquinolin-1(2H)-one hydrochloride<br>$^1$H NMR (400 MHz, DMSO-d$_6$): δ 11.50 (d, 1H), 8.57 (broad s, 3H), 8.46 (d, 1H), 7.73 (d, 1H), 7.59 (m, 2H), 7.58 (t, 1H), 7.30 (m, 1H), 6.92 (d, 1H), 4.65 (quad, 1H), 2.27 (s, 3H), 1.50 (d, 3H)<br>IR (cm$^{-1}$): 3500-2000, 1650-1630<br>HRMS (ESI): theoretical m/z for C$_{19}$H$_{18}$FN$_2$O$_2$ [M + H]$^+$ 325.1352, measured 325.1363.<br>Optical purity (ASH 5 μM column 4.6 × 250 mm; eluant: EtOH/heptane/diethylamine: 70/30/0.1; detection: 620 nm): >99%. (absence P36) |
| P37 | 223 | 5-[4-(Aminomethyl)-2-fluorobenzoyl]isoquinolin-1(2H)-one hydrochloride<br>$^1$H NMR (400 MHz, DMSO-d$_6$): δ 11.55 (d, 1H), 8.60 (m, 3H), 8.47 (d, 1H), 7.77 (d, 1H), 7.70 (t, 1H), 7.60-7.49 (m, 2H), 7.58 (t, 1H), 7.30 (m, 1H), 6.90 (d, 1H), 4.15 (s, 2H)<br>IR (cm$^{-1}$): 2970, 1680-1655, 1622<br>HRMS (ESI): theoretical m/z for C$_{17}$H$_{14}$FN$_2$O$_2$ [M + H]$^+$ 297.1093, measured 297.1024 |
| P39 | 227 | 5-{[(1S)-1-Amino-2,3-dihydro-1H-inden-5-yl]-carbonyl}isoquinolin-1(2H)-one hydrochloride<br>$^1$H NMR (400 MHz, DMSO-d$_6$): δ 11.50 (s, 1H), 8.55 (broad s, 3H), 8.40 (d, 1H), 7.78 (d, 1H), 7.70 (d, 1H), 7.65 (m, 2H), 7.60 (t, 1H), 7.20 (d, 1H), 6.40 (m, 1H), 4.78 (t, 1H), 3.10-2.90 (m, 2H), 2.50-2.00 (m, 2H)<br>IR (cm$^{-1}$): 3300-2400, 1687-1665<br>HRMS (ESI): theoretical m/z for C$_{19}$H$_{17}$N$_2$O$_2$ [M + H]$^+$ 305.1290, measured 305.1311.<br>Optical purity (ASH 5 μM column 4.6 × 250 mm; eluant: heptane/propanol/diethylamine: 70/30/0.1; detection: 270 nm): >99%. |
| P40 | 232 | 5-[4-(Aminomethyl)-2,5-difluorobenzoyl]isoquinolin-1(2H)-one hydrochloride<br>$^1$H NMR (400 MHz, DMSO-d$_6$): δ 11.60 (s, 1H), 8.60 (broad s, 3H), 8.49 (d, 1H), 7.80 (d, 1H), 7.70-7.60 (m, 2H), 7.59 (t, 1H), 7.30 (m, 1H), 7.00 (d, 1H), 4.15 (s, 2H)<br>IR (cm$^{-1}$): 3200-2400, 1689-1658 |

| Product | Obtained from | Nomenclature Analytical description |
|---|---|---|
| P42 | 247 | HRMS (ESI): theoretical m/z for $C_{17}H_{13}F_2N_2O_2$ [M + H]$^+$ 315.0945, measured 315.0934<br>5-[4-(1-Aminoethyl)-2-fluoro-3-methoxybenzoyl]-isoquinolin-1(2H)-one hydrochloride<br>$^1$H NMR (400 MHz, DMSO-d$_6$): δ 12.60 (s, 1H), 8.65 (broad s, 3H), 8.50 (d, 1H), 7.80 (d, 1H), 7.55 (m, 2H), 7.45 (m, 1H), 7.30 (d, 1H), 7.00 (d, 1H), 4.65 (q, 1H), 3.95 (s, 3H), 1.50 (d, 3H)<br>IR (cm$^{-1}$): 3359-2437, 1690, 1656<br>HRMS (ESI): theoretical m/z for $C_{19}H_{18}FN_2O_3$ [M + H]$^+$ 341.1031, measured 341.1318 |
| P43 | 257 | 5-[4-(1-Aminoethyl)-2,3-dimethylbenzoyl]isoquinolin-1(2H)-one hydrochloride<br>$^1$H NMR (400 MHz, DMSO-d6): δ 11.58 (broad d, 1H), 8.57 (m, 3H), 8.46 (d, 1H), 7.63 (d, 1H), 7.52 (m, 2H), 7.34 (dd, 1H), 7.22 (d, 1H), 7.18 (d, 1H), 4.71 (m, 1H), 2.31 (s, 3H), 2.20 (s, 3H), 1.51 (d, 3H)<br>IR (cm$^{-1}$): 3300-2400, 1642, 1626<br>HRMS (ESI): theoretical m/z for $C_{20}H_{21}N_2O_2$ [M + H]$^+$ 321.1603, measured 321.1594 |
| P47 | 273 | 5-{4-[(1R)-1-Aminoethyl]-2-methylbenzoyl}isoquinolin-1(2H)-one hydrochloride<br>$^1$H NMR (400 MHz, DMSO-d$_6$): δ 11.60-11.50 (m, 1H), 8.60-8.40 (m, 3H), 8.45 (m, 1H), 7.65 (dd, 1H), 7.60 (m, 1H), 7.50 (m, 1H), 7.40 (dd, 1H), 7.35 (d, 1H), 7.30 (m, 1H), 6.90 (d, 1H), 4.45 (quad, 1H), 2.35 (s, 3H), 1.55 (d, 3H)<br>IR (cm$^{-1}$): 3500, 3300-1950, 1685, 1653<br>HRMS (ESI): theoretical m/z for $C_{19}H_{19}N_2O_2$ [M + H]$^+$ 307.1441, measured 307.1455<br>theoretical m/z for $C_{19}H_{16}NO_2$ [M + H—NH$_3$]$^+$ 290.1176, measured 290.1175<br>Optical purity: (AD 5 μm column 4.6 × 250 mm, eluant: EtOH/heptane/diethylamine 40/60/0.1, detection: 255 nm): >99%, (absence of P52)<br>α$_D$ (589 nM) = 5.7 (c = 0.01 g/mL, MeOH) at 20° C. |
| P51 | 312 | 5-[4-(1-Aminoethyl)-3-ethoxy-2-fluorobenzoyl]-isoquinolin-1(2H)-one hydrochloride<br>$^1$H NMR (400 MHz, DMSO-d$_6$): δ 11.60 (m, 1H), 8.70-8.30 (m, 3H), 8.50 (d, 1H), 7.80 (d, 1H), 7.65 (m, 1H), 7.50 (m, 1H), 7.40 (m, 1H), 7.30 (d, 1H), 6.95 (d, 1H), 4.70 (quad, 1H), 4.15 (q, 2H), 1.50 (d, 3H), 1.30 (t, 3H)<br>IR (cm$^{-1}$): 3200-2300, 1667, 1626<br>HRMS (ESI): theoretical m/z for $C_{20}H_{20}FN_2O_3$ [M + H]$^+$ 355.1489, measured 355.1489 |
| P52 | 315 | 5-{4-[(1S)-1-Aminoethyl]-2-methylbenzoyl}isoquinolin-1(2H)-one hydrochloride<br>$^1$H NMR (400 MHz, DMSO-d$_6$): δ 11.60-11.50 (m, 1H), 8.60-8.40 (m, 3H), 8.45 (m, 1H), 7.65 (dd, 1H), 7.60-7.50 (2m, 2H), 7.40 (dd, 1H), 7.35 (d, 1H), 7.30 (m, 1H), 6.90 (d, 1H), 4.45 (quad, 1H), 2.35 (s, 3H), 1.55 (d, 3H)<br>IR (cm$^{-1}$): 3200-2340, 1652, 1615<br>HRMS (ESI): theoretical m/z for $C_{19}H_{19}N_2O_2$ [M + H]$^+$ 307.1447, measured 307.1455.<br>Optical purity: (AD 5 μm column 4.6 × 250 mm, eluant: EtOH/heptane/diethylamine 40/60/0.1, detection: 255 nm): >99%. (absence of P47) |
| P61 | 351 | 5-({8-[(1R)-1-Aminoethyl]-2,3-dihydro-1,4-benzo-dioxin-5-yl}carbonyl)isoquinolin-1(2H)-one hydrochloride<br>$^1$H NMR (300 MHz, DMSO-d$_6$): δ 11.50 (broad s, 1H), 8.45 (d, 1H), 8.38 (broad s, 3H), 7.72 (d, 1H), 7.52 (t, 1H), 7.29 (m, 1H), 7.18 (d, 1H), 7.09 (d, 1H), 7.05 (d, 1H), 4.59 (quad, 1H), 4.30 (m, 2H), 4.10 (m, 2H), 1.51 (d, 3H)<br>IR (cm$^{-1}$): 3211, 3100-2500, 1669, 1219, 1076, 777<br>HRMS (ESI): theoretical m/z for $C_{20}H_{19}N_2O_4$ [M + H]$^+$ 351.1345, measured 351.1341<br>Optical purity (SFC: Chiralpak IA 3 μM 4.6 × 250 mm; eluant: CO$_2$/(ethanol/butylamine: 100/0.5): 70/30; detection: 260 nm): >99%.<br>(absence of P64)<br>α$_D$ (589 nM) = −15.1 (c = 0.009 g/mL, MeOH) at 20° C. |
| P64 | 373 | 5-({8-[(1S)-1-Aminoethyl]-2,3-dihydro-1,4-benzo-dioxin-5-yl}carbonyl)isoquinolin-1(2H)-one hydrochloride<br>$^1$H NMR (400 MHz, DMSO-d$_6$): δ 11.52 (m, 1H), 8.43 |

| Product | Obtained from | Nomenclature Analytical description |
|---|---|---|
| | | (d, 1H), 8.36 (m, 3H), 7.73 (d, 1H), 7.53 (t, 1H), 7.29 (broad d 1H), 7.16 (d, 1H), 7.08 (d, 1H), 7.05 (d, 1H), 4.58 (quad, 1H), 4.31 (m, 2H), 4.10 (m, 2H), 1.51 (d, 3H) <br> IR (cm$^{-1}$): 3221, 3200-2300, 1669 <br> HRMS (ESI): theoretical m/z for $C_{20}H_{19}N_2O_4$ [M + H]$^+$ 351.1345, measured 351.1353. <br> theoretical m/z for $C_{20}H_{19}N_2O_4$ [M + H]$^+$ 351.1345, measured 351.1353. <br> Optical purity (SFC: Chiralpak IA 3 μM 4.6 × 250 mm; eluant: $CO_2$/(ethanol/butylamine: 100/0.5): 70/30; detection: 260 nm): >99%. <br> (absence of P61) <br> $\alpha_D$ (589 nM) = 15.41 (c = 1, DMSO) at 20° C. |
| P68 | 391 | 5-{4-[(1R)-1-Aminoethyl]-2-methylbenzoyl}-3-methyl-isoquinolin-1(2H)-one methanesulphonate <br> $^1$H NMR (400 MHz, DMSO-d$_6$): δ 8.40 (d, 1H), 7.60 (d, 1H), 7.50 (broad s, 1H), 7.45 (t, 1H), 7.40 (m, 2H), 6.80 (broad s, 1H), 4.50 (m, 1H), 2.40-2.20 (3s, 9H), 1.50 (d, 3H) <br> IR (cm$^{-1}$): 3400-2450, 1684, 1637, 1600, 1550, 1315, 1239, 1149, 825-681 <br> HRMS (ESI): theoretical m/z for $C_{20}H_{21}N_2O_2$ [M + H]$^+$ 321.1603, measured 321.1591 <br> theoretical m/z for $C_{40}H_{41}N_4O_4$ [2M + H]$^+$ 641.3128, measured 641.3080 <br> theoretical m/z for $C_{40}H_{40}N_4NaO_4$ [2M + Na]$^+$ 663.2947, measured 663.2919 <br> Optical purity (capillary electrophoresis: standard CE, phosphate buffer/HS α-cyclodextrin, detection 210 nm): >99%. |
| P74 | 408 | 5-{4-[(1S)-1-Aminoethyl]-2-methylbenzoyl}-4-methyl-isoquinolin-1(2H)-one hydrochloride <br> $^1$H NMR (500 MHz, DMSO-d$_6$): δ 11.62 (d, 1H), 8.61 (broad s, 3H), 8.44 (dd, 1H), 7.61 (d, 1H), 7.55 (t, 1H), 7.50 (dd, 1H), 7.42 (dd, 1H), 7.39 (d, 1H), 7.06 (d, 1H), 4.43 (quad, 1H), 2.63 (s, 3H), 1.89 (s, 3H), 1.52 (d, 3H) <br> IR (cm$^{-1}$): 3200-2000, 1677, 1645 <br> HRMS (ESI): theoretical m/z for $C_{20}H_{21}N_2O_2$ [M + H]+ 321.1603, measured 321.1579. <br> m/z measured for $C_{20}H_{20}N_2O_2$ [M]+ 320.20. <br> Optical purity (SFC: (S,S) Whelk 5 μM 4.6 × 250 mm; eluant: $CO_2$/(ethanol/butylamine: 100/0.5): 75/25; detection: 255 nm): >99%. <br> (absence of P87) |
| P87 | 462 | 5-{4-[(1R)-1-Aminoethyl]-2-methylbenzoyl}-4-methyl-isoquinolin-1(2H)-one hydrochloride <br> $^1$H NMR (400 MHz, DMSO-d$_6$): δ 11.40 (broad s, 1H), 8.45 (broad s, 3H), 8.45 (dd, 1H), 7.60 (s, 1H), 7.56 (t, 1H), 7.50 (dd, 1H), 7.40 (2m, 2H), 7.06 (broad s, 1H), 4.42 (quad, 1H), 2.63 (s, 3H), 1.90 (s, 3H), 1.50 (d, 3H) <br> IR (cm$^{-1}$): 3000-2500, 1677, 1645 <br> HRMS (ESI): theoretical m/z for $C_{20}H_{21}N_2O_2$ [M + H]$^+$ 321.1603, measured 321.1589, <br> Optical purity (SFC: (S,S) Whelk 5 μM 4.6 × 250 mm; eluant: $CO_2$/(ethanol/butylamine: 100/0.5): 75/25; detection: 255 nm): >99%. <br> (absence of P74) |
| P102 | 542 | 5-{4-[(1R)-1-Aminoethyl]-2-fluoro-6-methoxy-benzoyl}isoquinolin-1(2H)-one hydrochloride <br> $^1$H NMR (400 MHz, DMSO-d$_6$): δ 11.63 (m, 1H), 8.80-8.50 (m, 3H), 8.50 (d, 1H), 7.78 (d, 1H), 7.55 (t, 1H), 7.52 (d, 1H), 7.38 (dd, 1H), 7.35 (s, 1H), 7.18 (d, 1H), 4.49 (quad, 1H), 3.74 (s, 3H), 1.57 (d, 3H) <br> IR (cm$^{-1}$): 3300-2000, 1674, 1648, 1617 <br> HRMS (ESI): theoretical m/z for $C_{19}H_{18}FN_2O_3$ [M + H]$^+$ 341.1301, measured 341.1292. |
| P110 | 591 | [4-(1-Aminoethyl)phenyl](isoquinolin-5-yl)methanone dihydrochloride <br> $^1$H NMR (300 MHz, DMSO-d$_6$): δ 9.80 (s, 1H), 8.75 (m, 3H), 8.65 (2d, 2H), 8.20 (d, 1H), 8.15 (d, 1H), 8.00 (t, 1H), 7.88 (d, 2H), 7.75 (d, 2H), 4.50 (m, 1H), 1.55 (d, 3H) <br> IR (cm$^{-1}$): 3000-2500, 2051, 1665-1645, 1604, 819-746 <br> HRMS (ESI): theoretical m/z for $C_{18}H_{16}N_2O$ [M + H]$^+$ 277.1341, measured 277.1356 <br> theoretical m/z for $C_{18}H_{17}N_2O$ [M + H—NH$_3$]$^+$ 260.1075, measured 260.1078 |

| Product | Obtained from | Nomenclature Analytical description |
|---|---|---|
| P111 | 596 | {4-[(1S)-1-Aminoethyl]phenyl}(isoquinolin-5-yl)-methanone dihydrochloride<br>$^1$H NMR (300 MHz, DMSO-$d_6$): δ 9.80 (s, 1H), 8.75 (m, 3H), 8.65 (2d, 2H), 7.20 (d, 1H), 8.15 (d, 1H), 8.00 (t, 1H), 7.88 (d, 2H), 7.75 (d, 2H), 4.50 (m, 1H), 1.55 (d, 3H)<br>IR (cm$^{-1}$): 3000-2000, 1650<br>HRMS (ESI): theoretical m/z for $C_{18}H_{17}N_2O$ [M + H]$^+$ 277.1341, measured 277.1353<br>Optical purity: (ADH 5 μm column 4.6 × 250 mm, eluant: EtOH/triethylamine 1000/1, detection: 265 nm): >99%.<br>(absence of P1) |
| P112 | 603 | [4-(2-Aminopropan-2-yl)phenyl](isoquinolin-5-yl)-methanone dihydrochloride<br>$^1$H NMR (300 MHz, DMSO-$d_6$): δ 10.00 (s, 1H), 9.00 (m, 3H), 8.70 (m, 2H), 8.30-8.20 (2d, 2H), 8.05 (t, 1H), 7.85 (dd, 4H), 1.70 (s, 6H)<br>IR (cm$^{-1}$): 2800, 1651<br>HRMS (ESI): theoretical m/z for $C_{19}H_{19}N_2O$ [M + H]$^+$ 291.1497, measured 291.1514 |
| P113 | 610 | [4-(1-Aminocyclobutyl)phenyl](isoquinolin-5-yl)-methanone dihydrochloride<br>$^1$H NMR (300 MHz, DMSO-$d_6$): δ 9.95 (s, 1H), 9.00 (m, 3H), 8.70 (m, 2H), 8.25 (d, 1H), 8.20 (d, 1H), 8.05 (t, 1H), 7.85-7.75 (dd, 4H), 2.65 (m, 4H), 2.25-1.80 (m, 2H)<br>IR (cm$^{-1}$): 3000-2500, 1650<br>HRMS (ESI): theoretical m/z for $C_{20}H_{19}N_2O$ [M + H]$^+$ 303.1497, measured 303.1528 |
| P114 | 617 | [(1R)-1-Amino-2,3-dihydro-1H-inden-5-yl](isoquinolin-5-yl)methanone dihydrochloride<br>$^1$H NMR (300 MHz, DMSO-$d_6$): δ 9.90 (s, 1H), 8.90 (broad s, 3H), 8.68 (2d, 2H), 8.25 (d, 1H), 8.18 (d, 1H), 8.05 (t, 1H), 7.90 (d, 1H), 7.72 (m, 2H), 4.78 (m, 1H), 3.10 (m, 1H), 2.90 (m, 1H), 2.50 (m, 1H), 2.10 (m, 1H)<br>IR (cm$^{-1}$): 2484-2077, 2077-1955-1866, 1662-1651, 1607, 820-754<br>HRMS (ESI): theoretical m/z for $C_{19}H_{17}N_2O$ [M + H]$^+$ 289.1341, measured 289.1348<br>Optical purity (capillary electrophoresis: standard CE, phosphate buffer/HS α-cyclodextrin, detection 210 nm): >99%.<br>(absence of P115) |
| P115 | 619 | [(1S)-1-Amino-2,3-dihydro-1H-inden-5-yl](isoquinolin-5-yl)methanone dihydrochloride<br>$^1$H NMR (300 MHz, DMSO-$d_6$): δ 9.85 (s, 1H), 8.80 (broad s, 3H), 8.65 (m, 2H), 8.20 (d, 1H), 8.15 (d, 1H), 8.05 (m, 1H), 7.85 (d, 1H), 7.75 (m, 2H), 4.80 (m, 1H), 3.15-2.90 (2m, 2H), 2.55-2.05 (2m, 2H)<br>IR (cm$^{-1}$): 2725-2150, 2076, 1957, 1866, 1664, 1651, 1606-1590<br>HRMS (ESI): theoretical m/z for $C_{19}H_{17}N_2O$ [M + H]$^+$ 289.1341, measured 289.1364<br>Optical purity (capillary electrophoresis: standard CE, phosphate buffer/HS α-cyclodextrin, detection 210 nm): >99%.<br>(absence of P114)<br>$α_D$ (589 nM) = −12.83 (c = 0.013 g/mL, MeOH) at 20° C. |
| P116 | 625 | [4-(4-Aminotetrahydro-2H-pyran-4-yl)phenyl]-(isoquinolin-5-yl)methanone dihydrochloride<br>$^1$H NMR (400 MHz, DMSO-$d_6$): δ 9.80 (s, 1H), 8.95-8.75 (broad m, 3H), 8.67 (d, 1H), 8.63 (d, 1H), 8.21 (d, 1H), 8.15 (d, 1H), 8.00 (t, 1H), 7.88 (m, 4H), 3.92-3.40 (2m, 4H), 2.45-2.20 (2m, 4H)<br>IR (cm$^{-1}$): 3700-3200, 3300-1800, 1659<br>HRMS (ESI): theoretical m/z for $C_{21}H_{21}N_2O_2$ [M + H]$^+$ 333.1603, measured 333.2 |
| P117 | 635 | (1-Amino-1-methyl-2,3-dihydro-1H-inden-5-yl)-(isoquinolin-5-yl)methanone dihydrochloride<br>$^1$H NMR (300 MHz, DMSO-$d_6$): δ 9.90 (s, 1H), 8.88 (broad s, 3H), 8.68 (m, 2H), 8.20 (d, 1H), 8.15 (d, 1H), 8.01 (t, 1H), 7.85 (d, 1H), 7.75 (m, 2H), 3.13 (m, 1H), 2.99 (m, 1H), 2.35 (m, 1H), 2.25 (m, 1H), 1.63 (s, 3H)<br>IR (cm$^{-1}$): 3200-2000, 1659<br>HRMS (ESI): theoretical m/z for $C_{20}H_{19}N_2O$ [M + H]$^+$ 303.1497, measured 303.1511 |
| P118 | 637 | {4-[(1S)-1-Aminoethyl]-2-methylphenyl}(isoquinolin-5-yl)methanone hydrochloride<br>$^1$H NMR (400 MHz, DMSO-$d_6$): δ 9.88 (s, 1H), 8.74 (m, 4H), 8.68 (d, 1H), 8.59 (d, 1H), 8.04 (d, 1H), 7.98 (t, 1H), |

| Product | Obtained from | Nomenclature Analytical description |
|---|---|---|
| | | 7.62 (broad s, 1H), 7.48 (broad d, 1H), 7.42 (d, 1H), 4.46 (m, 1H), 2.43 (s, 3H), 1.56 (d, 3H)<br>IR (cm$^{-1}$): 3468, 3000-2000, 1657<br>HRMS (ESI): theoretical m/z for $C_{19}H_{19}N_2O$ [M + H]$^+$ 291.1497, measured 291.1521<br>Optical purity: (ADH 5 μm column 4.6 × 250 mm, eluant: EtOH/diethylamine 100/0.1, detection: 270 nm): >99%. (absence of P2) |
| P120 | 647 | (1-Amino-6-methoxy-2,3-dihydro-1H-inden-5-yl)-(isoquinolin-5-yl)methanone dihydrochloride<br>$^1$H NMR (300 MHz, DMSO-d$_6$): δ 9.70 (broad s, 1H), 8.90-8.60 (m, 3H), 8.65 (d, 1H), 8.60-8.50 (2m, 2H), 7.95 (d, 1H), 7.85 (t, 1H), 7.70 (s, 1H), 7.50 (s, 1H), 4.75 (m, 1H), 3.50 (s, 3H), 3.10 (m, 1H), 2.85 (m, 1H), 2.50 (m, 1H), 2.10 (m, 1H)<br>IR (cm$^{-1}$): 3600-3300, 3100-2000, 1647<br>HRMS (ESI): theoretical m/z for $C_{20}H_{19}N_2O_2$ [M + H]$^+$ 319.1447, measured 319.1432 |
| P126 | 688 | [4-(1-Aminoethyl)-2-hydroxyphenyl](isoquinolin-5-yl)-methanone dihydrochloride<br>$^1$H NMR (400 MHz, DMSO-d$_6$): δ 11.03 (m, 1H), 9.87 (s, 1H), 8.72 (m, 3H), 8.69 (d, 1H), 8.64 (d, 1H), 8.38 (d, 1H), 8.14 (d, 1H), 8.00 (t, 1H), 7.52 (d, 1H), 7.18 (d(fine), 1H), 7.14 (dd(fine), 1H), 4.41 (m, 1H), 1.53 (d, 3H)<br>IR (cm$^{-1}$): 3600-2000, 1630<br>HRMS (ESI): theoretical m/z for $C_{18}H_{17}N_2O_2$ [M + H]$^+$ 293.1290, measured 293.1284 |
| P132 | 718 | 5-[4-(1-Aminoethyl)-2-fluoro-3-(2-methylpropoxy)-benzoyl] isoquinolin-1(2H)-one hydrochloride<br>$^1$H NMR (400 MHz, DMSO-d$_6$): δ 12.60 (s, 1H), 8.50 (s, 3H), 8.50 (d, 1H), 7.80 (d, 1H), 7.60 (d, 1H), 7.55 (m, 1H), 7.45 (m, 1H), 7.35 (m, 1H), 7.00 (d, 1H), 4.70 (quad, 1H), 3.95-3.80 (m, 2H), 2.05 (m, 1H), 1.55 (d, 3H), 1.00 (d, 6H).<br>IR (cm$^{-1}$): 3220-2450, 1664, 1628<br>HRMS (ESI): theoretical m/z for $C_{22}H_{24}FN_2O_3$ [M + H]$^+$ 383.1771, measured 383.1760 |
| P141 | 757 | {4-[(1R)-1-Aminoethyl]phenyl}(8-chloroisoquinolin-5-yl)-1(2H)-one dihydrochloride<br>$^1$H NMR (400 MHz, DMSO-d$_6$): δ 9.76 (s, 1H), 8.72 (d, 1H), 8.68 (broad s, 1H), 8.02 (d, 1H), 7.98 (d, 1H), 7.92 (d, 1H), 7.87 (d, 1H), 7.71 (d, 2H), 4.53 (m, 1H), 1.54 (d, 3H)<br>IR (cm$^{-1}$): 3200-2000, 1655-1643<br>HRMS (ESI): theoretical m/z for $C_{18}H_{15}ClN_2O$ [M + H]$^+$ 311.095, measured 311.093 |

Products P9, P10, P22 and P23 were obtained by separation of the corresponding racemic products:

Product P6 in the form of the free base (3.4 g) was chromatographed by high pressure chromatography on a chiral support (OD column, eluant $CH_3CN$, detection: 255 nm) to give, after salt formation, products P9 and P10.

| Product | Obtained from | Nomenclature Analytical description |
|---|---|---|
| P9 | P6 | {4-[(1R)-1-Aminoethyl]-2,6-difluorophenyl}-(isoquinolin-5-yl)methanone dihydrochloride<br>$^1$H NMR (300 MHz; DMSO-d6): δ 9.79 (s, 1H); 8.90 (d, 1H); 8.85 (broad s, 3H); 8.80 (d, 1H); 8.70 (d, 1H); 8.27 (d, 1H); 7.96 (t, 1H); 7.61 (d, 2H); 4.57 (m, 1H); 1.59 (d, 3H)<br>IR (cm$^{-1}$): 3200-2200, 1668<br>HRMS (ESI): m/z calculated for $C_{18}H_{14}F_2N_2O$ [M + H]$^+$; 313.1152 found 313.1140<br>Optical purity: (Kromasil Cellucoat column 4.6 × 250 mm, eluant: heptane/EtOH/diethylamine 70/30/0.1, detection: 252 nm): >99%. (absence of P10)<br>α$_D$ (589 nM) = 2.49 (c = 0.008 g/mL, MeOH) at 20° C. |

-continued

| Product | Obtained from | Nomenclature Analytical description |
|---|---|---|
| P10 | P6 | {4-[(1S)-1-Aminoethyl]-2,6-difluorophenyl}-(isoquinolin-5-yl)methanone dihydrochloride<br>$^1$H NMR (300 MHz; DMSO-d6): δ 9.79 (s, 1H); 8.90 (d, 1H); 8.85 (broad s, 3H); 8.80 (d, 1H); 8.70 (d, 1H); 8.27 (d, 1H); 7.96 (t, 1H); 7.61 (d, 2H); 4.57 (m, 1H); 1.59 (d, 3H)<br>IR (cm$^{-1}$): 3200-2200, 1670<br>HRMS (ESI): m/z calculated for $C_{18}H_{14}F_2N_2O$ [M + H]$^+$; 313.1152 found 313.1141<br>Optical purity: (Kromasil Cellucoat column 4.6 × 250 mm, eluant: heptane/EtOH/diethylamine 70/30/0.1, detection: 252 nm): >99%. (absence of P9)<br>$α_D$ (589 nM) = −2.2 (c = 0.008 g/mL, CHCl$_3$) at 20° C. |

Product P11 in the form of the free base (1.8 g) was chromatographed by high pressure chromatography on a chiral support (AD column, eluant MeOH, detection: 295 nm) to give, after salt formation, products P22 and P23.

| Product | Obtained from | Nomenclature Analytical description |
|---|---|---|
| P22 | P11 | {4-[(1S)-1-Aminoethyl]-2-chlorophenyl}(isoquinolin-5-yl)methanone dihydrochloride<br>$^1$H NMR (400 MHz; DMSO-d$_6$): δ 9.90 (s, 1H); 9.90 (d and m, 4H); 8.80 (d, 1H); 8.70 (d, 2H); 8.10 (d, 1H); 8.00 (t, 1H); 7.90 (broad s, 1H); 7.70 (m, 2H); 4.55 (m, 1H); 1.60 (d, 3H)<br>IR (cm$^{-1}$): 3000-2500, 1661<br>MS (DEI 70 eV): m/z measured for $C_{18}H_{15}Cl_1F_1N_2O$ 310.1<br>Optical purity: (ADH 5 μm column 4.6 × 250 mm, eluant: EtOH/heptane/diethylamine 70/30/0.1, detection: 235 nm): >99%. (absence of P23) |
| P23 | P11 | {4-[(1R)-1-Aminoethyl]-2-chlorophenyl}(isoquinolin-5-yl)methanone dihydrochloride<br>$^1$H NMR (400 MHz; DMSO-d6): δ 9.90 (s, 1H); 9.90 (d and m, 4H); 8.80 (d, 1H); 8.70 (d, 2H); 8.10 (d, 1H); 8.00 (t, 1H); 7.90 (broad s, 1H); 7.70 (m, 2H); 4.55 (m, 1H); 1.60 (d, 3H)<br>IR (cm$^{-1}$): 3000-2500, 1660<br>MS (DEI 70 eV): m/z measured for $C_{18}H_{15}Cl_1F_1N_2O$ 310.1<br>Optical purity: (ADH 5 μm column 4.6 × 250 mm, eluant: EtOH/heptane/diethylamine 70/30/0.1, detection: 235 nm): >99%. (absence of P22) |

Protocol XXI: Alternative Method for the Preparation of Compounds of Formula (I) Wherein X Represents —C(=O)

Compounds of formula (I) wherein X represents —C(=O)— can also be prepared by coupling reaction via directed ortho-metalation according to the example of the synthesis of intermediate 333 below:

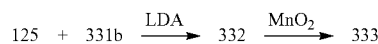

Intermediate 332:

tert-Butyl [(1R)-1-{3-[(1-ethoxyisoquinolin-5-yl)(hydroxy) methyl]-2,4-difluorophenyl}ethyl]carbamate To a solution of intermediate 331b (35 g, 137 mmoles) in THF (700 mL), cooled to −78° C. under a nitrogen atmosphere, there is added a 2N solution of LDA in heptane/THF/ethylbenzene (170 mL, 342 mmoles), the temperature being maintained below −75° C. The reaction mixture is stirred at −78° C. for 30 minutes, and then a solution of intermediate 125 (28.8 g, 143 mmoles) in THF (330 mL) is added in the course of 1 hour, the temperature being maintained below −75° C. The reaction mixture is stirred for 30 minutes. The reaction mixture is hydrolysed with water and then allowed to return to ambient temperature. The THF is removed under reduced pressure. The aqueous phase is extracted with 2×350 mL of AcOEt, and then the organic phases are combined and evaporated in vacuo. The residue is purified by flash chromatography on silica (eluant=CH$_2$Cl$_2$/AcOEt: 70/30). Intermediate 332 (56.3 g) is obtained in the form of a yellowish solid.

$^1$H NMR (400 MHz, DMSO-d$_6$): δ 8.15 (m, 2H), 7.92 (d, 1H), 7.64 (t, 1H), 7.35 (m, 1H), 7.26 (m, 1H), 6.98 (m, 1H), 6.60 (s, 1H), 6.11 (broad s, 1H), 4.81 (m, 1H), 4.53 (quad, 2H), 1.42 (t, 3H), 1.38-1.22 (m, 12H), 1.35 (d, 3H).

$^{19}$F NMR: −119, −115

IR (cm$^{-1}$): 3331, 1689, 1572, 1161

Intermediate 333:

tert-Butyl [(1R)-1-{3-[(1-ethoxyisoquinolin-5-yl)carbonyl]-2,4-difluorophenyl}ethyl]-carbamate Intermediate 332 is converted into intermediate 333 according to the protocol described for intermediate 127 (Protocol XX).

$^1$H NMR (300/400 MHz, DMSO-$d_6$): δ 8.55 (d, 1H), 8.05 (d, 1H), 8.20 (m, 2H), 7.75 (t, 1H), 7.65 (quad, 1H), 7.55 (broad d, 1H), 7.30 (t, 1H), 4.85 (m, 1H), 4.55 (quad, 2H), 1.45 (t, 3H), 1.40 (m, 9H), 1.3 (d, 3H)

IR (cm$^{-1}$): 3300, 1676, 1250

This sequence was used to prepare the following intermediates:

Intermediate 236:

N-{5-[(1-Ethoxyisoquinolin-5-yl)carbonyl]-4,6-difluoro-2,3-dihydro-1H-inden-1-yl}-2-methylpropane-2-sulphinamide Obtained by oxidation of the intermediate resulting from the coupling of 234 and 125

$^1$H NMR (400 MHz, DMSO-$d_6$): δ 8.53 (d, 1H), 8.19 (2d, 2H), 8.00 (d, 1H), 7.71 (t, 1H), 7.48 (d, 1H), 6.01 (d, 1H), 4.89 (m, 1H), 4.58 (quad, 1H), 2.96-2.78 (m, 2H), 2.50-2.05 (m, 2H), 1.47 (t, 3H), 1.19 (s, 9H)

IR (cm$^{-1}$): 3200, 1668

Intermediate 262:

N-{6-[(1-Ethoxyisoquinolin-5-yl)carbonyl]-5,7-difluoro-2,3-dihydro-1H-inden-1-yl}-2-methylpropane-2-sulphinamide Obtained by oxidation of the intermediate resulting from the coupling of 260 and 125

$^1$H NMR (400 MHz, DMSO-$d_6$): δ 8.55 (d, 1H), 8.20 (d, 1H), 8.15 (d, 1H), 8.00 (d, 1H), 7.70 (m, 1H), 7.25 (d, 1H), 5.75 (d, 1H), 4.95 (m, 1H), 4.55 (quad, 2H), 3.20-2.90 (2m, 2H), 2.40-2.20 (2m, 2H), 1.45 (t, 3H), 1.05 (s, 9H)

IR (cm$^{-1}$): 3215, 1738, 1670.

Intermediate 271:

tert-Butyl (1-{4-[(1-ethoxyisoquinolin-5-yl)carbonyl]-2,3-difluorophenyl}ethyl)-carbamate Obtained by oxidation of the intermediate resulting from the coupling of 269 and 125

$^1$H NMR (300/400 MHz, DMSO-$d_6$): δ 8.47 (d, 1H), 8.11 (d, 1H), 7.95 (d, 1H), 7.70 (t, 1H), 7.70 (d, 1H), 7.70 (broad d, 1H), 7.49 (t, 1H), 7.32 (t, 1H), 4.95 (quint, 1H), 4.55 (quad, 2H), 1.45 (t, 3H), 1.40 (broad s, 9H), 1.35 (d, 3H)

IR (cm$^{-1}$): 3345, 1671, 1523

Intermediate 296:

tert-Butyl [(1R)-1-{4-[(1-ethoxy-3-methylisoquinolin-5-yl)carbonyl]-3,5-difluorophenyl}ethyl]carbamate Obtained by oxidation of the intermediate resulting from the coupling of 288 and 294

$^1$H NMR (400 MHz, DMSO-$d_6$): δ 8.50 (d, 1H), 8.05 (s, 1H), 8.00 (d, 1H), 7.65 (t, 1H), 7.55 (broad d, 1H), 7.15 (broad d, 2H), 4.75 (m, 1H), 4.55 (quad, 2H), 2.55 (s, 3H), 1.45 (t, 3H), 1.40 (s, 9H), 1.40 (d, 6H)

IR (cm$^{-1}$): 3400, 1679, 1260

Intermediate 305:

tert-Butyl [(1R)-1-{4-[(1-ethoxy-4-methylisoquinolin-5-yl)carbonyl]-3,5-difluorophenyl}ethyl]carbamate Obtained by oxidation of the intermediate resulting from the coupling of 288 and 303

$^1$H NMR (400 MHz, DMSO-$d_6$): δ 8.45 (d, 1H), 8.00 (s, 1H), 7.80 (d, 1H), 7.65 (m, 1H), 7.55 (d, 1H), 7.20 (d, 2H), 4.75 (m, 1H), 4.55 (quad, 2H), 2.20 (s, 3H), 1.45 (t, 3H), 1.40 (s, 9H), 1.30 (t, 3H)

IR (cm$^{-1}$): 3387, 1686, 1668

Intermediate 319:

N-{5-[(1-Ethoxyisoquinolin-5-yl)carbonyl]-4,6-difluoro-2,3-dihydro-1H-inden-1-yl}-2-methylpropane-2-sulphinamide Obtained by oxidation of the intermediate resulting from the coupling of 317 and 125

$^1$H NMR (400 MHz, DMSO-$d_6$): δ 8.53 (d, 1H), 8.19 (2d, 2H), 8.00 (d, 1H), 7.71 (t, 1H), 7.48 (d, 1H), 6.01 (d, 1H), 4.89 (m, 1H), 4.58 (quad, 1H), 2.96-2.78 (m, 2H), 2.50-2.05 (m, 2H), 1.47 (t, 3H), 1.19 (s, 9H)

IR (cm$^{-1}$): 3200, 1734, 1668, 1033

Intermediate 326:

tert-Butyl [(1S)-1-{3,5-difluoro-4-[(4-methylisoquinolin-5-yl)carbonyl]phenyl}ethyl]-carbamate Obtained by oxidation of the intermediate resulting from the coupling of 324 and 321

$^1$H NMR (400 MHz, DMSO-$d_6$): δ 9.30 (s, 1H), 8.50 (s, 1H), 8.35 (d, 1H), 7.90 (d, 1H), 7.70 (m, 1H), 7.60 (d, 1H), 7.25 (d, 2H), 4.75 (m, 1H), 2.35 (s, 3H), 1.40 (s, 9H), 1.35 (d, 3H)

IR (cm$^{-1}$): 3392, 1685, 1635

Intermediate 328:

tert-Butyl [(1S)-1-{4-[(1-ethoxy-4-methylisoquinolin-5-yl)carbonyl]-3,5-difluorophenyl}ethyl]carbamate Obtained starting from 326 according to the protocol described for 182

$^1$H NMR (400 MHz, DMSO-$d_6$): δ 8.53 (d, 1H), 8.05 (s, 1H), 7.90 (broad d, 1H), 7.75 (t, 1H), 7.62 (broad d, 1H), 7.30 (m, 2H), 4.81 (quint, 1H), 4.64 (quad, 2H), 2.29 (s, 3H), 1.55 (t, 3H), 1.48 (broad s, 9H), 1.41 (d, 3H)

LCMS [M+H]+=471.

Intermediate 336:

N-[(1S)-1-{3-[(1-Ethoxyisoquinolin-5-yl)carbonyl]-2,4-difluorophenyl}ethyl]-2-methylpropane-2-sulphinamide Obtained by oxidation of the intermediate resulting from the coupling of 334 and 125

$^1$H NMR (300/400 MHz, DMSO-$d_6$): δ 8.55 (d, 1H), 8.02 (dd, 2H), 8.00 (d, 1H), 7.75 (t, 2H), 7.35 (t, 1H), 5.55 (d, 1H), 4.7 (m, 1H), 4.55 (quad, 2H), 1.55 (d, 3H), 1.48 (t, 3H), 1.12 (s, 9H)

IR (cm$^{-1}$): 1669, 1048

Intermediate 339:

N-{5-[(1-Ethoxyisoquinolin-5-yl)carbonyl]-4,6-difluoro-2,3-dihydro-1H-inden-1-yl}-2-methylpropane-2-sulphinamide Obtained by oxidation of the intermediate resulting from the coupling of 337 and 125

$^1$H NMR (400 MHz, DMSO-d$_6$): δ 8.60 (ddd, 1H), 8.20 (d, 1H), 8.20 (dd, 1H), 8.00 (d, 1H), 7.75 (t, 1H), 7.50 (d, 1H), 6.05 (d, 1H), 4.90 (quad, 1H), 4.60 (quad, 2H), 3.00 (m, 1H), 2.80 (m, 1H), 2.50 (m, 1H), 2.05 (m, 1H), 1.50 (t, 3H), 1.20 (s, 9H)

IR (cm$^{-1}$): 3240, 1667, 1633, 1605, 1568, 815, 758

Intermediate 345:

tert-Butyl {(1R)-6-[(1-ethoxyisoquinolin-5-yl)carbonyl]-5,7-difluoro-2,3-dihydro-1H-inden-1-yl}carbamate Obtained by oxidation of the intermediate resulting from the coupling of 343 and 125

$^1$H NMR (400 MHz, DMSO-d$_6$): δ 8.55 (d, 1H), 8.20 (2d, 2H), 8.05 (d, 1H), 7.70 (t, 1H), 7.35 (d, 1H), 7.20 (d, 1H), 5.20 (quad, 1H), 4.60 (quad, 2H), 3.10 (m, 1H), 2.90 (m, 1H), 2.45 (m, 1H), 1.95 (m, 1H), 1.50 (t, 3H), 1.35 (s, 9H)

IR (cm$^{-1}$): 3430, 1672, 1635, 1575, 1517, 1162

Intermediate 348:

tert-Butyl {(1S)-6-[(1-ethoxyisoquinolin-5-yl)carbonyl]-5,7-difluoro-2,3-dihydro-1H-inden-1-yl}carbamate Obtained by oxidation of the intermediate resulting from the coupling of 346 and 125

$^1$H NMR (400 MHz, DMSO-d$_6$): δ 8.55 (d, 1H), 8.20 (2d, 2H), 8.05 (d, 1H), 7.70 (t, 1H), 7.35 (d, 1H), 7.20 (d, 1H), 5.20 (quad, 1H), 4.60 (quad, 2H), 3.10 (m, 1H), 2.90 (m, 1H), 2.45 (m, 1H), 1.95 (m, 1H), 1.50 (t, 3H), 1.35 (m, 9H)

IR (cm$^{-1}$): 3430, 1673, 1636, 1575, 1517, 1162

Intermediate 369:

tert-Butyl (1-{4-[(1-ethoxyisoquinolin-5-yl)carbonyl]-3,5-difluoro-2-methoxyphenyl}-ethyl)carbamate Obtained by oxidation of the intermediate resulting from the coupling of 367 and 125

$^1$H NMR (300 MHz, DMSO-d$_6$): δ 8.55 (d, 1H), 8.20 (2d, 2H), 8.10 (d, 1H), 7.75 (t, 1H), 7.50 (d, 1H), 7.20 (d, 1H), 5.00 (m, 1H), 4.60 (quad, 2H), 3.90 (s, 3H), 1.45 (t, 3H), 1.40 (m, 9H), 1.30 (d, 3H)

$^{19}$F NMR: −118, −129

IR (cm$^{-1}$): 3390, 1682, 1675, 1517, 1162, 851-738

Intermediate 375:

tert-Butyl (1-{4-[(1-ethoxy-3-methylisoquinolin-5-yl)carbonyl]-3,5-difluoro-2-methoxyphenyl}ethyl)carbamate Obtained by oxidation of the intermediate resulting from the coupling of 367 and 294

$^1$H NMR (300 MHz, DMSO-d$_6$): δ 8.50 (d, 1H), 8.05 (s, 1H), 8.05 (d, 1H), 7.65 (t, 1H), 7.50 (d, 1H), 7.20 (d, 1H), 5.00 (m, 1H), 4.55 (quad, 2H), 3.90 (s, 3H), 2.55 (s, 3H), 1.50 (t, 3H), 1.40 (m, 9H), 1.30 (d, 3H)

$^{19}$F NMR: −118, −129

IR (cm$^{-1}$): 3400, 1679, 1665, 1616, 1571, 1520, 1148, 860-691

Intermediate 380:

tert-Butyl (2-{4-[(1-ethoxy-4-methylisoquinolin-5-yl)carbonyl]-3,5-difluorophenyl}-propan-2-yl)carbamate Obtained by oxidation of the intermediate resulting from the coupling of 378 and 303

$^1$H NMR (400 MHz, DMSO-d$_6$): δ 8.45 (m, 1H), 7.95 (s, 1H), 7.80 (m, 1H), 7.65 (t, 1H), 7.35 (m, 1H), 7.15 (d, 2H), 4.55 (quad, 2H), 2.20 (s, 3H), 1.50 (s, 6H), 1.45 (t, 3H), 1.35 (broad s, 9H)

IR (cm$^{-1}$): 3310, 1718, 1688, 1627

Intermediate 389:

tert-Butyl [1-{4-[(1-ethoxyisoquinolin-5-yl)carbonyl]-3-fluoro-2-methoxyphenyl}-ethyl]carbamate Obtained by oxidation of the intermediate resulting from the coupling of 387 and 125

$^1$H NMR (400 MHz, DMSO-d$_6$): δ 8.46 (d, 1H), 8.10 (d, 1H), 7.93 (d, 1H), 7.70 (m, 2H), 7.56 (d, 1H), 7.37 (dd, 1H), 7.30 (d, 1H), 4.99 (m, 1H), 4.57 (quad, 2H), 3.86 (s, 3H), 1.46 (t, 3H), 1.37 (s, 9H), 1.29 (d, 3H)

IR (cm$^{-1}$): 3354, 1703, 1660

Intermediate 403:

N-[(1R)-1-{4-[(1-Ethoxyisoquinolin-5-yl)carbonyl]-3,5-difluoro-2-methoxyphenyl}-ethyl]-2-methylpropane-2-sulphinamide Obtained by oxidation of the intermediate resulting from the coupling of 401 and 125

$^1$H NMR (400 MHz, DMSO-d$_6$): δ 8.55 (d, 1H), 8.20 (2d, 2H), 8.10 (d, 1H), 7.75 (t, 1H), 7.40 (dd, 1H), 5.80 (d, 1H), 4.75 (quint, 1H), 4.60 (quad, 2H), 3.90 (s, 3H), 1.50 (t, 3H), 1.40 (d, 3H), 1.15 (s, 9H)

IR (cm$^{-1}$): 3245, 1668, 1617, 1569, 816, 757

Intermediate 406:

N-[(1S)-1-{4-[(1-Ethoxyisoquinolin-5-yl)carbonyl]-3,5-difluoro-2-methoxyphenyl}-ethyl]-2-methylpropane-2-sulphinamide Obtained by oxidation of the intermediate resulting from the coupling of 404 and 125

$^1$H NMR (400 MHz, DMSO-d$_6$): δ 8.55 (d, 1H), 8.20 (2d, 2H), 8.10 (d, 1H), 7.75 (t, 1H), 7.30 (dd, 1H), 5.55 (d, 1H), 4.80 (quint, 1H), 4.60 (quad, 2H), 3.90 (s, 3H), 1.50 (t, 3H), 1.50 (d, 3H), 1.15 (s, 9H)

IR (cm$^{-1}$): 3230, 1668, 1617, 1569, 815, 757

Intermediate 417:

tert-Butyl {5-[(1-ethoxyisoquinolin-5-yl)carbonyl]-4,6-difluoro-2,3-dihydro-1H-inden-1-yl}carbamate Obtained by oxidation of the intermediate resulting from the coupling of 415 and 125

$^1$H NMR (400 MHz, DMSO-d$_6$): δ 8.55 (dd, 1H), 8.20 (2d, 2H), 8.00 (dd, 1H), 7.70 (t, 1H), 7.50 (d, 1H), 7.00 (d, 1H), 5.10 (m, 1H), 4.60 (quad, 2H), 3.00 (m, 1H), 2.80 (m, 1H), 2.45 (m, 1H), 1.95 (m, 1H), 1.45 (t, 3H), 1.45 (s, 9H)

IR (cm$^{-1}$): 3385, 1680, 1662, 1569, 1511, 1162

Intermediate 425:

tert-Butyl {5-[(1-ethoxyisoquinolin-5-yl)carbonyl]-4,6-difluoro-2,3-dihydro-1H-inden-1-yl}carbamate Obtained by oxidation of the intermediate resulting from the coupling of 423 and 125

$^1$H NMR (400 MHz, DMSO-d$_6$): δ 8.55 (dd, 1H), 8.20 (2d, 2H), 8.00 (dd, 1H), 7.70 (t, 1H), 7.50 (d, 1H), 7.00 (d, 1H), 5.10 (m, 1H), 4.60 (quad, 2H), 3.00 (m, 1H), 2.80 (m, 1H), 2.45 (m, 1H), 1.95 (m, 1H), 1.45 (t, 3H), 1.45 (s, 9H)

IR (cm$^{-1}$): 3385, 1680, 1662, 1569, 1510

Intermediate 432:

tert-Butyl (1-{4-[(1-ethoxyisoquinolin-5-yl)carbonyl]-2-ethyl-3,5-difluorophenyl}-ethyl)carbamate Obtained by oxidation of the intermediate resulting from the coupling of 430 and 125

$^1$H NMR (400 MHz, DMSO-d$_6$): δ 8.54 (d, 1H), 8.19 (d, 1H), 8.15 (d, 1H), 8.03 (d, 1H), 7.72 (dd, 1H), 7.60 (d, 1H), 7.25 (d, 1H), 4.94 (m, 1H), 4.57 (quad, 2H), 2.74 (m, 1H), 2.64 (m, 1H), 1.46 (t, 3H), 1.38 (s, 9H), 1.33 (d, 3H), 1.16 (t, 3H)

IR (cm$^{-1}$): 3358, 1677, 1631

Intermediate 446:

tert-Butyl (1-{6-(benzyloxy)-3-[(1-ethoxyisoquinolin-5-yl)carbonyl]-2,4-difluorophenyl}ethyl)carbamate Obtained by oxidation of the intermediate resulting from the coupling of 444 and 125

$^1$H NMR (300 MHz, DMSO-d$_6$): δ 8.50 (d, 1H), 8.15 (d, 1H), 8.0 (m, 2H), 7.70 (t, 1H), 7.6-7.3 (m, 5H), 7.05 (d, 1H), 6.95 (m, 1H), 5.30 (s, 2H), 5.10 (m, 1H), 4.55 (quad, 2H), 1.45 (t, 3H), 1.30 (m, 12H)

$^{19}$F NMR: −112.5, −115.5

IR (cm$^{-1}$): 3490, 1709

Intermediate 467:

tert-Butyl (2-{3-[(1-ethoxyisoquinolin-5-yl)carbonyl]-2,4-difluorophenyl}propan-2-yl)-carbamate Obtained by oxidation of the intermediate resulting from the coupling of 465 and 125

$^1$H NMR (400 MHz, DMSO-d$_6$): δ 8.54 (d, 1H), 8.20 (s, 2H), 7.92 (d, 1H), 7.69 (t, 1H), 7.50 (m, 1H), 7.30 (broad s, 1H), 7.22 (t, 1H), 4.58 (quad, 2H), 1.55 (s, 6H), 1.45 (t, 3H), 1.30 (m, 9H)

$^{19}$F NMR: −117.2, −116.2

IR (cm$^{-1}$): 3345, 1697, 1672

Intermediate 480:

N-(1-{3-[(1-Ethoxyisoquinolin-5-yl)carbonyl]-2,4-difluorophenyl}propyl)-2-methylpropane-2-sulphinamide Obtained by oxidation of the intermediate resulting from the coupling of 478 and 125

$^1$H NMR (300 MHz, DMSO-d$_6$): δ 8.56 (d, 1H), 8.19 (2d, 2H), 7.99 (d, 1H), 7.72 (2m, 2H), 7.31 (t, 1H), 5.50 (d, 1H), 4.59 (quad., 2H), 4.40 (m, 1H), 1.92 (m, 1H), 1.78 (m, 1H), 1.48 (t, 3H), 1.08 (s, 9H), 0.87 (t, 3H)

IR (cm$^{-1}$): 3197, 1670, 1264, 1050, 1018

Intermediate 486:

tert-Butyl 2-{3-[(1-ethoxyisoquinolin-5-yl)carbonyl]-2,4-difluorophenyl}pyrrolidine-1-carboxylate Obtained by oxidation of the intermediate resulting from the coupling of 484 and 125

$^1$H NMR (300 MHz, DMSO-d$_6$): δ 8.45 (d, 1H), 8.17 (2d, 2H), 7.98 (d, 1H), 7.80 (t, 1H), 7.45 (m, 1H), 7.21 (t, 1H), 4.95 (m, 1H), 4.61 (quad, 2H), 3.52 (m, 2H), 2.33 (m, 1H), 1.89 (m, 2H), 1.80 (m, 1H), 1.48 (t, 3H), 1.29 (s, 9H)

IR (cm$^{-1}$): 1694, 1674, 1159

Optical purity (SFC: ID 3 μM column 4.6×250 mm; CO$_2$/(isopropanol/n-butylamine: 100/0.5): 75/25; Detection: 254 nm): >99%.

Intermediate 494:

tert-Butyl [(1R)-1-{4-[(1-ethoxyisoquinolin-5-yl)carbonyl]-3,5-difluorophenyl}propyl]-carbamate Obtained by oxidation of the intermediate resulting from the coupling of 492 and 125

$^1$H NMR (400 MHz, DMSO-d$_6$): δ 8.55 (d, 1H), 8.20 (d, 1H), 8.15 (d, 1H), 8.05 (broad d, 1H), 7.25 (d, 2H), 4.55 (m and quad, 3H), 1.7 (m, 2H), 1.45 (t, 3H), 1.4 (s, 9H), 0.9 (t, 3H)

Intermediate 501:

tert-Butyl (1-{4-[(1-ethoxyisoquinolin-5-yl)carbonyl]-3,5-difluorophenyl}-2-methyl-propyl)carbamate Obtained by oxidation of the intermediate resulting from the coupling of 499 and 125

$^1$H NMR (400 MHz, DMSO-d$_6$): δ 8.54 (d, 1H), 8.19 (d, 1H), 8.11 (d, 1H), 8.05 (d, 1H), 7.71 (t, 1H), 7.22 (m, 2H), 4.58 (quad, 2H), 4.39 (t, 1H), 1.95 (m, 1H), 1.48 (t, 3H), 1.38 (broad s, 9H), 0.9-0.79 (2d, 6H)

$^{19}$F NMR: −113.1

IR (cm$^{-1}$): 3354, 1678, 1633

Intermediate 507:

tert-Butyl (1-{4-[(1-ethoxyisoquinolin-5-yl)carbonyl]-3,5-difluorophenyl}butyl)-carbamate Obtained by oxidation of the intermediate resulting from the coupling of 505 and 125

$^1$H NMR (400 MHz, DMSO-d$_6$): δ 8.55 (d, 1H), 8.15 (d, 1H), 8.2 (d, 1H), 8.05 (d, 1H), 7.7 (t, 1H), 7.45 (broad d, 1H), 7.2 (broad d, 2H), 4.6 (m, 1H), 4.58 (quad, 2H), 1.65 (m, 2H), 1.45 (t, 3H), 1.4 (broad s, 9H), 1.3 (m, 2H), 0.9 (t, 3H)

IR (cm$^{-1}$): 3350, 1676, 1160

Intermediate 512:

tert-Butyl (1-{4-[(1-ethoxyisoquinolin-5-yl)carbonyl]-3,5-difluorophenyl}-3-methyl-butyl)carbamate Obtained by oxidation of the intermediate resulting from the coupling of 510 and 125

$^1$H NMR (400 MHz, DMSO-d$_6$): δ 8.55 (d, 1H), 8.15 (dd, 1H), 8.05 (d, 1H), 7.7 (t, 1H), 7.25 (d, 2H), 4.65 (m, 1H), 4.55 (quad, 2H), 1.65-1.45 (m, 3H), 1.45 (t, 3H), 1.4 (s, 9H), 0.95 (2d, 6H)

IR (cm$^{-1}$): 3380, 1681, 1673, 1663

Intermediate 523:

tert-Butyl 2-{3-[(1-ethoxyisoquinolin-5-yl)carbonyl]-2,4-difluorophenyl}pyrrolidine-1-carboxylate Obtained by oxidation of the intermediate resulting from the coupling of 521 and 125

$^1$H NMR (400 MHz, DMSO-$d_6$): δ 8.56 (d, 1H), 8.18 (2d, 2H), 7.98 (d, 1H), 7.7 (t, 1H), 7.46 (m, 1H), 7.22 (m, 1H), 4.96 (m, 1H), 4.62 (quad, 2H), 3.52 (m, 2H), 2.35-1.8 (2m, 2H), 1.90 (m, 2H), 1.5 (t, 3H), 1.29 (s, 9H)

IR (cm$^{-1}$): 1682, 1667

Optical purity (SFC: ID 3 μM column 4.6×250 mm; CO$_2$/(isopropanol/n-butylamine: 100/0.5): 75/25; Detection: 254 nm): >99%.

Intermediate 528:

N-(1-{3-[(1-Ethoxyisoquinolin-5-yl)carbonyl]-2-fluorophenyl}ethyl)-2-methylpropane-2-sulphinamide Obtained by oxidation of the intermediate resulting from the coupling of 526 and 125

$^1$H NMR (300/400 MHz, DMSO-$d_6$): δ 8.50 (broad d, 1H), 8.10 (d, 1H), 7.87 (broad d, 1H), 7.69 (dd, 1H), 7.71 (dd, 1H), 7.77 (td, 1H), 7.57 (td, 1H), 7.38 (t, 1H), 4.64 (quint., 1H), 4.56 (quad, 2H), 1.47 (d, 3H), 1.46 (t, 3H), 1.07 (s, 9H)

$^{19}$F NMR: −118

IR (cm$^{-1}$): 1663, 1051, 3203

Intermediate 552:

tert-Butyl (1-{2-(benzyloxy)-4-[(1-ethoxyisoquinolin-5-yl)carbonyl]-3,5-difluorophenyl}ethyl)carbamate Obtained by oxidation of the intermediate resulting from the coupling of 550 and 125

$^1$H NMR (400 MHz, DMSO-$d_6$): δ 8.56 (d, 1H), 8.2-8.16 (2d, 2H), 8.06 (d, 1H), 7.74 (t, 1H), 7.54 (d, 1H), 7.48 (d, 2H), 7.41 (t, 2H), 7.37 (t, 1H), 7.24 (d, 1H), 5.11 (AB, 2H), 5.12 (m, 1H), 4.58 (quad, 2H), 1.46 (t, 3H), 1.39 (broad s, 12H), 1.27 (d, 3H)

IR (cm$^{-1}$): 3358, 1679

Intermediate 560:

tert-Butyl (1-{3-[(1-ethoxyisoquinolin-5-yl)carbonyl]-2,4-difluoro-6-methylphenyl}-ethyl)carbamate Obtained by oxidation of the intermediate resulting from the coupling of 558 and 125

$^1$H NMR (400 MHz, DMSO-$d_6$): δ 8.53 (d, 1H), 8.19-8.12 (2d, 2H), 7.96 (d, 1H), 7.69 (t, 1H), 7.33 (d, 1H), 7.11 (d, 1H), 4.88 (quint, 1H), 4.58 (quad, 2H), 2.49 (s, 3H), 1.46 (t, 3H), 1.36 (d, 3H), 1.33-1.25 (2 broad s, 9H)

IR (cm$^{-1}$): 3340, 1705, 1670, 1258, 1162

Intermediate 698:

tert-Butyl [{4-[(1-ethoxyisoquinolin-5-yl)carbonyl]-3,5-difluorophenyl}(3-methoxyphenyl)methyl]carbamate Obtained by oxidation of the intermediate resulting from the coupling of 696 and 125

$^1$H NMR (300 MHz, DMSO-$d_6$): δ 8.55 (d, 1H), 8.20 (d, 1H), 8.15 (d, 1H), 8.05 (d, 1H), 7.70 (t, 1H), 7.35 (d, 2H), 7.25 (t, 1H), 7.00 (m, 2H), 6.85 (dd, 1H), 5.95 (m, 1H), 4.55 (quad, 2H), 3.75 (s, 3H), 1.45 (t, 3H), 1.40 (broad s, 9H)

IR (cm$^{-1}$): 3342, 2980, 1675, 1632-1612, 1568, 1250, 1159

Intermediate 704:

tert-Butyl (2-cyclohexyl-1-{4-[(1-ethoxyisoquinolin-5-yl)carbonyl]-3,5-difluorophenyl}ethyl)carbamate Obtained by oxidation of the intermediate resulting from the coupling of 702 and 125

$^1$H NMR (300 MHz, DMSO-$d_6$): δ 8.55 (d, 1H), 8.20 (d, 1H), 8.15 (d, 1H), 8.05 (d, 1H), 7.80 (d, 1H), 7.45 (dl, 1H, NH), 7.20 (d, 2H), 4.70 (m, 1H), 4.55 (quad., 2H), 1.85-0.90 (m, 13H), 1.45 (t, 3H), 1.40 (s, 9H)

IR (cm$^{-1}$): 3359, 2924-2854, 1680-1634, 1616, 1526, 1252, 1164

Intermediate 708:

tert-Butyl (cyclohexylmethyl)(1-{4-[(1-ethoxyisoquinolin-5-yl)carbonyl]-3,5-difluorophenyl}ethyl)carbamate Obtained by oxidation of the intermediate resulting from the coupling of 706 and 125

$^1$H NMR (300 MHz, DMSO-$d_6$): δ 8.53 (d, 1H), 8.18 (d, 1H), 8.13 (d, 1H), 8.00 (d, 1H), 7.70 (t, 1H), 7.15 (m, 2H), 4.92 (m, 1H), 4.56 (quad., 2H), 3.10 (m, 2H), 1.75-0.75 (m, 11H), 1.58 (d, 3H), 1.45 (t, 3H), 1.30 (broad s, 9H)

IR (cm$^{-1}$): 1674, 1632, 1254-1150, 957, 816, 757

Intermediate 710:

tert-Butyl (1-{4-[(1-ethoxy-3-methylisoquinolin-5-yl)carbonyl]-3,5-difluorophenyl}-ethyl)carbamate Obtained by oxidation of the intermediate resulting from the coupling of intermediate 278 and 294

$^1$H NMR (400 MHz, DMSO-$d_6$): δ 8.50 (m, 1H), 8.05 (s, 1H), 8.00 (d, 1H), 7.60 (t, 1H), 7.50 (d, 1H), 7.20 (d, 2H), 4.75 (m, 1H), 4.55 (quad., 2H), 2.55 (s, 3H), 1.45 (t, 3H), 1.40 (broad s, 9H), 1.35 (d, 3H)

IR (cm$^{-1}$): 3349, 1672

Intermediate 732:

tert-Butyl (2-{4-[(1-ethoxy-3-methylisoquinolin-5-yl)carbonyl]-3,5-difluorophenyl}propan-2-yl)carbamate Obtained by oxidation of the intermediate resulting from the coupling of 378 and 294

$^1$H NMR (400 MHz, DMSO-$d_6$): δ 8.45 (d, 1H), 8.00 (s, 1H), 7.95 (d, 1H), 7.65 (t, 1H), 7.35 (m, 1H, NH), 7.20 (d, 2H), 4.55 (quad., 2H), 2.55 (s, 3H), 1.50 (s, 6H), 1.45 (t, 3H), 1.35 (broad s, 9H)

IR (cm$^{-1}$): 3331, 1687, 1669

Intermediate 734:

tert-Butyl (1-{4-[(1-ethoxy-3-methylisoquinolin-5-yl)carbonyl]-3,5-difluoro-2-methoxyphenyl}ethyl)carbamate Obtained by oxidation of the intermediate resulting from the coupling of 367 and 294

$^1$H NMR (300 MHz, DMSO-$d_6$): δ 8.50 (d, 1H), 8.05 (s and d, 2H), 7.65 (t, 1H), 7.50 (d, 1H), 7.20 (d, 1H), 5.0 (m, 1H), 4.55 (quad, 2H), 3.90 (s, 3H), 2.55 (s, 3H), 1.50 (t, 3H), 1.40 (m, 9H), 1.30 (d, 3H)

$^{19}$F NMR: −118, −129
IR (cm$^{−1}$): 3259, 1697-1663
Intermediate 741:

tert-Butyl [1-{4-[(1-ethoxyisoquinolin-5-yl)carbonyl]-3-fluoro-2-methoxyphenyl}-ethyl]carbamate Obtained by oxidation of the intermediate resulting from the coupling of 739 and 125
$^1$H NMR (400 MHz, DMSO-d$_6$): δ 8.50 (d, 1H), 8.10 (d, 1H), 7.95 (d, 1H), 7.70 (m, 2H), 7.55 (d, 1H, NH), 7.40 (d, 1H), 7.30 (dd, 1H), 5.00 (quint., 1H), 4.60 (quad., 2H), 3.85 (s, 3H), 1.50 (t, 3H), 1.35 (m, 9H), 1.30 (d, 3H)
IR (cm$^{−1}$): 3410, 1709, 1665, 1616, 1570, 1265, 1160, 813, 757
Intermediates 448, 546, 555, 562 and 730 were obtained starting from intermediates prepared using coupling protocol XXI and described above.
Intermediate 546:

tert-Butyl (1-{4-[(1-ethoxyisoquinolin-5-yl)carbonyl]-2-fluoro-3-methoxyphenyl}-ethyl)carbamate Intermediate 546 was obtained by nucleophilic substitution reaction (MeONa/DMF) starting from intermediate 271: 4.8 g (10.5 mmoles) of intermediate 271 are dissolved in 150 mL of DMF under a stream of nitrogen. 1.5 g (27.75 mmoles, 2.6 eq.) of powdered sodium methoxide are added in a single batch. Stirring is carried out at ambient temperature overnight. HPLC monitoring after 16 h at ambient temperature shows only 40% of product formed. A further 1.5 g (27.75 mmoles, 2.6 eq.) of powdered sodium methoxide are added, and stirring is carried out for a further 6 hours. The mixture is hydrolysed by addition of ice-water. Extraction is carried out with 3 times 250 mL of ethyl acetate, and the organic phase is dried over MgSO$_4$ and then filtered and evaporated to dryness. 18 g of an oil still containing DMF are obtained. The residue is taken up in 200 mL of water and extracted with 5 times 200 mL of ether. The organic phase is dried over MgSO$_4$, filtered and evaporated to dryness. There are obtained 4.89 g of an orange oil, which is purified by flash chromatography on silica (eluant: CH$_2$Cl$_2$—AcOEt gradient: 99-1 to 90-10) to give 1.55 g of intermediate 546 in the form of a yellow meringue and 1.6 g of impure fractions.
$^1$H NMR (400 MHz, DMSO-d$_6$): δ 8.44 (d, 1H), 8.11 (d, 1H), 7.84 (d, 1H), 7.80 (d, 1H), 7.68 (t, 1H), 7.35 (d, 1H), 7.25 (t, 1H), 4.94 (quint, 1H), 4.56 (quad, 2H), 3.49 (s, 3H), 1.45 (t, 3H), 1.38 (s, 9H), 1.36 (d, 3H)
$^{19}$F NMR: −137.1
IR (cm$^{−1}$): 3342, 1701, 1664
Intermediate 554 was obtained starting from 552 according to the following sequence: Intermediate 553:

tert-Butyl (1-{4-[(1-ethoxyisoquinolin-5-yl)carbonyl]-3,5-difluoro-2-hydroxyphenyl}-ethyl)carbamate A solution of 552 (6.7 g, 12 mmoles) in an ethanol/AcOEt mixture (500 mL, 1/1) is hydrogenated at atmospheric pressure of H$_2$ and at 60° C. in the presence of 10% Pd/C (0.2 g) for 7 hours. The catalyst is filtered off, and concentration of the filtrate yields intermediate 553 in the form of a solid (5.7 g).
$^1$H NMR (400 MHz, DMSO-d$_6$): δ 9.88 (broad s, 1H), 8.53 (d, 1H), 8.19-8.13 (2d, 2H), 8.06 (d, 1H), 7.72 (t, 1H), 7.47 (broad d, 1H), 7.07 (d, 1H), 5.03 (quint, 1H), 4.57 (quad, 2H), 1.46 (t, 3H), 1.39 (broad s and d, 12H), 1.29 (d, 3H)
IR (cm$^{−1}$): 3350, 3500-2600, 1675
Intermediate 554:

6-{1-[(tert-Butoxycarbonyl)amino]ethyl}-3-[(1-ethoxyisoquinolin-5-yl)carbonyl]-2,4-difluorophenyl trifluoromethanesulphonate A solution at 0° C. of 553 (5.6 g, 11 mmoles) in pyridine (45 mL) is treated with triflic anhydride (3.36 g, 11 mmoles). The reaction mixture is stirred at ambient temperature for 2 hours and then cooled to 0° C. again and treated with triflic anhydride (0.2 eq.) until conversion is complete. The pyridine is evaporated off in vacuo, and the residue is taken up in water and AcOEt. The organic phase is washed with a saturated NaCl solution, dried over MgSO$_4$ and then concentrated. By chromatography on silica (eluant CH$_2$Cl$_2$/AcOEt 100/0 to 95/5), intermediate 554 is obtained in the form of a solid (6.2 g).
$^1$H NMR (300 MHz, DMSO-d$_6$): δ 8.59 (d, 1H), 8.23-8.19 (2d, 2H), 8.17 (d, 1H), 7.74 (t, 1H), 7.71 (broad d, 1H), 7.5 (d, 1H), 4.97 (quint, 1H), 4.57 (quad, 2H), 1.47 (t, 3H), 1.4 (d, 3H), 1.38 (broad s, 9H)
IR (cm$^{−1}$): 3375, 1675
LCMS [M+H]+: 604
Intermediate 448 was obtained in two steps starting from intermediate 446: intermediate 446 was converted into phenol 447 according to the protocol described for obtaining 553. The phenol 447 was treated with methyl iodide according to the protocol described for intermediate 93.
Intermediate 448:

tert-Butyl (1-{3-[(1-ethoxyisoquinolin-5-yl)carbonyl]-2,4-difluoro-6-methoxyphenyl}-ethyl)carbamate $^1$H NMR (400 MHz, DMSO-d$_6$): δ 8.50 (d, 1H), 8.15 (d, 1H), 7.97 (2m, 2H), 7.69 (tt, 1H), 6.99 (d, 1H), 7.0-6.7 (broad s, 1H), 5.1-4.9 (m, 1H), 4.57 (quad, 2H), 3.92 (s, 3H), 1.45 (t, 3H), 1.4-1.3 (broad s, 12H)
IR (cm$^{−1}$): 3455, 1707, 1163
Intermediate 554 was used to prepare intermediates 555 and 562:
Intermediate 555:

tert-Butyl (1-{4-[(1-ethoxyisoquinolin-5-yl)carbonyl]-3,5-difluoro-2-methylphenyl}-ethyl)carbamate A mixture of 554 (1 g, 1.65 mmoles), trimethyl-boroxine (0.42 g, 3.3 mmoles), K$_2$CO$_3$ (0.91 g, 6 mmoles) in 1,4-dioxane (15 mL) degassed with N$_2$ for 15 minutes is treated with Pd(PPh$_3$)$_4$(0.38 g, 0.3 mmole). The mixture is heated at reflux for 1 hour. After return to ambient temperature, the solid is filtered off and the filtrate is concentrated in vacuo. By chromatography on silica (eluant CH$_2$Cl$_2$/AcOEt 100/0 to 50/50), 0.7 g of intermediate 555 is obtained.
$^1$H NMR (400 MHz, DMSO-d$_6$): δ 8.54 (d, 1H), 8.2-8.15 (2d, 2H), 8.03 (d, 1H), 7.72 (t, 1H), 7.59 (broad d, 1H), 7.21 (d, 1H), 4.9 (quint, 1H), 4.57 (quad, 2H), 2.22 (broad s, 3H), 1.46 (t, 3H), 1.38-1.26 (2 broad s, 9H), 1.3 (d, 3H)
IR (cm$^{−1}$): 3369, 1682-1672
LCMS [M+H]$^+$: 470

Intermediate 562 was obtained starting from intermediate 554 according to the sequence:

Intermediate 561:

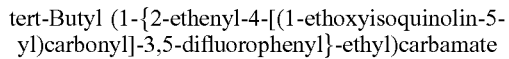

tert-Butyl (1-{2-ethenyl-4-[(1-ethoxyisoquinolin-5-yl)carbonyl]-3,5-difluorophenyl}-ethyl)carbamate To a solution, degassed with $N_2$, of intermediate 554 (1. g) in 1,4-dioxane (20 mL) there are added vinyl-tributyl-tin (0.58 g) and Pd(PPh$_3$)$_4$(50 mg) and LiCl (0.2 g). The mixture is heated at 100° C. for 2 hours. After return to ambient temperature, the mixture is treated with a 10% aqueous KF solution, the salts are filtered off and the filtrate is extracted with AcOEt. The organic phase is dried over MgSO4 and concentrated in vacuo. By chromatography on silica (eluant CH$_2$Cl$_2$/AcOEt 100/0 to 90/5), intermediate 561 is obtained in the form of an amorphous solid (0.7 g).

$^1$H NMR (400 MHz, DMSO-d$_6$): δ 8.55 (d, 1H), 8.21-8.18 (2d, 2H), 8.09 (d, 1H), 7.72 (t, 1H), 7.62 (broad d, 1H), 7.28 (d, 1H), 6.73 (dd, 1H), 5.69 (d, 1H), 5.66 (d, 1H), 4.98 (quint, 1H), 4.57 (quad, 2H), 1.46 (t, 3H), 1.38-1.26 (2 broad s, 9H), 1.3 (d, 3H)

IR (cm$^{-1}$): 3367, 1683-1670

Treatment of intermediate 561 according to the protocol described for intermediate 395 yielded 562.

Intermediate 562:

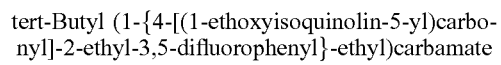

tert-Butyl (1-{4-[(1-ethoxyisoquinolin-5-yl)carbonyl]-2-ethyl-3,5-difluorophenyl}-ethyl)carbamate $^1$H NMR (400 MHz, DMSO-d$_6$): δ 8.54 (d, 1H), 8.2-8.15 (2d, 2H), 8.03 (d, 1H), 7.72 (t, 1H), 7.6 (broad d, 1H), 7.25 (d, 1H), 4.94 (quint, 1H), 4.57 (quad, 2H), 2.74-2.64 (2m, 2H), 1.46 (t, 3H), 1.38 (broad s, 9H), 1.33 (d, 3H), 1.16 t, 3H)

LCMS [M+H]+: 484

Intermediate 412 was obtained according to the following protocol:

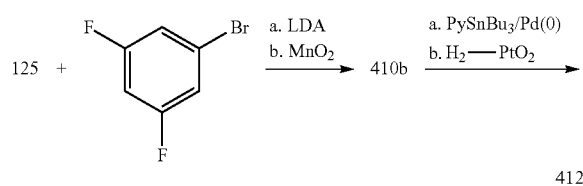

Intermediate 410b:

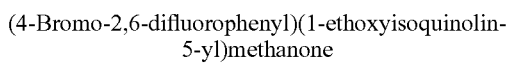

(4-Bromo-2,6-difluorophenyl)(1-ethoxyisoquinolin-5-yl)methanone

Obtained by oxidation of the intermediate resulting from the coupling of 1-bromo-3,5-difluorobenzene and 125

$^1$H NMR (400 MHz, DMSO-d$_6$): δ 8.55 (d, 1H), 8.20 (m, 2H), 8.15 (d, 1H), 7.70 (m, 3H), 4.60 (quad, 2H), 1.45 (t, 3H)

IR (cm$^{-1}$): 1668.

Intermediate 412:

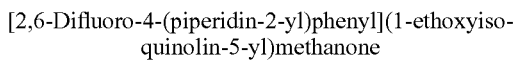

[2,6-Difluoro-4-(piperidin-2-yl)phenyl](1-ethoxyisoquinolin-5-yl)methanone

Step 1:

To a solution, degassed with nitrogen, of intermediate 410b (1.1 g) in anhydrous DMF (20 mL) there are added 2-(tributylstannyl)-pyridine (1 g, 2.7 mmoles) and Pd(PPh$_3$)$_4$ (500 mg, 0.43 mmole). The reaction mixture is heated at 100° C. for 20 hours and is then diluted with ethyl acetate and water. The organic phase is decanted, washed with water, dried over MgSO$_4$, filtered and evaporated in vacuo. The residue is purified by flash chromatography on silica (eluant: CH$_2$Cl$_2$—AcOEt gradient: 99-1 to 85-15). The expected intermediate (700 mg) is obtained in the form of a white solid.

$^1$H NMR (400 MHz, DMSO-d$_6$): δ 8.75 (dd, 1H), 8.56 (d, 1H), 8.21 (dd, 2H), 8.18 (m, 2H), 8.04 (d, 2H), 7.99 (td, 1H), 7.73 (t, 1H), 7.50 (dd, 1H), 4.58 (quad, 2H), 1.46 (t, 3H)

IR (cm$^{-1}$): 1668

Step 2:

To a solution of the intermediate obtained above (700 mg, 1.79 mmoles) in 45 mL of methanol there are added 0.4 mL of a concentrated 37% HCl solution and 140 mg of PtO$_2$. The reaction mixture is hydrogenated at ambient temperature and under atmospheric pressure of H$_2$ for 15 hours. The catalyst is filtered off and the filtrate is concentrated in vacuo. The residue is suspended in water and treated with a 10N aqueous sodium hydroxide solution and extracted with ethyl acetate. The organic phase is washed with water, dried over MgSO$_4$, filtered and evaporated in vacuo. The product is purified on Phase Strategy RP 15 µm, eluant: water-acetonitrile-trifluoroacetic acid. After evaporation of the acetonitrile, the aqueous phase is rendered basic by addition of 10N sodium hydroxide and is then extracted with ethyl acetate. The organic phase is washed with water, dried over MgSO$_4$, filtered and evaporated in vacuo. Intermediate 412 (180 mg) is obtained in the form of an oil, which crystallises at ambient temperature.

$^1$H NMR (400 MHz, DMSO-d$_6$): δ 8.54 (d, 1H), 8.20 (d, 1H), 8.14 (d, 1H), 8.01 (d, 1H), 7.72 (t, 1H), 7.30 (d, 2H), 4.57 (quad., 2H), 3.78 (m, 1H), 3.12 (m, 1H), 2.72 (m, 1H), 1.84 (m, 2H), 1.62 (m, 1H), 1.46 (t, 3H), 1.60-1.30 (m, 3H)

IR (cm$^{-1}$): 1667

Products P66 and P134 were obtained starting from intermediates 380 and 732, respectively, according to the procedure described for product P68.

The other ketone intermediates obtained by protocol XXI were deprotected in an acidic medium (4N HCl to 2N HCl in ether) to yield the final products, according to the procedures described for products P17 and P110.

| Product | Obtained from | Nomenclature Analytical description |
|---|---|---|
| P41 | 236 | 5-[(1-Amino-4,6-difluoro-2,3-dihydro-1H-inden-5-yl)carbonyl]isoquinolin-1(2H)-one hydrochloride<br>$^1$H NMR (400 MHz, DMSO-d$_6$): δ 11.60 (s, 1H), 8.65 (m, 3H), 8.52 (d, 1H), 7.90 (d, 1H), 7.60 (d and t, 2H), 7.40 (s, 2H), 4.85 (m, 1H), 3.10 (m, 1H), 2.92 (m, 1H), 2.60 (m, 1H), 2.12 (m, 1H)<br>IR (cm$^{-1}$): 1687-1671, 1629 |

| Product | Obtained from | Nomenclature Analytical description |
|---|---|---|
| | | HRMS (ESI): theoretical m/z for $C_{19}H_{15}F_2N_2O_2$ [M + H]$^+$ 341.1102, measured 341.1107 |
| P44 | 262 | 5-[(3-Amino-4,6-difluoro-2,3-dihydro-1H-inden-5-yl)carbonyl]isoquinolin-1(2H)-one hydrochloride<br>$^1$H NMR (400 MHz, CDCl$_3$): δ 11.70 (s, 1H), 8.65 (broad s, 3H), 8.55 (d, 1H), 7.95 (d, 1H), 7.60 (m, 1H), 7.40 (2d, 2H), 7.30 (d, 1H), 4.90 (dd, 1H), 3.35-3.00 (2m, 2H), 2.55-2.20 (2m, 2H)<br>IR (cm$^{-1}$): 3250-2480, 1687-1672<br>HRMS (ESI): theoretical m/z for $C_{19}H_{15}F_2N_2O_2$ [M + H]$^+$ 341.1102, measured 341.1107 |
| P46 | 271 | 5-[4-(1-Aminoethyl)-2,3-difluorobenzoyl]isoquinolin-1(2H)-one hydrochloride<br>$^1$H NMR (400 MHz, DMSO-d$_6$): δ 11.60 (m, 1H), 9.00-8.50 (m, 3H), 8.50 (broad d, 1H), 7.85 (broad d, 1H), 7.65 (broad t, 1H), 7.60-7.50 (m, 2H), 7.30 (m, 1H), 7.00 (d, 1H), 4.70 (quad, 1H), 1.6 (d, 3H)<br>IR (cm$^{-1}$): 3200-1950, 1671, 1632<br>HRMS (ESI): theoretical m/z for $C_{18}H_{15}F_2N_2O_2$ [M + H]$^+$ 329.1101, measured 329.1102 |
| P49 | 296 | 5-{4-[(1R)-1-Aminoethyl]-2,6-difluorobenzoyl}-3-methylisoquinolin-1(2H)-one hydrochloride<br>$^1$H NMR (400 MHz, DMSO-d$_6$): δ 11.80 (s, 1H), 8.75 (s, 3H), 8.50 (d, 1H), 7.85 (d, 1H), 7.55 (d, 2H), 7.50 (m, 1H), 7.30 (s, 1H), 4.55 (quad, 1H), 2.30 (s, 3H), 1.55 (d, 3H)<br>IR (cm$^{-1}$): 3237-2450, 1687-1672, 1622<br>HRMS (ESI): theoretical m/z for $C_{19}H_{17}F_2N_2O_2$ [M + H]$^+$ 343.1258, measured 343.1256 |
| P50 | 305 | 5-{4-[(1R)-1-Aminoethyl]-2,6-difluorobenzoyl}-4-methylisoquinolin-1(2H)-one hydrochloride<br>$^1$H NMR (400 MHz, DMSO-d$_6$): δ 11.60 (s, 1H), 8.75 (s, 3H), 8.50 (d, 1H), 7.70 (d, 1H), 7.55 (m, 1H), 7.55 (m, 2H), 7.20 (s, 1H), 4.55 (quad, 1H), 1.95 (s, 3H), 1.55 (d, 3H)<br>IR (cm$^{-1}$): 3158, 3120-2432, 1676, 1633<br>HRMS (ESI): theoretical m/z for $C_{19}H_{17}F_2N_2O_2$ [M + H]$^+$ 343.1258, measured 343.1274 |
| P53 | 319 | 5-[(1-Amino-4,6-difluoro-2,3-dihydro-1H-inden-5-yl)carbonyl]isoquinolin-1(2H)-one hydrochloride<br>$^1$H NMR (400 MHz, DMSO-d$_6$): δ 11.60 (s, 1H), 8.65 (m, 3H), 8.52 (d, 1H), 7.90 (d, 1H), 7.60 (d, 1H), 7.60 (t, 1H), 7.40 (s, 2H), 4.85 (m, 1H), 3.10 (m, 1H), 2.92 (m, 1H), 2.60 (m, 1H), 2.12 (m, 1H)<br>IR (cm$^{-1}$): 3600-2600, 1687, 1633<br>HRMS (ESI): theoretical m/z for $C_{19}H_{15}F_2N_2O_2$ [M + H]$^+$ 341.1101, measured 341.1101<br>Optical purity (SFC: AD 3 μM column 4.6 × 250 mm; eluant: CO$_2$/(isopropanol/diethylamine: 100/0.5): 70/30; detection: 255 nm): >99%.<br>(absence of P58) |
| P55 | 328 | 5-{4-[(1S)-1-Aminoethyl]-2,6-difluorobenzoyl}-4-methylisoquinolin-1(2H)-one hydrochloride<br>$^1$H NMR (400 MHz, DMSO-d$_6$): δ 11.50 (s, 1H), 8.65 (m, 3H), 8.48 (dd, 1H), 7.70 (d, 1H), 7.50 (t, 1H), 7.50 (d, 2H), 7.15 (d, 1H), 4.55 (broad s, 1H), 1.99 (s, 3H), 1.55 (d, 3H)<br>$^{19}$F NMR: −108.2<br>IR (cm$^{-1}$): 3500-2500, 1680, 1632<br>MS (DEI 70 eV): m/z 342.1 |
| P56 | 333 | 5-{3-[(1R)-1-Aminoethyl]-2,6-difluorobenzoyl}-isoquinolin-1(2H)-one hydrochloride<br>$^1$H NMR (400 MHz, DMSO-d$_6$): δ 11.80 (broad s, 1H), 8.80 (broad s, 3H), 8.55 (d, 1H), 8.00 (d and dd, 2H), 7.60 (t, 1H), 7.40 (t and d, 3H), 4.62 (quad, 1H), 1.60 (d, 3H)<br>$^{19}$F NMR: −112, −115<br>IR (cm$^{-1}$): 3450-2480, 1668, 1619, 1589, 1273-1237<br>HRMS (ESI): theoretical m/z for $C_{18}H_{15}F_2N_2O_2$ [M + H]$^+$ 329.1102, measured 329.1115<br>Optical purity (SFC: ID 5 μM column 4.6 × 250 mm; eluant: CO$_2$/(isopropanol/n-butylamine: 100/0.5): 75/25; detection: 254 nm): >99%.<br>(absence of P57)<br>α$_D$ (589 nM) = −3.09 (c = 0.0097 g/mL, DMSO) at 20° C. |
| P57 | 336 | 5-{3-[(1S)-1-Aminoethyl]-2,6-difluorobenzoyl}-isoquinolin-1(2H)-one hydrochloride |

| Product | Obtained from | Nomenclature Analytical description |
|---|---|---|
|  |  | $^1$H NMR (400 MHz, DMSO-d$_6$): δ 11.80 (broad s, 1H), 8.80 (broad s, 3H), 8.60 (d, 1H), 8.00 (d and dd, 2H), 7.65 (t, 1H), 7.50 (t and d, 3H), 4.68 (quad, 1H), 1.62 (d, 3H)<br>$^{19}$F NMR: −111, −115<br>IR (cm$^{-1}$): 3450-2480, 1674, 1612, 1589, 1262-1222<br>HRMS (ESI): theoretical m/z for C$_{18}$F$_2$H$_{15}$N$_2$O$_2$ [M + H]$^+$ 329.1102, measured 329.1105<br>Optical purity (SFC: ID 5 μM column 4.6 × 250 mm; eluant: CO$_2$/(isopropanol/n-butylamine: 100/0.5): 75/25; detection: 254 nm): >99%.<br>(absence of P56)<br>α$_D$ (589 nM) = 3.43 (c = 1, DMSO) at 20° C. |
| P58 | 339 | 5-[(1-Amino-4,6-difluoro-2,3-dihydro-1H-inden-5-yl)carbonyl]isoquinolin-1(2H)-one hydrochloride<br>$^1$H NMR (400 MHz, DMSO-d$_6$): δ 11.60 (s, 1H), 8.65 (m, 3H), 8.52 (d, 1H), 7.90 (d, 1H), 7.60 (d, 1H), 7.60 (t, 1H), 7.40 (s, 2H), 4.85 (m, 1H), 3.10 (m, 1H), 2.92 (m, 1H), 2.60 (m, 1H), 2.12 (m, 1H)<br>IR (cm$^{-1}$): 3410-2390, 1675, 1632, 1600, 879-740<br>HRMS (ESI): theoretical m/z for C$_{19}$H$_{15}$F$_2$N$_2$O$_2$ [M + H]$^+$ 341.1101, measured 341.1104<br>Optical purity (SFC: AD 3 μM column 4.6 × 250 mm; eluant: CO$_2$/(isopropanol/diethylamine: 100/0.5): 70/30; detection: 255 nm): >99%. (absence of P53) |
| P59 | 345 | 5-{[(3R)-3-Amino-4,6-difluoro-2,3-dihydro-1H-inden-5-yl]carbonyl}isoquinolin-1(2H)-one hydrochloride<br>$^1$H NMR (400 MHz, DMSO-d$_6$): δ 11.70 (m, 1H), 8.65 (m, 3H), 8.50 (d, 1H), 7.95 (d, 1H), 7.60 (t, 1H), 7.40 (2d, 2H), 7.30 (d, 1H), 4.90 (m, 1H), 3.30 (m, 1H), 3.00 (m, 1H), 2.55 (m, 1H), 2.20 (m, 1H)<br>IR (cm$^{-1}$): 3200-2300, 1657, 1628<br>HRMS (ESI): theoretical m/z for C$_{19}$H$_{15}$F$_2$N$_2$O$_2$ [M + H]$^+$ 341.1102, measured 341.1104<br>Optical purity (SFC: AD-H 3 μM column 4.6 × 250 mm; eluant: CO$_2$/(methanol/butylamine: 100/0.5): 65/35; detection: 308 nm): >99%.<br>(absence of P60)<br>α$_D$ (589 nM) = −27.7 (c = 0.009 g/mL, MeOH) at 20° C.□ |
| P60 | 348 | 5-{[(3S)-3-Amino-4,6-difluoro-2,3-dihydro-1H-inden-5-yl]carbonyl}isoquinolin-1(2H)-one hydrochloride<br>$^1$H NMR (400 MHz, DMSO-d$_6$): δ 11.70 (m, 1H), 8.65 (m, 3H), 8.50 (d, 1H), 7.95 (d, 1H), 7.60 (t, 1H), 7.40 (2d, 2H), 7.30 (d, 1H), 4.90 (m, 1H), 3.30 (m, 1H), 3.00 (m, 1H), 2.55 (m, 1H), 2.2 (m, 1H)<br>IR (cm$^{-1}$): 3200-2300, 1657, 1627<br>HRMS (ESI): theoretical m/z for C$_{19}$H$_{15}$F$_2$N$_2$O$_2$ [M + H]$^+$ 341.1102, measured 341.1101<br>Optical purity (SFC: AD-H 3 μM column 4.6 × 250 mm; eluant: CO$_2$/(methanol/butylamine:100/0.5): 65/35; detection: 308 nm): >99%.<br>(absence of P59) |
| P63 | 369 | 5-[4-(1-Aminoethyl)-2,6-difluoro-3-methoxybenzoyl]-isoquinolin-1(2H)-one hydrochloride<br>$^1$H NMR (300 MHz, DMSO-d$_6$): δ 11.70 (m, 1H), 8.80 (m, 3H), 8.55 (d, 1H), 7.95 (d, 1H), 7.60 (dd, 1H), 7.60 (t, 1H), 7.40 (broad s, 2H), 4.70 (quad, 1H), 3.95 (s, 3H), 1.55 (d, 3H)<br>IR (cm$^{-1}$): 3410-2080, 1666, 1629, 1610, 1589, 832-702<br>HRMS (ESI): theoretical m/z for C$_{19}$H$_{17}$F$_2$N$_2$O$_3$ [M + H]$^+$ 359.1207, measured 359.1232 |
| P65 | 375 | 5-[4-(1-Aminoethyl)-2,6-difluoro-3-methoxybenzoyl]-3-methylisoquinolin-1(2H)-one hydrochloride<br>$^1$H NMR (300 MHz, DMSO-d$_6$): δ 11.70 (m, 1H), 8.70 (m, 3H), 8.50 (d, 1H), 7.95 (d, 1H), 7.65 (dd, 1H), 7.50 (t, 1H), 7.30 (s, 1H), 4.70 (quad, 1H), 3.90 (s, 3H), 2.30 (s, 3H), 1.55 (d, 3H)<br>IR (cm$^{-1}$): 3430-2250, 1666, 1632, 1595, 838-687<br>HRMS (ESI): theoretical m/z for C$_{20}$H$_{19}$F$_2$N$_2$O$_3$ [M + H]$^+$ 373.1364, measured 373.1365 |
| P66 | 380 | 5-[4-(2-Aminopropan-2-yl)-2,6-difluorobenzoyl]-4-methylisoquinolin-1(2H)-one methanesulphonate<br>$^1$H NMR (400 MHz, DMSO-d$_6$): δ 11.50 (d, 1H), 8.70-8.50 (m, 3H), 8.50 (d, 1H), 7.70 (d, 1H), 7.55 (t, 1H), 7.50 (d, 2H), 7.15 (broad d, 1H), 1.95 (broad s, 3H), 1.65 (s, 6H)<br>IR (cm$^{-1}$): 3300-2200, 1682, 1634, 1162, 1035 |

| Product | Obtained from | Nomenclature Analytical description |
|---|---|---|
| | | HRMS (ESI): theoretical m/z for $C_{20}F_2H_{19}N_2O_2$ [M + H]$^+$ 357.1415, measured 357.1423 theoretical m/z for $C_{20}F_2H_{19}N_2O_2$ [M + H—NH$_3$]$^+$ 340.1149, measured 340.1142 |
| P67 | 389 | 5-{4-[-1-Aminoethyl]-2-fluoro-3-methoxybenzoyl}-isoquinolin-1(2H)-one hydrochloride, enantiomer 1 $^1$H NMR (400 MHz, DMSO-d$_6$): δ 11.57 (d, 1H), 8.55 (m, 3H), 8.47 (d, 1H), 7.80 (d, 1H), 7.57 (t, 1H), 7.54 (d, 1H), 7.42 (dd, 1H), 7.31 (dd, 1H), 6.96 (d, 1H), 4.67 (quad, 1H), 3.93 (d, 3H), 1.52 (d, 3H) IR (cm$^{-1}$): 3300-2500, 1665, 1627 HRMS (ESI): theoretical m/z for $C_{19}H_{18}FN_2O_3$ [M + H]$^+$ 341.1301, measured 341.1297; theoretical m/z for $C_{19}FH_{18}N_2O_3$ [M + H—NH$_3$]$^+$ 324.1036, measured 324.1014 Optical purity (AD-H 5 μM column 4.6 × 250 mm; eluant: EtOH/CH$_3$CN/butylamine: 95/5/0.1); detection: 260 nm): >99%. α$_D$ (589 nM) = −6.99 (c = 0.01 g/mL, MeOH) at 20° C. |
| P70 | 395 | 5-[4-(1-Aminoethyl)-2,6-difluorobenzoyl]-4-ethyl-isoquinolin-1(2H)-one hydrochloride $^1$H NMR (400 MHz, DMSO-d$_6$): δ 11.60 (d, 1H), 8.75 (broad s, 3H), 8.47 (d, 1H), 7.70 (dd, 1H), 7.52 (t, 1H), 7.52 (d, 2H), 7.08 (d, 1H), 4.52 (broad s, 1H), 2.33 (quad, 2H), 1.55 (d, 3H), 1.10 (t, 3H) $^{19}$F NMR: −108.7 IR (cm$^{-1}$): 3300-2000, 1676, 1631 HRMS (ESI): theoretical m/z for $C_{20}H_{19}F_2N_2O_2$ [M + H]$^+$ 357.1415, measured 357.1415 |
| P72 | 403 | 5-{4-[(1R)-1-Aminoethyl]-2,6-difluoro-3-methoxy-benzoyl}isoquinolin-1(2H)-one hydrochloride $^1$H NMR (400 MHz, DMSO-d$_6$): δ 11.70 (m, 1H), 8.55 (d, 1H), 8.55 (m, 3H), 7.95 (dd, 1H), 7.60 (t and dd, 2H), 7.40 (m, 2H), 4.70 (quad, 1H), 3.90 (s, 3H), 1.50 (d, 3H) IR (cm$^{-1}$): 3300-2300, 1687, 1649, 1630, 1589 HRMS (ESI): theoretical m/z for $C_{19}H_{17}F_2N_2O_3$ [M + H]$^+$ 359.1207, measured 359.1189. Optical purity (SFC: ID 5 μM column 4.6 × 250 mm; eluant: CO$_2$/(isopropanol/butylamine: 100/0.5): 70/30; detection: 256 nm): >99%. (absence of P73) |
| P73 | 406 | 5-{4-[(1S)-1-Aminoethyl]-2,6-difluoro-3-methoxy-benzoyl}isoquinolin-1(2H)-one hydrochloride $^1$H NMR (400 MHz, DMSO-d$_6$): δ 11.70 (m, 1H), 8.60 (m, 3H), 8.55 (d, 1H), 7.95 (dd, 1H), 7.60 (t, 1H), 7.60 (dd, 1H), 7.40 (m, 2H), 4.70 (quad, 1H), 3.90 (s, 3H), 1.50 (d, 3H) IR (cm$^{-1}$): 3300-2300, 1687, 1649, 1630, 1589 HRMS (ESI): theoretical m/z for $C_{19}H_{17}F_2N_2O_3$ [M + H]$^+$ 359.1207, measured 359.1215. Optical purity (ID 5 μM column 4.6 × 250 mm; eluant: CO$_2$/(isopropanol/butylamine: 100/0.5): 70/30; detection: 256 nm): >99%. (absence of P72) |
| P75 | 412 | 5-[2,6-Difluoro-4-(piperidin-2-yl)benzoyl]isoquinolin-1(2H)-one hydrochloride $^1$H NMR (400 MHz, DMSO-d$_6$): δ 11.67 (broad s, 1H), 9.46 (m, 2H), 8.54 (d, 1H), 7.90 (d, 1H), 7.59 (m, 1H), 7.59 (m, 2H), 7.41 (m, 2H), 4.37 (dd, 1H), 3.39 (m, 1H), 3.03 (m, 1H), 2.02 (m, 1H), 2.00-1.50 (m, 5H) IR (cm$^{-1}$): 3200-2400, 1673, 1632 HRMS (ESI): theoretical m/z for $C_{21}H_{19}F_2N_2O_2$ [M + H]$^+$ 369.1415, measured 369.1415. |
| P80 | 432 | 5-[4-(1-Aminoethyl)-3-ethyl-2,6-difluorobenzoyl]-isoquinolin-1(2H)-one hydrochloride $^1$H NMR (400 MHz, DMSO-d$_6$): δ 11.70 (m, 1H), 8.80 (m, 3H), 8.50 (dd, 1H), 7.90 (dd, 1H), 7.75 (d, 1H), 7.60 (t, 1H), 7.40 (m, 1H), 7.40 (broad s, 2H), 4.65 (quad, 1H), 2.70 (m, 2H), 1.60 (d, 3H), 1.10 (t, 3H) IR (cm$^{-1}$): 3500-2250, 1673-1624, 1594, 788-697 HRMS (ESI): theoretical m/z for $C_{20}H_{19}F_2N_2O_2$ [M + H]$^+$ 357.1415, measured 357.1396. |
| P81 | 433 | 5-{4-[(1R)-1-Aminoethyl]-2,6-difluorobenzoyl}-4-chloroisoquinolin-1(2H)-one hydrochloride $^1$H NMR (400 MHz, DMSO-d$_6$): δ 12.10-11.60 (broad s, 1H), 8.90-8.40 (broad s, 3H), 8.42 (d, 1H), 7.77 (d, 1H), 7.63 (t, 1H), 7.53 (s, 1H), 7.47 (m, 2H), 4.50 (quad, 1H), |

| Product | Obtained from | Nomenclature Analytical description |
|---|---|---|
| | | 1.51 (d, 3H)<br>IR (cm$^{-1}$): 3600-2400, 1671, 1648<br>HRMS (ESI): theoretical m/z for C$_{18}$H$_{14}$ClF$_2$N$_2$O$_2$<br>[M + H]$^+$ 363.0712, measured 363.0706.<br>α$_D$ (589 nM) = 4.39 (c = 1, DMSO) at 20° C. |
| P82 | 434 | 5-{4-[(1,S)-1-Aminoethyl]-2,6-difluorobenzoyl}-4-chloroisoquinolin-1(2H)-one hydrochloride<br>$^1$H NMR (400 MHz, DMSO-d$_6$): δ 12.10-11.60 (broad s, 1H), 8.90-8.40 (broad s, 3H), 8.42 (d, 1H), 7.77 (d, 1H), 7.63 (t, 1H), 7.53 (s, 1H), 7.47 (m, 2H), 4.50 (quad, 1H), 1.51 (d, 3H)<br>$^{19}$F NMR: −107.2<br>IR (cm$^{-1}$): 3600-2400, 1681, 1634<br>HRMS (ESI): theoretical m/z for C$_{18}$H$_{14}$ClF$_2$N$_2$O$_2$<br>[M + H]$^+$ 363.0712, measured 363.0701.<br>α$_D$ (589 nM) = −4.4 (c = 1, DMSO) at 20° C. |
| P85 | 448 | 5-[3-(1-Aminoethyl)-2,6-difluoro-4-methoxybenzoyl]-isoquinolin-1(2H)-one hydrochloride<br>$^1$H NMR (400 MHz, DMSO-d$_6$): δ 11.60 (broad s, 1H), 8.50 (d, 1H), 8.29 (broad s, 3H), 7.93 (d, 1H), 7.58 (t, 1H), 7.37 (d, 1H), 7.23 (d, 1H), 7.23 (d, 1H), 4.60 (quad, 2H), 3.97 (s, 3H), 1.52 (d, 6H)<br>$^{19}$F NMR: −109, −115<br>IR (cm$^{-1}$): 3200-2600, 1674, 1650, 1625, 1144, 1052, 781<br>HRMS (ESI): theoretical m/z for C$_{19}$H$_{17}$F$_2$N$_2$O$_3$ [M + H]$^+$ 359.1207, measured 359.1212. |
| P88 | 467 | 5-[3-(2-Aminopropan-2-yl)-2,6-difluorobenzoyl]-isoquinolin-1(2H)-one hydrochloride<br>$^1$H NMR (400 MHz, DMSO-d$_6$): δ 11.70 (s, 1H), 8.83 (broad s, 3H), 8.54 (d, 1H), 7.97 (d, 1H), 7.74 (m, 1H), 7.59 (t, 1H), 7.45 (2d, 2H), 7.40 (m, 1H), 1.70 (s, 6H)<br>$^{19}$F NMR: −109.7, −112.6<br>IR (cm$^{-1}$): 3200-2500, 1684, 1625<br>HRMS (ESI): theoretical m/z for C$_{19}$H$_{17}$F$_2$N$_2$O$_2$ [M + H]$^+$ 343.1258, measured 343.1265. |
| P90 | 480 | 5-[3-(1-Aminopropyl)-2,6-difluorobenzoyl]isoquinolin-1(2H)-one hydrochloride<br>$^1$H NMR (400 MHz, DMSO-d$_6$): δ 11.70 (broad s, 1H), 8.54 (broad s, 3H), 8.53 (d, 1H), 7.93 (2m, 2H), 7.59 (t, 1H), 7.45 (t, 1H), 7.42 (s, 2H), 4.39 (dd, 1H), 2.01 (m, 1H), 1.88 (m, 1H), 0.82 (t, 3H)<br>IR (cm$^{-1}$): 3350-2500, 1675, 1630, 1026, 1006<br>HRMS (ESI): theoretical m/z for C$_{19}$H$_{17}$F$_2$N$_2$O$_2$ [M + H]$^+$ 343.1258, measured 343.1248<br>Optical purity (SFC: (S,S) Whelk 5 μM column 4.6 × 250 mm; eluant: CO$_2$/(isopropanol/diethylamine: 100/0.5): 70/30; detection: 254 nm): >99%. |
| P91 | 486 | 5-[2,6-Difluoro-3-(pyrrolidin-2-yl)benzoyl]isoquinolin-1(2H)-one hydrochloride<br>$^1$H NMR (400 MHz, DMSO-d$_6$): δ 11.70 (broad s, 1H), 9.50 (broad s, 2H), 8.54 (d, 1H), 8.00 (d, 1H), 7.92 (m, 1H), 7.59 (t, 1H), 7.42 (m, 3H), 4.76 (dd, 1H), 3.30 (m, 2H), 2.38-2.13-1.99 (m, 4H)<br>IR (cm$^{-1}$): 3250-2400, 1687, 1667, 787<br>HRMS (ESI): theoretical m/z for C$_{20}$H$_{17}$F$_2$N$_2$O$_2$ [M + H]$^+$ 355.1258, measured 355.1267.<br>Optical purity (SFC: ID 5 μM column 4.6 × 250 mm; eluant: CO$_2$/(isopropanol/diethylamine: 100/0.5): 70/30; detection: 255 nm): >99%. (absence of P99) |
| P92 | 494 | 5-{4-[(1R)-1-Aminopropyl]-2,6-difluorobenzoyl}-isoquinolin-1(2H)-one hydrochloride<br>$^1$H NMR (400 MHz, DMSO-d$_6$): δ 11.80 (broad s, 1H), 8.70 (m, 3H), 8.50 (d, 1H), 7.90 (d, 1H), 7.60 (t, 1H), 7.55 (d, 2H), 7.40 (m, 2H), 4.30 (dd, 1H), 2.05-1.85 (m, 2H), 0.85 (t, 3H)<br>IR (cm$^{-1}$): 3300-2100, 1670, 1624<br>HRMS (ESI): theoretical m/z for C$_{19}$H$_{17}$F$_2$N$_2$O$_2$ [M + H]$^+$ 343.1258, measured 343.1248. |
| P93 | 501 | 5-[4-(1-Amino-2-methylpropyl)-2,6-difluorobenzoyl]-isoquinolin-1(2H)-one hydrochloride<br>$^1$H NMR (300-500 MHz, DMSO-d$_6$): δ 11.67 (broad s, 1H), 8.61 (broad s, 3H), 8.54 (d, 1H), 7.90 (d, 1H), 7.59 (t, 1H), 7.49 (d, 2H), 7.39 (s, 2H), 4.13 (d, 1H), 2.21 (m, 1H), 1.06-0.81 (d, 6H)<br>IR (cm$^{-1}$): 3500-2500, 1626, 1524, 1480<br>$^{19}$F NMR: −111.3 |

| Product | Obtained from | Nomenclature Analytical description |
|---|---|---|
| | | HRMS (ESI): theoretical m/z for $C_{20}H_{19}F_2N_2O_2$ [M + H]$^+$ 357.1415, measured 357.1409. |
| P94 | 507 | 5-[4-(1-Aminobutyl)-2,6-difluorobenzoyl]isoquinolin-1(2H)-one hydrochloride<br>$^1$H NMR (400 MHz, DMSO-d$_6$): δ 11.70 (s, 1H), 8.80 (m, 3H), 8.55 (d, 1H), 7.90 (d, 1H), 7.60 (m, 3H), 7.40 (m, 2H), 4.35 (m, 1H), 1.90 (m, 2H), 1.25 (m, 2H), 0.90 (t, 3H)<br>IR (cm$^{-1}$): 3200, 2800, 1632<br>HRMS (ESI): theoretical m/z for $C_{20}H_{19}F_2N_2O_2$ [M + H]$^+$ 357.1415, measured 357.1422. |
| P95 | 512 | 5-[4-(1-Amino-3-methylbutyl)-2,6-difluorobenzoyl]-isoquinolin-1(2H)-one hydrochloride<br>$^1$H NMR (400 MHz, DMSO-d$_6$): δ 11.70 (m, 1H), 8.75 (m, 3H), 8.55 (d, 1H), 7.90 (d, 1H), 7.60 (m, 3H), 7.40 (m, 2H), 4.40 (t, 1H), 1.85 (dd, 2H), 1.45 (m, 1H), 0.90 (2d, 6H)<br>IR (cm$^{-1}$): 3165, 2870, 1658, 1216<br>HRMS (ESI): theoretical m/z for $C_{21}H_{21}F_2N_2O_2$ [M + H]$^+$ 371.1571, measured 371.1576. |
| P99 | 523 | 5-[2,6-Difluoro-3-(pyrrolidin-2-yl)benzoyl]isoquinolin-1(2H)-one hydrochloride<br>$^1$H NMR (400 MHz, DMSO-d$_6$): δ 11.69 (d, 1H), 9.64 (m, 2H), 8.55 (broad d, 1H), 8.01 (d, 1H), 7.92 (m, 1H), 7.60 (t, 1H), 7.5-7.35 (m, 3H), 4.8 (dd, 1H), 3.3 (m, 2H), 2.38 (m, 1H), 2.2-2.05 (2m, 2H), 2.00 (m, 1H)<br>IR (cm$^{-1}$): 3300-2000, 1686, 1666<br>HRMS (ESI): theoretical m/z for $C_{20}H_{17}F_2N_2O_2$ [M + H]$^+$ 355.1258, measured 355.1266.<br>Optical purity (SFC: ID 5 μM column 4.6 × 250 mm; eluant: CO$_2$/(isopropanol/diethylamine: 100/0.5): 70/30; detection: 255 nm): >99%. (absence of P91) |
| P100 | 528 | 5-[3-(1-Aminoethyl)-2-fluorobenzoyl]isoquinolin-1(2H)-one hydrochloride<br>$^1$H NMR (400 MHz, DMSO-d$_6$): δ 11.57 (d, 1H), 8.48 (d, 1H), 7.96 (m, 1H), 7.80 (d, 1H), 7.66 (m, 1H), 7.55 (t, 1H), 7.50 (t, 1H), 7.30 (dd, 1H), 6.98 (d, 1H), 6.65 (m, 3H), 4.62 (quad, 1H), 1.55 (d, 3H)<br>IR (cm$^{-1}$): 3167, 3000-2000, 1664, 1630<br>HRMS (ESI): theoretical m/z for $C_{18}H_{16}FN_2O_2$ [M + H]$^+$ 311.1196, measured 311.1195.<br>Optical purity (SFC: ID 3 μM column 4.6 × 250 mm; eluant: CO$_2$/(isopropanol/diethylamine: 100/0.5): 70/30; detection: 253 nm): >99%. (absence of P108) |
| P104 | 546 | 5-[4-(1-Aminoethyl)-3-fluoro-2-methoxybenzoyl]-isoquinolin-1(2H)-one hydrochloride<br>$^1$H NMR (400 MHz, DMSO-d$_6$): δ 11.57 (m, 1H), 8.59 (broad s, 3H), 8.46 (broad d, 1H), 7.71 (dd, 1H), 7.55 (t, 1H), 7.50 (dd, 1H), 7.42 (d, 1H), 7.32 (dd, 1H), 7.08 (d, 1H), 4.68 (quad, 1H), 3.57 (s, 3H), 1.57 (d, 3H)<br>IR (cm$^{-1}$): 3650-2400, 1678, 1651, 783, 752<br>HRMS (ESI): theoretical m/z for $C_{19}H_{18}FN_2O_3$ [M + H]$^+$ 341.1301, measured 341.1292 |
| P105 | 555 | 5-[4-(1-Aminoethyl)-2,6-difluoro-3-methylbenzoyl]-isoquinolin-1(2H)-one hydrochloride<br>$^1$H NMR (400 MHz, DMSO-d$_6$): δ 11.67 (broad s, 1H), 8.62 (broad s, 3H), 8.53 (dd, 1H), 7.88 (broad d, 1H), 7.59 (d, 1H), 7.58 (t, 1H), 7.41 (m, 2H), 4.69 (quad, 1H), 2.26 (s, 3H), 1.53 (d, 3H).<br>IR (cm$^{-1}$): 3350-2000, 1672, 1626<br>HRMS (ESI): theoretical m/z for $C_{19}H_{17}F_2N_2O_2$ [M + H]$^+$ 343.1253, measured 343.1244 |
| P106 | 560 | 5-[3-(1-Aminoethyl)-2,6-difluoro-4-methylbenzoyl]-isoquinolin-1(2H)-one hydrochloride<br>$^1$H NMR (400 MHz, DMSO-d$_6$): δ 11.7 (m, 1H), 8.55 (m, 4H), 8.00 (d, 1H), 7.60 (t, 1H), 7.40 (m, 2H), 7.25 (d, 1H), 4.60 (m, 1H), 1.50 (m, 6H).<br>IR (cm$^{-1}$): 2859, 1622, 789-747-709<br>HRMS (ESI): theoretical m/z for $C_{19}H_{17}F_2N_2O_2$ [M + H]$^+$ 343.1253, measured 343.1246 |
| P107 | 562 | 5-[4-(1-Aminoethyl)-3-ethyl-2,6-difluorobenzoyl]-isoquinolin-1(2H)-one hydrochloride<br>$^1$H NMR (400 MHz, DMSO-d$_6$): δ 11.68 (broad s, 1H), 8.59 (broad s, 3H), 8.54 (broad d, 1H), 7.88 (broad d, 1H), 7.64 (d, 1H), 7.59 (t, 1H), 7.41 (m, 2H), 4.67 (quad, 1H), 2.70 (m, 2H), 1.55 (d, 3H), 1.13 (t, 3H) |

| Product | Obtained from | Nomenclature Analytical description |
|---|---|---|
| | | IR (cm$^{-1}$): 3200-2500, 1674, 789<br>HRMS (ESI): theoretical m/z for C$_{20}$H$_{19}$F$_2$N$_2$O$_2$ [M + H]$^+$ 357.1409, measured 357.1403. |
| P128 | 698 | 5-{4-[Amino(3-methoxyphenyl)methyl]-2,6-difluoro-benzoyl}isoquinolin-1(2H)-one hydrochloride<br>$^1$H NMR (300 MHz, DMSO-d$_6$): δ 11.65 (broad s, 1H), 9.30 (broad s, 3H), 8.50 (d, 1H), 7.90 (d, 1H), 7.55 (m, 3H), 7.40 (m, 3H), 7.30 (s, 1H), 7.15 (d, 1H), 7.00 (dd, 1H), 5.75 (s, 1H), 3.80 (s, 3H)<br>IR (cm$^{-1}$): 3300-2400, 1661, 1627-1591, 1259, 783<br>HRMS (ESI): theoretical m/z for C$_{24}$H$_{19}$F$_2$N$_2$O$_3$ [M + H]$^+$ 421.1364, measured 421.1346 |
| P129 | 704 | 5-[4-(1-Amino-2-cyclohexylethyl)-2,6-difluorobenzoyl]-isoquinolin-1(2H)-one hydrochloride<br>$^1$H NMR (300 MHz, DMSO-d$_6$): δ 11.70 (broad s, 1H), 8.75 (m, 3H), 8.55 (d, 1H), 7.90 (d, 1H), 7.60 (m, 3H), 7.40 (m, 2H), 4.45 (m, 1H), 1.95-0.85 (3m, 13H)<br>IR (cm$^{-1}$): 3387, 3150-2600, 2923-2851, 1661-1631, 1591, 1260<br>HRMS (ESI): theoretical m/z for C$_{24}$H$_{25}$F$_2$N$_2$O$_2$ [M + H]$^+$ 411.1884, measured 411.1869 |
| P130 | 708 | 5-(4-{1-[(Cyclohexylmethyl)amino]ethyl}-2,6-difluorobenzoyl)isoquinolin-1(2H)-one hydrochloride<br>$^1$H NMR (300 MHz, DMSO-d$_6$): δ 8.50 (d, 1H), 7.85 (d, 1H), 7.55 (m, 3H), 7.35 (s, 2H), 4.45 (m, 1H), 2.75 (m, 1H), 2.60 (m, 1H), 1.75-0.90 (3m, 11H), 1.65 (d, 3H)<br>IR (cm$^{-1}$): 3163, 3019, 2921-2854, 2661, 1692-1673, 1634-1592, 1437, 1237<br>HRMS (ESI): theoretical m/z for C$_{25}$H$_{27}$F$_2$N$_2$O$_2$ [M + H]$^+$ 425.2041, measured 425.2042 |
| P131 | 710 | 5-[4-(1-Aminoethyl)-2,6-difluorobenzoyl]-3-methylisoquinolin-1(2H)-one hydrochloride<br>$^1$H NMR (400 MHz, DMSO-d$_6$): δ 11.80-11.60 (m, 1H), 9.00-8.60 (m, 3H), 8.50 (dd, 1H), 7.85 (dd, 1H), 7.55 (d, 2H), 7.50 (t, 1H), 7.30 (broad s, 1H), 4.55 (quad, 1H), 2.30 (s, 3H), 1.55 (d, 3H)<br>IR (cm$^{-1}$): 3200-2300, 1672<br>HRMS (ESI): theoretical m/z for C$_{19}$F$_2$H$_{17}$N$_2$O$_2$ [M + H]$^+$ 343.1258, measured 343.1268; theoretical m/z for C$_{19}$H$_{17}$F$_2$N$_2$O$_2$ [M + H—NH$_3$]$^+$ 326.0993, found 326.0991 |
| P133 | 730 | 5-{4-(1-Aminoethyl)-5-[2-(dimethylamino)ethoxy]-2-fluorobenzoyl}isoquinolin-1(2H)-one hydrochloride<br>$^1$H NMR (400 MHz, DMSO-d$_6$): δ 11.70 (m, 1H), 10.80 (m, 1H), 8.60 (m, 3H), 8.50 (d, 1H), 7.80 (d, 1H), 7.60 (t, 1H), 7.60 (d, 1H), 7.40 (d, 1H), 7.35 (dd, 1H), 7.00 (t, 1H), 5.00 (quad, 1H), 4.45 (m, 2H), 3.60 (m, 2H), 2.85 (broad s, 6H), 1.55 (d, 3H)<br>IR (cm$^{-1}$): 3367, 2800-2300, 1655, 1627, 1481<br>HRMS (ESI): theoretical m/z for C$_{22}$H$_{25}$FN$_3$O$_3$ [M + H]$^+$ 398.1880, measured 398.1881 |
| P134 | 732 | 5-[4-(2-Aminopropan-2-yl)-2,6-difluorobenzoyl]-3-methylisoquinolin-1(2H)-one methanesulphonate<br>$^1$H NMR (400 MHz, DMSO-d$_6$): δ 11.80-11.60 (m, 1H), 8.50 (d, 1H), 8.50-8.30 (m, 3H), 7.85 (d, 1H), 7.55-7.45 (m, 3H), 7.30 (s, 1H), 2.30 (broad s, 3H), 1.70 (s, 6H)<br>IR (cm$^{-1}$): 3300-2000, 1675, 1632, 1176<br>HRMS (ESI): theoretical m/z for C$_{20}$H$_{19}$F$_2$N$_2$O$_2$ [M + H]$^+$ 357.1415, measured 357.1412 |
| P135 | 734 | 5-[4-(1-Aminoethyl)-2,6-difluoro-3-methoxybenzoyl]-3-methylisoquinolin-1(2H)-one hydrochloride<br>$^1$H NMR (300 MHz, DMSO-d$_6$): δ 11.70 (m, 1H), 8.70 (m, 3H), 8.50 (d, 1H), 7.95 (d, 1H), 7.65 (dd, 1H), 7.50 (t, 1H), 7.30 (s, 1H), 4.70 (quad, 1H), 3.90 (s, 3H), 2.30 (s, 3H), 1.55 (d, 3H)<br>IR (cm$^{-1}$): 3430-2250, 1666, 1632, 1595, 838-687<br>HRMS (ESI): theoretical m/z for C$_{20}$H$_{19}$F$_2$N$_2$O$_3$ [M + H]$^+$ 373.1364, measured 373.1365 |
| P137 | 741 | 5-{4-[-1-Aminoethyl]-2-fluoro-3-methoxybenzoyl}-isoquinolin-1(2H)-one hydrochloride, enantiomer 2<br>$^1$H NMR (400 MHz, DMSO-d$_6$): δ 11.60 (d, 1H), 8.70 (broad s, 3H), 8.45 (d, 1H), 7.80 (d, 1H), 7.58 (t, 1H), 7.45 (dd, 1H), 7.42 (dd, 1H), 7.30 (dd, 1H), 6.95 (d, 1H), 4.68 (quad, 1H), 3.93 (s, 3H), 1.55 (d, 3H)<br>IR (cm$^{-1}$): 3300-2200, 1664, 1621<br>HRMS (ESI): theoretical m/z for C$_{19}$FH$_{18}$N$_2$O$_3$ [M + H]$^+$ 341.1301, measured 341.1298; theoretical m/z for |

| Product | Obtained from | Nomenclature Analytical description |
|---|---|---|
| | | $C_{19}H_{18}FN_2O_3$ [M + H—NH$_3$]$^+$ 324.1012, found 324.1036<br>Optical purity (AD-H 5 µM column 4.6 × 250 mm; eluant:<br>EtOH/CH$_3$CN/butylamine: 95/5/0.1); detection: 260 nm): >99%.<br>(absence of P67)<br>$\alpha_D$ (589 nM) = 6.85 (c = 0.01 g/mL, MeOH) at 20° C. |

Protocol XXII: Alternative Method for the Preparation of Compounds of Formula (I) Wherein X Represents —C(═O)

Compounds of formula (I) wherein X represents —C(═O) can also be prepared by coupling reaction by halogen-metal exchange of a halo-isoquinoline compound according to the example of the synthesis of intermediate 106:

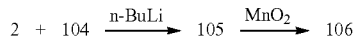

Intermediate 105:

2,2,2-Trifluoro-N-(1-{3-fluoro-4-[hydroxy(isoquinolin-5-yl)methyl]-5-methoxyphenyl}ethyl)acetamide To a solution of intermediate 2 (1 g, 4.8 mmoles) in anhydrous THF (15 mL), under N$_2$ and cooled to −78° C., there is added a solution of n-BuLi (2.5N/hexane) (2.1 mL), the temperature being maintained below −70° C. The resulting solution is stirred for 20 minutes at −78° C., and then a solution of intermediate 104 (1.3 g, 4.4 mmoles) in anhydrous THF (15 mL) is added, the temperature being maintained below −70° C. The reaction mixture is stirred for 1 hour at −78° C. and then for 1½ h at −50° C., and it is then hydrolysed and extracted with AcOEt. The organic phase is washed with water, dried over MgSO$_4$ and evaporated in vacuo. The residue is purified by flash chromatography on silica (eluant: CH$_2$Cl$_2$/AcOEt: gradient: 100/0 to 90/10). Intermediate 105 (1 g) is obtained.

$^1$H NMR (300 MHz, DMSO-d$_6$): δ 9.80 (broad s, 1H), 9.27 (s, 1H), 8.42 (d, 1H), 8.14 (broad d, 1H), 8.00 (d, 1H), 7.75 (d, 1H), 7.71 (t, 1H), 6.94 (broad s, 1H), 6.70 (broad d, 1H), 6.65 (dl, 1H), 5.98 (d, 1H), 4.97 (m, 1H), 3.93 (s, 3H), 1.41 (2d, 3H).

IR (cm$^{-1}$): 3400-3100, 1707, 1209-1183-1157, 733

Intermediate 106:

2,2,2-Trifluoro-N-{1-[3-fluoro-4-(isoquinolin-5-ylcarbonyl)-5-methoxyphenyl]ethyl}-acetamide To a solution of (0.68 g, 1.61 mmoles) of intermediate 105 in methylene chloride (100 mL) there is added MnO$_2$ (2.6 g, 30 mmoles). The mixture is stirred for 17 hours at ambient temperature, and then the MnO$_2$ is filtered off. Evaporation of the filtrate yields intermediate 106 (450 mg) in the form of a solid.

$^1$H NMR (300 MHz, DMSO-d$_6$): δ 9.90 (m, 1H), 9.50 (s, 1H), 8.75 and 8.70 (2d, 2H), 8.45 (d, 1H), 8.00 (d, 1H), 7.80 (t, 1H), 7.10 (broad s, 1H), 7.00 (broad d, 1H), 5.10 (q, 1H), 3.70 (s, 3H), 1.50 (d, 3H)

IR (cm$^{-1}$): 3125 (weak), 1717, 1677, 1621 and 1590, 1570, 1208-1095, 833-667 This sequence was used to prepare the following intermediates:

Intermediate 20:

2,2,2-Trifluoro-N-{(1R)-1-[4-(isoquinolin-5-ylcarbonyl)-3-methoxyphenyl]ethyl}-acetamide Obtained by oxidation of the intermediate resulting from the coupling of 18 and 2

$^1$H NMR (300 MHz, DMSO-d$_6$): δ 9.90 (broad s, 1H), 9.40 (s, 1H), 8.60 (d, 1H), 8.35 (d, 1H), 8.30 (d, 1H), 7.80 (d, 1H), 7.42 (t, 1H), 7.50 (d, 1H), 7.15 (s, 1H), 7.10 (d, 1H), 5.10 (m, 1H), 3.53 (s, 3H), 1.50 (d, 3H)

IR (cm$^{-1}$): 3125, 1708, 1653, 1608, 1568, 1204-1181-1149, 831-760-734

Intermediate 96

2,2,2-Trifluoro-N-{(1R)-1-[8-(isoquinolin-5-ylcarbonyl)-3,4-dihydro-2H-chromen-5-yl]ethyl}acetamide Obtained by oxidation of the intermediate resulting from the coupling of 94 and 2

$^1$H NMR (300 MHz, DMSO-d$_6$): δ 10.00 (broad s, 1H), 9.50 (s, 1H), 8.60 (d, 1H), 8.35 (m, 2H), 7.85 (d, 1H), 7.70 (t, 1H), 7.35 (d, 1H), 7.10 (d, 1H), 5.15 (quad, 1H), 3.80 (t, 2H), 2.80 (2m, 2H), 1.85 (quint, 2H), 1.45 (d, 3H)

IR (cm$^{-1}$): 3395, 1708, 1652, 1610, 1595, 1572. 1200-1148, 830-700

Intermediate 264:

N-[(1R)-1-{8-[(1-Ethoxyisoquinolin-5-yl)carbonyl]-3,4-dihydro-2H-chromen-5-yl}ethyl]-2,2,2-trifluoroacetamide Obtained by oxidation of the intermediate resulting from the coupling of 94 and 124

$^1$H NMR (300 MHz, DMSO-d$_6$): δ 10.0 (m, 1H), 8.40 (d, 1H), 8.10 (d, 1H), 7.9-7.75 (2d, 2H), 7.65 (t, 1H), 7.35 (d, 1H), 7.10 (d, 1H), 5.15 (m, 1H), 4.55 (quad, 2H), 3.80 (m, 2H), 2.9-2.65 (m, 2H), 1.95-1.8 (m, 2H), 1.5-1.35 (d and t, 6H)

IR (cm$^{-1}$): 3294, 1724, 1700, 1656, 1100-1280

LCMS [M+H]+=472

Optical purity (SFC: IA 3 µM column 4.6×250 mm; CO$_2$/(ethanol/diethylamine: 100/0.5): 80/20; Detection: 215 nm): >99%.

$\alpha_D$ (589 nM)=+65.93 (c=0.010 g/mL, MeOH, 20° C.).

Intermediate 359:

N-[(1S)-1-{8-[(1-Ethoxyisoquinolin-5-yl)carbonyl]-3,4-dihydro-2H-chromen-5-yl}ethyl]-2,2,2-trifluoroacetamide Obtained by oxidation of the intermediate resulting from the coupling of 357 and 124

$^1$H NMR (400 MHz, DMSO-d$_6$): δ 9.99 (s, 1H), 8.41 (d, 1H), 8.09 (d, 1H), 7.84 (d, 1H), 7.80 (d, 1H), 7.66 (dd, 1H), 7.36 (d, 1H), 7.09 (d, 1H), 5.16 (quad, 1H), 4.56 (quad, 2H), 3.80 (m, 2H), 2.87 (dt, 1H), 2.76 (dt, 1H), 1.88 (m, 2H), 1.47 (m, 6H)

IR (cm$^{-1}$): 3286, 1702, 1651

Optical purity (SFC: IA 3 µM column 4.6×250 mm; CO$_2$/(ethanol/diethylamine: 100/0.5): 80/20; Detection: 215 nm): >99%.

Intermediate 399:

tert-Butyl (2-{3-chloro-4-[(1-ethoxy-4-methylisoquinolin-5-yl)carbonyl]phenyl}-propan-2-yl)carbamate Obtained by oxidation of the intermediate resulting from the coupling of 193 and 301

$^1$H NMR (400 MHz, DMSO-d$_6$): δ 8.45 (d, 1H), 7.92 (s, 1H), 7.65 (d and t, 3H), 7.50 (d, 1H), 7.45 (dd, 1H), 7.38 (broad s, 1H), 4.52 (quad, 2H), 2.18 (s, 3H), 1.55 (s, 6H), 1.45 (t, 3H), 1.35 (broad s, 9H)

IR (cm$^{-1}$): 3313, 1684-1658

Intermediate 455:

N-{8-[(1-Ethoxyisoquinolin-5-yl)carbonyl]-3,4-dihydro-2H-chromen-4-yl}-2,2,2-trifluoroacetamide Obtained by oxidation of the intermediate resulting from the coupling of 453 and 124

$^1$H NMR (400 MHz, DMSO-d$_6$): δ 9.95 (broad s, 1H), 8.42 (d, 1H), 8.10 (d, 1H), 7.90 (d, 1H), 7.82 (d, 1H), 7.67 (d, 1H), 7.41 (d, 1H), 7.38 (d, 1H), 7.09 (t, 1H), 5.15 (m, 1H), 4.57 (quad, 2H), 3.98 (t, 2H), 2.05 (m, 1H), 1.92 (m, 1H), 1.46 (t, 3H)

IR (cm$^{-1}$): 3280, 1703, 1655

Intermediate 514:

N-[(1R)-1-{8-[(1-Ethoxy-4-methylisoquinolin-5-yl)carbonyl]-3,4-dihydro-2H-chromen-5-yl}ethyl]-2,2,2-trifluoroacetamide Obtained by oxidation of the intermediate resulting from the coupling of 94 and 302

$^1$H NMR (300 MHz, DMSO-d$_6$): δ 10.00 (m, 1H), 7.85 (s, 1H), 7.60 (m, 2H), 7.50 (dd, 1H), 7.10 (d, 1H), 5.15 (quad, 1H), 4.50 (quad, 2H), 3.70 (t, 2H), 2.80 (m, 2H), 2.10 (s, 3H), 1.80 (m, 2H), 1.45 (t, 6H)

$^{19}$F NMR: -73, IR (cm$^{-1}$): 3270, 1722

Intermediate 544:

N-[(1R)-1-{4-[(1-Ethoxyisoquinolin-5-yl)carbonyl]-3-methoxyphenyl}ethyl]-2,2,2-trifluoroacetamide Obtained by oxidation of the intermediate resulting from the coupling of 18 and 124

$^1$H NMR (400 MHz, DMSO-d$_6$): δ 10.00 (m, 1H), 8.4 (d, 1H), 8.05 (d, 1H), 7.8-7.75 (d and dd, 2H), 7.65 (dd, 1H), 7.5 (d, 1H), 7.15 (d, 1H), 7.05 (d, 1H), 5.01 (quad, 1H), 4.55 (quad, 2H), 3.5 (s, 3H), 1.5 (d, 3H), 1.45 (t, 3H)

IR (cm$^{-1}$): 3290, 1698, 1651

Intermediate 641:

2,2,2-Trifluoro-N-{(1S)-1-[4-(isoquinolin-5-ylcarbonyl)-3-methoxyphenyl]ethyl}-acetamide Obtained by oxidation of the intermediate resulting from the coupling of 639 and 2

$^1$H NMR (300 MHz, DMSO-d6): δ 10.00 (broad s, 1H, NH), 9.45 (s, 1H), 8.60 (d, 1H), 8.35 (d, 1H), 8.30 (d, 1H), 7.85 (d, 1H), 7.75 (t, 1H), 7.52 (d, 1H), 7.20 (s, 1H), 7.10 (d, 1H), 5.10 (m, 1H), 3.55 (s, 3H), 1.53 (d, 3H)

IR (cm$^{-1}$): 3222, 1710, 1651, 1608, 1569

Intermediate 736:

tert-Butyl (2-{3-chloro-4-[(1-ethoxy-3-methylisoquinolin-5-yl)carbonyl]phenyl}-propan-2-yl)carbamate Obtained by oxidation of the intermediate resulting from the coupling of 397 and 293

$^1$H NMR (400 MHz, DMSO-d$_6$): δ 8.42 (d, 1H), 7.85 (s, 1H), 7.70 (d, 1H), 7.60 (t, 1H), 7.52 (d, 1H), 7.45 (s and d, 2H), 7.35 (broad s, 1H, NH), 4.52 (quad, 2H), 2.50 (s, 3H), 1.55 (s, 6H), 1.45 (t, 3H), 1.30 (broad s, 9H)

IR (cm$^{-1}$): 3259, 1697-1663

Intermediate 750:

N-({8-[(1-Ethoxyisoquinolin-5-yl)carbonyl]-3,4-dihydro-2H-chromen-4-yl}methyl)-2,2,2-trifluoroacetamide Obtained by oxidation of the intermediate resulting from the coupling of 748 and 125

$^1$H NMR (300 MHz, DMSO-d$_6$): δ 9.65 (s, 1H, NH), 8.40 (d, 1H), 8.09 (d, 1H), 7.82 (d, 1H), 7.81 (dd, 1H), 7.65 (t, 1H), 7.40-7.37 (2d, 2H), 7.07 (t, 1H), 4.55 (quad., 2H), 3.83 (m, 2H), 3.55 (dd, 1H), 3.38 (dd, 1H), 3.08 (m, 1H), 1.87 (m, 1H), 1.70 (m, 1H), 1.47 (t, 3H)

IR (cm$^{-1}$): 3307, 1709, 1653, 1568, 1277, 1155

Intermediate 221 was obtained by oxidation of 220 resulting from the coupling between 4-bromo-2-fluorobenzaldehyde and intermediate 124.

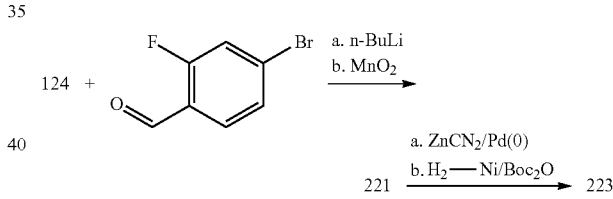

Intermediate 221:

(4-Bromo-2-fluorophenyl)(1-ethoxyisoquinolin-5-yl)methanone

Step 1:

To a solution of intermediate 124 (2 g, 7.94 mmoles) in anhydrous THF (40 mL), cooled to -70° C., there is added, in the course of 20 minutes, a 2.5N solution of n-BuLi in hexane (3.2 mL, 8 mmoles). The resulting solution is stirred for 10 minutes at -70° C., and then a solution of commercial 4-bromo-2-fluoro-benzaldehyde (1.66 g, 8.17 mmoles) in THF (15 mL) is added in the course of 15 minutes. The reaction mixture is stirred at -70° C. until the starting product has disappeared, and is hydrolysed with a saturated aqueous ammonium chloride solution. The organic phase is extracted with ethyl ether, washed with a saturated aqueous NaCl solution, dried over MgSO$_4$, filtered and evaporated in vacuo. By recrystallisation from acetonitrile, the expected intermediate (1.8 g) is obtained.

$^1$H NMR (400 MHz, DMSO-d$_6$): δ 8.16 (d, 1H), 7.98 (d, 1H), 7.80 (d, 1H), 7.62 (t, 1H), 7.50 (d, 1H), 7.42 (d, 1H), 7.38 (m, 2H), 6.52 (d, 1H), 6.32 (d, OH), 4.50 (quad., 2H), 1.40 (t, 3H)

IR (cm$^{-1}$): 3252, 1620-1602-1571, 1209-1163, 1038, 867-801-755

Step 2:

Oxidation of the intermediate obtained above in the presence of MnO$_2$ yields intermediate 221.

$^1$H NMR (400 MHz, DMSO-d$_6$): δ 8.48 (d, 1H), 8.10 (d, 1H), 7.95 (d, 1H), 7.78 to 7.6 (m, 5H), 4.57 (quad, 2H), 1.45 (t, 3H)

IR (cm$^{-1}$): 1650

Intermediate 223 was obtained starting from 221:

Intermediate 222:

4-[(1-Ethoxyisoquinolin-5-yl)carbonyl]-3-fluorobenzonitrile

To a solution of intermediate 221 (2 g, 5.34 mmoles) in DMF (10 mL), degassed with nitrogen, at ambient temperature, there are added Zn(CN)$_2$ (0.75 g, 6.41 mmoles) and Pd(PPh$_3$)$_4$(0.31 g). The reaction mixture is heated at 100° C. for 45 minutes and is then hydrolysed with water. The organic phase is extracted with ethyl acetate, washed 4 times with water and with a saturated aqueous NaCl solution, dried over MgSO$_4$, filtered and evaporated in vacuo. The residue is purified by flash chromatography on silica (eluant: CH$_2$Cl$_2$—AcOEt gradient: 100/0 to 95-5. The expected intermediate 222 (1.6 g) is obtained in the form of a solid.

$^1$H NMR (400 MHz, DMSO-d$_6$): δ 8.51 (d, 1H), 8.17 (d, 1H), 8.08 (d, 1H), 7.99 (d, 1H), 7.94 (d, 1H), 7.89 (m, 2H), 7.70 (t, 1H), 4.58 (quad, 2H), 1.46 (t, 3H)

IR (cm$^{-1}$): 1651, 2239

Intermediate 223:

tert-Butyl {4-[(1-ethoxyisoquinolin-5-yl)carbonyl]-3-fluorobenzyl}carbamate

To a solution of intermediate 222 (250 mg, 0.78 mmole) in ethanol (5 mL) there are added di-tert-butyl dicarbonate (220 mg, 1.04 mmoles) and Raney nickel (200 mg). The mixture is hydrogenated at atmospheric pressure and ambient temperature for 18 hours and then heated at 70° C. for 212 hours. After cooling, the catalyst is filtered off. The filtrate is evaporated to dryness and purified by flash chromatography on silica (eluant: CH$_2$Cl$_2$—AcOEt gradient: 99-1 to 90-10). Intermediate 223 (190 mg) is obtained.

$^1$H NMR (400 MHz, DMSO-d$_6$): δ 8.45 (d, 1H), 8.08 (d, 1H), 7.89 (d, 1H), 7.72 to 7.62 (m, 3H), 7.53 (t, 1H), 7.25 (dl, 1H), 7.16 (dl, 1H), 4.56 (quad., 2H), 4.23 (d, 2H), 1.46 (t, 3H), 1.40 (broad s, 9H)

IR (cm$^{-1}$): 3360, 1740, 1683-1662, 1525, 1278-1159, 810-783-752

The ketone intermediates protected in the form of trifluoro-acetamides were deprotected in a basic medium according to the example of intermediate 56.

Intermediate 21:

{4-[(1R)-1-Aminoethyl]-2-methoxyphenyl}(isoquinolin-5-yl)methanone $^1$H NMR (300 MHz, DMSO-d$_6$): δ 9.50 (s, 1H), 8.60 (d, 1H), 8.35 (d, 1H), 8.25 (d, 1H), 7.80 (d, 1H), 7.70 (t, 1H), 7.50 (d, 1H), 7.20 (d, 1H), 7.12 (d, 1H), 4.10 (quad, 1H), 3.52 (s, 3H), 2.10 (m, 2H), 1.35 (d, 3H)

IR (cm$^{-1}$): 3344, 3277, 1646, 1609

Intermediate 265:

{5-[(1R)-1-Aminoethyl]-3,4-dihydro-2H-chromen-8-yl}(1-ethoxyisoquinolin-5-yl)methanone Obtained starting from intermediate 264

$^1$H NMR (400 MHz, DMSO-d$_6$): δ 8.40 (d, 1H), 8.05 (d, 1H), 7.80 (m, 1H), 7.70 (m, 1H), 7.65 (t, 1H), 7.30 (d, 1H), 7.25 (d, 1H), 4.55 (q, 2H), 4.20 (q, 1H), 3.75 (m, 2H), 2.85-2.70 (2m, 2H), 2.30-1.90 (m, 2H), 1.80 (m, 2H), 1.25 (d, 3H), 1.45 (t, 3H)

IR (cm$^{-1}$): 3383, 3269, 1643

Intermediate 360:

{5-[(1S)-1-Aminoethyl]-3,4-dihydro-2H-chromen-8-yl}(1-ethoxyisoquinolin-5-yl)methanone $^1$H NMR (400 MHz, DMSO-d$_6$): δ 8.40 (d, 1H), 8.07 (d, 1H), 7.77 (m, 2H), 7.65 (dd, 1H), 7.32 (d, 1H), 7.27 (d, 1H), 4.56 (quad, 2H), 4.19 (quad, 1H), 3.75 (t, 2H), 2.85 (dt, 1H), 2.69 (dt, 1H), 1.83 (m, 4H), 1.47 (t, 3H), 1.24 (d, 3H)

IR (cm$^{-1}$): 3387, 3290, 1643, 1612

Intermediate 456:

(4-Amino-3,4-dihydro-2H-chromen-8-yl)(1-ethoxyisoquinolin-5-yl)methanone $^1$H NMR (400 MHz, DMSO-d$_6$): δ 8.40 (d, 1H), 8.08 (d, 1H), 7.81 (d, 1H), 7.79 (d, 1H), 7.64 (t, 1H), 7.62 (dd, 1H), 7.31 (dd, 1H), 7.00 (t, 1H), 4.55 (quad, 2H), 3.94 (m, 1H), 3.90 (m, 1H), 3.83 (m, 1H), 2.04 (broad s, 2H), 1.90 (m, 1H), 1.64 (m, 1H), 1.45 (t, 3H)

IR (cm$^{-1}$): 3361, 3285, 1651, 1585, 1272, 1235, 807, 756

Intermediate 515:

{5-[(1R)-1-Aminoethyl]-3,4-dihydro-2H-chromen-8-yl}(1-ethoxy-4-methylisoquinolin-5-yl)methanone $^1$H NMR (500 MHz, DMSO-d$_6$): δ 8.31 (d, 1H), 7.86 (s, 1H), 7.57 (t, 1H), 7.52 (d, 1H), 7.52 (d, 1H), 7.28 (d, 1H), 4.51 (quad, 2H), 4.17 (quad, 1H), 3.66 (m, 2H), 2.81 (m, 1H), 2.66 (m, 1H), 2.17 (s, 3H), 1.79 (m, 2H), 1.45 (t, 3H), 1.22 (d, 3H), 1.95 (broad s, 2H)

IR (cm$^{-1}$): 3379, 3310, 1653

Intermediate 545:

{4-[(1R)-1-Aminoethyl]-2-methoxyphenyl}(1-ethoxyisoquinolin-5-yl)methanone $^1$H NMR (400 MHz, DMSO-d$_6$): δ 8.39 (dt, 1H), 8.05 (d, 1H), 7.74 (dd, 1H), 7.70 (dd, 1H), 7.64 (dd, 1H), 7.45 (d, 1H), 7.18 (d, 1H), 7.10 (dd, 1H), 4.55 (quad, 2H), 4.05 (quad, 1H), 3.50 (s, 3H), 1.90 (broad s, 2H), 1.46 (t, 3H), 1.29 (d, 3H)

IR (cm$^{-1}$): 3365, 3300, 1657, 1245, 1033, 810, 788

Intermediate 751:

[4-(Aminomethyl)-3,4-dihydro-2H-chromen-8-yl](1-ethoxyisoquinolin-5-yl)-methanone $^1$H NMR (400 MHz, DMSO-d$_6$): δ 8.40 (d, 1H), 8.05 (d, 1H), 7.78 (d, 1H), 7.78 (d, 1H), 7.62 (t, 1H), 7.45 (d, 1H), 7.30 (d, 1H), 6.98 (t, 1H), 4.53 (quad, 2H), 3.80 (m, 2H), 2.90-2.65 (2dd, 2H), 2.74 (m, 1H), 1.93-1.80 (2m, 2H), 1.50 (broad s, 2H), 1.48 (t, 3H)

IR (cm$^{-1}$): 3381, 1654

Intermediates 223, 265, 360, 399, 456, 515, 545 and 751 were treated in an acidic medium to yield the final products, according to the procedures described for product P17.

| Product | Obtained from | Nomenclature Analytical description |
|---|---|---|
| P3 | 20 | {4-[(1R)-1-Aminoethyl]-2-methoxyphenyl}(isoquinolin-5-yl)methanone dihydrochloride<br>$^1$H NMR (400 MHz, DMSO-d$_6$): δ 9.90 (s, 1H), 8.75 (d, 1H), 8.56 (dl, 2H), 8.05 (dd, 1H), 8.00 (t, 1H), 7.65 (d, 1H), 7.55 (d, 1H), 7.30 (dd, 1H), 4.50 (m, 1H), 3.55 (s, 3H), 1.60 (d, 3H)<br>IR (cm-1): 3300-1980, 1656<br>HRMS (ESI): theoretical m/z for C19H19N2O2 [M + H]+ 307.1447, measured 307.1472<br>Optical purity (ADH 3 μm column 4.6 × 250 mm; eluant: CH$_3$CN/isopropanol/triethylamine): 85/15/0.1; Detection: 325 nm: >99%. (absence of P119)<br>α$_D$ (589 nM) = 1.15 (c = 0.011 g/mL, MeOH) at 20° C. |
| P13 | 96 | {5-[(1R)-1-Aminoethyl]-3,4-dihydro-2H-chromen-8-yl}(isoquinolin-5-yl)methanone dihydrochloride<br>$^1$H NMR (400 MHz, DMSO-d$_6$): δ 9.80 (s, 1H), 8.70 (d, 1H), 8.60 (m, 5H), 8.05 (d, 1H), 7.90 (t, 1H), 7.50 (d, 1H), 7.30 (d, 1H), 4.55 (m, 1H), 3.80 (t, 2H), 2.80 (dd, 2H), 1.90 (m, 2H), 1.50 (d, 3H)<br>IR (cm$^{-1}$): 3000-2500, 1650<br>HRMS (ESI): theoretical m/z for C$_{21}$H$_{21}$N$_2$O$_2$ [M + H]$^+$ 333.1603, measured 333.1593 |
| P14 | 106 | [4-(1-Aminoethyl)-2-fluoro-6-methoxyphenyl]-(isoquinolin-5-yl)methanone dihydrochloride<br>$^1$H NMR (400 MHz, DMSO-d$_6$): δ 9.76 (s, 1H), 8.98 (d, 1H), 8.79 (d, 1H), 8.76 (broad s, 3H), 8.65 (d, 1H), 8.13 (d, 1H), 7.93 (t, 1H), 7.42 (s, 1H), 7.23 (d, 1H), 4.51 (quint, 1H), 3.72 (s, 3H), 1.59 (d, 1H)<br>IR (cm$^{-1}$): 3000-2500, 1673<br>HRMS (ESI): theoretical m/z for C$_{19}$H$_{18}$FN$_2$O$_2$ [M + H]$^+$ 352.1352, measured 325.1352 |
| P45 | 265 | 5-({5-[(1R)-1-Aminoethyl]-3,4-dihydro-2H-chromen-8-yl}carbonyl)isoquinolin-1(2H)-one hydrochloride<br>$^1$H NMR (400 MHz, DMSO-d$_6$): δ 11.60 (s, 1H), 8.80-8.30 (m, 3H), 8.40 (broad d, 1H), 7.65 (dd, 1H), 7.50 (t, 1H), 7.40 (d, 1H), 7.30 (2m, 2H), 7.10 (d, 1H), 4.50 (quad, 1H), 3.85 (m, 2H), 2.85-2.75 (2m, 2H), 1.90 (m, 2H), 1.50 (d, 2H)<br>IR (cm$^{-1}$): 3500-1950, 1632<br>HRMS (ESI): theoretical m/z for C$_{21}$H$_{21}$N$_2$O$_3$ [M + H]$^+$ 349.1552, measured 349.1543.<br>αD 589 nM = −19.28 (c = 0.00688 g/mL, MeOH) at 21° C. |
| P62 | 359 | 5-({5-[(1S)-1-Aminoethyl]-3,4-dihydro-2H-chromen-8-yl}carbonyl)isoquinolin-1(2H)-one hydrochloride<br>$^1$H NMR (400 MHz, DMSO-d$_6$): δ 11.50 (d, 1H), 8.48 (m, 3H), 8.41 (d, 1H), 7.66 (d, 1H), 7.51 (t, 1H), 7.38 (d, 1H), 7.27 (m, 2H), 7.09 (d, 1H), 4.54 (quad, 1H), 3.86 (t, 2H), 2.88 (m, 1H), 2.73 (m, 1H), 1.88 (m, 2H), 1.50 (d, 3H)<br>IR (cm-1): 3600-2300, 1632<br>HRMS (ESI): theoretical m/z for C21H21N2O3 [M + H]+ 349.1552, measured 349.1564<br>Optical purity (SFC: AD 3 μm column 4.6 × 250 mm; Composition: CO$_2$/(ethanol/n-butylamine: 100/0.5): 65/35; Detection: 254 nm: >99%. (absence of P45) |
| P71 | 399 | 5-[4-(2-Aminopropan-2-yl)-2-chlorobenzoyl]-4-methylisoquinolin-1(2H)-one hydrochloride<br>$^1$H NMR (400 MHz, DMSO-d$_6$): δ 11.50 (d, 1H), 8.82 (m, 3H), 8.46 (m, 1H), 7.85 (d, 1H), 7.78 (d, 1H), 7.68 (dd, 1H), 7.52 (m, 2H), 7.14 (d, 1H), 1.96 (s, 3H), 1.67 (s, 6H).<br>IR (cm$^{-1}$): 3300-2300, 1684, 1662<br>HRMS (ESI): theoretical m/z for C$_{20}$H$_{20}$ClN$_2$O$_2$ [M + H]+ 355.1213, measured 355.1212; theoretical m/z for C$_{20}$H$_{20}$ClN$_2$O$_2$ [M + H—NH3]+ 338.0948, measured 338.0934 |
| P86 | 455 | 5-[(4-Amino-3,4-dihydro-2H-chromen-8-yl)carbonyl]-isoquinolin-1(2H)-one hydrochloride<br>$^1$H NMR (400 MHz, DMSO-d$_6$): δ 11.50 (broad s, 1H), 8.61 (broad s, 3H), 8.42 (d, 1H), 7.75 (2d, 2H), 7.50 (t, 1H), 7.45 (d, 1H), 7.29 (m, 1H), 7.12 (d + t, 2H), 4.55 (t, 1H), 4.10 (m, 1H), 4.00 (m, 1H), 2.20 (m, 1H), 2.05 (m, 1H)<br>IR (cm$^{-1}$): 3100-2700, 1686, 1667, 1237, 793, 761<br>HRMS (ESI): theoretical m/z for C$_{19}$H$_{17}$N$_2$O$_3$ [M + H]+ 321.1239, measured 321.1212. |

| Product | Obtained from | Nomenclature Analytical description |
|---|---|---|
| P96 | 514 | 5-({5-[(1R)-1-Aminoethyl]-3,4-dihydro-2H-chromen-8-yl}carbonyl)-4-methylisoquinolin-1(2H)-one hydrochloride<br>$^1$H NMR (300 MHz, DMSO-d$_6$): δ 11.35 (d, 1H), 8.50 (m, 3H), 8.36 (dd, 1H), 7.60 (d, 1H), 7.48 (t, 1H), 7.37 (dd, 1H), 7.29 (d, 1H), 7.03 (m, 1H), 4.53 (m, 1H), 3.78 (m, 2H), 2.82 + 2.71 (m, 2H), 1.91 (s, 3H), 1.82 (m, 2H), 1.49 (d, 3H).<br>IR (cm$^{-1}$): 3500-2300, 3350, 1635<br>HRMS (ESI): theoretical m/z for C$_{22}$H$_{23}$N$_2$O$_3$ [M + H]+ 363.1709, measured 363.1706. |
| P103 | 544 | 5-{4-[(1R)-1-Aminoethyl]-2-methoxybenzoyl}-isoquinolin-1(2H)-one hydrochloride<br>$^1$H NMR (400 MHz, DMSO-d$_6$): δ 11.50 (broad s, 1H), 8.46 (broad s, 3H), 8.41 (d, 1H), 7.63 (d, 1H), 7.52 (d, 1H), 7.51 (t, 1H), 7.41 (broad s, 1H), 7.21 (dl, 1H), 7.27 (m, 1H), 7.03 (d, 1H), 4.47 (quad, 1H), 3.61 (s, 3H), 1.56 (d, 3H)<br>IR (cm−1): 3300-2400, 1665, 1643, 1617, 794<br>HRMS (ESI): theoretical m/z for C$_{19}$H$_{19}$N$_2$O$_3$ [M + H]+ 323.1396, measured 323.1386. |
| P119 | 641 | {4-[(1S)-1-Aminoethyl]-2-methoxyphenyl}(isoquinolin-5-yl)methanone dihydrochloride<br>$^1$H NMR (300 MHz, DMSO-d$_6$): δ 9.92 (s, 1H), 8.88 (broad s, 3H), 8.76 (dd, 1H), 8.70 (m, 2H), 8.10 (dd, 1H), 8.00 (t, 1H), 7.64 (d, 1H), 7.60 (d fine, 1H), 7.30 (dd, 1H), 4.50 (m, 1H), 3.55 (s, 3H), 1.60 (d, 3H)<br>IR (cm$^{-1}$): 3000-2000, 1656<br>HRMS (ESI): theoretical m/z for C19H19N2O2 [M + H]+ 307.1447, measured 307.1447.<br>Optical purity (ADH 3 μm column 4.6 × 250 mm; eluant: CH$_3$CN/isopropanol/triethylamine): 85/15/0.1; Detection: 325 nm: >99%. (absence of P3) |
| P136 | 736 | 5-[4-(2-Aminopropan-2-yl)-2-chlorobenzoyl]-3-methylisoquinolin-1(2H)-one hydrochloride<br>$^1$H NMR (400 MHz, DMSO-d$_6$): δ 11.66 (s, 1H), 8.80 (m, 3H), 8.43 (d, 1H), 7.81 (d, 1H), 7.69 (dd, 1H), 7.65 (d, 1H), 7.60 (d, 1H), 7.45 (t, 1H), 7.17 (broad s, 1H), 2.28 (s, 3H), 1.68 (s, 6H)<br>IR (cm$^{-1}$): 3200-2300, 1639.<br>HRMS (ESI): theoretical m/z for C20H20ClN2O2 [M + H]+ 355.1213, measured 355.1212 |
| P139 | 750 | 5-{[4-(Aminomethyl)-3,4-dihydro-2H-chromen-8-yl]-carbonyl}isoquinolin-1(2H)-one hydrochloride<br>$^1$H NMR (400 MHz, DMSO-d$_6$): δ 11.50 (s, 1H), 8.40 (d, 1H), 8.20 (m, 3H), 7.70 (d, 1H), 7.50 (t, 1H), 7.50 (d, 1H), 7.35 (d, 1H), 7.30 (dd, 1H), 7.05 (t, 1H), 7.05 (d, 1H), 3.95 (m, 2H), 3.25 (m, 1H), 3.20-3.05 (m, 2H), 2.00 (m, 2H)<br>IR (cm$^{-1}$): 3400, 3100, 2900-2800, 1647-1626<br>HRMS (ESI): theoretical m/z for C20H19N2O3 [M + H]+ 335.1396, measured 335.1400 |

Protocol XXIII: Alternative Method for the Preparation of Compounds of Formula (I) Wherein X Represents —C(=O)

Compounds of formula (I) wherein X represents —C(=O) can be prepared by aromatic electrophilic substitution reaction.

By way of example, the synthesis of intermediate 54 is described below:

Intermediate 54:

2,2,2-Trifluoro-N-{1-[3-hydroxy-4-(isoquinolin-5-ylcarbonyl)-5-methylphenyl]ethyl}-acetamide To a mixture of 53 (8.7 g, 33 mmoles) and 655 (7.6 g, 33 mmoles) in methylene chloride (700 mL) at 30° C. there is added AlCl$_3$ (8.8 g). The mixture is heated for 1 hour at 50° C. and then, after return to ambient temperature, AlCl$_3$ (8.8 g) is again added. The mixture is heated at 50° C. for 24 hours, and AlCl$_3$ (8.8 g) is again added. After heating for 24 hours at 50° C. and for two days at ambient temperature, the mixture is hydrolysed carefully on a mixture of ice and water. The product is extracted with methylene chloride, and the organic phase is dried and then concentrated in vacuo. The product is purified by chromatography on silica (eluant CH$_2$Cl$_2$AcOEt 90/1). Intermediate 54 (3.8 g) is thus obtained.

$^1$H NMR (400 MHz, DMSO-d$_6$): δ 9.50, 8.72, 8.70, 8.40, 7.90, 7.75, 6.80, 6.70, 4.97, 2.15, 1.50.

IR (cm$^{-1}$): 3331, 3000-2500, 1692-1663, 1165

Compounds 652, 656, 665 and 673 were obtained according to the same protocol.

Intermediate 652:

2,2,2-Trifluoro-N-{1-[4-(isoquinolin-5-ylcarbonyl)-3,5-dimethylphenylethyl}-acetamide Obtained by reaction of 655 with 651
$^1$H NMR (300/500 MHz, DMSO-d$_6$): δ 9.90 (broad s, 1H, NH), 9.48 (s, 1H), 8.85 (broad d, 1H), 8.72 (d, 1H), 8.45 (d, 1H), 7.82 (d, 1H), 7.75 (t, 1H), 7.15 (s, 2H), 5.03 (quad, 1H), 2.10 (s, 6H), 1.51 (d, 3H)
IR (cm$^{-1}$): 3208, 1712, 1653, 1571, 1145, 1185, 1208

Intermediate 656:

2,2,2-Trifluoro-N-{(1R)-1-[3-hydroxy-4-(isoquinolin-5-ylcarbonyl)phenyl]ethyl}-acetamide Obtained by reaction of 655 with 17
$^1$H NMR (300/500 MHz, DMSO-d$_6$): δ 9.40 (s, 1H), 8.52 (d, 1H), 8.32 (d, 1H), 7.88 (m, 2H), 7.78 (t, 1H), 7.38 (d, 1H), 6.98 (s, 1H), 6.88 (d, 1H), 5.00 (quint, 1H), 1.78 (d, 3H)
IR (cm$^{-1}$): 3295, 1707, 1629, 1147 broad Intermediate 665:

2,2,2-Trifluoro-N-{(1R)-1-[7-(isoquinolin-5-ylcarbonyl)-2,3-dihydro-1-benzofuran-4-yl]ethyl}acetamide Obtained by reaction of 655 and 664
$^1$H NMR (300 MHz, DMSO-d$_6$): δ 10.00 (NH), 9.40, 8.55, 8.30, 8.00, 7.88, 7.75, 7.45, 6.98, 5.00, 4.45, 3.20, 1.48
IR (cm$^{-1}$): 3300, 1709, 1650, 1230-1150

Intermediate 673:

2,2,2-Trifluoro-N-{1-[3-hydroxy-4-(isoquinolin-5-ylcarbonyl)-5-methoxyphenyl]-ethyl}acetamide Obtained by reaction of 655 and 672
$^1$H NMR (400 MHz, DMSO-d$_6$): δ 10.1-9.85 (m, 2H), 8.75 (d, 1H), 8.65 (d, 1H), 8.35 (t, 2H), 7.95 (d, 1H), 7.75 (t, 1H), 6.65-6.55 (2s, 2H), 4.98 (m, 1H), 3.60 (s, 3H), 1.50 (d, 3H)
IR (cm$^{-1}$): 3287, 3120-1980, 1706-1625

Intermediate 55:

2,2,2-Trifluoro-N-{1-[4-(isoquinolin-5-ylcarbonyl)-3-methoxy-5-methylphenyl]ethyl}-acetamide Obtained by reaction of methyl iodide with intermediate 54 according to the protocol described for intermediate 93 (Protocol XVII)
$^1$H NMR (300 MHz, DMSO-d$_6$): δ 9.90 (broad s, 1H), 9.40 (s, 1H), 8.80 (d, 1H), 8.70 (d, 1H), 8.40 (broad d, 1H), 7.85 (broad d, 1H), 7.75 (t, 1H), 7.00 (broad s, 1H), 6.95 (broad s, 1H), 5.05 (quad, 1H), 3.60 (s, 3H), 2.10 (s, 3H), 1.50 (d, 3H)
IR (cm$^{-1}$): 3215, 1724-1658, 1178

Intermediate 659:

N-{(1R)-1-[3-Ethyl-4-(isoquinolin-5-ylcarbonyl)phenyl]ethyl}-2,2,2-trifluoroacetamide Obtained starting from 656 according to the sequence described for obtaining 562
$^1$H NMR (300 MHz, DMSO-d$_6$): δ 9.80 (broad s, 1H, NH), 9.50 (s, 1H), 8.62 (d, 1H), 8.40 (d, 1H), 8.30 (d, 1H), 7.82 (d, 1H), 7.74 (t, 1H), 7.40 (s, 2H), 7.25 (m, 2H), 5.05 (quad., 1H), 2.70 (quad, 2H), 1.52 (d, 3H), 1.12 (t, 3H)
IR (cm$^{-1}$): 3296, 1705, 1657

Intermediate 674:

2,2,2-Trifluoro-N-{1-[4-(isoquinolin-5-ylcarbonyl)-3,5-dimethoxyphenyl]ethyl}-acetamide Obtained by reaction of methyl iodide with intermediate 673 according to the protocol described for intermediate 93 (Protocol XVII)
$^1$H NMR (400 MHz, DMSO-d$_6$): δ 9.90 (broad s, 1H, NH), 9.45 (s, 1H), 8.82 (d, 1H), 8.68 (d, 1H), 8.40 (d, 1H), 7.92 (d, 1H), 7.75 (t, 1H), 6.85 (s, 2H), 5.10 (quad., 1H), 3.65 (s, 6H), 1.52 (d, 3H)
IR (cm$^{-1}$): 3233, 1726-1664, 1118, 852, 763, 614

The ketone intermediates protected in the form of trifluoro-acetamides were deprotected in a basic medium to yield the final products, according to the example of intermediate 56.

Intermediate 56:

[4-(1-Aminoethyl)-2-methoxyphenyl](isoquinolin-5-yl)methanone

To a solution of 55 (2.67 g, 6.41 mmoles) in methanol there is added a 1N NaOH solution (46 mL), and the reaction mixture is stirred at ambient temperature until conversion is complete. The solvent is evaporated off in vacuo, the residue is taken up in water (150 mL) and extracted with methylene chloride, and the organic phase is dried and then concentrated in vacuo. The residue is chromatographed on silica gel (eluant CH$_2$Cl$_2$/EtOH/NH$_4$OH 28% (95/05/0.5)). Intermediate 56 (0.8 g) is obtained in the form of an oil.
$^1$H NMR (300 MHz, DMSO-d$_6$): δ 9.40 (s, 1H), 8.80 (d, 1H), 8.70 (d, 1H), 8.40 (dl, 1H), 7.85 (broad d, 1H), 7.70 (t, 1H), 7.00 (broad s, 1H), 6.95 (broad s, 1H), 4.00 (quad, 1H), 3.55 (s, 3H), 2.10 (s, 3H), 1.90 (m, 2H), 1.30 (d, 3H)
IR (cm$^{-1}$): 3500-3250, 1654, 1610, 1571, 834-672 The intermediates obtained are converted into hydrochlorides by treatment with a 2N HCl solution in ethyl ether.

| Product | Obtained from | Nomenclature Analytical description |
|---|---|---|
| P7 | 56 | [4-(1-Aminoethyl)-2-methoxy-6-methylphenyl]-(isoquinolin-5-yl)methanone dihydrochloride<br>$^1$H NMR (300 MHz, DMSO-d$_6$): δ 9.80 (s, 1H), 9.10 (s, 1H), 8.80 (d, 1H), 8.70 (d, 1H), 8.65 (d, 1H), 8.00 (d, 1H), 7.98 (t, 1H), 7.35 (s, 1H), 7.12 (s, 1H), 4.40 (m, 1H), 3.60 (s, 3H), 2.20 (s, 3H), 1.60 (d, 3H)<br>IR (cm$^{-1}$): 2710-2076, 1667<br>HRMS (ESI): m/z calculated for C$_{20}$H$_{20}$N$_2$O$_2$ [M + H]$^+$ 321.1603, found 321.1612 |

-continued

| Product | Obtained from | Nomenclature Analytical description |
|---|---|---|
| P121 | 652 | [4-(1-Aminoethyl)-2,6-dimethylphenyl](isoquinolin-5-yl)methanone dihydrochloride<br>$^1$H NMR (400 MHz, DMSO-$d_6$): δ 9.80 (s, 1H), 9.10 (d, 1H), 8.85 (d, 1H), 8.68 (d, 1H), 8.60 (broad s, 3H), 7.96 (d, 1H), 7.90 (t, 1H), 7.38 (s, 2H), 4.40 (m, 1H), 2.10 (s, 6H), 1.58 (d, 3H)<br>IR (cm$^{-1}$): 3000-2000, 1659, 910-832<br>HRMS (ESI): theoretical m/z for $C_{20}H_{21}N_2O$ $M^{+\cdot}$304.1576, measured 304.2 |
| P122 | 659 | {4-[(1R)-1-Aminoethyl]-2-ethylphenyl}(isoquinolin-5-yl)methanone dihydrochloride<br>$^1$H NMR (400 MHz, DMSO-$d_6$): δ 9.80 (s, 1H), 8.78 (d, 1H), 8.65 (broad s, 3H), 8.65 (m, 2H), 7.95 (m, 2H), 7.65 (s, 1H), 7.48 (dd, 1H), 7.40 (d, 1H), 4.48 (m, 1H), 2.72 (quad, 2H), 1.58 (d, 3H), 1.18 (t, 3H)<br>IR (cm$^{-1}$): 3000-2000, 1662, 918-821<br>HRMS (ESI): theoretical m/z for $C_{20}H_{21}N_2O$ $M^{+\cdot}$304.1576, measured 304.2 |
| P123 | 665 | {4-[(1R)-1-Aminoethyl]-2,3-dihydro-1-benzofuran-7-yl}(isoquinolin-5-yl)methanone dihydrochloride<br>$^1$H NMR (400 MHz, DMSO-$d_6$): δ 9.90 (s, 1H), 8.70 (2d, 2H), 8.40 (d, 1H), 8.20 (broad d, 1H), 8.00 (t, 1H), 7.60 (d, 1H), 7.30 (d, 1H), 4.40 (t and m, 3H), 3.30 (2m, 2H), 1.50 (d, 3H)<br>IR (cm$^{-1}$): 3250-2000, 1651, 1604, 833, 658<br>HRMS (ESI): theoretical m/z for $C_{20}H_{19}N_2O_2$ $[M + H]^+$ 319.1447, measured 319.1442 |
| P124 | 674 | [4-(1-Aminoethyl)-2,6-dimethoxyphenyl](isoquinolin-5-yl)methanone dihydrochloride<br>$^1$H NMR (400 MHz, DMSO-$d_6$): δ 9.80 (s, 1H), 9.10 (d, 1H), 8.80 (d, 1H), 8.65 (broad d, 1H), 8.10 (broad d, 1H), 7.95 (t, 1H), 7.10 (s, 2H), 4.45 (quint, 1H), 3.70 (s, 6H), 1.60 (d, 3H)<br>IR (cm$^{-1}$): 3340, 1970, 1673, 1607, 1582, 831, 759<br>HRMS (ESI): theoretical m/z for $C_{20}H_{21}N_2O_3$ $[M + H]^+$ 337.1552, measured 337.1566 |

Protocol XXIV: Alternative Method for the Preparation of Compounds of Formula (I) Wherein X Represents —C(═O)

Compounds of formula (I) wherein X represents —C(═O) can be prepared by reaction of boronic intermediates with carbonylated intermediates, the intermediate alcohol obtained is then oxidised to the ketone, and the protecting group of the amine function is removed.

By way of example, the synthesis of intermediate 569 is described below:

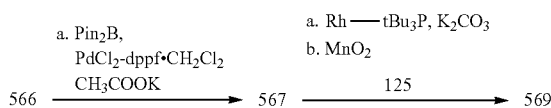

Intermediate 567:

tert-Butyl {1-[2-fluoro-3-(4,4,5,5-tetramethyl-1,3,2-dioxaborolan-2-yl)phenyl]ethyl}-carbamate To a mixture of intermediate 566 (2 g, 6.2 mmoles), potassium acetate (1.2 g) and bis(pinacolato)diborane (1.75 g, 6.9 mmoles) in 1,4-dioxane degassed with nitrogen (20 mL), there is added PdCl$_2$-dppf.CH$_2$Cl$_2$ (0.15 g, 3%). The reaction mixture is heated at reflux for 4 hours. After return to ambient temperature, the mixture is hydrolysed, and then toluene is added. After filtration, the filtrate is washed with water and a saturated aqueous NaCl solution; the organic phase is dried over MgSO$_4$ and concentrated. The residue is chromatographed on silica gel using an iPr$_2$O/cyclohexane eluant mixture (10/90 to 100/0). Intermediate 567 (1.9 g) is obtained in the form of an oil.

$^1$H NMR (400 MHz, DMSO-$d_6$): δ 7.50 (2m, 3H), 7.16 (t, 1H), 4.85 (m, 1H), 1.35 (broad s, 9H), 1.3 (s, 12H), 1.28 (d, 3H)
$^{19}$F NMR: −108.6
IR (cm$^{-1}$): 3341, 1700, 1361
GC-EI (70 eV): M+.=365.2

Intermediate 569:

tert-Butyl (1-{3-[(1-ethoxyisoquinolin-5-yl)carbonyl]-2-fluorophenyl}ethyl)carbamate Step 1:

To a mixture of intermediate 567 (1.8 g, 4.9 mmoles), intermediate 125 (0.986 g, 4.9 mmoles) and K$_2$CO$_3$ (1.36 g, 9.8 mmoles) in dioxane (18 mL) degassed with argon, there are added bis(ethylene)rhodium(I) chloride dimer (38 mg) and tri-tert-butylphosphine as a 1M solution in toluene (0.196 mL). The reaction mixture is heated for 6 hours at 60° C. and then stirred for 3 days at ambient temperature. After hydrolysis and extraction with Et$_2$O, the organic phase is washed in succession with water to pH=7 and then with a saturated aqueous NaCl solution, dried over MgSO$_4$, filtered and evaporated in vacuo. The residue is purified by flash chromatography on silica (eluant: CH$_2$Cl$_2$-THF: 95-5) to give the expected intermediate (1.1 g) in the form of a beige solid.

$^1$H NMR (400 MHz, DMSO-$d_6$): δ 8.15 (d, 1H), 7.95 (d, 1H), 7.80 (d, 1H), 7.60 (t, 1H), 7.50 (d, 1H), 7.45 (m, 1H), 7.30-7.15 (m, 1H), 7.10 (m, 1H), 6.53 (m, 1H), 6.18 (m, 1H), 4.85 (m, 1H), 4.50 (quad, 2H), 1.40 (t, 3H), 1.35 (broad s, 9H), 1.25 (d, 3H)

IR (cm$^{-1}$): 3315, 1683

Step 2:

The intermediate obtained above is oxidised in the presence of MnO$_2$ (according to protocol described above) to give intermediate 569.

$^1$H NMR (400 MHz, DMSO-d$_6$): δ 8.47 (d, 1H), 8.1 (d, 1H), 7.89 (d, 1H), 7.75-7.6 (3m, 3H), 7.6-7.5 (2m, 2H), 7.37 (t, 1H), 4.85 (m, 1H), 4.57 (quad, 2H), 1.46 (t, 3H), 1.36 (broad s, 9H), 1.26 (d, 3H)

IR (cm$^{-1}$): 3348, 1680-1661

Intermediate 587:

tert-Butyl (1-{4-[(1-ethoxyisoquinolin-5-yl)(hydroxy)methyl]-2-methoxy-3-methylphenyl}ethyl) carbamate Obtained starting from 586 and 125 according to the same protocol.

$^1$H NMR (400 MHz, DMSO-d$_6$): δ 8.15 (d, 1H), 7.95 (d, 1H), 7.61 (m, 2H), 7.36-7.29 (2 broad d, 1H), 7.34 (d, 1H), 7.14-7.11 (2d, 1H), 6.85-6.81 (m, 1H), 6.4 (s, 1H), 4.93 (m, 1H), 4.51 (quad, 2H), 3.73-3.69 (2s, 3H), 2.2 (broad s, 3H), 1.43 (t, 3H), 1.34 (broad s, 9H), 1.22-1.2 (2d, 3H)

IR (cm$^{-1}$): 3343, 1689

Intermediate 587 is oxidised in the presence of MnO$_2$ (according to protocol described above) to give intermediate 588:

Intermediate 588:

tert-Butyl (1-{4-[(1-ethoxyisoquinolin-5-yl)carbonyl]-2-methoxy-3-methylphenyl}-ethyl)carbamate $^1$H NMR (400 MHz, DMSO-d$_6$): δ 8.44 (d, 1H), 7.79 (d, 1H), 7.67 (t, 1H), 8.10 (d, 1H), 7.74 (d, 1H), 7.50 (broad d, 1H), 7.29 (d, 1H), 7.07 (d, 1H), 5.0 (m, 1H), 4.58 (quad, 2H), 3.80 (s, 3H), 2.27 (s, 3H), 1.46 (t, 3H), 1.36 (s, 9H), 1.27 (d, 3H)

IR (cm$^{-1}$): 3352, 1708, 1660

The ketone intermediates obtained by protocol XXIV were deprotected in an acidic medium to yield the final product, according to the procedures described for products P17 and P110 when they are protected in the form of tert-butyl-carbamates.

| Product | Obtained from | Nomenclature Analytical description |
|---|---|---|
| P108 | 569 | 5-[3-(1-Aminoethyl)-2-fluorobenzoyl]isoquinolin-1(2H)-one hydrochloride<br>$^1$H NMR (400 MHz, DMSO-d$_6$): δ 11.57 (d, 1H), 8.80-8.40 (m, 3H), 8.47 (d, 1H), 7.96 (td, 1H), 7.81 (d, 1H), 7.66 (td, 1H), 7.56 (t, 1H), 7.47 (t, 1H), 7.31 (dd, 1H), 6.98 (d, 1H), 4.62 (m, 1H), 1.54 (d, 3H)<br>IR (cm$^{-1}$): 3300-2000, 1663, 1615<br>HRMS (ESI): theoretical m/z for C$_{18}$H$_{16}$FN$_2$O$_2$ [M + H]$^+$ 311.1190, measured 311.1184.<br>Optical purity (SFC: ID 3 μM column 4.6 × 250 mm; eluant: CO$_2$/(isopropanol/diethylamine: 100/0.5): 70/30; detection: 253 nm): >99%.<br>(absence of P100) |
| P109 | 588 | 5-[4-(1-Aminoethyl)-3-methoxy-2-methylbenzoyl]-isoquinolin-1(2H)-one hydrochloride<br>$^1$H NMR (400 MHz, DMSO-d$_6$): δ 11.58 (d, 1H), 8.51 (m, 3H), 8.46 (d, 1H), 7.66 (d, 1H), 7.55 (t, 1H), 7.55 (d, 1H), 7.32 (dd, 1H), 7.19 (d, 1H), 7.05 (d, 1H), 4.66 (quad, 1H), 3.79 (s, 3H), 2.25 (s, 3H), 1.53 (d, 3H)<br>IR (cm$^{-1}$): 3400-2300, 1681, 1650<br>HRMS (ESI): theoretical m/z for C$_{20}$H$_{21}$N$_2$O$_3$ [M + H]$^+$ 337.1547, measured 337.1541.<br>theoretical m/z for C$_{20}$H$_{18}$NO$_3$ [M + H—NH$_3$]$^+$ 320.1281, measured 320.1277.<br>m/z measured for C$_{20}$H$_{19}$N$_2$O$_3$ [M − H]$^-$ 335.30. |

Protocol XXV: Preparation of Compounds of Formula (I) Wherein X Represents —CH(OH)—

Compounds of formula (I) wherein X represents —CH(OH)— can be synthesised according to protocol XX, without the final oxidation step.

Intermediate 147 was prepared starting from intermediate 3 and intermediate 145 according to the procedure described for obtaining product P17.

Intermediate 147:

tert-Butyl [(1R)-1-{3,5-difluoro-4-[hydroxy(isoquinolin-5-yl)methyl]phenyl}ethyl]-carbamate $^1$H NMR (300 MHz, DMSO-d$_6$): 9.30 (s, 1H), 8.45 (d, 1H), 8.20 (d, 1H), 8.05 (broad d, 1H), 7.75 (t, 1H), 7.65 (broad d, 1H), 7.40 (broad d, 1H), 6.95 (d, 1H), 6.60 (d, 1H), 6.40 (d, 1H), 4.60 (quint, 1H), 1.35 (s, 9H), 1.20 (d, 3H)

Intermediate 147 (1.44 g) was chromatographed by high pressure chromatography on a chiral support (ChiralCell OJ column, eluant: n-propyl alcohol/heptane/diethylamine 10/90/0.1, detection 270 nm) to give the two optical antipodes 148 (0.6 g) and 149 (0.53 g).

Intermediate 148:

Optical purity (OJ-H column, eluant: n-propyl alcohol/heptane/diethylamine 10/90/0.1, detection 270 nm): >99%.

Intermediate 149:

Optical purity (OJ-H column, eluant: n-propyl alcohol/heptane/diethylamine 10/90/0.1, detection 270 nm): 98%.

To a solution of intermediate 149 (0.5 g) in methylene chloride (30 mL) there is added in the course of 10 minutes TFA (1.7 mL). The reaction mixture is stirred at ambient temperature for 20 h before being concentrated in vacuo. The residue is taken up in water and treated with 20% sodium hydroxide and extracted with methylene chloride, and the organic phase is dried over MgSO$_4$. Evaporation under reduced pressure yields intermediate 150 (0.25 g).
Intermediate 150:

{4-[(1R)-1-Aminoethyl]-2,6-difluorophenyl}(isoquinolin-5-yl)methanol, enantiomer 1

Optical purity (capillary electrophoresis: standard CE, NaH$_2$PO$_4$ 0.05M, pH2.5—H$_3$PO$_4$cc/HS ca-cyclodextrin, detection 233 nm): 99%.

Intermediate 148, treated according to the protocol described for intermediate 150, yielded intermediate 692:
Intermediate 692:

{4-[(1R)-1-Aminoethyl]-2,6-difluorophenyl}(isoquinolin-5-yl)methanol, enantiomer 2

Optical purity (capillary electrophoresis: standard CE, NaH$_2$PO$_4$ 0.05M, pH2.5—H$_3$PO$_4$cc/HS α-cyclodextrin, detection 233 nm): >99%.

Intermediate 151 was prepared starting from intermediate 3 and intermediate 146 according to the procedure described for obtaining product P17.
Intermediate 151:

tert-Butyl [(1S)-1-{3,5-difluoro-4-[hydroxy(isoquinolin-5-yl)methyl]phenyl}ethyl]-carbamate $^1$H NMR (300 MHz, DMSO-d$_6$): 9.30 (s, 1H), 8.45 (d, 1H), 8.20 (d, 1H), 8.05 (broad d, 1H), 7.75 (t, 1H), 7.65 (broad d, 1H), 7.40 (broad d, 1H), 6.95 (d, 1H), 6.60 (d, 1H), 6.40 (d, 1H), 4.60 (quint, 1H), 1.35 (s, 9H), 1.20 (d, 3H)

Intermediate 151 (1.2 g) was chromatographed by high pressure chromatography on a chiral support (ChiralCell OJ column, eluant: n-propyl alcohol/heptane/diethylamine 10/100/0.1, detection 270 nm) to give the two optical antipodes 152 (0.42 g) and 153 (0.59 g).

Intermediate 152:

Optical purity (OJ-H column, eluant: ethanol/heptane/diethylamine 70/30/0.1 to 5/95/0.1, detection 275 nm): >98%

Intermediate 153:

Optical purity (OJ-H column, eluant: ethanol/heptane/diethylamine 70/30/0.1 to 5/95/0.1, detection 275 nm): >99%.

Intermediate 153, treated according to the protocol described for intermediate 150, yielded intermediate 154 (0.25 g).

Intermediate 154:

{4-[(1S)-1-Aminoethyl]-2,6-difluorophenyl}(isoquinolin-5-yl)methanol, enantiomer 1

Optical purity (capillary electrophoresis: standard CE, NaH$_2$PO$_4$ 0.05M, pH2.5—H$_3$PO$_4$cc/HS α-cyclodextrin, detection 233 nm): >99%.

Intermediates 150, 154 and 692 are converted into hydrochlorides by treatment with a 2N solution of HCl in ethyl ether:

| Product | Obtained from | Nomenclature Analytical description |
|---|---|---|
| P20 | 150 | {4-[(1R)-1-Aminoethyl]-2,6-difluorophenyl}-(isoquinolin-5-yl)methanol dihydrochloride, enantiomer 1<br>$^1$H NMR (400 MHz, DMSO-d$_6$): δ 9.82 (s, 1H), 8.73 (m, 3H), 8.66 (d, 1H), 8.45 (m, 2H), 8.14 (d, 1H), 8.04 (t, 1H), 7.35 (d, 2H), 6.75 (s, 1H), 4.40 (m, 1H), 1.48 (d, 3H).<br>IR (cm$^{-1}$): 3231<br>HRMS (ESI): theoretical m/z for C$_{18}$H$_{17}$F$_2$N$_2$O [M + H]$^+$ 315.1309, measured 315.1294.<br>Optical purity (capillary electrophoresis: standard CE, NaH$_2$PO$_4$ 0.05M, pH 2.5 —H$_3$PO$_4$cc/HS α-cyclodextrin, detection 233 nm): 99%. |
| P21 | 154 | {4-[(1S)-1-Aminoethyl]-2,6-difluorophenyl}-(isoquinolin-5-yl)methanol dihydrochloride, enantiomer 1<br>$^1$H NMR (400 MHz, DMSO-d$_6$): δ 9.78 (s, 1H), 8.68 (broad s, 3H), 8.65 (d, 1H), 8.44-8.41 (2d, 2H), 8.10 (d, 1H), 8.02 (t, 1H), 7.34 (d, 2H), 6.75 (s, 1H), 4.40 (m, 1H), 1.47 (d, 3H)<br>IR (cm$^{-1}$): 3300-1900<br>HRMS (ESI): theoretical m/z for C$_{18}$H$_{17}$F$_2$N$_2$O [M + H]$^+$ 315.1309, measured 315.1297.<br>Optical purity (capillary electrophoresis: standard CE, NaH$_2$PO$_4$ 0.05M, pH 2.5 —H$_3$PO$_4$cc/HS α-cyclodextrin, detection 233 nm): 99%. |
| P127 | 692 | {4-[(1R)-1-Aminoethyl]-2,6-difluorophenyl}-(isoquinolin-5-yl)methanol dihydrochloride, enantiomer 2<br>$^1$H NMR (400 MHz, DMSO-d$_6$): δ 9.82 (s, 1H), 8.73 (m, 3H), 8.66 (d, 1H), 8.45 (m, 2H), 8.14 (d, 1H), 8.04 (t, 1H), 7.35 (d, 2H), 6.75 (s, 1H), 4.40 (m, 1H), 1.48 (d, 3H)<br>IR (cm$^{-1}$): 3231, 3200-2300<br>HRMS (ESI): theoretical m/z for C$_{18}$H$_{17}$F$_2$N$_2$O [M + H]$^+$ 315.1309, measured 315.1309.<br>Optical purity (capillary electrophoresis: standard CE, |

| Product | Obtained from | Nomenclature Analytical description |
|---|---|---|
| | | NaH$_2$PO$_4$ 0.05M, pH 2.5 —H$_3$PO$_4$cc/HS α-cyclodextrin, detection 233 nm): 99%. |

Protocol XXVI: Preparation of Compounds of Formula (I) Wherein X Represents —CH$_2$—

Compounds of formula (I) wherein X represents —CH$_2$— can be synthesised according to the procedures described below:

By way of example, the synthesis of intermediate 144 (1-[3,5-difluoro-4-(isoquinolin-5-ylmethyl) phenyl] ethanamine):

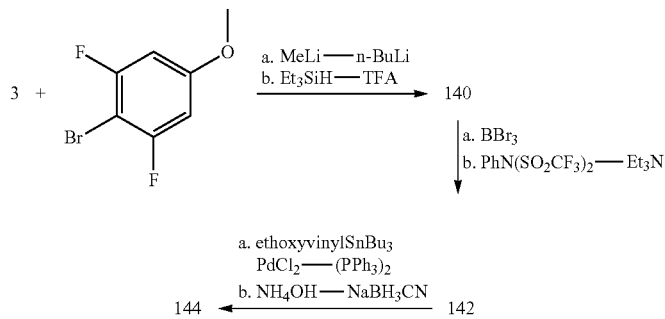

Intermediate 140:

(5-(2,6-Difluoro-4-methoxybenzyl)isoquinoline)

Step 1:

To a solution of commercial 4-bromo-3,5-difluoroanisole (25 g, 112 mmoles) in anhydrous THF (44 mL) cooled to −70° C. there is added a 2.5 N solution of n-BuLi in cyclohexane (44 mL, 110 mmoles) in the course of 35 minutes. The resulting mixture is stirred at −70° C. for 35 minutes, and then a solution (17 g, 108 mmoles) of intermediate 3 in THF (300 mL) is added, the temperature being maintained below −70° C. The reaction mixture is stirred for one hour at −70° C. and then hydrolysed with water. The organic phase is extracted with Et$_2$O, dried over MgSO$_4$, filtered and evaporated in vacuo. The residue is purified on Lichroprep RP18 40-60 (CH$_3$CN/H$_2$O/TFA 95/5/0.1). The expected intermediate (15.7 g) is obtained in the form of a white solid.

$^1$H NMR (300 MHz, DMSO-d$_6$): δ 9.60 (s, 1H), 8.55 (dd, 1H), 8.35 (m, 1H), 8.25 (m, 1H), 7.85-7.95 (2m, 2H), 6.65-6.75 (d, 2H), 6.60 (s, 1H), 3.75 (s, 3H), 6.0-8.0 (m, 1H)

IR (cm$^{-1}$): 3248, 1050-1200, 1705, 1666

Step 2:

The intermediate obtained above (850 mg, 2.82 mmoles) dissolved in trifluoroacetic acid (35 mL) is treated with triethylsilane (4.5 mL, 28.2 mmoles) at ambient temperature. The resulting mixture is heated for 1 hour at 70° C. The reaction mixture is poured into a mixture of water and ice, and then a 40% aqueous sodium hydroxide solution is added. The organic phase is extracted with ethyl acetate and washed with water, dried over MgSO$_4$, filtered and evaporated in vacuo. The residue obtained is purified by flash chromatography on silica (eluant: CH$_2$Cl$_2$/AcOEt, gradient 100-0 to 70-30). Intermediate 140 (400 mg) is obtained in the form of a white solid.

$^1$H NMR (300 MHz, DMSO-d$_6$): δ 9.30 (s, 1H), 8.60 (d, 1H), 8.10 (d, 1H), 8.00 (d, 1H), 7.60 (t, 1H), 7.30 (d, 1H), 6.80 (d, 2H), 4.35 (s, 2H), 3.80 (s, 3H)

IR (cm$^{-1}$): 1138

Intermediate 142:

3,5-Difluoro-4-(isoquinolin-5-ylmethyl)phenyl trifluoromethanesulphonate

Step 1:

To a solution of intermediate 140 (8 g, 20 mmoles) in methylene chloride (160 mL) cooled to −70° C. there is added a 1N BBr$_3$/CH$_2$Cl$_2$ solution (48 mL, 48 mmoles). The reaction mixture is stirred for 2 days at ambient temperature. The reaction mixture is cooled to −70° C. and treated with 50 mL of methanol in the course of 20 minutes and is then returned to ambient temperature and then concentrated in vacuo. The residue is heated at reflux in 160 mL of methanol for 1/2 h and is then concentrated in vacuo. The expected intermediate (6.9 g) is obtained in the form of its hydrobromide.

$^1$H NMR (300 MHz, DMSO-d$_6$): δ 10.35 (broad s, 1H), 9.80 (s, 1H), 8.77 (d, 1H), 8.60 (d, 1H), 8.35 (d, 1H), 7.89 (t, 1H), 7.69 (d, 1H), 6.54 (d, 2H), 4.41 (s, 2H)

IR (cm$^{-1}$): 1647-1633, 2500-3100

Step 2:

To a solution of the intermediate obtained above (500 mg, 1.8 mmoles) and triethylamine (1.8 g, 18 mmoles) in 35 mL of methylene chloride cooled to −78° C. there is added N-phenyl-bistrifluoromethanesulphonimide (1 g, 2.8 mmoles) in the course of one minute. The reaction mixture is stirred for 1 hour at −78° C. and a further 1 mL of Et$_3$N is added. After stirring for 1 hour at −78° C., the reaction mixture is hydrolysed at −78° C. by addition of water. The organic phase is washed with a saturated aqueous NaCl solution, dried over MgSO$_4$, filtered and evaporated in vacuo. The residue is purified by flash chromatography on silica (eluant CH$_2$Cl$_2$—AcOEt: 100-0 to 80-20). There are obtained 230 mg of intermediate 142 in the form of an oil.

¹H NMR (300 MHz, DMSO-d₆): δ 9.40 (s, 1H), 8.60 (d, 1H), 8.05 (m, 2H), 7.65 (m, 3H), 7.35 (m, 1H), 4.50 (s, 2H)
IR (cm⁻¹): 1427-1138, 1210

Intermediate 144:

1-[3,5-Difluoro-4-(isoquinolin-5-ylmethyl)phenyl]ethanamine

Step 1:

To a solution, degassed with nitrogen, of intermediate 142 (500 mg, 1.23 mmoles) in DMF (5 mL) there are added 60 mg (0.22 mmole) of triphenylphosphine, 15 mg (0.066 mmole) of Pd(OAc)₂, 160 mg (3.77 mmoles) of LiCl and 530 mg (1.46 mmoles) of (1-ethoxy-vinyl)-tributyltin. The mixture is heated at 70° C. for 5 hours and then stirred overnight at ambient temperature. The mixture is treated with a 1N aqueous HCl solution and stirred at ambient temperature and is then rendered basic with a 28% NH₄OH solution. The organic phase is extracted with AcOEt and washed with an aqueous NaCl solution, dried over MgSO₄, filtered and evaporated to dryness. The residue is purified by flash chromatography on silica (eluant: CH₂Cl₂—AcOEt gradient: 100-0 to 90-10). The expected intermediate (150 mg) is obtained.

¹H NMR (300 MHz, DMSO-d₆): δ 9.35 (s, 1H), 8.60 (d, 1H), 8.10 (d, 1H), 8.05 (d, 1H), 7.70 (d, 2H), 7.60 (t, 1H), 7.35 (d, 1H), 4.50 (s, 2H), 2.60 (s, 3H)
IR (cm⁻¹): 1685, 1620, 1579, 1315, 860-831-761

Step 2:

To a solution of the intermediate obtained above (650 mg, 2.18 mmoles) in 13 mL of methanol there are added ammonium acetate (2.4 g, 31 mmoles) and then 4 Å powdered molecular sieve. After 20 minutes, sodium cyanoborohydride (120 mg, 1.9 mmoles) is added. The reaction mixture is stirred overnight at ambient temperature. The solution is filtered to remove the molecular sieve, and then the filtrate is evaporated in vacuo. The residue is treated with 20% HCl to which ethyl acetate is added. The aqueous phase is decanted, rendered basic by addition of 20% NaOH and extracted twice with methylene chloride. The organic phase is then dried over MgSO₄, filtered and evaporated in vacuo. The residue is purified by flash chromatography on silica (eluant: CH₂Cl₂-EtOH gradient: 97-3 to 90-10). Intermediate 144 (260 mg) is obtained in the form of an oil.

¹H NMR (300 MHz, DMSO-d₆): δ 9.40 (s, 1H), 8.60 (d, 1H), 8.10 (d, 1H), 8.00 (d, 1H), 7.60 (t, 1H), 7.35 (d, 1H), 7.15 (d, 2H), 4.45 (s, 2H), 3.95 (quad., 1H), 1.25 (d, 3H), 1.95 (m, 2H)
IR (cm⁻¹): 1309, 3200-3400

Intermediate 530:

N-[(1R)-1-{4-[(1-Ethoxyisoquinolin-5-yl)methyl]-3-methoxyphenyl}ethyl]-2,2,2-trifluoroacetamide Obtained by dehydroxylation (according to the conditions described for intermediate 140) of alcohol 677, prepared by coupling of 676 and 3

¹H NMR (300 MHz, DMSO-d₆): δ 9.2 (s, 1H), 8.1 (d, 1H), 8.00 (d, 1H), 7.55 (m, 1H), 7.5 (m, 1H), 7.4 (d, 1H), 7.05 (s, 1H), 6.8 (m, 2H), 5.0 (m, 1H), 4.5 (quad., 2H), 4.25 (s, 2H), 3.85 (s, 3H), 1.45 (m, 6H)
19F NMR: −73

Intermediate 678:

2,2,2-Trifluoro-N-{1-[3-fluoro-4-(isoquinolin-5-ylmethyl)phenyl]ethyl}acetamide

Obtained by dehydroxylation (according to the conditions described for intermediate 140) of alcohol 543, prepared by coupling of 18 and 124

¹H NMR (300 MHz, DMSO-d₆): δ 9.80 (d, 1H), 9.30 (s, 1H), 8.50 (d, 1H), 8.00 (broad d, 1H), 7.95 (d, 1H), 7.60 (t, 1H), 7.55 (dd, 1H), 7.20 (dd, 1H), 7.15 (t, 1H), 7.05 (dd, 1H), 5.0 (quint., 1H), 4.40 (s, 2H), 1.40 (d, 3H)
IR (cm⁻¹): 3430, 3050, 1703, 1555

The ketone intermediates protected in the form of trifluoro-acetamides were deprotected in a basic medium to yield the final products, according to the example of intermediate 56. The intermediates obtained are converted into hydrochlorides by treatment with a 2N HCl solution in ethyl ether.

| Product | Obtained from | Nomenclature Analytical description |
|---|---|---|
| P19 | 144 | 1-[3,5-Difluoro-4-(isoquinolin-5-ylmethyl)phenyl]-ethanamine dihydrochloride<br>¹H NMR (400 MHz, DMSO-d₆): δ 9.90 (s, 1H), 8.80 (m, 3H), 8.80 (d, 1H), 8.35 (d, 1H), 7.90 (t, 1H), 7.70 (d, 1H), 7.45 (d, 2H), 4.60 (s, 2H), 4.45 (m, 1H), 1.55 (d, 3H)<br>IR (cm⁻¹): 3000-2500<br>HRMS (ESI): theoretical m/z for C₁₈H₁₇F₂N₂ [M + H]⁺ 299.1360, measured 299.1368 |
| P101 | 530 | 5-{4-[(1R)-1-Aminoethyl]-2-methoxybenzyl}-isoquinolin-1(2H)-one hydrochloride<br>¹H NMR (400 MHz, DMSO-d₆): δ 11.29 (m, 1H), 8.38 (broad s, 3H), 8.11 (broad d, 1H), 7.44 (broad d, 1H), 7.40 (t, 1H), 7.28 (broad s, 1H), 7.16 (m, 1H), 6.94 (broad d, 1H), 6.88 (d, 1H), 6.56 (d, 1H), 4.34 (quad, 1H), 4.15 (s, 2H), 3.86 (s, 3H), 1.50 (d, 3H)<br>IR (cm⁻¹): 3300-2400, 3173, 1641, 1263, 1036, 782<br>HRMS (ESI): theoretical m/z for C₁₉H₂₁N₂O₂ [M + H]⁺ 309.1603, measured 309.1614. |
| P125 | 678 | 1-[3-Fluoro-4-(isoquinolin-5-ylmethyl)phenyl]-ethanamine dihydrochloride<br>¹H NMR (400 MHz, DMSO-d₆): δ 9.80 (s, 1H), 8.70 (s, 1H), 8.62 (broad s, 3H), 8.48 (d, 1H), 8.40 (dd, 1H), 7.90 (m, 2H), 7.48 (d, 1H), 7.28 (m, 2H), 4.58 (s, 2H), 4.38 (m, 1H), 1.50 (d, 3H)<br>IR (cm⁻¹): 2552-2505, 2083-1984-1855, 1645-1609, 877-839-815<br>HRMS (ESI): theoretical m/z for C₁₈H₁₈FN₂ [M + H]⁺ 281.1454, measured 281.1466 |

Protocol XXVII

When Ry$_3$ represents:
- a group —C(=O)—CHRy$_4$-NHRy$_5$ wherein Ry$_4$ represents a hydrogen atom or a (C$_1$-C$_6$)alkyl group and Ry$_5$ represents a hydrogen atom or a methyl group, or
- a —(C$_1$-C$_6$)alkyl group which can be substituted by a hydroxyl group, or
- a —O(C$_1$-C$_3$)alkyl group, or
- a cyclohexyl group, or
- a methylsulphonyl group, the following protocols were used.

The final products were prepared starting from intermediates or final products described above:

Intermediate 418:

(1-Amino-4,6-difluoro-2,3-dihydro-1H-inden-5-yl)(1-ethoxyisoquinolin-5-yl)methanone To a solution of intermediate 417 (2.6 g, 5.5 mmoles) in methylene chloride (20 mL) there is added trifluoroacetic acid (2 times 2.07 mL). The mixture is stirred at ambient temperature for 18 h and is then diluted with CH$_2$Cl$_2$ and treated with 1N sodium hydroxide. The organic phase is washed with water and then dried over MgSO$_4$ and concentrated in vacuo. Intermediate 418 (2 g) so obtained is used in the following step without additional purification.

$^1$H NMR (400 MHz, DMSO-d$_6$): δ 8.50 (d, 1H), 8.20 (2d, 2H), 8.00 (d, 1H), 7.70 (t, 1H), 7.25 (d, 1H), 4.60 (quad, 2H), 4.30 (t and s, 1H), 2.90 (m, 1H), 2.70 (m, 1H), 2.45 (m, 1H), 2.30 (m, 2H), 1.75 (m, 1H), 1.45 (t, 3H)

IR (cm$^{-1}$): 3390, 1667, 1633, 1567, 814-757

Intermediate 421:

[4-(2-Aminopropan-2-yl)-2,6-difluorophenyl](1-ethoxyisoquinolin-5-yl)methanone

Obtained starting from 172 according to protocol XXVII $^1$H NMR (400 MHz, DMSO-d$_6$): δ 8.50 (d, 1H), 8.2-8.1 (dd, 2H), 8.00 (dd, 1H), 7.75 (dd, 1H), 7.45 (d, 1H), 4.55 (quad, 2H), 2.05 (m, 1H), 2.70 (m, 2H), 1.45 (t, 3H), 1.40 (s, 6H)

IR (cm$^{-1}$): 3371, 3302, 1668

Intermediate 426:

(1-Amino-4,6-difluoro-2,3-dihydro-1H-inden-5-yl)(1-ethoxyisoquinolin-5-yl)-methanone Obtained starting from 425 according to protocol XXVII $^1$H NMR (400 MHz, DMSO-d$_6$): δ 8.50 (d, 1H), 8.20 (2d, 2H), 8.00 (d, 1H), 7.70 (t, 1H), 7.25 (d, 1H), 4.60 (quad, 2H), 4.30 (t and s, 1H), 2.90 (m, 2H), 2.70 (m, 1H), 2.45 (m, 1H), 2.30 (m, 2H), 1.75 (m, 1H), 1.45 (t, 3H)

IR (cm$^{-1}$): 3390, 1666, 1633, 1567, 814-757

Intermediate 435:

{4-[(1S)-1-Aminoethyl]-2,6-difluorophenyl}(1-ethoxyisoquinolin-5-yl)methanone

Obtained starting from 165 according to protocol XXVII $^1$H NMR (400 MHz, DMSO-d$_6$): δ 8.55 (d, 1H), 8.20 (d, 1H), 8.15 (d, 1H), 8.00 (d, 1H), 7.70 (t, 1H), 7.30 (d, 2H), 4.60 (quad, 2H), 4.05 (quad, 1H), 2.05 (m, 2H), 1.45 (t, 3H), 1.30 (d, 3H)

IR (cm$^{-1}$): 3380, 3317, 1669, 1633

Intermediate 468:

{4-[(1R)-1-Aminoethyl]-2,6-difluorophenyl}(1-ethoxyisoquinolin-5-yl)methanone

Obtained starting from 170 according to protocol XXVII $^1$H NMR (400 MHz, DMSO-d$_6$): δ 8.55 (d, 1H), 8.20 (d, 1H), 8.15 (d, 1H), 8.02 (d, 1H), 7.72 (t, 1H), 7.30 (d, 2H), 4.60 (quad, 2H), 4.05 (quad, 1H), 2.02 (m, 2H), 1.45 (t, 3H), 1.30 (d, 3H)

IR (cm$^{-1}$): 3381, 3314, 1670

Intermediate 752:

[4-(1-Aminoethyl)-2,6-difluorophenyl](1-ethoxyisoquinolin-5-yl)methanone

Obtained starting from 127 according to protocol XXVII $^1$H NMR (400 MHz, DMSO-d$_6$): δ 8.54 (broad d, 1H), 8.19 (d, 1H), 8.13 (broad d, 1H), 8.02 (broad d, 1H), 7.72 (dd, 1H), 7.31 (m, 2H), 4.57 (quad, 2H), 4.06 (quad, 1H), 2.01 (broad s, 2H), 1.46 (t, 3H), 1.30 (d, 3H)

IR (cm$^{-1}$): 3375-3310, 1671

LCMS [M+H]+=356

The amines obtained were converted into amide intermediates according to the following protocols:

Intermediate 419:

tert-Butyl [2-({5-[(1-ethoxyisoquinolin-5-yl)carbonyl]-4,6-difluoro-2,3-dihydro-1H-inden-1-yl}amino)-2-oxoethyl]carbamate To a solution of 418 (0.8 g, 2.1 mmoles) in CH$_3$CN (16 mL) there are added in succession 1-hydroxybenzotriazole (0.03 g, 0.1 eq.), N,N'-dicyclohexylcarbodiimide (0.71 g), N-tert-butoxy-carbonyl-glycine (0.38 g). The mixture is stirred at ambient temperature for 3 days.

The precipitate is filtered off and washed with CH$_3$CN, and the filtrate is concentrated in vacuo. The residue is chromatographed on silica gel using a CH$_2$Cl$_2$/AcOEt eluant: 80/20 to 60/40. Intermediate 419 (1.16 g) is obtained in the form of an amorphous solid.

$^1$H NMR (300 MHz, DMSO-d$_6$): δ 8.55 (d, 1H), 8.35 (d, 1H), 8.20 (2d, 2H), 8.0 (d, 1H), 7.70 (t, 1H), 7.10 (d, 1H), 7.00 (t, 1H), 5.40 (quad, 1H), 4.60 (quad, 2H), 3.60 (d, 2H), 3.0 (m, 1H), 2.80 (m, 1H), 2.45 (m, 1H), 2.00 (m, 1H), 1.50 (t, 3H), 1.40 (m, 9H)

IR (cm$^{-1}$): 3350, 1720, 1667, 1586

Intermediate 427:

tert-Butyl [2-({5-[(1-ethoxyisoquinolin-5-yl)carbonyl]-4,6-difluoro-2,3-dihydro-1H-inden-1-yl}amino)-2-oxoethyl]carbamate Obtained according to the same protocol starting from 426

$^1$H NMR (400 MHz, DMSO-d$_6$): δ 8.55 (d, 1H), 8.35 (d, 1H), 8.20 (2d, 2H), 8.0 (d, 1H), 7.70 (t, 1H), 7.10 (d, 1H), 7.00 (t, 1H), 5.40 (quad, 1H), 4.60 (quad, 2H), 3.60 (d, 2H), 3.0 (m, 1H), 2.80 (m, 1H), 2.45 (m, 1H), 2.00 (m, 1H), 1.50 (t, 3H), 1.40 (m, 9H)

IR (cm$^{-1}$): 3350, 1720, 1667, 1586

Intermediate 765:

tert-Butyl (2-{[(1R)-1-{4-[(1-ethoxyisoquinolin-5-yl)carbonyl]-3,5-difluorophenyl}-ethyl]amino}-2-oxoethyl)carbamate To a solution of 468 (1 g, 2.8 mmoles) in CH$_2$Cl$_2$ (20 mL) there are added in succession 1-hydroxybenzotriazole (0.37 g, 2.8 mmoles), 1-[3-(dimethylamino)propyl]-3-ethylcarbodiimide hydrochloride (0.59 g, 2.8 mmoles), N-tert-butoxy-carbonyl-glycine (0.49 g, 2.8 mmoles) and Et$_3$N (0.78 mL, 5.6 mmoles). The mixture is stirred at ambient temperature for 1 h. The mixture is diluted with methylene chloride and washed with 1N sodium hydroxide, 1N HCl and water. The organic phase is dried over MgSO$_4$ and then concentrated in vacuo. Product 765 (1.1 g) is obtained in the form of a white solid.

$^1$H NMR (300 MHz, DMSO-d$_6$): δ 8.55 (d, 1H), 8.35 (d, 1H), 8.2 (dd, 2H), 8.15 (d, 1H), 8.02 (d, 1H), 7.70 (d, 1H), 7.25 (d, 2H), 7.0 (t, 1H), 5.02 (quint, 1H), 4.55 (quad, 2H), 3.58 (dd, 2H), 1.48 (t, 3H), 1.45 (d, 3H), 1.4 (s, 9H)

IR (cm$^{-1}$): 3304, 1714, 1675, 1654

Intermediate 436:

tert-Butyl (2-{[(1S)-1-{4-[(1-ethoxyisoquinolin-5-yl)carbonyl]-3,5-difluorophenyl}-ethyl]amino}-2-oxoethyl)carbamate Obtained according to the same protocol starting from 435

$^1$H NMR (400 MHz, DMSO-d$_6$): δ 8.55 (d, 1H), 8.35 (d, 1H), 8.2-8.1 (dd, 2H), 8.05 (dd, 1H), 7.70 (dd, 1H), 7.25 (d, 2H), 5.00 (m, 1H), 4.55 (quad, 2H), 3.65-3.5 (m, 2H), 1.45 (t, 3H), 1.40 (d, 3H), 1.35 (s, 9H)

IR (cm$^{-1}$): 3311, 1717, 1672, 1637

Intermediate 742:

tert-Butyl {2-[(2-{4-[(1-ethoxyisoquinolin-5-yl)carbonyl]-3,5-difluorophenyl}propan-2-yl)amino]-2-oxoethyl}carbamate Obtained according to the same protocol starting from 421

$^1$H NMR (400 MHz, DMSO-d$_6$): δ 8.55 (m, 1H), 8.20 (d, 1H), 8.15 (d, 1H), 8.00 (d, 1H), 7.75 (dd, 1H), 7.25 (d, 2H), 4.55 (quad, 2H), 3.55 (d, 2H), 1.60 (s, 6H), 1.45 (t, 3H), 1.35 (s, 9H)

IR (cm$^{-1}$): 3500-3200, 1667

Intermediates 419, 427, 468, 436, 742 obtained were deprotected in an acidic medium to yield the final products, according to the procedure described for product P17.

The amides were also obtained by reaction according to the following protocols:

Intermediate 224:

tert-Butyl {2-[(1-{3,5-difluoro-4-[(1-oxo-1,2-dihydroisoquinolin-5-yl)carbonyl]-phenyl}ethyl)amino]-2-oxoethyl}carbamate To a solution, at −10° C., of N-tert-butoxy-carbonyl-glycine (0.48 g, 2.8 mmoles), Et$_3$N (0.38 mL, 2.7 mmoles) in THF (5 mL) treated with ethyl chloroformate (0.26 mL, 2.7 mmoles) there is added slowly a solution of P17 (1 g, 2.7 mmoles) and Et$_3$N (0.42 mL, 3 mmoles) in a DMF/THF mixture (13 mL/7.6 mL). The mixture is stirred at ambient temperature for 20 h. The reaction mixture is poured into water and extracted with AcOEt, dried and then concentrated. The residue is chromatographed on silica gel via a solid deposit using a CH$_2$Cl$_2$/EtOH eluant: 97/3. Product 224 (0.46 g) is obtained.

$^1$H NMR (400 MHz, DMSO-d$_6$): δ 11.62 (m, 1H), 8.51 (d, 1H), 8.36 (d, 1H), 7.90 (d, 1H), 7.57 (t, 1H), 7.37 (m, 2H), 7.24 (m, 2H), 6.97 (t, 1H), 4.99 (quint, 1H), 3.58 (d, 1H), 1.38 (broad s, 12H)

IR (cm$^{-1}$): 3305

LCMS [M+H]+=485

Intermediate 320:

tert-Butyl {(2S,3S)-1-[(1-{3,5-difluoro-4-[(1-oxo-1,2-dihydroisoquinolin-5-yl)-carbonyl]phenyl}ethyl)amino]-3-methyl-1-oxopentan-2-yl}carbamate Obtained according to the same protocol starting from P17 using N-tert-butoxy-carbonyl-(L)-isoleucine. Intermediate 320 was converted directly into P55 by treatment according to the protocol described for P17.

Intermediate 392:

tert-Butyl {2-[(1-{3,5-difluoro-4-[(1-oxo-1,2-dihydroisoquinolin-5-yl)carbonyl]-phenyl}ethyl)amino]-2-oxoethyl}methylcarbamate Obtained according to the same protocol starting from P17 using methyl-N-tert-butoxy-carbonyl-glycine $^1$H NMR (300 MHz, DMSO-d$_6$): δ 11.32 (m, 1H), 8.52 (d, 1H), 8.15 (broad d, 1H), 7.87 (d, 1H), 7.55 (t, 1H), 7.32 (dd, 2H), 7.21 (d, 2H), 5.03 (m, 1H), 3.83 (dd, 1H), 2.85 (s, 3H), 1.44 (d, 3H), 1.38 (s, 9H)

IR (cm$^{-1}$): 3303, 3200-2500, 1699, 1672, 1660, 1632

Intermediate 420:

tert-Butyl (2-{[(1S)-1-{3-methyl-4-[(1-oxo-1,2-dihydroisoquinolin-5-yl)carbonyl]-phenyl}ethyl]amino}-2-oxoethyl)carbamate Obtained according to the same protocol starting from P53 using N-tert-butoxy-carbonyl-glycine $^1$H NMR (400 MHz, DMSO-d$_6$): δ 11.50 (m, 1H), 8.40 (d, 1H), 8.35 (d, 1H), 7.65 (dd, 1H), 7.50 (t, 1H), 7.30 (d, 1H), 7.25 (d, 1H), 7.20 (m, 2H), 6.90 (t, 1H), 6.75 (d, 1H), 4.95 (m, 1H), 3.60 (d, 2H), 1.40 (s, 3H), 1.35 (m, 12H)

IR (cm$^{-1}$): 3600-2500, 1695, 1633, 1505

LCMS [M+H]+=463

The intermediates so obtained were deprotected in an acidic medium to yield the final products, according to the procedure described for product P110 when they are protected in the form of tert-butyl-carbamates.

The amines obtained were converted into alkyl intermediates according to the following protocols:

Intermediate 469:

{2,6-Difluoro-4-[(1R)-1-{[2-(tetrahydro-2H-pyran-2-yloxy)ethyl]amino}ethyl]phenyl}-(1-ethoxyisoquinolin-5-yl)methanone

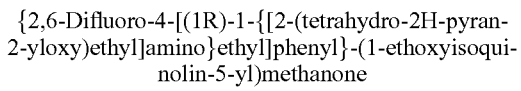

To a solution of 468 (1 g, 2.8 mmoles) in DMF (10 mL) there are added $K_2CO_3$ (1.2 g, 8.4 mmoles) and 2-(2-bromoethoxy)-tetrahydro-2H-pyran (0.46 mL, 3.08 mmoles). The mixture is heated at 80° C. for 20 h. The solvent is evaporated off in vacuo, the residue is taken up in water and extracted with methylene chloride, and the organic phase is dried over $MgSO_4$ and then concentrated in vacuo. The residue is chromatographed on silica gel using a $CH_2Cl_2$/EtOH eluant: 98-2. Product 469 (0.59 g) is obtained in the form of an oil.

$^1$H NMR (400 MHz, DMSO-$d_6$): δ 8.55 (d, 1H), 8.20 (d, 1H), 8.15 (d, 1H), 8.05 (d, 1H), 7.72 (d, 1H), 7.30 (d, 2H), 4.58 (quad and m, 3H), 3.85 (quad, 1H), 3.75-3.45 (2m, 2H), 3.68-3.45 (2m, 2H), 2.65-2.5 (m, 2H), 2.30 (m, 1H), 1.75-1.65 (2m, 2H), 1.50 (t and m, 7H), 1.30 (d, 3H)

IR (cm$^{-1}$): 3333, 1674

Intermediate 437:

{2,6-Difluoro-4-[(1S)-1-{[2-(tetrahydro-2H-pyran-2-yloxy)ethyl]amino}ethyl]phenyl}-(1-ethoxyisoquinolin-5-yl)methanone

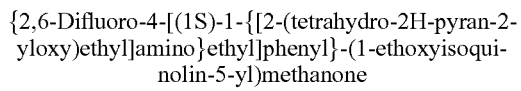

Obtained according to the same protocol starting from intermediate 435

$^1$H NMR (400 MHz, DMSO-$d_6$): δ 8.55 (d, 1H), 8.20 (d, 1H), 8.15 (d, 1H), 8.05 (d, 1H), 7.72 (d, 1H), 7.30 (d, 2H), 4.58 (quad and m, 3H), 3.85 (quad, 1H), 3.75-3.45 (2m, 2H), 3.68-3.45 (2m, 2H), 2.65-2.5 (m, 2H), 2.30 (m, 1H), 1.75-1.65 (2m, 2H), 1.50 (t and m, 7H), 1.30 (d, 3H)

IR (cm$^{-1}$): 3328, 1671

Intermediate 285:

[2,6-Difluoro-4-(1-{[2-(tetrahydro-2H-pyran-2-yloxy)ethyl]amino}ethyl)phenyl](1-ethoxyisoquinolin-5-yl)methanone

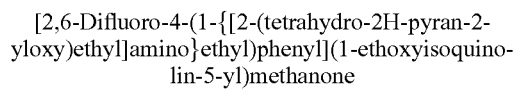

This procedure was also used to prepare intermediate 285, racemic mixture of intermediates 469 and 437.

Intermediate 422:

[2,6-Difluoro-4-(2-{[2-(tetrahydro-2H-pyran-2-yloxy)ethyl]amino}propan-2-yl)-phenyl](1-ethoxyisoquinolin-5-yl)methanone

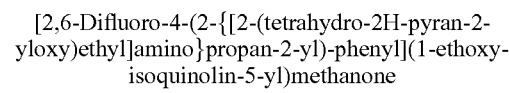

Obtained according to the same protocol starting from 421

$^1$H NMR (400 MHz, DMSO-$d_6$): δ 8.55 (d, 1H), 8.20 (d, 1H), 8.15 (d, 1H), 8.05 (d, 1H), 7.72 (t, 1H), 7.35 (d, 2H), 4.57 (quad and m, 3H), 3.75-3.45 (2m, 2H), 3.65-3.45 (2m, 2H), 2.48 (m, 2H), 2.30 (m, 1H), 1.8-1.4 (m, 4H), 1.6-1.45 (2m, 2H), 1.50 (t, 3H), 1.4 (s, 6H)

Intermediate 516:

(2,6-Difluoro-4-{(1R)-1-[(2-methoxyethyl)amino]ethyl}phenyl)(1-ethoxyisoquinolin-5-yl)methanone

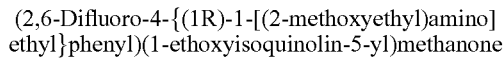

To a solution of 468 (1 g, 2.8 mmoles) in DMF (15 mL) there are added $Et_3N$ (1.18 mL, 8.4 mmoles) and 2-bromoethyl methyl ether (0.29 mL, 3.1 mmoles). The mixture is heated at 70° C. for 4 days. The mixture is decanted in the presence of water and of methylene chloride, and the organic phase is washed with water and then with a saturated NaCl solution. After drying over $MgSO_4$ and concentration in vacuo, the residue is chromatographed on silica gel using a $CH_2Cl_2$/AcOEt eluant: 50/50. Product 516 (0.46 g) is obtained in the form of an oil.

$^1$H NMR (400 MHz, DMSO-$d_6$): δ 8.55 (d, 1H), 8.20 (d, 1H), 8.15 (d, 1H), 8.05 (d, 1H), 7.75 (m, 1H), 7.30 (m, 2H), 4.6 (quad, 2H), 3.85 (m, 1H), 3.4 (t, 2H), 3.25 (s, 3H), 2.55 (m, 2H), 2.25 (s, 1H), 1.45 (t, 3H), 1.30 (d, 3H)

IR (cm$^{-1}$): 3325

LCMS [M+H]+=414

Optical purity (OJ-H column, eluant: methanol/diethylamine 100/0.1, detection 254 nm): >98.8%.

Intermediate 517:

(2,6-Difluoro-4-{(1S)-1-[(2-methoxyethyl)amino]ethyl}phenyl)(1-ethoxyisoquinolin-5-yl)methanone

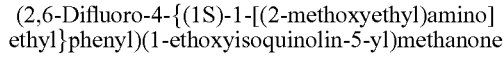

Obtained according to the same protocol starting from 435

$^1$H NMR (400 MHz, DMSO-$d_6$): δ 8.55 (d, 1H), 8.20 (d, 1H), 8.15 (d, 1H), 8.05 (d, 1H), 7.75 (m, 1H), 7.30 (m, 2H), 4.6 (quad, 2H), 3.85 (m, 1H), 3.4 (t, 2H), 3.25 (s, 3H), 2.55 (m, 2H), 2.25 (s, 1H), 1.45 (t, 3H), 1.30 (d, 3H)

IR (cm$^{-1}$): 3325

LCMS [M+H]+=414

Optical purity (OJ-H column, eluant: methanol/diethylamine 100/0.1, detection 254 nm): >99%.

Intermediate 753:

[2,6-Difluoro-4-(1-{[2-(methylsulphonyl)ethyl]amino}ethyl)phenyl](1-ethoxyisoquinolin-5-yl)methanone

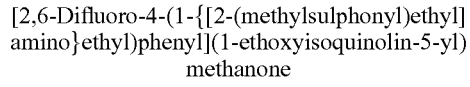

To a solution of 752 (0.7 g, 2.09 mmoles) in 1,4-dioxane (7.5 mL) there are added diisopropyl-ethyl-amine (0.47 mL, 3.3 mmoles) and methyl-vinyl-sulphone (1.09 mL, 1.2 mmoles). The mixture is heated at 90° C. for 8 days. The mixture is decanted in the presence of water and of methylene chloride, and the organic phase is washed with a saturated $NH_4Cl$ solution and then with a saturated $Na_2CO_3$ solution. After drying over $MgSO_4$ and concentration in vacuo, the residue is chromatographed on silica gel using a $CH_2Cl_2$/EtOH eluant: 100/0 to 95/5. Product 753 (0.46 g) is obtained in the form of an oil.

$^1$H NMR (400 MHz, DMSO-$d_6$): δ 8.53 (d, 1H), 8.20 (d, 1H), 8.12 (d, 1H), 8.06 (d, 1H), 7.72 (t, 1H), 7.30 (d, 2H), 4.58 (quad, 2H), 3.88 (quad, 1H), 3.23 (quad, 2H), 3.03 (s, 3H), 2.78 (t, 2H), 1.47 (t, 3H), 1.29 (d, 3H)

IR (cm$^{-1}$): 3339, 1671, 1371, 1119

Intermediates 422, 437, 469, 516, 517, 753 obtained were deprotected in an acidic medium to yield the final products, according to the procedure described for product P17.

| Product | Obtained from | Nomenclature Analytical description |
|---------|---------------|---------------------------------------|
| P38 | P17 | N-(1-{3,5-Difluoro-4-[(1-oxo-1,2-dihydroisoquinolin-5-yl)carbonyl]phenyl}ethyl)glycinamide hydrochloride |

| Product | Obtained from | Nomenclature Analytical description |
|---|---|---|
| | | $^1$H NMR (400 MHz, DMSO-d$_6$): δ 10.70 (m, 1H), 9.20 (d, 1H), 8.55 (d, 1H), 8.20 (m, 3H), 7.90 (d, 1H), 7.60 (t, 1H), 7.40 (m, 2H), 7.35 (m, 2H), 5.05 (m, 1H), 3.70 (m, 2H), 1.45 (d, 3H)<br>IR (cm$^{-1}$): 3100-3000, 3000-2800, 1672<br>HRMS (ESI): theoretical m/z for C$_{20}$H$_{18}$F$_2$N$_3$O$_3$ [M + H]$^+$ 386.1316, measured 386.1315 |
| P48 | 285 | 5-(2,6-Difluoro-4-{1-[(2-hydroxyethyl)amino]ethyl}-benzoyl)isoquinolin-1(2H)-one hydrochloride<br>$^1$H NMR (400 MHz, DMSO-d$_6$): δ 11.70-11.60 (s, 1H), 10.0-9.0 (2m, 2H), 8.55 (m, 1H), 8.00 (m, 1H), 7.77-7.55 (m, 3H), 7.40 (m, 2H), 5.5-5.0 (m, 1H), 4.55 (m, 1H), 3.70 (m, 2H), 2.95-2.80 (2m, 2H)<br>IR (cm$^{-1}$): 3350, 2844-2400, 1687-1674, 1633<br>HRMS (ESI): theoretical m/z for C$_{19}$H$_{19}$F$_2$N$_2$O$_3$ [M + H]$^+$ 373.1364, measured 373.1362 |
| P54 | P17 | N-(1-{3,5-Difluoro-4-[(1-oxo-1,2-dihydroisoquinolin-5-yl)carbonyl]phenyl}ethyl)-L-isoleucinamide hydrochloride<br>$^1$H NMR (400 MHz, DMSO-d$_6$): δ 11.65 (broad s, 1H), 9.25 (2d, 1H), 8.55 (d, 1H), 8.12 (unresolved peak, 3H), 7.90 (2d, 1H), 7.60 (2t, 1H), 5.10 (quint, 1H), 3.72 (m, 1H), 1.90 (m, 1H), 1.60-1.05 (m, 3H), 0.95-0.85 (m, 6H)<br>IR (cm$^{-1}$): 3600-2300, 1689, 1661, 1630<br>HRMS (ESI): theoretical m/z for C$_{24}$H$_{26}$F$_2$N$_3$O$_3$ [M + H]$^+$ 442.194223, measured 442.1939 |
| P69 | P17 | N-(1-{3,5-Difluoro-4-[(1-oxo-1,2-dihydroisoquinolin-5-yl)carbonyl]phenyl}ethyl)-N$^2$-methylglycinamide hydrochloride<br>$^1$H NMR (400 MHz, DMSO-d$_6$): δ 11.70 (s, 1H), 9.15 (d, 1H), 8.80 (m, 2H), 8.52 (d, 1H), 7.90 (d, 1H), 7.60 (t, 1H), 7.40 (m, 2H), 7.30 (d, 2H), 5.05 (quint, 1H), 3.80 (AB, 2H), 2.60 (s, 3H), 1,45 (d, 3H)<br>IR (cm$^{-1}$): 3700-2000, 1689, 1672, 1632<br>HRMS (ESI): theoretical m/z for C$_{21}$H$_{20}$F$_2$N$_3$O$_3$ [M + H]$^+$ 400.1473, measured 400.1456 |
| P76 | 419 | N-{4,6-Difluoro-5-[(1-oxo-1,2-dihydroisoquinolin-5-yl)carbonyl]-2,3-dihydro-1H-inden-1-yl}glycinamide hydrochloride<br>$^1$H NMR (300 MHz, DMSO-d$_6$): δ 11.60 (m, 1H), 8.90 (d, 1H), 8.50 (dd, 1H), 8.00 (m, 3H), 7.90 (d, 1H), 7.60 (t, 1H), 7.40 (m, 2H), 7.15 (d, 1H), 5.40 (quad, 1H), 3.65 (2d, 2H), 3 (m, 1H), 2.85 (m, 1H), 2.55 (m, 1H), 2.00 (m, 1H)<br>IR (cm$^{-1}$): 3300-2300, 3289, 1652, 1628, 1544<br>HRMS (ESI): theoretical m/z for C$_{21}$H$_{18}$F$_2$N$_3$O$_3$ [M + H]$^+$ 398.1316, found 398.1304.<br>Optical purity (SFC: AD 5 μM column 4.6 × 250 mm; eluant: CO$_2$/(methanol/butylamine: 100/0.5): 65/35; detection: 255 nm): >99%.<br>(absence of P79) |
| P77 | P53 | N-[(1S)-1-{3-Methyl-4-[(1-oxo-1,2-dihydroisoquinolin-5-yl)carbonyl]phenyl}ethyl]glycinamide hydrochloride<br>$^1$H NMR (400 MHz, DMSO-d$_6$): δ 11.50 (m, 1H), 9.00 (d, 1H), 8.45 (d, 1H), 8.10 (m, 3H), 7.65 (dd, 1H), 7.55 (t, 1H), 7.40 (d, 1H), 7.30 (m, 2H), 7.30 (m, 1H), 6.80 (d, 1H), 5.00 (quint, 1H), 3.60 (s, 2H), 2.40 (s, 3H), 1.40 (d, 3H)<br>IR (cm$^{-1}$): 3650-2080, 1675-1660, 1600, 1557, 832-688<br>HRMS (ESI): theoretical m/z for C$_{21}$H$_{22}$N$_3$O$_3$ [M + H]$^+$ 364.1661, measured 364.1648 |
| P78 | 422 | 5-(2,6-Difluoro-4-{2-[(2-hydroxyethyl)amino]propan-2-yl}benzoyl)isoquinolin-1(2H)-one hydrochloride<br>$^1$H NMR (400 MHz, DMSO-d$_6$): δ 11.70 (broad s, 1H), 9.80-9.30 (m, 2H), 8.55 (m, 1H), 8.00 (m, 1H), 7.65 (d, 2H), 7.60 (t, 1H), 7.40 (m, 2H), 5.25 (t, 1H), 3.65 (quad, 2H), 2.75 (m, 2H), 1.80 (broad s, 6H)<br>IR (cm$^{-1}$): 3500-2000, 1660, 1627<br>HRMS (ESI): theoretical m/z for C$_{21}$H$_{21}$F$_2$N$_2$O$_3$ [M + H]$^+$ 387.1520, measured 387.1517. |
| P79 | 427 | N-{4,6-Difluoro-5-[(1-oxo-1,2-dihydroisoquinolin-5-yl)carbonyl]-2,3-dihydro-1H-inden-1-yl}glycinamide hydrochloride<br>$^1$H NMR (400 MHz, DMSO-d$_6$): δ 11.60 (m, 1H), 9.10 (d, 1H), 8.50 (dd, 1H), 8.20 (m, 3H), 7.90 (d, 1H), 7.60 (t, 1H), 7.40 (m, 2H), 7.15 (d, 1H), 5.40 (quad, 1H), 3.65 (2d, 2H), 3.00 (m, 1H), 2.85 (m, 1H), 2.55 (m, 1H), 2.00 (m, 1H)<br>IR (cm$^{-1}$): 3300-2300, 3289, 1652, 1628, 1544 |

-continued

| Product | Obtained from | Nomenclature Analytical description |
|---|---|---|
| | | HRMS (ESI): theoretical m/z for $C_{21}H_{18}F_2N_3O_3$ $[M + H]^+$ 398.1316, measured 398.1334.<br>Optical purity (SFC: AD 5 μM column 4.6 × 250 mm; eluant: $CO_2$/(methanol/butylamine: 100/0.5): 65/35; detection: 255 nm): >99%. (absence of P76) |
| P83 | 436 | N-[(1S)-1-{3,5-Difluoro-4-[(1-oxo-1,2-dihydroisoquinolin-5-yl)carbonyl]phenyl}ethyl]-glycinamide hydrochloride<br>$^1$H NMR (400 MHz, DMSO-$d_6$): δ 11.65 (broad s, 1H), 9.10 (d, 1H), 8.50 (dd, 1H), 8.30-7.90 (broad s, 3H), 7.90 (dd, 1H), 7.55 (t, 1H), 7.35 (dd, 2H), 7.30 (d, 2H), 5.05 (m, 1H), 3.65 (m, 2H), 1.45 (d, 3H)<br>IR (cm$^{-1}$): 3318, 3200-2500, 1692, 1674<br>HRMS (ESI): theoretical m/z for $C_{20}H_{18}F_2N_3O_3$ $[M + H]^+$ 386.1316, measured 386.1300.<br>$α_D$ (589 nM) = −59.93 (c = 1, DMSO) at 20° C. |
| P84 | 437 | 5-(2,6-Difluoro-4-{(1S)-1-[(2-hydroxyethyl)amino]-ethyl}benzoyl)isoquinolin-1(2H)-one hydrochloride<br>$^1$H NMR (400 MHz, DMSO-$d_6$): δ 11.70 (d, 1H), 8.53 (d, 1H), 7.99 (d, 1H), 7.60 (m, 3H), 7.41 (m, 2H), 5.24 (t, 1H), 4.53 (q, 1H), 3.69 (m, 2H), 2.95 (m, 1H), 2.80 (m, 1H), 1.63 (d, 3H)<br>IR (cm$^{-1}$): 3500-3200, 3200-2200, 1685, 1620<br>HRMS (ESI): theoretical m/z for $C_{20}H_{19}F_2N_2O_3$ $[M + H]^+$ 373.1364, measured 373.1350.<br>$α_D$ (589 nM) = −1.7 (c = 0.01, DMSO) at 20° C. |
| P89 | 469 | 5-(2,6-Difluoro-4-{(1R)-1-[(2-hydroxyethyl)amino]-ethyl}benzoyl)isoquinolin-1(2H)-one hydrochloride<br>$^1$H NMR (400 MHz, DMSO-$d_6$): δ 11.80 (broad s, 1H), 10.80-10.30 (2 broad s, 2H), 8.52 (d, 1H), 8.00 (d, 1H), 7.60 (d + t, 3H), 7.40 (d, 2H), 5.25 (t, 1H), 4.50 (m, 1H), 3.70 (m, 2H), 2.95-2.70 (m, 2H), 1.65 (d, 3H)<br>IR (cm$^{-1}$): 3500-2700, 3200-2700, 1685-1672<br>HRMS (ESI): theoretical m/z for $C_{20}H_{19}F_2N_2O_3$ $[M + H]^+$ 373.1364, measured 373.1348.<br>$α_D$ (589 nM) = 1.29 (c = 1, DMSO) at 20° C. |
| P97 | 468 | 5-(2,6-Difluoro-4-{(1R)-1-[(2-methoxyethyl)amino]-ethyl}benzoyl)isoquinolin-1(2H)-one hydrochloride<br>$^1$H NMR (400 MHz, DMSO-$d_6$): δ 11.66 (m, 1H), 9.67-9.38 (2m, 2H), 8.54 (dd, 1H), 7.98 (broad d, 1H), 7.58 (t, 1H), 7.56 (d, 2H), 7.42 (m, 2H), 4.50 (m, 1H), 3.60 (m, 2H), 3.30 (s, 3H), 3.05-2.90 (2m, 2H), 1.62 (d, 3H)<br>IR (cm$^{-1}$): 3500-2000, 1671, 1630<br>HRMS (ESI): theoretical m/z for $C_{21}H_{21}F_2N_2O_3$ $[M + H]^+$ 387.1520, measured 387.1524.<br>Optical purity (SFC: OZ-H 5 μM column 4.6 × 250 mm; eluant: $CO_2$/(methanol/diethylamine: 100/0.5): 73/27; detection: 254 nm): 98.7%. |
| P98 | 495 | 5-(2,6-Difluoro-4-{(1S)-1-[(2-methoxyethyl)amino]-ethyl}benzoyl)isoquinolin-1(2H)-one hydrochloride<br>$^1$H NMR (400 MHz, DMSO-$d_6$): δ 11.68 (m, 1H), 9.90-9.56 (2m, 2H), 8.54 (dd, 1H), 7.99 (broad d, 1H), 7.61 (d, 2H), 7.57 (t, 1H), 7.42 (m, 2H), 4.51 (m, 1H), 3.63 (m, 2H), 3.30 (s, 3H), 3.05-2.90 (2m, 2H), 1.64 (d, 3H)<br>IR (cm$^{-1}$): 3500-2000, 1693, 1662, 1627<br>HRMS (ESI): theoretical m/z for $C_{21}H_{21}F_2N_2O_3$ $[M + H]^+$ 387.1520, measured 387.1524.<br>Optical purity (SFC: OZ-H 5 μM column 4.6 × 250 mm; eluant: $CO_2$/(methanol/diethylamine: 100/0.5): 73/27; detection: 254 nm): >99%. (absence of P97) |
| P138 | 742 | N-(2-{3,5-Difluoro-4-[(1-oxo-1,2-dihydroisoquinolin-5-yl)carbonyl]phenyl}propan-2-yl)glycinamide hydrochloride<br>$^1$H NMR (400 MHz, DMSO-$d_6$): δ 11.90-11.50 (m, 1H), 8.85 (m, 1H), 8.50 (dd, 1H), 8.20-7.85 (m, 3H), 7.90 (dd, 1H), 7.60 (dd, 1H), 7.40 (m, 2H), 7.25 (d, 2H), 3.65 (s, 2H), 1.65 (s, 6H)<br>IR (cm$^{-1}$): 3600-2000, 3303, 1672, 1628<br>HRMS (ESI): theoretical m/z for $C_{21}H_{20}F_2N_3O_3$ $[M + H]^+$ 400.1473, measured 400.14518 |
| P140 | 753 | 5-[2,6-Difluoro-4-(1-{[2-(methylsulphonyl)ethyl]-amino}ethyl)benzoyl]isoquinolin-1(2H)-one hydrochloride<br>$^1$H NMR (400 MHz, DMSO-$d_6$): δ 10.70 (m, 1H), 10.50-10.00 (m, 2H), 8.55 (d, 1H), 7.95 (d, 1H), 7.65 (d, 2H), |

-continued

| Product | Obtained from | Nomenclature Analytical description |
|---------|---------------|-------------------------------------|
|         |               | 7.60 (t, 1H), 7.40 (m, 2H), 4.60 (m, 1H), 3.65 (m, 2H), 3.40-3.10 (m, 2H), 3.15 (s, 3H), 1.65 (d, 3H) $^{19}$F NMR: −111.7 IR (cm$^{-1}$): 3100, 2800-2600, 1674-1634, 1276-1139 HRMS (ESI): theoretical m/z for $C_{21}H_{21}F_2N_2O_4S$ [M + H]$^+$ 435.1190, measured 435.1152. |
| P142    | 765           | N-[(1R)-1-{3,5-Difluoro-4-[(1-oxo-1,2-dihydroiso-quinolin-5-yl)carbonyl]phenyl}ethyl]glycinamide hydrochloride $^1$H NMR (400 MHz, DMSO-d$_6$): δ 12.0-11.5 (m, 1H), 9.0 (d, 1H), 8.50 (dd, 1H), 7.90 (dd, 1H), 8.2-7.8 (m, 3H), 7.55 (t, 1H), 7.35 (dd, 2H), 7.30 (d, 2H), 5.05 (m, 1H), 3.65 (m, 2H), 1.45 (d, 3H) IR (cm$^{-1}$): 3307, 3300-2000, 1691, 1673 HRMS (ESI): theoretical m/z for $C_{20}H_{18}F_2N_3O_3$ [M + H]$^+$ 386.1316, measured 386.1300. $α_D$ (589 nM) = +62.5 (c = 1, DMSO) at 20° C. |

Pharmacological Studies

ROCK1 Enzymatic Test

Evaluation of the effects of compounds on human ROCK1 activity quantified by measuring the phosphorylation of the substrate Ulight-RRRSLLE (PLK) using a human recombinant enzyme and the LANCE® detection method.

Experimental Protocol

The test compound, the reference compound or water (control) is mixed with the enzyme (8.2 ng) in a buffer comprising 40 mM Hepes/Tris (pH 7.4), 0.8 mM EGTA/Tris, 8 mM MgCl$_2$, 1.6 mM DTT and 0.008% Tween 20.

The reaction is then started by adding 50 nM of Ulight-RRRSLLE (PLK) substrate and 1 µM of ATP, and the mixture is incubated for 30 minutes at ambient temperature. For the basal control measurements, the enzyme is excluded from the reaction mixture.

After the incubation, the reaction is stopped by adding 13 mM of EDTA. After 5 minutes, the anti-phospho-PLK antibody labelled with europium chelate is added. After a further 60 minutes, the fluorescence transfer is measured at lex=337 nm, lem=620 nm and lem=665 nm using a microplate reader (Envision, Perkin Elmer). The enzymatic activity is determined by dividing the signal measured at 665 nm by that measured at 620 nm (ratio). The results are expressed in the form of a percentage inhibition of the control enzymatic activity. The standard reference inhibition compound is staurosporine, which is tested in each experiment at several concentrations in order to obtain an inhibition curve on the basis of which the value of the IC$_{50}$ (concentration that induces 50% inhibition) is calculated.

BIBLIOGRAPHICAL REFERENCE

Doe, C., Bentley, R., Behm, D. J., Lafferty, R., Stavenger, R., Jung, D., Bamford, M., Panchal, T., Grygielko, E., Wright, L. L., Smith, G. K., Chen, Z., Webb, C., Khandekar, S., YI, T., Kirkpatrick, R., Dul, E., Jolivette, L., Marino, J. P. JR., Willette, R., Lee, D. and Hu, E. (2007), Novel Rho kinase inhibitors with anti-inflammatory and vasodilatory activities. J. Pharmacol. Exp. Ther., 320: 89.

| Compound of formula (I) | ROCK1(h), IC$_{50}$ (M) |
|-------------------------|--------------------------|
| P9                      | 5.87E−09                 |
| P17                     | 4.20E−09                 |
| P19                     | 6.30E−08                 |
| P24                     | 2.30E−08                 |
| P27                     | 8.70E−09                 |
| P42                     | 9.60E−09                 |
| P45                     | 5.00E−09                 |
| P47                     | 6.78E−09                 |
| P48                     | 7.45E−09                 |
| P50                     | 5.40E−09                 |
| P56                     | 1.65E−08                 |
| P58                     | 3.85E−09                 |
| P59                     | 1.95E−09                 |
| P61                     | 5.35E−09                 |
| P75                     | 1.04E−08                 |
| P129                    | 2.05E−08                 |
| P139                    | 8.75E−08                 |

Functional Test (Rat Aorta)

Study of Vascular Reactivity on Aortic Segments of the Rat.

After anaesthesia of the animal, the thoracic aorta is removed and immediately placed in a physiological saline solution (PSS). The proximal thoracic aorta is cleaned of adherent conjunctive tissue and 4 aortic rings (3-4 mm) are cut. The endothelium is removed mechanically without damaging the smooth muscle cells.

The rings without endothelium are placed in PSS medium in isolated organ baths maintained at 37° C. in the presence of carbogen. The isometric tension of the rings is recorded by means of a force sensor. At their optimum tension, the rings are subjected to an equilibration period during which the physiological medium is replaced regularly. The preparations are then contracted twice by means of a hyperpotassic solution (KCl 60 mM), each of the 2 contractions being followed by successive washings in order to return to the original tension. The absence of endothelium is verified after contraction by an al-adrenergic receptor agonist, phenylephrine (PHE, 10$^{-6}$M), followed by the addition of carbachol (10$^{-5}$M), a muscarinic receptor agonist, which induces a relaxation only in the presence of endothelium. The rings are then washed regularly with PSS for 60 minutes in order to remove the pharmacological agents.

The rings are recontracted with PHE (10$^{-6}$M) and then, after stabilisation of the contraction, the product or its solvent is added in cumulative concentrations, 5 concentrations are tested: 10M$^{-8}$, 10$^{-7}$M, 10$^{-6}$M, 10M$^{-5}$ and 3×10$^-$ 5M (if the product is dissolved in DMSO) or $10^{-4}$M (if $H_2O$ is the solvent of the product).

Analysis of the Results

The contractile response is obtained in milligrams (mg). The results are expressed by the mean±SEM of the contractile responses obtained on at least 2 rats. The variations in tension of each product are calculated as a percentage of the maximum contraction induced by PHE before the product is added, according to the formula:

% contraction $B(t)=[\times(mg)$ tension(compound)$B(t)/y$ (mg) maximum tension (PHE)$B]\times100$.

The concentration-response curves obtained are analysed and allow the $IC_{50}$ value of each product to be determined ($IC_{50}$: concentration of product necessary to inhibit 50% of the maximum contraction induced by PHE), the estimation of the $IC_{50}$ value of the concentration-response curves being obtained by non-linear regression.

| Compound of formula (I) | Relaxation (rat aorta + PHE), $IC_{50}$ (M) |
|---|---|
| P6 | 2.00E−07 |
| P9 | 3.30E−08 |
| P17 | 1.40E−08 |
| P19 | 2.30E−07 |
| P21 | 1.00E−06 |
| P24 | 1.00E−08 |
| P27 | 5.00E−08 |
| P42 | 2.00E−07 |
| P45 | 1.00E−07 |
| P47 | 4.00E−08 |
| P48 | 1.50E−07 |
| P50 | 1.00E−07 |
| P56 | 1.50E−07 |
| P58 | 7.00E−08 |
| P59 | 5.50E−07 |
| P61 | 1.70E−07 |
| P75 | 2.00E−07 |
| P129 | 2.00E−06 |
| P139 | 2.00E−06 |

Evaluation on the Arterial Pressure (SHR Rats)

The effect of the ROCK inhibitors was tested by the reduction of the arterial pressure (AP) that they induce in spontaneously hypertensive rats (SHR) after intravenous (i.v.) and/or oral administration. In summary, the SHRs were anaesthetised with 2% isoflurane, and a telemetry probe (PAC40, Data Science International) was implanted in the abdominal aorta to record the AP and a polyethylene catheter was implanted in the jugular vein for the i.v. administration.

After recovery from the surgery (2 to 3 weeks), the AP was recorded continuously for 24 hours after administration of the ROCK inhibitors at doses of 1, 3, 10 and 30 mg/kg by the i.v. route and/or by the oral route. The effect on the AP was expressed as the percentage reduction relative to the basal arterial pressure before administration of the product.

| Compound of formula (I) | SHR rat ΔAP % max, IV 3 mg/kg | SHR rat ΔAP % max, PO 3 mg/kg |
|---|---|---|
| P6 | −73.4 | −35.6 |
| P9 | −67 | −53.7 |
| P17 | −72.8 | −56.6 |
| P19 | −39.6 | — |
| P24 | −68.2 | −52.5 |
| P27 | −69 | −54 |
| P42 | −59.9 | −12.3 |
| P45 | −60.6 | −24 |
| P47 | −62.7 | −26.4 |
| P48 | −67.3 | −29.2 |
| P50 | −58 | −16.8 |
| P56 | −54.7 | — |
| P58 | −65.1 | −52.7 |
| P59 | −40.3 | — |
| P61 | −59 | — |
| P75 | −49.8 | −12.4 |
| P129 | −30.2 | −18.4 |

Pharmaceutical Compositions

Tablets obtained by wet granulation

| Constituents | Quantity % |
|---|---|
| Compound of formula (I) | 10 |
| Normal lactose powder | qs 100 |
| Maize starch | 20 |
| PVP K30 | 7 |
| Carboxymethyl potato starch, weakly cross-linked sodium salt | 3 |
| Colloidal silica | 0.2 |
| Magnesium stearate | 0.5 |

Tablets obtained by direct compression

| Constituents | Quantity % |
|---|---|
| Compound of formula (I) | 10 |
| Agglomerated lactose | qs 100 |
| Microcrystalline cellulose | 25 |
| Carboxymethyl potato starch, weakly cross-linked sodium salt | 3 |
| Colloidal silica | 0.2 |
| Magnesium stearate | 0.5 |

The invention claimed is:

1. A compound of formula (I):

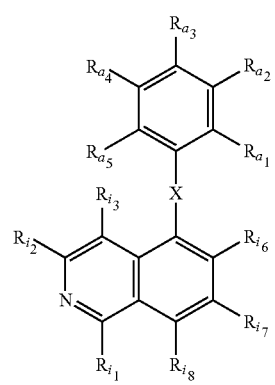

wherein:
X represents —C(=O), —CH(OH)— or —CH$_2$—,
Ri$_1$ represents a hydrogen atom or a hydroxyl group,
it being understood that the compound of formula (I) wherein Ri$_1$ represents a hydroxyl group may be represented by the following tautomeric form:

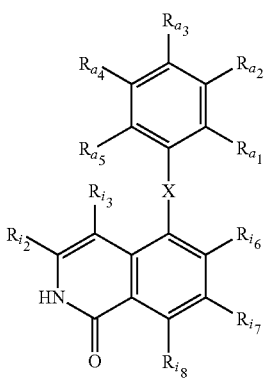

$Ri_2$ and $Ri_3$, which may be identical or different, each represent a hydrogen atom, a $(C_1-C_6)$alkyl group or a halogen atom, $Ri_6$, $Ri_7$ and $Ri_8$, which may be identical or different, each represent a hydrogen atom or a halogen atom, $Ra_1$ and $Ra_5$, which may be identical or different, each represent a hydrogen atom, a halogen atom, an —O($C_1-C_6$)alkyl group or a ($C_1-C_6$)alkyl group, $Ra_2$ represents a hydrogen or halogen atom, a hydroxyl group, a —O($C_1-C_6$)alkyl group, a —($C_1-C_6$)alkyl group, a nitrogen-containing heterocycle having from 3 to 7 ring members, or —O—(CH2)$_m$—NR'R", $Ra_3$ represents a hydrogen atom, an —O($C_1-C_6$)alkyl group, a —($C_1-C_6$)alkyl group, a nitrogen-containing heterocycle having from 3 to 7 ring members, or —CRy$_1$Ry$_2$NH(Ry$_3$), $Ra_4$ represents a hydrogen atom a halogen atom, an —O($C_1-C_6$)alkyl group, a —($C_1-C_6$)alkyl group, or —CRy$_1$Ry$_2$NH(Ry$_3$), it being understood that:

$Ra_1$, $Ra_2$, $Ra_3$, $Ra_4$ and $Ra_5$ may not simultaneously represent a hydrogen atom, $Ra_3$ and $Ra_4$ may not simultaneously represent —CRy$_1$Ry$_2$NH(Ry$_3$), $Ra_1$ and $Ra_2$, together with the carbon atoms carrying them, may form a heterocycle having from 4 to 7 ring members chosen from tetrahydrofuran, 1,4-dioxane, tetrahydropyran, tetrahydro-2H-pyran-4-amine and 1-(tetrahydro-2H-pyran-4-yl)methanamine, and $Ra_2$ and $Ra_3$, together with the carbon atoms carrying them, may form a hydrocarbon ring having from 4 to 7 ring members chosen from cyclopentane, cyclopentanamine, N-cyclopentylglycinamide and 1-methylcyclopentanamine, m is an integer, the value of which is fixed at 1, 2 or 3, R' and R", which may be identical or different, each represent —($C_1-C_6$)alkyl groups or, together with the nitrogen atom carrying them, form a heterocycle having from 3 to 7 ring members, Ry$_1$ represents a hydrogen atom, a —($C_1-C_6$)alkyl group, a —CH$_2$-cyclohexyl group, or a 3-methoxyphenyl group, Ry$_2$ represents a hydrogen atom or a —($C_1-C_6$)alkyl group, Ry$_3$ represents:
a hydrogen atom,
—C(=O)—CHRy$_4$-NHRy$_5$ wherein Ry$_4$ represents a hydrogen atom or a ($C_1-C_6$)alkyl group and Ry$_5$ represents a hydrogen atom or a methyl group, or
a —($C_1-C_6$)alkyl group which may be substituted by a hydroxyl group, an —O($C_1-C_3$)alkyl group, a cyclohexyl group or a methylsulphonyl group, or Ry$_1$ and Ry$_2$, together with the carbon atom carrying them, form a cyclopropane, cyclobutane or tetrahydropyran group, or Ry$_2$ and Ry$_3$, together with the carbon and nitrogen atoms carrying them, respectively, form a pyrrolidine or piperidine group, or an optical isomer thereof, where it exists, an addition salt thereof with a pharmaceutically acceptable acid or a hydrate thereof.

2. The compound according to claim 1, wherein X represents —C(=O).

3. The compound of according to claim 1, wherein $Ri_1$ represents a hydroxyl group, it being understood that said compound may be represented in its tautomeric form.

4. The compound according to claim 1, wherein $Ri_2$, $Ri_6$, $Ri_7$ and $Ri_8$ each represent a hydrogen atom.

5. The compound according to claim 1, Wherein $Ra_1$ and $Ra_5$ each represent a fluorine atom.

6. The compound according to claim 1, wherein $Ra_3$ or $Ra_4$ represents —CRy$_1$Ry$_2$NH(Ry$_3$).

7. The compound according to claim 6, wherein:
Ry$_1$ represents a hydrogen atom or a —($C_1-C_6$)alkyl group,
Ry$_2$ represents a —($C_1-C_6$)alkyl group, and
Ry$_3$ represents a hydrogen atom.

8. The compound according to claim 1, wherein:
X represents —C(=O)—,
$Ri_1$ represents a hydrogen atom or a hydroxyl group,
$Ri_2$, $Ri_6$, $Ri_7$ and $Ri_8$ each represent a hydrogen atom and $Ri_3$ represents a hydrogen atom or a ($C_1-C_6$)alkyl group,
$Ra_1$ and $Ra_5$, which may be identical or different, each represent a hydrogen atom, a fluorine atom or a ($C_1-C_6$)alkyl group,
$Ra_2$ represents a hydrogen atom or a —($C_1-C_6$)alkyl group,
$Ra_3$ represents a hydrogen atom, a piperidine group or —CRy$_1$Ry$_2$NH(Ry$_3$),
$Ra_4$ represents a hydrogen atom or —CRy$_1$Ry$_2$NH(Ry$_3$), it being understood that $Ra_3$ and $Ra_4$ may not simultaneously represent —CRy$_1$Ry$_2$NH(Ry$_3$), and that:
when $Ra_3$ represents —CRy$_1$Ry$_2$NH(Ry$_3$), $Ra_1$ and $Ra_2$, together with the carbon atoms carrying them, may form a tetrahydrofuran, 1,4-dioxane or tetrahydropyran group, or
when $Ra_3$ represents a hydrogen atom, $Ra_1$ and $Ra_2$, together with the carbon atoms carrying them, may form a tetrahydro-2H-pyran-4-amine or 1-(tetrahydro-2H-pyran-4-yl)methanamine group, or
$Ra_2$ and $Ra_3$, together with the carbon atoms carrying them, may form a cyclopentanamine or 1-methylcyclopentanamine group, Ry$_1$ represents a hydrogen atom, a —($C_1-C_6$)alkyl group or —CH$_2$-cyclohexyl group,
Ry$_2$ represents a hydrogen atom or a —($C_1-C_6$)alkyl group,
Ry$_3$ represents a hydrogen atom or a —($C_1-C_6$)alkyl group which may be substituted by a hydroxyl group.

9. The compound according to claim 1, which is selected from:
- [4-(1-aminoethyl)-2,6-difluorophenyl](isoquinolin-5-yl)methanone,
- [4-((1R)-1-aminoethyl)-2,6-difluorophenyl](isoquinolin-5-yl)methanone,
- [4-(1-aminoethyl)-2,6-difluorophenyl](1-hydroxyisoquinolin-5-yl)methanone,
- 1-[3,5-difluoro-4-(isoquinolin-5-ylmethyl)phenyl]ethanamine,
- {4-[(1S)-1-aminoethyl]-2,6-difluorophenyl}(isoquinolin-5-yl)methanol,
- [4-(2-aminopropan-2-yl)-2,6-difluorophenyl](isoquinolin-5-yl)methanone,
- 5-[4-(2-aminopropan-2-yl)-2,6-difluorobenzoyl]isoquinolin-1(2H)-one,
- 5-[4-(1-aminoethyl)-2-fluoro-3-methoxybenzoyl]isoquinolin-1(2H)-one,
- 5-({5-[(1R)-1-aminoethyl]-3,4-dihydro-2H-chromen-8-yl}carbonyl)isoquinolin-1(2H)-one,
- 5-{4-[(1R)-1-aminoethyl]-2-methylbenzoyl}isoquinolin-1(2H)-one,
- 5-(2,6-difluoro-4-{1-[(2-hydroxyethyl)amino]ethyl}benzoyl)isoquinolin-1(2H)-one,
- 5-{4-[(1R)-1-aminoethyl]-2,6-difluorobenzoyl}-4-methylisoquinolin-1(2H)-one,
- 5-{3-[(1R)-1-aminoethyl]-2,6-difluorobenzoyl}isoquinolin-1(2H)-one,
- 5-[(1-amino-4,6-difluoro-2,3-dihydro-1H-inden-5-yl)carbonyl]isoquinolin-1(2H)-one,
- 5-{[(3R)-3-amino-4,6-difluoro-2,3-dihydro-1H-inden-5-yl]carbonyl}isoquinolin-1(2H)-one,
- 5-({8-[(1R)-1-aminoethyl]-2,3-dihydro-1,4-benzodioxin-5-yl}carbonyl)isoquinolin-1(2H)-one,
- 5-[2,6-difluoro-4-(piperidin-2-yl)benzoyl]isoquinolin-1(2H)-one,
- 5-[4-(1-amino-2-cyclohexylethyl)-2,6-difluorobenzoyl]isoquinolin-1(2H)-one, and
- 5-{[4-(aminomethyl)-3,4-dihydro-2H-chromen-8-yl]carbonyl}isoquinolin-1(2H)-one, or an optical isomer thereof, where it exists, an addition salt thereof with a pharmaceutically acceptable acid or a hydrate thereof.

10. The compound according to claim 1, which is 5-({5-8 (1R)-1-Aminoethyl]-3,4-dihydro-2H-chromen-8-yl}carbonyl)isoquinolin-1(2H)-one or an addition salt thereof with a pharmaceutically acceptable acid or a hydrate thereof.

11. The compound according to claim 1, which is 5-{4-[(1R)-1-Aminoethyl]-2-methylbenzoyl}isoquinolin-1(2H)-one or an addition salt thereof with a pharmaceutically acceptable acid or a hydrate thereof.

12. The compound according to claim 1, which is 5-{4-[(1R)-1-Aminoethyl]-2,6-difluorobenzoyl}-4-methylisoquinolin-1(2H)-one or an addition salt thereof with a pharmaceutically acceptable acid or a hydrate thereof.

13. The compound according to claim 1, which is 5-{3-[(1R)-1-Aminoethyl]-2,6-difluorobenzoyl}-isoquinolin-1(2H)-one or an addition salt thereof with a pharmaceutically acceptable acid or a hydrate thereof.

14. The compound according to claim 1, which is 5-{[(3R)-3-Amino-4,6-difluoro-2,3-dihydro-1H-inden-5-yl]carbonyl}isoquinolin-1(2H)-one or an addition salt thereof with a pharmaceutically acceptable acid or a hydrate thereof.

15. The compound according to claim 1, which is 5({8-[(1R)-1-Aminoethyl}-2,3-dihydro-1,4-benzo-dioxin-5-yl}carbonyl)isoquinolin-1(2H)-one or an addition salt thereof with a pharmaceutically acceptable acid or a hydrate thereof.

16. A pharmaceutical composition comprising as active ingredient the compound according to claim 1, in combination with one or more inert, non-toxic, pharmaceutically acceptable excipients or carriers.

17. A method for the treatment of pathologies which are the result of activation of the RhoA/ROCK pathway and phosphorylation of the myosin light chain in a subject in need thereof, wherein the pathology which is the result of activation of the RhoA/ROCK pathway and phosphorylation of the myosin light chain is a condition selected from systemic arterial hypertension, pulmonary arterial hypertension, angina, myocardial infarction, post-angioplasty restenosis, aortic aneurysm, occlusion of the peripheral arteries, atherosclerosis, cardiac fibrosis and heart failure, comprising administration of an effective amount of the compound according to claim 1.

18. The method according to claim 11, wherein the condition is systemic arterial hypertension.

19. A method for the treatment of pathologies which are the result of activation of the RhoA/ROCK pathway and phosphorylation of the myosin light chain in a subject in need thereof, wherein the pathology which is the result of activation of the RhoA/ROCK pathway and phosphorylation of the myosin light chain is a condition selected from glaucoma and pathologies of the cornea, comprising administration of an effective amount of the compound according to claim 1.

20. A method for the treatment of pathologies which are the result of activation of the RhoA/ROCK pathway and phosphorylation of the myosin light chain in a subject in need thereof, wherein the pathology which is the result of activation of the RhoA/ROCK pathway and phosphorylation of the myosin light chain is a condition selected from erectile dysfunction, broncho-obstructive pulmonary diseases, post-radiation intestinal fibrosis, cutaneous systemic sclerosis, pulmonary fibrosis associated with pulmonary arterial hypertension, hepatic diseases, renal fibrosis and glomerulosclerosis, diabetes, hyperglycaemia, insulin resistance, diabetic nephropathies induced or not induced by hypertension, thrombotic diseases, cerebral vasospasm and resulting cerebral ischaemia, comprising administration of an effective amount of the compound according to claim 1.

* * * * *

UNITED STATES PATENT AND TRADEMARK OFFICE
CERTIFICATE OF CORRECTION

PATENT NO. : 9,809,553 B2
APPLICATION NO. : 15/119173
DATED : November 7, 2017
INVENTOR(S) : Stéfano Chimenti et al.

Page 1 of 1

It is certified that error appears in the above-identified patent and that said Letters Patent is hereby corrected as shown below:

In the Claims

Column 195, Line 44: "5-({5-8" should be "5-({5-[".

Column 196, Line 30: "claim 11" should be "claim 17".

Signed and Sealed this
Fourth Day of September, 2018

Andrei Iancu
*Director of the United States Patent and Trademark Office*